(12) United States Patent
Mitchell et al.

(10) Patent No.: US 9,815,846 B2
(45) Date of Patent: Nov. 14, 2017

(54) TRKA KINASE INHIBITORS, COMPOSITIONS AND METHODS THEREOF

(71) Applicants: Merck Sharp & Dohme Corp., Rahway, NJ (US); MSD R & D (China) Co., LTD., Shanghai (CN)

(72) Inventors: Helen Mitchell, Richboro, PA (US); Mark E. Fraley, North Wales, PA (US); Andrew J. Cooke, West Point, PA (US); Craig A. Stump, West Point, PA (US); Yi-Heng Chen, Whippany, NJ (US); Xu-Fang Zhang, Dresher, PA (US); Casey C. McComas, Phoenixville, PA (US); Kathy Schirripa, Quakertown, PA (US); Melody McWherter, Boyertown, PA (US); Swati P. Mercer, Philadelphia, PA (US); Kerim Babaoglu, Lansdale, PA (US); Dongfang Meng, Morganville, NJ (US); Jane Wu, Marlboro, NJ (US); Ping Liu, Westfield, NJ (US); Harold B. Wood, Westfield, NJ (US); Jianming Bao, Shanghai (CN); Chun Sing Li, Shanghai (CN); Qinghua Mao, Shanghai (CN); Zhiqi Qi, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/128,689

(22) PCT Filed: Mar. 23, 2015

(86) PCT No.: PCT/US2015/021936
§ 371 (c)(1),
(2) Date: Sep. 23, 2016

(87) PCT Pub. No.: WO2015/148344
PCT Pub. Date: Oct. 1, 2015

(65) Prior Publication Data
US 2017/0114071 A1 Apr. 27, 2017

(30) Foreign Application Priority Data

Mar. 26, 2014 (WO) ................ PCT/CN2014/074145

(51) Int. Cl.
*C07D 491/107* (2006.01)
*C07C 233/66* (2006.01)
(Continued)

(52) U.S. Cl.
CPC ........ *C07D 491/107* (2013.01); *C07C 233/66* (2013.01); *C07D 213/75* (2013.01); *C07D 239/42* (2013.01); *C07D 401/04* (2013.01); *C07D 401/06* (2013.01); *C07D 401/12* (2013.01); *C07D 401/14* (2013.01); *C07D 403/06* (2013.01); *C07D 403/12* (2013.01); *C07D 403/14* (2013.01); *C07D 405/12* (2013.01); *C07D 405/14* (2013.01); *C07D 413/06* (2013.01); *C07D 413/12* (2013.01); *C07D 413/14* (2013.01);
(Continued)

(58) Field of Classification Search
CPC .................. C07D 491/107; C07C 233/66
See application file for complete search history.

(56) References Cited

U.S. PATENT DOCUMENTS

| | | | |
|---|---|---|---|
| 4,638,014 A | 1/1987 | Clark | |
| 6,022,884 A * | 2/2000 | Mantlo | ............... C07D 213/73 514/352 |

(Continued)

FOREIGN PATENT DOCUMENTS

| | | |
|---|---|---|
| EP | 1181318 | 5/2000 |
| EP | 1388341 | 8/2002 |

(Continued)

OTHER PUBLICATIONS

Karra et al (2013):STN International, HCAPLUS database (Columbus, Ohio), Accession No. 2013: 571270.*

(Continued)

*Primary Examiner* — Golam M M Shameem
(74) *Attorney, Agent, or Firm* — Sylvia A. Ayler; John C. Todaro

(57) ABSTRACT

The present invention is directed to six membered heteroaryl benzamide compounds of formula (I), which are tropomyosin-related kinase (Trk) family protein kinase inhibitors, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

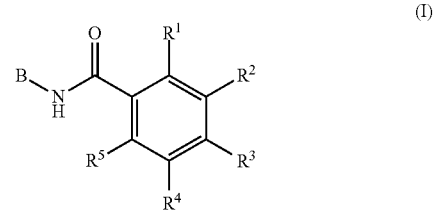

(I)

16 Claims, No Drawings

(51) Int. Cl.

| | | |
|---|---|---|
| C07D 213/75 | (2006.01) | |
| C07D 403/12 | (2006.01) | |
| C07D 401/12 | (2006.01) | |
| C07D 417/12 | (2006.01) | |
| C07D 239/42 | (2006.01) | |
| C07D 401/04 | (2006.01) | |
| C07D 413/12 | (2006.01) | |
| C07D 417/14 | (2006.01) | |
| C07D 401/14 | (2006.01) | |
| C07D 405/12 | (2006.01) | |
| C07D 413/14 | (2006.01) | |
| C07D 403/14 | (2006.01) | |
| C07D 405/14 | (2006.01) | |
| C07D 471/04 | (2006.01) | |
| C07D 401/06 | (2006.01) | |
| C07D 413/06 | (2006.01) | |
| C07D 403/06 | (2006.01) | |

(52) U.S. Cl.
CPC ......... *C07D 417/12* (2013.01); *C07D 417/14* (2013.01); *C07D 471/04* (2013.01)

(56) References Cited

U.S. PATENT DOCUMENTS

| | | |
|---|---|---|
| 6,372,767 B1 | 4/2002 | McNaughton-Smith et al. |
| 6,458,813 B1 * | 10/2002 | Mantlo ................ C07D 213/73 514/335 |
| 2002/0103203 A1 | 8/2002 | Bender et al. |
| 2005/0143384 A1 | 6/2005 | Sartori et al. |
| 2009/0163476 A1 | 6/2009 | Millburn et al. |
| 2010/0120862 A1 | 5/2010 | Tafesse |

FOREIGN PATENT DOCUMENTS

| | | |
|---|---|---|
| EP | 2151435 | 2/2010 |
| NO | WO2007069773 A1 | 6/2007 |
| WO | WO0178698 A2 | 10/2001 |
| WO | WO2004058184 | 7/2004 |
| WO | WO2004096122 | 11/2004 |
| WO | WO2004098518 A2 | 11/2004 |
| WO | WO2005019266 | 3/2005 |
| WO | WO2005030128 | 4/2005 |
| WO | WO2005061540 | 7/2005 |
| WO | WO2005110994 | 11/2005 |
| WO | WO2006137106 | 6/2006 |
| WO | WO2006087538 | 8/2006 |
| WO | WO2006115452 | 11/2006 |
| WO | WO2006123113 | 11/2006 |
| WO | WO2006131952 | 12/2006 |
| WO | WO2007013673 | 2/2007 |
| WO | WO2007025540 A2 | 3/2007 |
| WO | WO2007042321 | 4/2007 |
| WO | 2008003770 A1 | 1/2008 |
| WO | WO2008052734 | 5/2008 |
| WO | WO2008124610 A1 | 10/2008 |
| WO | WO2009003999 A2 | 1/2009 |
| WO | WO2009046802 A1 | 4/2009 |
| WO | WO2009003998 | 8/2009 |
| WO | WO2010033941 | 3/2010 |
| WO | WO2010077680 A2 | 7/2010 |
| WO | WO2010111653 | 9/2010 |
| WO | WO2012003387 A1 | 1/2012 |
| WO | WO2012028579 A1 | 3/2012 |
| WO | WO2012100223 A1 | 7/2012 |
| WO | WO2012107434 A1 | 8/2012 |
| WO | WO2012158413 | 11/2012 |
| WO | WO2012159565 A1 | 11/2012 |
| WO | WO2012161879 A1 | 11/2012 |
| WO | WO2013171641 | 11/2013 |
| WO | WO2013176970 | 11/2013 |
| WO | WO2014016434 | 1/2014 |

OTHER PUBLICATIONS

Mantlo et al (1999):STN International, HCAPLUS database (Columbus, Ohio), Accession No. 1999: 325908.*
Truong et al (2013):STN International, HCAPLUS database (Columbus, Ohio), Accession No. 2013: 943306.*
Assumi et al., Expression of Neurotrophins and Their Receptors (TRK) During Fracture Healing, Bone, 2000, pp. 625-633, 26.
Bardelli et al., Mutational Analysis of the Tryosine Kinome in Colorectal Cancers, Science, May 9, 2003, pp. 949, 300.
Brodeur et al., Neuroblastoma: Biological Insights into a Clincal Enigma, Nat. Rev Cancer, 2003, pp. 203-216, 3.
Cheung et al., Aurora Kinase Inhibitor Patents and Agents in Clinical Testing: An Update (Oct. 2009), Expert Opin. Investig. Drugs, 2009, 1-36, 19.
Dang et al., Expression of Nerve Growth Factor Receptors is Correlated with Progression and Prognosis of Human Pancreatic Cancer, J. of Gastroenterology and Hepatology, 2006, pp. 850-858, 21 (5).
Delafoy et al., Role of Nerve Growth Factor in the Trinitrobenzene Sulfonic Acid-Induced Colonic Hypersensitivity, Pain, 2003, pp. 489-497, 105.
Di Mola, Nerve Growth Factor and Trk Hihg Affinity Receptor (TRkA) Gene Expression in Inflammatory Bowel Disease, Gut, 2000, pp. 670-678, 46(5).
Dionne et al., Cell cycle-independent death of prostate adenocarcinoma is Induced by the trk Tyrosine Kinase Inhibitor CEP-751 (KT6587), Clinical Cancer Research, 1998, pp. 1887-1898, 4(8).
Dou et al., Increased nerve growth factor and its receptors in atopic dermatitis:, Archives of Dermatological Research, 2006, pp. 31-37 (1), 298.
Freund-Michel et al., The Nerve Growth Factor and Its Receptors in Airway Inflammatory Diseases, Pharmacology & Thereapeutics, 2008, pp. 52-76, 117 (1).
Hu et al., Decrease in Bladder Overactivity With REN1820 in Rats, J. of Urology, 2005, pp. 1016-1021, 173 (3).
Iannone, Increased Expression of Nerve Growth Factoer (NGF) and high Affinity NGF Receptor (p140 TrkA) in Human Osteoarthritic Chondrocytes, Rheumatology, 2002, pp. 1413-1418, 4.
Jaggar et al., Inflammation of the Rat Urinary Bladder is associated with a Referred Thermal Hyperalgesia Which is Nerve Growth Factor Dependent, Br. J. Anaesth., 1999, pp. 442-448, 83.
Kruettgen et al., The Dark Side of the NGF Family: Neurotrophin in Neoplasia, Brain Pathology, 2006, pp. 304-310, 16.
Lamb et al., Nerve Growth Factor and Gastric Hyperalgesia in the Rat, Neurogastroenterol Motil., 2003, pp. 355-361, 15.
Ma et al., The Progressive Tactile Hyperalgesia Induced by Peripheral Inflammation is Nerve Growth Factor Dependent, Neuroreport, 1997, pp. 807-810, 8.
Marchetti et al., Frequent Mutations in the Neuroptrophic Trrosine Receptor Kinase Gene Family in Large Cell Neuroendocrine Carcinioma of the Lung, Rapid Communication, 2008, pp. 609-616, 29 (5).
McMahon et al., The Biological Effects of Endogenous Nerve Growth Factor on Adult Sensory Neurons Revealed by a trkA-IgG Fusion Molecule, Nature Medicine, 1995, pp. 774-780, 1.
Raychaudhuri et al., K252a, a High-Affinity Nerve Growth Factor Receptor Blocker,, J. of Investigative Dermatology, 2004, pp. 812-819, 122 (3).
Shelton et al., Nerve growth factor mediates hyperalgesia and cachexia, Pain, 2005, pp. 8-16, 116.
Sohrabji et al., Estrogen-BDNF interactions: Implications, Frontiers in Neuroendocrinology, 2006, pp. 404-414, 27 (4).
Substance: Benzanilide. Royal Society of Chemistry. 2013. [retrieved on Sep. 3, 2015].Retrieved from the Internet. <URL: http://www.rsc.org/learn-chemistry/wiki/Substance:Benzanilide>. entire document.
Tripathy et al., TrkA kinase inhibitors from a library of modified and isosteric, Bioganic & Medicinal Chemistry Letters, 2008, pp. 3551-3555, 18.
Undevia et al., Phase I Clinical Trial of CEP-2563 Dihydrochloride, A Receptor Tyrosine Kinase Inhibitor, in Patients with Refractory

(56) References Cited

OTHER PUBLICATIONS

Solid Tumors, Investigational New Drugs, 2004, pp. 449-458, 22.
Woolf, Nerve Growth Factor Contributes to the Generation of Inflammatory Sensory Hypersenstivity, Neuroscience, 1994, pp. 327-331, 62.
Zhan et al., Effect of Blockade of Nerve Growth Factor and Tumor Necrosis Factor on Pain Behaviors After Plantar Incision, J. Pain, 2004, pp. 157-163, 5.
Zhu et al., Nerve Growth Factor Expression Correlation with Perineural Invasion and Pain in Human Pancreatic Cancer, J. of Clinicl Oncology, 1999, pp. 2419-2428, 17.
Sahu et al., Synthesis and Biological Evaluation of 3-(phthalimidomethyl)-4-(5-Substittued Isoxazoline and Pyrazoline) Substituted Benzanilides, J. of the Indian Chemical Society, 2007, pp. 1011-1015, 84.
Wacker et al, The Identification of Novel, High Affinity AQP9 Inhibitors in an Intracellular Binding site, Molecular Membrane Biology, 2013, pp. 246-260, 30.
Weisberg et al., Discovery and Characterization of Novel Mutant FLT3 Kinase Inhibitors, Therapeutic Discovery, 2010, pp. 2468-2477, 9.
Zhou et al, Synthesis and Sar of Novel, non-MPEP chemotype mGluR5 NAMs Identified by Functional HTS, Bioorganic & Medicinal Chemistry Letters, 2009, 6502-6506, 23.

\* cited by examiner

TRKA KINASE INHIBITORS, COMPOSITIONS AND METHODS THEREOF

CROSS REFERENCE TO RELATED APPLICATIONS

This application is the National Stage of International Application No. PCT/US2015/021936 filed on Mar. 23, 2015, which claims the benefit under 35 U.S.C. 119 (b) and 37 CFR 1.55, Application No. PCT/CN2014/074145, filed Mar. 26, 2014.

FIELD OF THE INVENTION

The invention is directed to a class of substituted six membered aryl or heteroaryl benzamide compounds, their salts, pharmaceutical compositions comprising them and their use in therapy of the human body. In particular, the invention is directed to a class of substituted heteroaryl benzamide compounds, which are tropomyosin-related kinase (Trk) family protein kinase inhibitors, and hence are useful in the treatment of pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA.

BACKGROUND OF THE INVENTION

Trk receptors are high affinity binding protein kinase receptors that are activated by Neurotrophins (NT), a group of soluble growth factors including Nerve Growth Factor (NGF), Brain-Derived Neurotrophic Factor (BDNF) and Neurotrophin 3-5 (NT 3-5). The Trk receptors consist of three family members TrkA, TrkB and TrkC that bind to and mediate the signal transduction derived from the Neurotrophins. NGF activates TrkA, BDNF and NT-4/5 activate TrkB and NT3 activates TrkC.

Inhibitors of the Trk/neutrophin pathway have been demonstrated to be highly effective in numerous pre-clinical animal models of pain. Antagonistic NGF and TrkA antibodies have been shown to be efficacious in inflammatory and neuropathic pain animal models and in human clinical trials. See Woolf, C. J. et al. (1994) Neuroscience 62, 327-331; Zahn, P. K. et al. (2004) J. Pain 5, 157-163; McMahon, S. B. et al., (1995) Nat. Med. 1, 774-780; Ma, Q. P. and Woolf, C. J. (1997) Neuroreport 8, 807-810; Shelton, D. L. et al. (2005) Pain 116, 8-16; Delafoy, L. et al. (2003) Pain 105, 489-497; Lamb, K. et al. (2003) Neurogastroenterol. Motil. 15, 355-361; and Jaggar, S. I. et al. (199) Br. J. Anaesth. 83, 442-448. Through gene disruption studies in mice the TrkA-NGF interaction was found to be required for the survival of certain peripheral neuron populations involved in mediating pain signaling in the case of pancreatic cancer—an increase in the expression of TrkA was shown to correlate with an increase level of pain signaling (Zhu et al., Journal of Clinical oncology, 17:2419-2428 (1999)). Increased expression of NGF and TrkA was also observed in human osteoarthritis chondrocytes (Iannone et al, Rheumatology 41:1413-1418 (2002)). In particular, anti-TrkA antibodies and anti-NGF antibodies have been demonstrated to be effective analgesics in in vivo models of inflammatory and neuropathic pain. See WO2006/131952, WO2005/061540, EP1181318 and WO01/78698, WO2004/058184 and WO2005/019266, respectively. See also WO2004/096122 and WO2006/137106 which describe the use of an anti-TrkA antibody in combination with an opioid analgesic for the treatment or prevention of pain.

Trk inhibitors that can induce apoptosis of proliferating osteoblasts may be useful in treating diseases related to an imbalance of the regulation of bone remodeling, such as osteoporosis, rheumatoid arthritis and bone metastases. The expression of TrkA and TrkC receptors in the bone forming area in mouse models of bone fracture and localization of NGF in almost all bone forming cells have been observed (K. Asaumi, et al., Bone (2000) 26(6) 625-633). See also Expert Opin. Ther. Patents (2009) 19(3)), WO2006/115452 and WO2006/087538, WO6123113, WO10033941, WO10077680, WO2005110994, Investigational New Drugs (2004), 22, 449-458 and R. Tripathy, et al., Bioorg. Med. Chem. Lett., 2008, 18, 3551-3555. The association between overexpression, activation, amplification and/or mutation of Trk receptors and several cancers as seen with studies conduct on neuroblastoma (Brodeur, G. M., Nat. Rev. Cancer 2003, 3, 203-216), ovarian cancer (Kruettgen et al., Brain Pathology 2006, 16: 304-310), prostate cancer (Dionne et al., Clin. Cancer Res. 1998, 4(8): 1887-1898), pancreatic cancer (Dang et al., J of Gastroenterology and Hepatology 2006, 21(5): 850-858), large cell neuroendocrine tumors (Marchetti et al., Human Mutation 2008, 29(5), 609-616, and colorectal cancer (Bardelli, A., Science 2003, 300, 949) support the reasoning that therapeutic implications of an effective Trk inhibitor may extend far beyond pain therapy. See also WO2005/030128, WO2012158413, WO07013673, WO07025540, WO08052734, WO2012028579, WO2012159565, WO2012107434, WO2012003387, WO2010111653, WO2008124610, WO2004098518, EP1388341, WO2012028579, WO2008003770, WO2012161879, WO2012100223, WO2009046802, WO2009003999, WO2007042321, US2005143384, WO2009003998, WO2007069773, WO2005/030128, and US2010120862.

Also promising is the utility of Trk inhibitors in the treatment of inflammatory lung diseases such as asthma (Freund-Michel, V; et al., Pharmacology & Therapeutics (2008), 117(1), 52-76), interstitial cystitis (Hu Vivian Y; et. al., J of Urology (2005, 173(3), 1016-21), inflammatory bowel disease including ulcerative colitis and Crohn's disease (Di Mola, F. F., et al., Gut (2000), 46(5), 670-678 and inflammatory skin diseases such as atopic dermatitis (Dou, Y. C., et. Al., Archives of Dermatological Research (2006), 298(1), 31-37, eczema and psoriasis (Raychaudhuri, S. P. et. al., J of Investigative Dermatology (2004), 122(3), 812-819).

Modulation of the neutrophin/Trk pathway also has been shown to have an effect in the etiology of neurodegenerative diseases including multiple sclerosis, Parkinson's disease and Alzheimer's disease (Sohrabji, et. al., Neuroendocrinology (2006), 27(4), 404-414).

Thus, the compounds of the invention, which are Trk inhibitors, are believed to be useful in the treatment of multiple types of acute and chronic pain including but not limited to inflammatory pain, neuropathic pain, and pain associated with cancer, surgery and bone fracture. The compounds may also be useful in the treatment of cancer, inflammation, neurodegenerative diseases and certain infectious diseases.

SUMMARY OF THE INVENTION

The present invention is directed to compounds of generic formula (I) below or pharmaceutically acceptable salts thereof that are useful as a Trk kinase mediator of NGF driven biological responses, an inhibitor of TrkA as well as other Trk kinases.

The invention is further directed to methods of treating a patient (preferably a human) for diseases or disorders in which the NGF receptor Trk kinases are involved, in particular TrkA. The invention further involves use of the compounds as NGF receptor TrkA inhibitor and/or antagonist for the preparation of a medicament for the treatment and/or prevention of diseases associated with inhibiting TrkA, which includes pain, cancer, restenosis, atherosclerosis, psoriasis, thrombosis, or a disease, disorder, or injury relating to dysmyelination or demyelination. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to compounds of general formula (I)

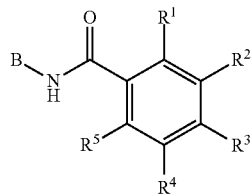

I or pharmaceutically acceptable salts thereof, wherein:
B represents phenyl, tetrahydronapthyridinyl, dihydropyrrolopyridinyl, or a six membered heteroaryl having at least one heteroatom that is nitrogen, said phenyl, tetrahydronapthyridinyl, dihydropyrrolopyridinyl, and heteroaryl optionally substituted with 1 to 3 groups of $R^a$;
R represents hydrogen, OH, or —$C_{1-6}$alkyl, said alkyl optionally substituted with 1 to 3 groups of $R^f$;
$R^1$ and $R^5$ are independently selected from the group consisting of hydrogen, CN, OH, —$C_{1-6}$alkyl and halogen;
$R^2$ and $R^4$ are independently selected from the group consisting of hydrogen, halogen, $C_{1-6}$ alkyl, $(CHR)_nC_{6-10}$ aryl and $(CHR)_nC_{5-10}$ heterocycle, said alkyl, aryl, and heterocycle optionally substituted with 1 to 3 groups of $R^a$,
$R^3$ represents hydrogen, $C_{1-6}$alkyl, $C_{1-4}$ haloalkyl, —$OC_{1-4}$ haloalkyl, and halogen;
$R^a$ is selected from the group consisting of hydrogen, —CN, $NO_2$, —$(CH_2)_nC(O)OR^f$, —$C_{1-4}$haloalkyl, —$OC_{1-4}$ halo alkyl, —$C_{1-6}$alkyl, —$C_{1-6}$alkenyl, —$C_{1-6}$alkynyl, —$(CH_2)_nC_{3-6}$ cycloalkyl, —$(CHR)_nC_{6-10}$ aryl, —$(CHR)_nC_{4-10}$ heterocycle, —$(CH_2)_nC(O)(CHR)_nC_{4-10}$ heterocycle, —O—$(CH_2)_nC_{6-10}$ aryl, —O—$(CH_2)_nC_{4-10}$ heterocycle, —O—, —$(CH_2)_nN(R^d)_2$, —$(CH_2)_nC(O)NH(CH_2)_nC_{4-10}$ heterocycle, $SO_2R^d$, $(CH_2)_nNHSO_2R^d$, —$(CH_2)_nSO_2N(R^d)_2$, $S(O)(NH)R^g$, —$C(O)CF_3$, COR, —$(CH_2)_n$halo, —$(CH_2)_nNHC(O)R^d$, —$(CH_2)_nNRC(O)NHR^d$, —$(CH_2)_nNHC(O)OR^d$, $CHR)_nC(O)N(R^d)_2$—$OC_{1-6}$alkyl, —O—, and —OH, said alkyl, cycloalkyl, aryl and heterocycle optionally substituted with 1 to 3 groups of $R^b$, wherein when two $R^d$ groups are attached to a nitrogen atom they may combine with that nitrogen to from a 4-8 membered heterocyle that is optionally substituted with 1 to 3 groups of $R^f$;
$R^b$ is selected from the group consisting of halogen, —$C_{1-6}$alkyl, —$C_{1-6}$alkylOR, —$C_{1-4}$ haloalkyl, —$(CH_2)_nN(R^d)_2$, —$OR^c$, —O—, —CN, $S(O)(NH)R^g$, —$SO_2R$, —$SO_2N(R^d)_2$, —$(CH_2)_nC(O)N(R^d)_2$, —$(CH_2)_nNHC(O)R^d$, COR, C(O)OR, $C_{3-6}$cycloalkyl, —O—$(CH_2)_nC_{4-10}$ heterocycle, and —$C_{1-6}$alkylN($R^d)_2$, said alkyl and heterocycle optionally substituted with 1 to 3 groups of $R^f$;
$R^c$ is selected from the group consisting of hydrogen, —$C_{1-6}$alkylOR$^g$, —$C_{1-4}$ haloalkyl and —$C_{1-6}$alkyl;
$R^d$ is independently selected from the group consisting of hydrogen, halogen, —$C_{1-4}$haloalkyl —$C_{1-6}$alkyl, COR, —$(CH_2)_nSO_2R$, —$(CH_2)_nNR^fC_{4-10}$ heterocycle, —$(CH_2)_nC_{3-6}$cycloalkyl, —$(CH_2)_nC_{4-10}$heterocycle said alkyl, cycloalkyl and heterocycle optionally substituted with 1 to 3 groups of $R^f$; wherein when two $R^d$ groups are attached to a nitrogen atom they may combine with that nitrogen to from a 4-8 membered heterocycle that is optionally substituted with 1 to 3 groups of $R^f$;
$R^f$ is selected from the group consisting of hydrogen, $C_{1-6}$alkyl, $OR^c$, CN, —$N(R^c)_2$, $C(O)N(R^g)_2$, $C(O)C_{1-6}$alkyl, —$SO_2R^g$, —O—, —$C_{1-6}$alkyl $SO_2R^g$, —$C_{1-6}$alkylOR$^g$, —$C_{1-6}$alkylN($R^g)_2$,
$R^g$ is selected from the group consisting of hydrogen, —$C_{1-6}$alkyl; and
n represents 0-6.

An embodiment of the invention of formula I is realized when B is unsubstituted or substituted phenyl. A subembodiment of this aspect of the invention is realized when B is unsubstituted phenyl. Another subembodiment of this aspect of the invention is realized when B is substituted phenyl.

An embodiment of the invention of formula I is realized when B is an optionally substituted six membered heteroaryl selected from the group consisting of pyridyl, pyrimidinyl pyridazinyl, and pyrazinyl. An embodiment of the invention of this aspect of formula I is realized when B is substituted pyridyl. A further embodiment of this aspect of the invention of formula I is realized when B is unsubstituted pyridyl. Still another embodiment of this aspect of the invention of formula I is realized when B is substituted pyrimidinyl. Another embodiment of the invention of formula I is realized when B is unsubstituted pyrimidinyl. Yet another embodiment of the invention of formula I is realized when B is optionally substituted pyrazinyl. Another embodiment of the invention of formula I is realized when B is unsubstituted pyrazinyl. Another embodiment of the invention of formula I is realized when B is unsubstituted or substituted pyridazinyl.

An embodiment of the invention of formula I is realized when B is an optionally substituted tetrahydronapthyridinyl.

An embodiment of the invention of formula I is realized when B is an optionally substituted dihydropyrrolopyridinyl.

Another embodiment of the invention of formula I is realized when $R^a$ selected from from the group consisting of —$C_{1-4}$ haloalkyl, —$OC_{1-4}$ haloalkyl, —$C_{1-6}$alkyl, —$(CHR)_nC_{6-10}$ aryl, —$(CHR)_nC_{4-10}$ heterocycle, —$C(O)(CHR)_nC_{4-10}$ heterocycle, —O—$(CH_2)_nC_{6-10}$ aryl, —O—$(CH_2)_nC_{4-10}$ heterocycle, —O—, —$(CH_{12})_nN(R^d)_2$, —$(CH_2)_nC(O)NH(CH_2)_nC_{4-10}$ heterocycle, COR, —$(CH_2)_n$halo, —$(CH_2)_nNHC(O)R^d$, —$(CH_2)_nNHC(O)NHR^d$, —$(CH_2)_nNHC(O)OR^d$, —$(CHR)_nC(O)N(R^d)_2$—$(CH_2)_nNHSO_2R^d$, and —OR, said alkyl, aryl and heterocycle optionally substituted with 1 to 3 groups of $R^b$. A subembodiment of this aspect of the invention is realized when $R^a$ selected from the group consisting of —$C_{1-4}$ haloalkyl, —$OC_{1-4}$ haloalkyl, —$C_{1-6}$alkyl, —(CHR)$_n$C$_{6-10}$ aryl, —(CHR)$_n$C$_{4-10}$ heterocycle, —(CH$_2$)$_n$N(R$^d$)$_2$, COR, —(CH$_2$)$_n$halo, and —OR, said alkyl, aryl and heterocycle optionally substituted with 1 to 3 groups of $R^b$.

Another embodiment of the invention of formula I is realized when $R^b$ is selected from the group consisting of halogen, —$C_{1-6}$alkyl, —$C_{1-6}$alkylOR, —$C_{1-4}$ haloalkyl, —(CH$_2$)$_n$N(R$^d$)$_2$, —OR$^c$, —(CH$_2$)$_n$C(O)N(R$^d$)$_2$, —(CH$_2$)$_n$NHC(O)R$^d$.

Still another embodiment of the invention of formula I is realized when $R^1$ and $R^5$ are both hydrogen. Another embodiment of the invention of formula I is realized when one of $R^1$ and $R^5$ is hydrogen and the other is halogen. Still another embodiment of the invention of formula I is realized when $R^1$ and $R^5$ are both halogen. Still another embodiment of the invention of formula I is realized when one of $R^1$ and $R^5$ hydrogen and the other is chlorine, fluorine, CN, OH, or —$C_{1-6}$alkyl. Yet another embodiment of the invention of formula I is realized when one of $R^1$ and $R^5$ hydrogen and the other is —$C_{1-6}$alkyl. Yet another embodiment of the invention of formula I is realized when one of $R^1$ and $R^5$ hydrogen and the other is chlorine, or fluorine.

Another embodiment of the invention of formula I is realized when both $R^2$ and $R^4$ are hydrogen.

Another embodiment of the invention of formula I is realized when one of $R^2$ and $R^4$ is hydrogen and the other is (CHR)$_n$C$_{5-10}$ heterocycle, said heterocycle unsubstituted or substituted with 1 to 3 groups of $R^a$. A subembodiment of this aspect of the invention is realized when the n in (CHR)$_n$C$_{5-10}$ heterocycle is zero. Another subembodiment of this aspect of the invention is realized when the optionally substituted heterocycle is a five or six membered ring containing one or more heteroatoms at least one of which is nitrogen. Still another subembodiment of this aspect of the invention is realized when the optionally substituted heterocycle is a five membered ring containing one or more heteroatoms at least one of which is nitrogen. Still another subembodiment of this aspect of the invention is realized when the optionally substituted heterocycle is a six membered ring containing one or more heteroatoms at least one of which is nitrogen. Another subembodiment of this aspect of the invention is realized when the heterocycle is selected from the group consisting of pyrazolyl, pyridyl, thiazolyl, triazolyl, oxazolyl, oxadiazolyl, and pyrimidinyl, said groups optionally substituted. Another subembodiment of this aspect of the invention is realized when the heterocycle is optionally substituted pyrazolyl. Another subembodiment of this aspect of the invention is realized when the heterocycle is substituted pyrazolyl. Still another subembodiment of this aspect of the invention is realized when the heterocycle is optionally substituted thiazolyl. Yet another subembodiment of this aspect of the invention is realized when the heterocycle is optionally substituted pyridyl. Yet another subembodiment of this aspect of the invention is realized when the heterocycle is optionally substituted oxadiazolyl. Yet another subembodiment of this aspect of the invention is realized when the heterocycle is optionally substituted oxazolyl. Yet another subembodiment of this aspect of the invention is realized when the heterocycle is optionally substituted triazolyl. Yet another subembodiment of this aspect of the invention is realized when the heterocycle is optionally substituted pyrimidinyl. Still another subembodiment of this aspect of the invention is realized when the heterocycle is optionally substituted with 1 to 3 groups of $R^a$ selected from —$C_{1-4}$ haloalkyl, —$OC_{1-4}$ haloalkyl, —$C_{1-6}$alkyl, —C(O)CF$_3$, C(O)R, C(O)N(R)$_2$, —(CH$_2$)$_n$halo, and —OR.

Another embodiment of the invention of formula I is realized when $R^3$ is selected from the group consisting of hydrogen, CF$_3$, OCF$_3$, CH$_3$, bromine, chlorine, and fluorine. A subembodiment of this aspect of the invention is realized when $R^3$ is CF$_3$. Still another subembodiment of this aspect of the invention is realized when $R^3$ is OCF$_3$. Yet another subembodiment of this aspect of the invention is realized when $R^3$ is CH$_3$. Yet another subembodiment of this aspect of the invention is realized when $R^3$ is hydrogen.

Another embodiment of the invention of formula I is realized when one of $R^1$ and $R^5$ is hydrogen and the other is halogen, one of $R^2$ and $R^4$ is hydrogen and the other is selected from optionally substituted pyrazolyl, pyridyl, thiazolyl, triazolyl, oxazolyl, oxadiazolyl, and pyrimidinyl, and $R^3$ is selected from the group consisting of hydrogen, CF$_3$, OCF$_3$, CH$_3$, bromine, chlorine, and fluorine. An aspect of this embodiment is realized when one of $R^1$ and $R^5$ is hydrogen and the other is fluorine, one of $R^2$ and $R^4$ is hydrogen and the other is selected from optionally substituted pyrazolyl, and pyrimidinyl, and $R^3$ is CF$_3$, or OCF$_3$.

Another embodiment of the invention of formula I is realized when B is a pyrimidinyl substituted with 1 to 3 groups of $R^a$ selected from the group consisting of —$C_{1-4}$haloalkyl, —$OC_{1-4}$ haloalkyl, —$C_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH(CH$_2$)$_n$C$_{4-10}$ heterocycle, COR, —(CH$_2$)$_n$halo, —(CH$_2$)$_n$NHC(O)R$^d$, —(CH$_2$)$_n$NHC(O)NHR$^d$, —(CH$_2$)$_n$NHC(O)OR$^d$, —(CHR)$_n$C(O)N(R$^d$)$_2$—(CH$_2$)$_n$NHSO$_2$R$^d$, and —OR, said alkyl, aryl and heterocycle optionally substituted with 1 to 3 groups of $R^b$, wherein n=0-2. A further subembodiment of this aspect of the invention is realized when the pyrimidinyl is substituted with 1 to 3 groups selected from halogen, CH$_2$OH, CH$_3$, chloro, and optionally substituted phenyl or pyrazolyl. Another embodiment of this aspect of the invention is realized when one of the substituents on the pyrimidinyl is an optionally substituted phenyl.

Another embodiment of the invention of formula I is realized when B is pyridyl substituted with 1 to 3 groups of $R^a$ selected from the group consisting of —$C_{1-4}$haloalkyl, —$OC_{1-4}$haloalkyl, —$C_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH(CH$_2$)$_n$C$_{4-10}$ heterocycle, COR, —(CH$_2$)$_n$halo, —(CH$_2$)$_n$NHC(O)R$^d$, —(CH$_2$)$_n$NHC(O)NHR$^d$, —(CH$_2$)$_n$NHC(O)OR$^d$, —(CHR)$_n$C(O)N(R$^d$)$_2$—(CH$_2$)$_n$NHSO$_2$R$^d$, and —OR, said alkyl, aryl and heterocycle optionally substituted with 1 to 3 groups of $R^b$, wherein n=0-2. A further subembodiment of this aspect of the invention is realized when the pyridyl is substituted with 1 to 3 groups selected from halogen, CH$_2$OH, CH$_3$, chloro, and optionally substituted phenyl or pyrazolyl. Another embodiment of this aspect of the invention is realized when one of the substituents on the pyridyl is an optionally substituted phenyl.

Another embodiment of the invention of formula I is realized when B is phenyl substituted with 1 to 3 groups of $R^a$ selected from the group consisting of —$C_{1-4}$haloalkyl, —$OC_{1-4}$haloalkyl, —$C_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH (CH$_2$)$_n$C$_{4-10}$ heterocycle, COR, —(CH$_2$)$_n$halo, —(CH$_2$)$_n$NHC(O)R$^d$, —(CH$_2$)$_n$NHC(O)NHR$^d$, —(CH$_2$)$_n$NHC(O)OR$^d$, —(CHR)$_n$C(O)N(R$^d$)$_2$—(CH$_2$)$_n$NHSO$_2$R$^d$, and —OR, said alkyl, aryl and heterocycle optionally substituted with 1 to 3 groups of R$^b$, wherein n=0-2. A further subembodiment of this aspect of the invention is realized when the phenyl is substituted with 1 to 3 groups selected from halogen, CH$_2$OH, CH$_3$, chloro, and optionally substituted phenyl or pyrazolyl. Another embodiment of this aspect of the invention is realized when one of the substituents on the phenyl is an optionally substituted phenyl.

Another embodiment of the invention of formula I is realized when B is pyrazinyl substituted with 1 to 3 groups of R$^a$ selected from the group consisting of —C$_{1-4}$haloalkyl, —OC$_{1-4}$haloalkyl, —C$_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH(CH$_2$)$_n$C$_{4-10}$ heterocycle, COR, —(CH$_2$)$_n$halo, —(CH$_2$)$_n$NHC(O)R$^d$, —(CH$_2$)$_n$NHC(O)NHR$^d$, —(CH$_2$)$_n$NHC(O)OR$^d$, —(CHR)$_n$C(O)N(R$^d$)$_2$—(CH$_2$)$_n$NHSO$_2$R$^d$, and —OR, said alkyl, aryl and heterocycle optionally substituted with 1 to 3 groups of R$^b$, wherein n=0-2. A further subembodiment of this aspect of the invention is realized when the pyrazinyl is substituted with 1 to 3 groups selected from halogen, CH$_2$OH, CH$_3$, chloro, and optionally substituted phenyl or pyrazolyl. Another embodiment of this aspect of the invention is realized when one of the substituents on the pyrazinyl is an optionally substituted phenyl.

An embodiment of the invention of formula I is wherein B is tetrahydronaphthyridinyl substituted with 1 to 3 groups of R$^a$ selected from the group consisting of —C$_{1-4}$haloalkyl, —OC$_{1-4}$haloalkyl, —C$_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH(CH$_2$)$_n$C$_{4-10}$ heterocycle, COR, —(CH$_2$)$_n$halo, —(CH$_2$)$_n$NHC(O)R$^d$, —(CH$_2$)$_n$NHC(O)NHR$^d$, —(CH$_2$)$_n$NHC(O)OR$^d$, —(CHR)$_n$C(O)N(R$^d$)$_2$—(CH$_2$)$_n$NHSO$_2$R$^d$, and —OR, said alkyl, aryl and heterocycle optionally substituted with 1 to 3 groups of R$^b$, wherein n=0-2. A further subembodiment of this aspect of the invention is realized when the tetrahydronaphthyridinyl is substituted with 1 to 3 groups selected from halogen, CH$_2$OH, CH$_3$, chloro, and optionally substituted phenyl or pyrazolyl. Another embodiment of this aspect of the invention is realized when one of the substituents on the tetrahydronaphthyridinyl is an optionally substituted phenyl.

An embodiment of the invention of formula I is wherein B is dihydropyrrolopyridinyl substituted with 1 to 3 groups of R$^a$ selected from the group consisting of —C$_{1-4}$haloalkyl, —OC$_{1-4}$haloalkyl, —C$_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH(CH$_2$)$_n$C$_{4-10}$ heterocycle, COR, —(CH$_2$)$_n$halo, —(CH$_2$)$_n$NHC(O)R$^d$, —(CH$_2$)$_n$NHC(O)NHR$^d$, —(CH$_2$)$_n$NHC(O)OR$^d$, —(CHR)$_n$C(O)N(R$^d$)$_2$—(CH$_2$)$_n$NHSO$_2$R$^d$, and —OR, said alkyl, aryl and heterocycle optionally substituted with 1 to 3 groups of R$^b$, wherein n=0-2. A further subembodiment of this aspect of the invention is realized when the dihydropyrrolopyridinyl is substituted with 1 to 3 groups selected from halogen, CH$_2$OH, CH$_3$, chloro, and optionally substituted phenyl or pyrazolyl. Another embodiment of this aspect of the invention is realized when one of the substituents on the dihydropyrrolopyridinyl is an optionally substituted phenyl.

Still another embodiment of the invention of formula I is represented by structural formula Ia:

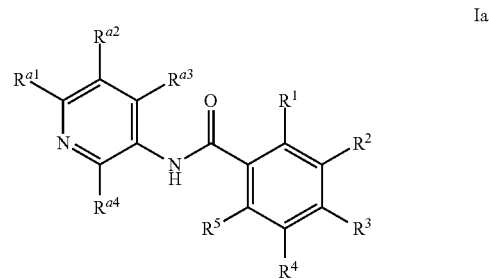

Ia or a pharmaceutically acceptable salt thereof, wherein R$^1$, R$^2$, R$^3$, R$^4$, and R$^5$ are as originally described and R$^{a1}$, R$^{a2}$, R$^{a3}$, and R$^{a4}$ all equal R$^a$ and R$^a$ is as originally described. A subembodiment of the invention of formula Ia is realized when R$^{a1}$, R$^{a2}$, R$^{a3}$, and R$^{a4}$ are independently selected from hydrogen, C$_{1-4}$haloalkyl, —OC$_{1-4}$haloalkyl, —C$_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH(CH$_2$)$_n$C$_{4-10}$ heterocycle, COR, —(CH$_2$)$_n$halo, —(CH$_2$)$_n$NHC(O)R$^d$, —(CH$_2$)$_n$NHC(O)NHR$^d$, —(CH$_2$)$_n$NHC(O)OR$^d$, —(CHR)$_n$C(O)N(R$^d$)$_2$—(CH$_2$)$_n$NHSO$_2$R$^d$, and —OR, said alkyl, aryl and heterocycle optionally substituted with 1 to 3 groups of R$^b$. Another subembodiment of the invention of formula Ia is realized when at least two of R$^{a1}$, R$^{a2}$, R$^{a3}$, and R$^{a4}$ on the pryidyl are hydrogen. Another subembodiment of the invention of formula Ia is realized when two of R$^{a1}$, R$^{a2}$, R$^{a3}$, and R$^{a4}$ on the pyridyl are hydrogen and two are not hydrogen. Another subembodiment of the invention of formula Ia is realized when one of R$^{a1}$, R$^{a2}$, R$^{a3}$, and R$^{a4}$ is always phenyl. Another subembodiment of the invention of formula Ia is realized when R$^{a4}$ is phenyl. Still another subembodiment of the invention of formula Ia is realized when R$^1$ and R$^5$ are independently selected from hydrogen and halogen, R$^3$ is CF$_3$, or halogen and one of R$^2$ and R$^4$ is hydrogen and the other is (CHR)$_n$C$_{5-10}$ heterocycle. Another subembodiment of the invention of formula Ia is realized when the heterocycle of R$^2$ and R$^4$ is optionally substituted oxodiazolyl, pyrazolyl, pyridyl, thiazolyl, oxazolyl, and pyrimidinyl.

Yet another embodiment of the invention of formula Ia is realized when one of R$^{a1}$, R$^{a2}$, R$^{a3}$, and R$^{a4}$ is always phenyl, one of R$^1$ and R$^5$ is hydrogen and the other is halogen, R$^3$ is CF$_3$, or halogen, and one of R$^2$ and R$^4$ is hydrogen and the other is optionally substituted oxodiazolyl, pyrazolyl, pyridyl, thiazolyl, oxazolyl, and pyrimidinyl. A further aspect of this embodiment is realized when R$^{a4}$ is phenyl, R$^1$ is hydrogen, R$^3$ is CF$_3$, R$^5$ is fluorine, R$^2$ is optionally substituted pyrazolyl, and R$^4$ is hydrogen Still another embodiment of the invention of formula I is represented by structural formula II:

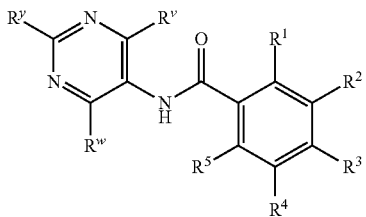

or a pharmaceutically acceptable salt thereof, wherein $R^1$, $R^2$, $R^3$, $R^4$, and $R^5$ are as originally described and $R^y$, $R^v$, and $R^w$ all equal $R^a$ and $R^a$ is as originally described A subembodiment of the invention of formula II is realized when $R^y$, $R^v$, and $R^w$ are independently selected from hydrogen, $C_{1-4}$haloalkyl, —$OC_{1-4}$haloalkyl, —$C_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH(CH$_2$)$_n$C$_{4-10}$ heterocycle, COR, —(CH$_2$)$_n$halo, —(CH$_2$)$_n$NHC(C)R$^d$, —(CH$_2$)$_n$NHC(O)NHR$^d$, —(CH$_2$)$_n$NHC(O)OR$^d$, —(CHR)$_n$C(O)N(R$^d$)$_2$—(CH$_2$)$_n$NHSO$_2$R$^d$, and —OR, said alkyl, aryl and heterocycle optionally substituted with 1 to 3 groups of $R^b$. Another subembodiment of the invention of formula II is realized when at least two of $R^y$, $R^v$, and $R^w$ on the pyrimidinyl are hydrogen. Another subembodiment of the invention of formula II is realized when two of $R^y$, $R^v$, and $R^w$ on the pyrimidinyl are hydrogen. Another subembodiment of the invention of formula II is realized when one of $R^y$, $R^v$, and $R^w$ is always phenyl. Another subembodiment of the invention of formula II is realized when $R^w$ is phenyl. Still another subembodiment of the invention of formula II is realized when $R^1$ and $R^5$ are independently selected from hydrogen and halogen, $R^3$ is CF$_3$, or halogen and one of $R^2$ and $R^4$ is hydrogen and the other is (CHR)$_n$C$_{5-10}$ heterocycle. Another subembodiment of the invention of formula II is realized when the heterocycle of $R^2$ and $R^4$ is optionally substituted oxodiazolyl, pyrazolyl, pyridyl, thiazolyl, oxazolyl, and pyrimidinyl.

Yet another embodiment of the invention of formula II is realized when one of $R^y$, $R^v$, and $R^w$ is always phenyl, one of $R^1$ and $R^5$ is hydrogen and the other is halogen, $R^3$ is CF$_3$, or halogen, and one of $R^2$ and $R^4$ is hydrogen and the other is optionally substituted oxodiazolyl, pyrazolyl, pyridyl, thiazolyl, oxazolyl, and pyrimidinyl. A further aspect of this embodiment is realized when $R^w$ is phenyl, $R^1$ is hydrogen, $R^3$ is CF$_3$, $R^5$ is fluorine, $R^2$ is optionally substituted pyrazolyl, and $R^4$ is hydrogen Still another embodiment of the invention of formula I is represented by structural formula III:

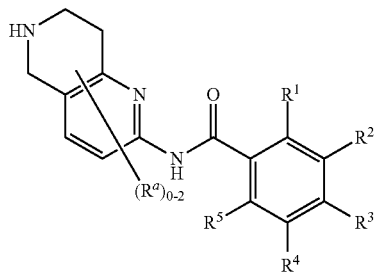

or a pharmaceutically acceptable salt thereof, wherein $R^1$, $R^2$, $R^3$, $R^4$, $R^a$, and $R^5$ are as originally described A subembodiment of the invention of formula III is realized when $R^a$ is independently selected from hydrogen, $C_{1-4}$haloalkyl, —$OC_{1-4}$haloalkyl, —$C_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH(CH$_2$)$_n$C$_{4-10}$ heterocycle, COR, —(CH$_2$)$_n$halo, —(CH$_2$)$_n$NHC(O)R$^d$, —(CH$_2$)$_n$NHC(O)NHR$^d$, —(CH$_2$)$_n$NHC(O)OR$^d$, —(CHR)$_n$C(O)N(R$^d$)$_2$—(CH$_2$)$_n$NHSO$_2$R$^d$, and —OR, said alkyl, aryl and heterocycle optionally substituted with 1 to 3 groups of $R^b$. Another subembodiment of the invention of formula III is realized when two of $R^a$ are present and are not hydrogen. Another subembodiment of the invention of formula III is realized when one of the two $R^a$'s that is present is always phenyl. Another subembodiment of the invention of formula III is realized when the $R^a$ that is phenyl is present on the pyridinyl portion of the ring. Still another subembodiment of the invention of formula II is realized when $R^1$ and $R^5$ are independently selected from hydrogen and halogen, $R^3$ is CF$_3$, or halogen and one of $R^2$ and $R^4$ is hydrogen and the other is (CHR)$_n$C$_{5-10}$ heterocycle. Another subembodiment of the invention of formula III is realized when the heterocycle of $R^2$ and $R^4$ is optionally substituted oxodiazolyl, pyrazolyl, pyridyl, thiazolyl, oxazolyl, and pyrimidinyl.

Yet another embodiment of the invention of formula III is realized when two $R^a$'s are present one of which is always phenyl, said phenyl attached on the pyridinyl portion of the ring, one of $R^1$ and $R^5$ is hydrogen and the other is halogen, $R^3$ is CF$_3$, or halogen, and one of $R^2$ and $R^4$ is hydrogen and the other is optionally substituted oxodiazolyl, pyrazolyl, pyridyl, thiazolyl, oxazolyl, and pyrimidinyl. A further aspect of this embodiment is realized when two $R^a$'s are present one of which is always phenyl, said phenyl attached on the pyridinyl portion of the ring, $R^1$ is hydrogen, $R^3$ is CF$_3$, $R^5$ is fluorine, $R^2$ is optionally substituted pyrazolyl, and $R^4$ is hydrogen The invention is also directed to methods of treating a patient (preferably a human) for diseases or disorders in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a therapeutically effective amount of a compound of the invention, or a pharmaceutically acceptable salt thereof.

The invention is also directed to the use of a compound of the invention for treating a disease or disorder in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA, by administering to the patient a compound of the invention, or a pharmaceutically acceptable salt thereof.

The invention is also directed to medicaments or pharmaceutical compositions for the treatment of diseases or disorders in a patient (preferably a human) in which the TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF)

receptor TrkA, which comprise a compound of the invention, or a pharmaceutically acceptable salt thereof, and a pharmaceutically acceptable carrier.

The invention is also directed to a method for the manufacture of a medicament or a pharmaceutical composition for treating diseases in which TrkA receptor is involved, such as pain, inflammation, cancer, restenosis, atherosclerosis, psoriasis, thrombosis, a disease, disorder, injury, or malfunction relating to dysmyelination or demyelination or a disease or disorder associated with abnormal activities of nerve growth factor (NGF) receptor TrkA comprising combining a compound of the invention or a pharmaceutically acceptable salt thereof, with a pharmaceutically acceptable carrier.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles as well as oxo substituted cycloalkyl groups.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

The term "heteroatom" means O, S or N, selected on an independent basis.

As used herein, the term "aryl," by itself or as part of another substituent, means an aromatic cyclic hydrocarbon radical. Preferred aryl groups have from six to ten carbon atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, triazolyl, N-oxides and —C═O derivatives thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, N-oxides thereof and —C═O derivatives thereof. Suitable heteroaryl groups are imidazopyridinyl, indazolyl, imidazothiazolyl, imidazopyrimidinyl, imidazopyridazinyl, imidazothiadiazolyl, quinoxalinyl, and imidazopyrrolyl.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

As used herein —O— includes oxo (e.g., an annular —CH— substituted with oxo is —C(O) or carbonyl.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulae (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formulae (I) can be prepared without undue experimentation by conventional techniques well known to those skilled in the art or by processes analogous to those described in the Schemes and Examples herein using appropriate isotopically-enriched reagents and/or intermediates.

The term "substantially pure" means that the isolated material is at least 90% pure, and preferably 95% pure, and even more preferably 99% pure as assayed by analytical techniques known in the art.

As used herein, the term TrkA refers to one of Trk high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5). The Trk receptors are made up of three family members, TrkA, TrkB and TrkC, that bind to and mediate the signal transduction derived from the Neurotrophins. Inhibitors of the Trk/neurotrophin pathway have been demonstrated to be highly effective in numerous pre-clinical animal models of pain. The compounds of the invention are modulators of the Trk receptors, particularly TrkA.

The term "pharmaceutically acceptable salts" refers to salts prepared from pharmaceutically acceptable non-toxic bases or acids including inorganic or organic bases and inorganic or organic acids. The compounds of the invention may be mono, di or tri salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formulae (I) disclosed herein as TrkA inhibitors in a patient or subject such as a mammal in need of such activity, comprising the administration of an effective amount of the compound. In addition to humans, a variety of other mammals can be treated according to the method of the present invention.

The compounds of the present invention have utility in treating or ameliorating pain disorders (including pain associated with cancer, surgery, and bone fracture, acute pain, inflammatory pain and neuropathic pain). The compounds of formula I are also useful for treating cancers including neuroblastoma, ovarian, pancreatic and colorectal cancer. Other conditions that may be treated by the compounds of the invention include inflammation and certain infectious diseases, interstitial cystitis, painful bladder syndrome, urinary incontinence, asthma, anorexia, atopic dermatitis, and psoriasis. Treatment of demyelination and dysmyelination, by promoting myelination, neuronal survival, and oligodendrocyte differentiation via blocking Sp35-TrkA interaction may also be possible with the compounds of the present invention.

The compounds of formula I may also be useful in the treatment of bone-related diseases (e.g., those involved in bone resorption). Examples of bone-related diseases include metastatic bone disease, treatment-induce bone loss, osteoporosis, rheumatoid arthritis, ankylosing spondylitis, Paget's disease, and periodontal disease. Another bone disorder or disease that can be treated with the compounds of the claimed invention is metastatic tumor-induced osteolysis. Cancers known to cause tumor induced osteolysis are hematological malignancies such as myeloma and lymphoma and solid tumors such as breast, prostate, lung, renal and thyroid.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally mammals such a human being, male or female, in whom TrkA and/or TrkB modulation is desired. Thus, an aspect of the present invention is a method of treating diseases with an inhibitor of TrkA and/or TrkB comprising administering to said mammal one or more compounds of formula I or a pharmaceutically acceptable salt thereof in an amount effective to treat or prevent said disorder. A particular aspect of the invention is directed to a method of treating pain, cancer, inflammation, neurodegenerative disease or *Typanosoma cruzi* infection by administering to said mammal a therapeutically effective amount of a compound of formula I or a pharmaceutically acceptable salt thereof. Still another aspect of the present invention is directed to a method of treating osteolytic disease in a mammal by administering a therapeutically effective amount of a compound of formula I or a pharmaceutically acceptable salt thereof. For purposes of this invention mammals include dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds include combinations with agents for the treatment of pain, for example steroids such as dexamethasone, cortisone, and fluticasone, non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib and valdecoxib; CB-2 agonists; VR-1 antagonists; bradykinin B 1 receptor antagonists; sodium channel blockers and antagonists; nitric oxide synthase (NOS) inhibitors (including iNOS and nNOS inhibitors); glycine site antagonists, including lacosamide; neuronal nicotinic agonists; NMDA antagonists; potassium channel openers; AMPA/kainate receptor antagonists; calcium channel blockers, such as ziconotide; GABA-A receptor IO modulators (e.g., a GABA-A receptor agonist); matrix metalloprotease (MMP) inhibitors; thrombolytic agents; chemotherapeutic agents, opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists; alpha agonists; neuronal nicotinic agonists; NMDA receptor agonists or antagonists; NK1 antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

Another aspect of the present invention is directed to a pharmaceutical composition comprising a compound of formula I or a pharmaceutically acceptable salt thereof and a pharmaceutically acceptable diluent or carrier. Still another aspect of the present invention is directed to a compound of formula I or a pharmaceutically acceptable salt thereof, for use in the treatment of a condition treatable with an inhibitor of TrkA and/or TrkB, such as the disorders, conditions and/or diseases described herein. Still another aspect is directed to use of a compound of formula I or a pharmaceutically acceptable salt thereof in the treatment of pain, cancer, inflammation, neurodegenerative disease or *typanosoma cruzi* infection.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringeability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the disease (i.e., arresting further development of the pathology and/or symptomatology), or (2) ameliorating the disease in an animal that is experiencing or displaying the pathology or symptomatology of the disease (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

During any of the synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

The following abbreviations are used throughout the text:
Me: methyl
Et: ethyl
Bu: butyl
t-Bu: tert-butyl
Ar: aryl
Ph: phenyl
Bn: benzyl
Ac: acetyl
DMF.DMA: N,N-dimethylformamide dimethyl acetal
DMSO: dimethylsulfoxide
DMF: N,N-dimethylformamide
THF: tetrahydrofuran
TEA: triethylamine
aq: aqueous
HPLC: high performance liquid chromatography
MS: mass spectrometry
CDI: 1,1'-carbonyldiimidazole
DCE: 1,2-dichloroethane
HCl: hydrochloric acid
° C.: degrees Celsius
BINAP: 2,2'-bis(diphenylphosphino)-1,1'-binaphthalene
ATP: adenosine triphosphate
i-Pr: isopropyl
Py: pyridyl
OAc: acetate
TFA: trifluoroacetic acid
TFAA: trifluoroacetic anhydride
Boc: tert-butoxycarbonyl
$Boc_2O$: di-tert-butyl dicarbonate
BOP: (benzotriazol-1-yloxy)tris(dimethylamino)phosphonium hexafluorophosphate
DEA: diethylamine DIEA: N,N-diisopropylethylamine
DIPEA: N,N-diisopropylethylamine
HOBT: 1-hydroxybenzotriazole
EDC: N-(3-dimethylaminopropyl)-N'-ethylcarbodiimide hydrochloride
EDCI: N-(3-dimethylaminopropyl)-N'-ethylcarbodiimide hydrochloride
PyCLU: chlorodipyrrolidinocarbenium
n-BuLi: n-butyllithium
HATU: O-(7-azabenzotriazol-1-yl)-N,N,N'N'-tetramethyluronium hexafluorophosphate
EDTA: ethylenediaminetetraacetic acid
HMDS: hexamethyldisilazane
min: minutes
h: hours
HPLC: high performance liquid chromatography
LCMS: liquid chromatography-mass spectrometry
SFC: supercritical fluid chromatography
TLC: thin layer chromatography
NMP: 1-methyl-2-pyrrolidinone
MTBE: methyl tert-butyl ether
DMA: N,N-dimethylacetamide
NBS: N-bromosuccinimide
CAN: ammonium cerium(IV) nitrate
dppf: 1,1'-bis(diphenylphosphino)ferrocene
dtbpf: 1,1'-bis(di-tert-butylphosphino)ferrocene
dba: dibenzylideneacetone
DMAP: 4-(dimethylamino)pyridine
PMBCl: 4-methoxybenzyl chloride
DIBAL: diisobutylaluminum hydride
DAST: (diethylamino)sulfur trifluoride
DBU: 1,8-diazabicyclo[5.4.0]undec-7-ene
AIBN: 2-2'-azobisisobutyronitrile
m-CPBA: 3-chloroperbenzoic acid
DABCO: diazabicyclo[2.2.2]octane
LDA: lithium diisopropylamide
HOAt: 1-hydroxy-7-azabenzotriazole
LAH: lithium aluminum hydride
AOP: 7-(azabenzotriazol-1-yloxy)tris(dimethylamino)phosphonium hexafluorophosphate
PyAOP: 7-(azabenzotriazol-1-yloxy)tripyrrolidinophosphonium hexafluorophosphate
DCM: dichloromethane
PE: petroleum ether
TMS: trimethylsilyl
Conc: concentrated
TIPS: triisopropylsilyl
OTf: trifluoromethanesulfonate
bis-pin: 4,4,4',4',5,5,5',5'-octamethyl-2,2'-bi(1,3,2-dioxaborolane)
NCS: N-chlorosuccinimide
DPPA: diphenylphosphoryl azide
PCC: pyridinium chlorochromate
DME: 1,2-dimethoxyethane
PMB: 4-methoxybenzyl
NMO: 4-methylmorpholine N-oxide
PyBop: benzotriazol-1-yl-oxytripyrrolidinophosphonium hexafluorophosphate
PS: polystyrene

REACTION SCHEMES

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Scheme 1 illustrates the general strategy for preparing the compounds of the present invention in which an carboxylic acid intermediate (1.1) may be activated (for example, via treatment with $POCl_3$, $(COCl)_2$, or $SOCl_2$ to generate the acid chloride) followed by coupling to an amine (1.2) to give the desired product amide 1.3. Various carboxylic acid intermediates, such as those described herein (vide infra), may be coupled to a variety of amines to give the compounds of the present invention. There are many known strategies for effecting such coupling chemistry, including use of coupling reagents, such as EDC with HOBT, PyBOP, HATU, AOP, PyAOP, CDI and the like.

SCHEME 1

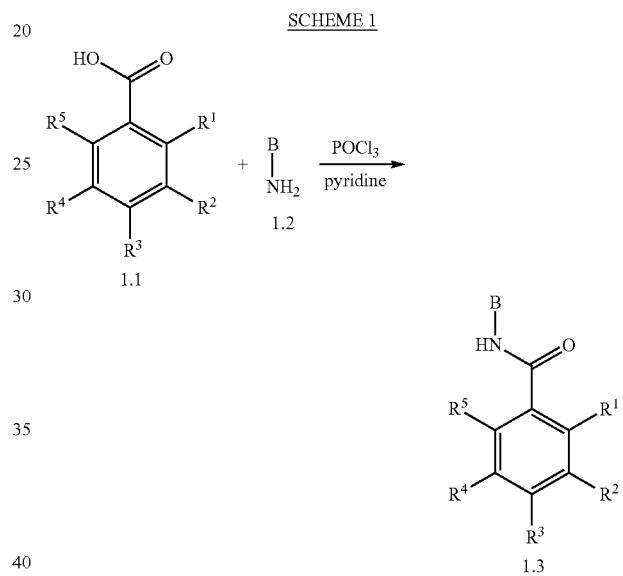

In some cases, various protecting group strategies familiar to one skilled in the art of organic synthesis may be employed to allow preparation of a particular compound of the present invention. This general approach may be successful for the preparation of a range of amide moieties, utilizing a variety of acids and amine intermediates.

SCHEME 2

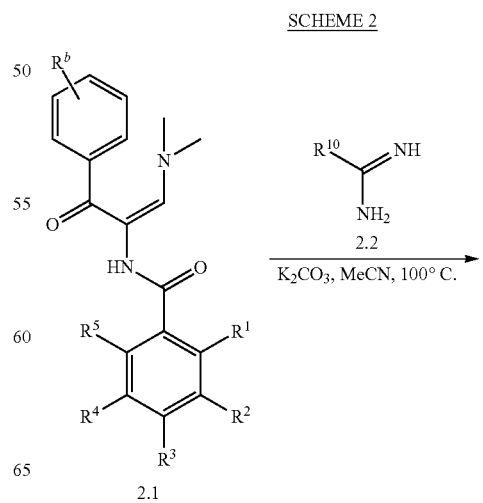

-continued

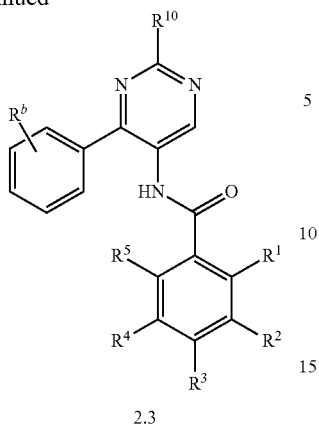
2.3

Reaction Scheme 2 illustrates a method of preparing the compounds of type 2.3 in which keto-enamine 2.1 is heated with amidine 2.2 in the presence of base to afford amide 2.3.

SCHEME 3

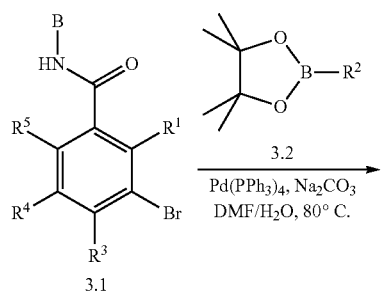

Reaction Scheme 3 illustrates an alternative method of preparing the compounds of type 1.3. Cross-coupling of bromide 3.1 with an aryl or heteroarylboronic ester 3.2 (or other suitable intermediate) in an aqueous solvent mixture in the presence of a suitable catalyst and base system (e.g., Pd(PPh$_3$)$_4$ and Na$_2$CO$_3$) furnishes amide 1.3.

Reaction Scheme 4 through 6 illustrate the preparation of the intermediate amines of the type 1.2 which are used to prepare compounds of the invention as described above.

SCHEME 4

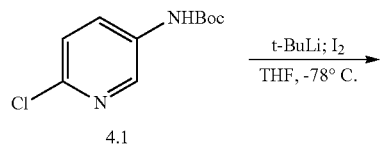

-continued

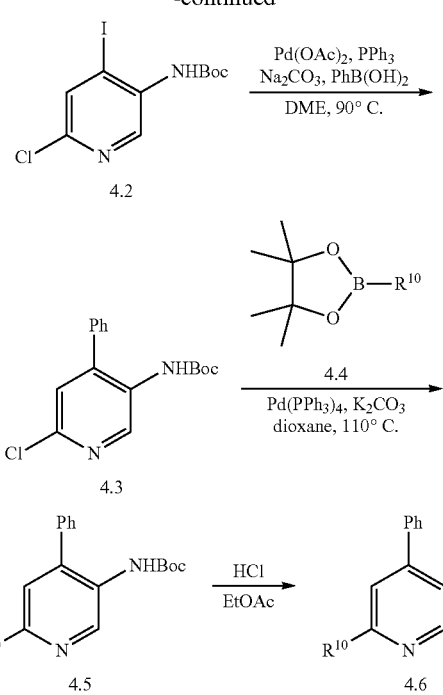

Reaction Scheme 4 illustrates the preparation of the intermediate amines of the type 4.6. Pyridine 4.1 is deprotonated with t-BuLi at low temperature followed by exposure to iodine to afford iodide 4.2. Selective cross-coupling of iodide 4.2 with phenylboronic acid (or other suitable intermediate) under Suzuki conditions in this case provides pyridine 4.3. A subsequent cross-coupling reaction of 4.3 with an alkyl or arylboronic ester 4.4 (or other suitable intermediate) furnishes pyridine 4.5. Removal of the Boc group is effected by exposure to HCl in EtOAc to afford amine 4.6.

SCHEME 5

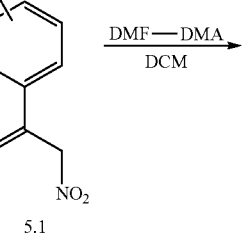
5.1

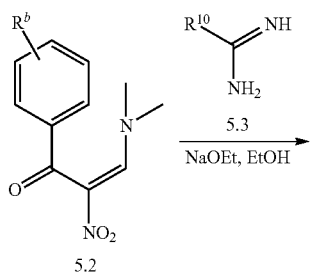
5.2

SCHEME 7

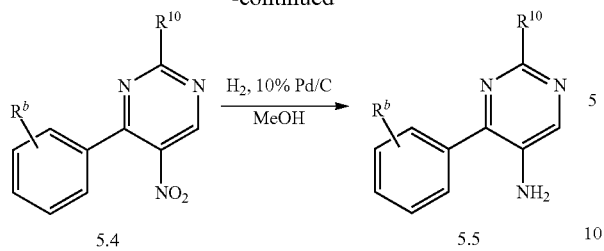

5.4 → 5.5

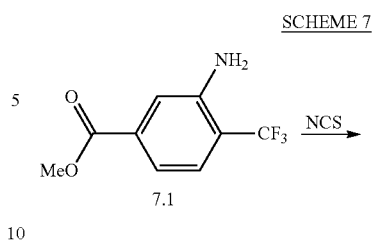

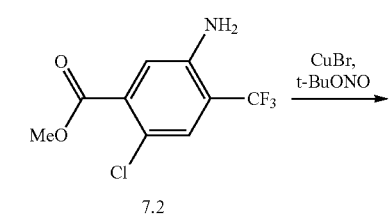

Reaction Scheme 5 illustrates the preparation of the intermediate amines of the type 5.5. Benzoylnitromethane 5.1 is treated with N,N-dimethylformamide dimethylacetal to afford 5.2. Conversion to pyrimidine 5.4 is effected by exposure of enamine 5.2 to amidine 5.3 in ethanol under basic conditions. The nitro group of 5.4 is reduced by $H_2$ in the presence of 10% Pd/C in MeOH to afford amine 5.5.

SCHEME 6

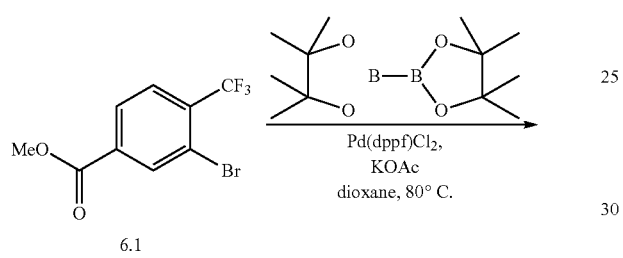

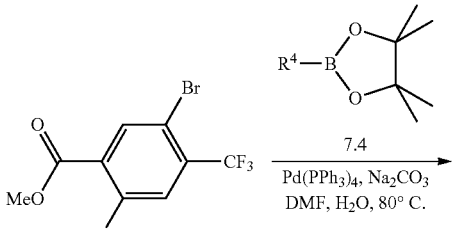

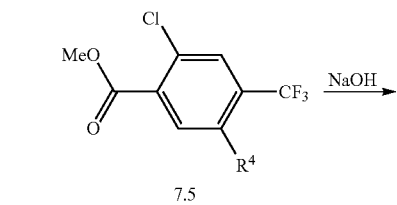

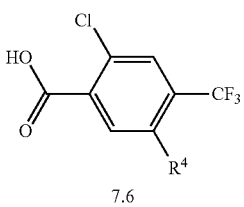

Reaction Scheme 6 illustrates the preparation of the intermediate acids of the type 6.5 which are used to prepare compounds of the invention. Bromide 6.1 is converted to the boronate ester with 4,4,4',4',5,5,5',5'-octamethyl-2,2'-bi(1,3,2-dioxaborolane) in the presence of a suitable catalyst and base system to afford 6.2. Cross-coupling of the ester 6.2 with a suitable aryl or heteroaryl bromide (6.3) is mediated by heating in an aqueous solvent system in the presence of a suitable catalyst and base (e.g., Pd(dppf)Cl$_2$ and Na$_2$CO$_3$ in aqueous DMF) to furnish ester 6.4. Hydrolysis of the ester under basic conditions then affords acid 6.5.

Reaction Scheme 7 illustrates the preparation of the intermediate acids of the type 7.6 which are used to prepare compounds of the invention. Amine 7.1 is treated with NCS to afford chloride 7.2, which is then converted to bromide 7.3 by exposure to t-butylnitrite and copper bromide. Cross-coupling of bromide 7.3 with an aryl or heteroarylboronic ester 7.4 (or other suitable intermediate) is mediated by heating in an aqueous solvent system in the presence of a suitable catalyst and base (e.g., Pd(dppf)Cl$_2$ and Na$_2$CO$_3$ in aqueous DMF) to furnish ester 7.5. Hydrolysis of the ester under basic conditions then affords acid 7.6.

SCHEME 8

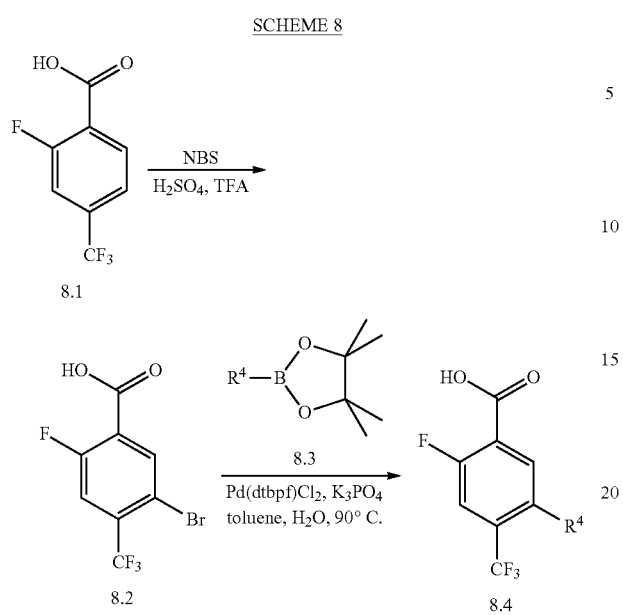

Reaction Scheme 8 depicts the synthesis of intermediates acids of the type 8.4. Bromination of 8.1 followed by cross-coupling of 8.2 and with an aryl or heteroarylboronic ester 8.3 (or other suitable intermediate) is mediated by heating in an aqueous solvent system in the presence of a suitable catalyst and base (e.g., Pd(dtbpf)Cl$_2$ and K$_3$PO$_4$ in aqueous toluene) to furnish 8.4.

SCHEME 9

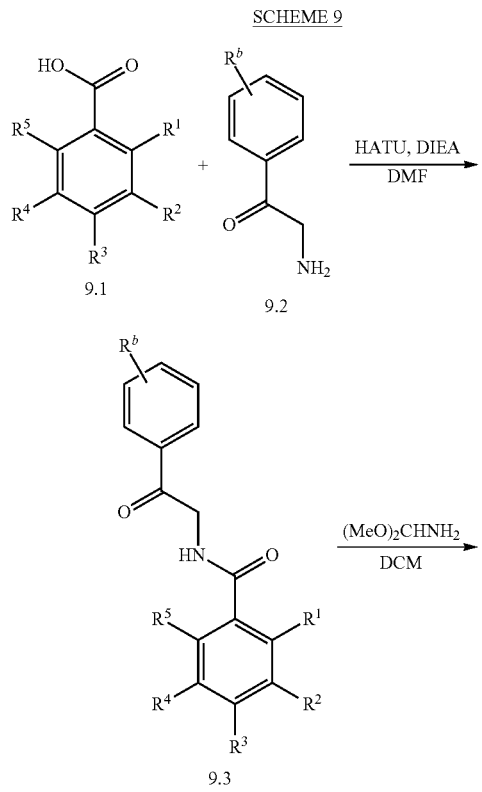

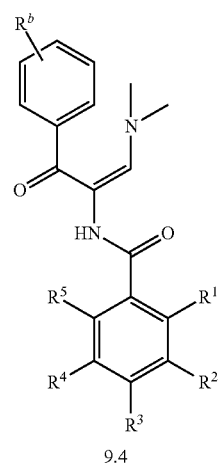

Reaction Scheme 8 illustrates the preparation of the intermediate enamines of the type 9.4 which are used to prepare compounds of the invention. Aminoacetophenone 9.2 is coupled with acid 9.1 under standard amide bond forming conditions (e.g., HATU, DIEA) to afford amide 9.3. Ketoamide 9.3 is then treated with dimethylformamide dimethylacetal to afford enamine 9.4.

SCHEME 10

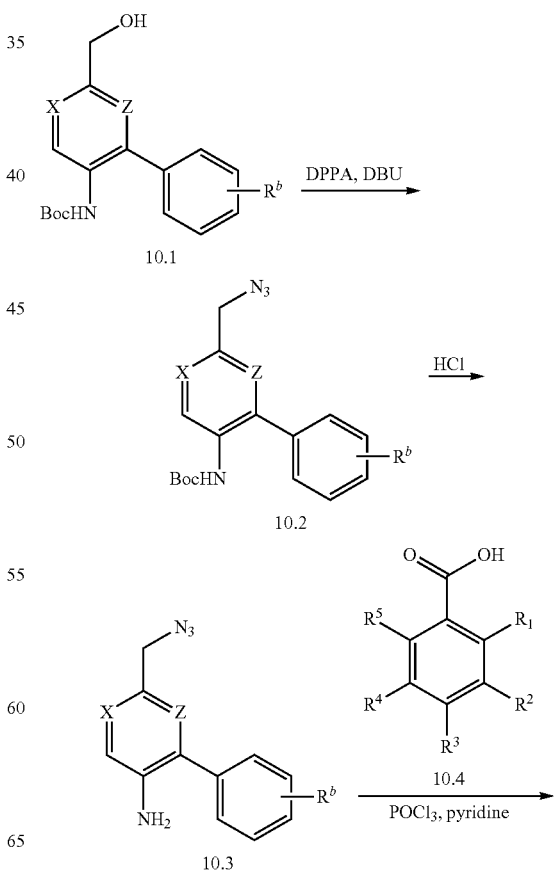

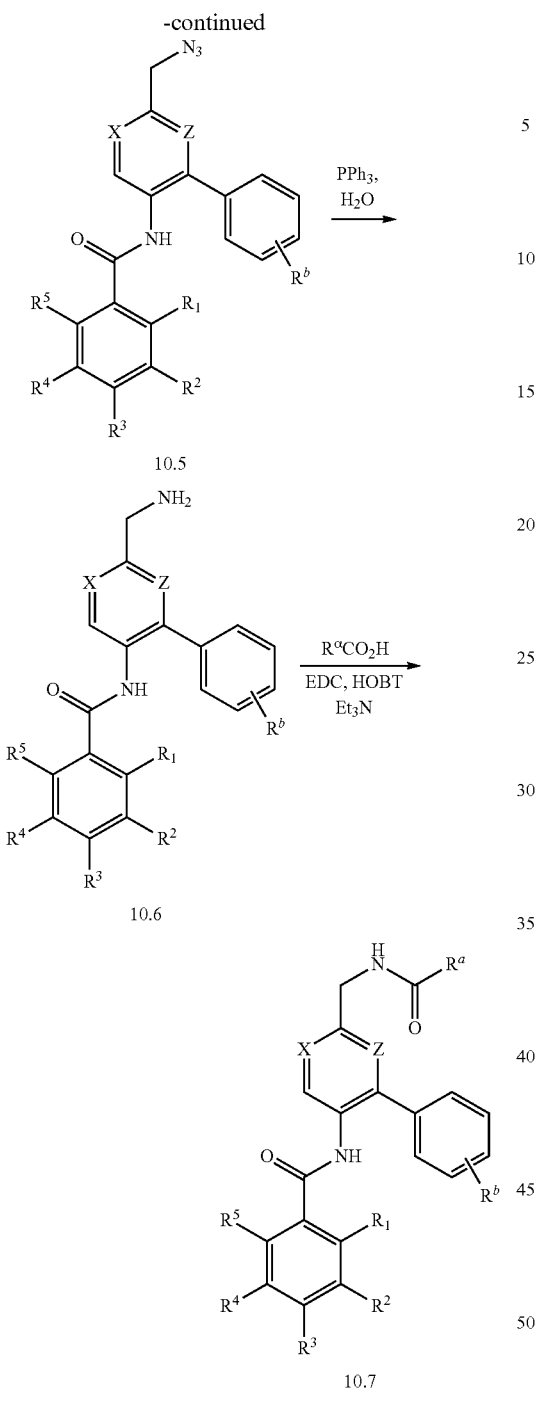

10.5

10.6

10.7

Reaction Scheme 10 depicts the preparation of benzylic amides of the invention of type 10.7. Alcohol 10.1 is converted to azide 10.2 with DPPA and DBU as base. The Boc protecting group is then removed with hydrochloric acid to provide 10.3 as a hydrochloride salt. Coupling of 10.3 with the benzoyl chloride generated from 10.4, in this case by treatment with POCl$_3$, affords benzamide 10.5. Reduction of the azide under Staudinger conditions yields amine 10.6 which can undergo a coupling with a carboxylic acid under a variety of conditions (e.g., EDC) to give 10.7.

SCHEME 11

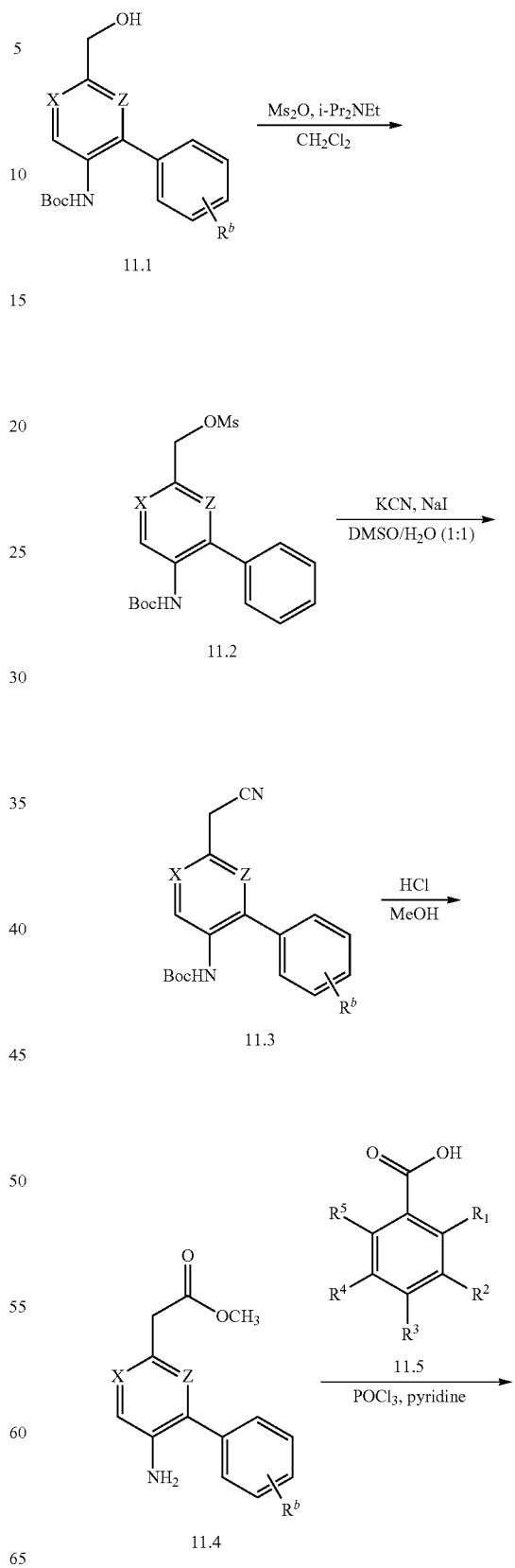

11.1

11.2

11.3

11.4

11.5 ment with POCl₃, affords benzamide 11.6. Saponification then provides carboxylic acid 11.7 which can be coupled with an amine to afford 11.8.

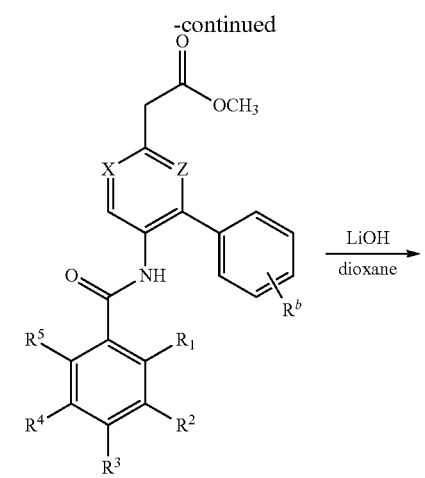

11.6

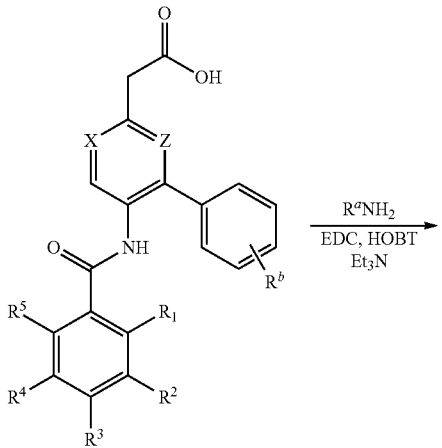

11.7

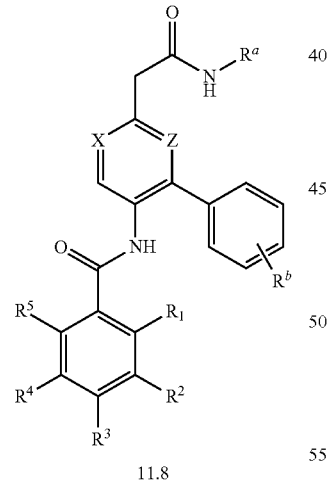

11.8

Reaction Scheme 11 describes the preparation of acetamides of the invention of type 11.8. Alcohol 11.1 is treated with methanesulfonic anhydride and N,N-diisopropylethylamine to provide mesylate 11.2, which is subsequently converted to the nitrile 11.3 with KCN in the presence of NaI. Hydrolysis of the nitrile with concomitant removal of the Boc group is achieved by heating 11.3 with hydrochloric acid to furnish aniline 11.4. Coupling of 11.4 with the benzoyl chloride generated from 11.5, in this case by treat-

SCHEME 12

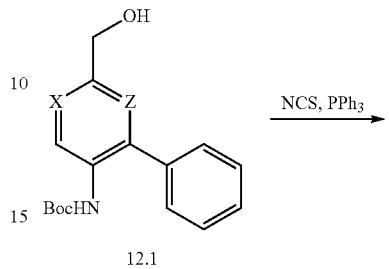

12.1

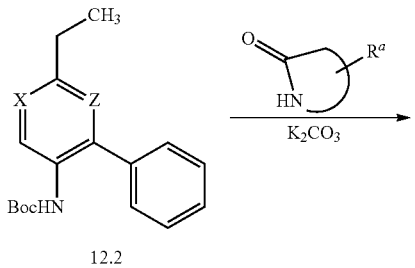

12.2

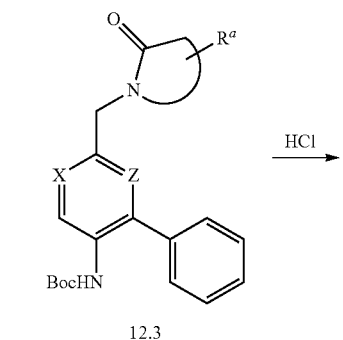

12.3

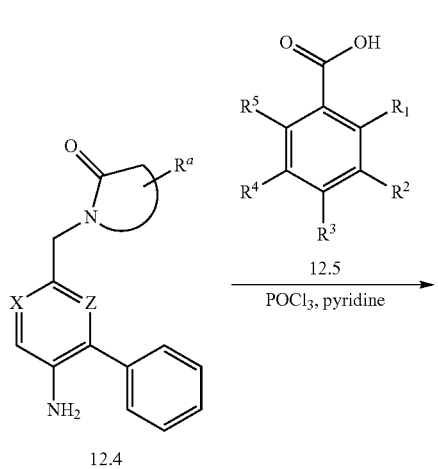

12.4

-continued

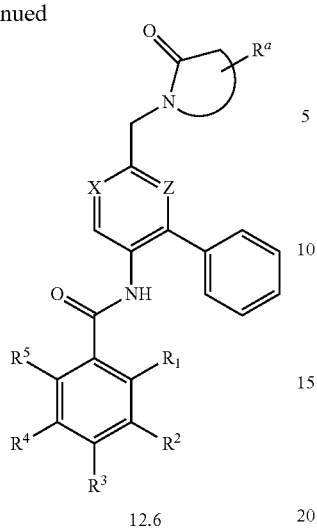

12.6

Reaction Scheme 12 illustrates compounds of the invention of type 12.6. Alcohol 12.1 is converted to chloride 12.2 with NCS and triphenylphosphine. N-Alkylation of heterocycles with 12.2 is mediated by base such as potassium carbonate to give 12.2. In some cases, deprotonation of the heterocycle with a stronger base such as sodium hydride, for example, may be required. C-alkylation may also be achieved with intermediates containing an acidic methylene subunit. Of note, chloride 12.2 may require an additional Boc protecting group on the aniline moiety for optimal yields in the alkylation reaction. Intermediate 12.3 is then treated with hydrochloric acid to remove the Boc protecting group(s) to provide aniline 12.4. Coupling of 12.4 with the benzoyl chloride generated from 12.5, in this case by treatment with POCl$_3$, affords benzamide 12.6.

Specific embodiments of the compounds of the invention, and methods of making them, are described in the Intermediates and Examples herein.

REACTION SCHEME FOR INTERMEDIATE A1

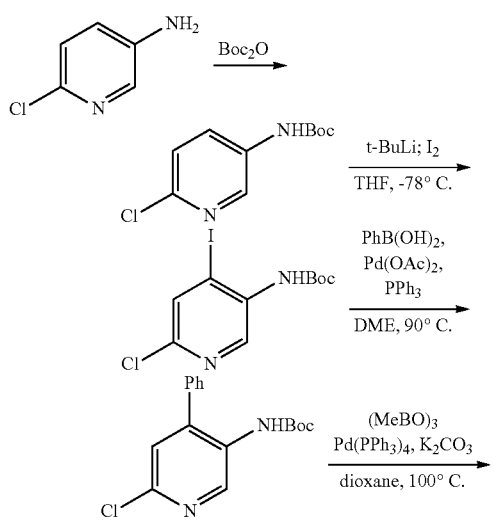

-continued

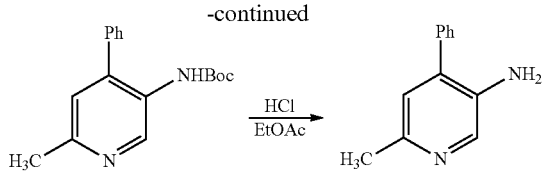

Intermediate A1

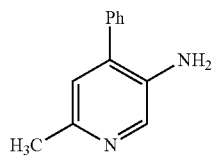

6-Methyl-4-phenylpyridin-3-amine

Step A: tert-Butyl (6-chloropyridin-3-yl)carbamate

A mixture of 6-chloropyridin-3-amine (58.0 g, 451 mmol) and Boc$_2$O (133 mL, 573 mmol) in dioxane (600 mL) was heated at 100° C. for 20 h. Additional Boc$_2$O (17 mL, 72 mmol) was added and the mixture was heated at 100° C. for 7 h. The mixture was cooled and concentrated, and the residue was partitioned between EtOAc (500 mL×3) and water (500 mL). The combined organic layers were washed with brine (500 mL×2), dried over Na$_2$SO$_4$ and concentrated. The residue was triturated with PE:EtOAc=15:1 (400 mL×3) and dried to give the title compound. MS: m/z=223 (M+1). $^1$H NMR (400 MHz, CDCl$_3$) δ 8.25 (d, J=3.0 Hz, 1H), 7.95 (d, J=6.3 Hz, 1H), 7.25 (d, J=8.8 Hz, 1H), 6.73 (s, 1H), 1.51 (s, 9H).

Step B: tert-Butyl (6-chloro-4-iodopyridin-3-yl)carbamate tert-Butyllithium (1.3 M in heptanes, 111 mL, 144 mmol) was added dropwise to a solution of t-butyl (6-chloropyridin-3-yl)carbamate (15.0 g, 65.6 mmol) in anhydrous THF (300 mL) at −78° C. over 30 min under N$_2$ atmosphere. The resulting mixture was stirred at −78° C. for 1 h, then at −10° C. for 1 h. The reaction mixture was cooled to −78° C. and a solution of I$_2$ (36.6 g, 144 mmol) in anhydrous THF (100 mL) was added. The resulting mixture was warmed to ambient temperature and stirred for 18 h. Excess t-butyllithium and I$_2$ were quenched with saturated aqueous NH$_4$Cl solution (150 mL) and saturated aqueous Na$_2$S$_2$O$_3$ solution (500 mL), respectively, and the resulting mixture was stirred for 30 min. The organic layer was separated and the aqueous layer was extracted with EtOAc (250 mL×2). The combined organic layers were washed with brine (250 mL), dried over Na$_2$SO$_4$ and concentrated. The residue was purified by column chromatography on silica gel (EtOAc:PE:Et$_3$N=2:98:1, then 2.5:97.5:1) to afford the title compound. MS: m/z=355 (M+1). $^1$H NMR (400 MHz, CDCl$_3$) δ 8.93 (s, 1H), 7.72 (s, 1H), 6.64 (s, 1H), 1.53 (s, 9H).

Step C: tert-Butyl (6-chloro-4-phenylpyridin-3-yl)carbamate

A deoxygenated mixture of t-butyl (6-chloro-4-iodopyridin-3-yl)carbamate (5.30 g, 14.9 mmol), phenylboronic acid (2.00 g, 16.4 mmol), Pd(OAc)$_2$ (0.168 g, 0.747 mmol), Ph$_3$P (0.392 g, 1.49 mmol), and aqueous Na$_2$CO$_3$ solution (2 M, 37.4 mL, 74.7 mmol) in DME (150 mL) was heated at 90° C. under N$_2$ atmosphere for 18 h. The mixture was cooled, silica gel (15 g) was added, and the resulting mixture was concentrated. The residue was purified by column chromatography on silica gel (PE:EtOAc:Et$_3$N=95:5:1) to give the title compound. MS: m/z=305 (M+1). $^1$H NMR (400 MHz, CDCl$_3$) δ 9.08 (s, 1H), 7.48-7.55 (m, 3H), 7.34-7.36 (m, 2H), 7.16 (s, 1H), 6.35 (s, 1H), 1.45 (s, 9H).

Step D: tert-Butyl (6-methyl-4-phenylpyridin-3-yl)carbamate

A deoxygenated mixture of t-butyl (6-chloro-4-phenylpyridin-3-yl)carbamate (2.30 g, 7.55 mmol), Pd(Ph$_3$P)$_4$ (0.872 g, 0.755 mmol), 2,4,6-trimethyl-1,3,5,2,4,6-trioxatriborinane (3.79 g, 30.2 mmol), and K$_2$CO$_3$ (3.13 g, 22.6 mmol) in dioxane (30 mL) was heated at 110° C. under N$_2$ atmosphere for 18 h. The mixture was cooled and filtered through Celite®. The filtrate was concentrated and the residue was purified by column chromatography on silica gel (PE:EtOAc:Et$_3$N=90:10:1, then 80:20:1) to give the title compound. MS: m/z=285 (M+1). $^1$H NMR (400 MHz, CDCl$_3$) δ 9.05 (s, 1H), 7.43-7.51 (m, 3H), 7.34-7.36 (m, 2H), 6.99 (s, 1H), 6.26 (s, 1H), 2.53 (s, 3H), 1.44 (s, 9H).

Step E: 6-Methyl-4-phenylpyridin-3-amine

A solution of HCl in EtOAc (4 M, 11.3 mL, 45.0 mmol) was added to a solution of t-butyl (6-methyl-4-phenylpyridin-3-yl)carbamate (1.28 g, 4.50 mmol) in EtOAc (15 mL). The resulting mixture was stirred at ambient temperature for 18 h, and then concentrated to give the title compound as an HCl salt. MS: m/z=185 (M+1).

Intermediate A2

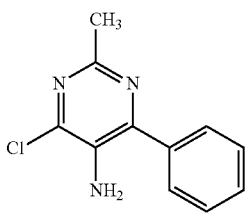

4-Chloro-2-methyl-6-phenylpyrimidin-5-amine

A deoxygenated mixture of 4,6-dichloro-2-methylpyrimidin-5-amine (536 mg, 3.01 mmol), phenylboronic acid (404 mg, 3.31 mmol), Pd(PPh$_3$)$_4$ (174 mg, 0.151 mmol), and aqueous sodium carbonate solution (2 M, 3.0 mL, 6.0 mmol) in DMF (9 mL) was heated at 110° C. under microwave irradiation for 1 h. The mixture was cooled and partitioned between water (100 mL) and Et$_2$O (3×70 mL). The combined organic layers were dried over Na$_2$SO$_4$ and concentrated. The residue was purified by column chromatography on silica gel (EtOAc:hexanes=0:100 to 50:50) to afford the title compound. MS: m/z=220.2 (M+1).

Intermediate A3

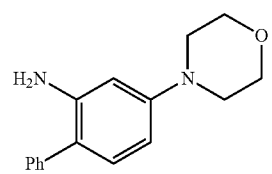 [SMILES: Nc1cc(N2CCOCC2)ccc1-c1ccccc1]

5-Morpholino-2-phenylpyridin-3-amine

Step A: Di-tert-butyl (5-chloro-2-phenylpyridin-3-yl)carbamate

A mixture of 5-chloro-2-phenylpyridin-3-amine (3.0 g, 15 mmol), Boc$_2$O (3.5 g, 16 mmol), TEA (4.0 mL, 29 mmol), and DMAP (122 mg, 1.00 mmol) in DCM (50 mL) was heated at 30° C. for 16 h, and then concentrated. The residue was partitioned between DCM (100 mL) and water (30 mL×2), and the organic layer was dried over Na$_2$SO$_4$ and concentrated. The residue was purified by column chromatography on silica gel (PE:EtOAc=15:1) to give the title compound. MS: m/z=405 (M+1). $^1$H NMR (400 MHz, DMSO-d$_6$) δ 8.72 (d, J=2.4 Hz, 1H), 8.19 (d, J=2.4 Hz, 1H), 7.49 (m, 5H), 1.41 (s, 18H).

Step B: tert-Butyl (5-morpholino-2-phenylpyridin-3-yl)carbamate

A deoxygenated mixture of di-tert-butyl (5-chloro-2-phenylpyridin-3-yl)carbamate (2.0 g, 4.9 mmol), morpholine (0.435 mL, 5.00 mmol), t-BuONa (768 mg, 8.00 mmol) and Pd$_2$(dba)$_3$ (100 mg, 0.11 mmol) in dioxane (20 mL) was heated at 80° C. for 16 h, and then concentrated. The residue was partitioned between DCM and H$_2$O (50 mL×3), and the organic layer was dried over Na$_2$SO$_4$ and concentrated. The residue was purified by preparative TLC (PE/EA=3:1) to give the title compound. MS: m/z=356 (M+1). $^1$H NMR (400 MHz, CDCl$_3$) δ 8.24 (s, 1H), 7.98 (d, J=2.4 Hz, 1H), 7.52 (m, 5H), 7.44 (s, 1H), 3.87 (m, 4H), 3.29 (m, 4H) 1.47 (s, 9H).

Step C: 5-Morpholino-2-phenylpyridin-3-amine

A solution of HCl in EtOAc (4 M, 5 mL, 20 mmol) was added to a solution of t-butyl (5-morpholino-2-phenylpyridin-3-yl)carbamate (160 mg, 0.40 mmol) in EtOAc (2 mL), and the resulting mixture was stirred at 25° C. for 2 h. The mixture was concentrated and the residue was partitioned between DCM (50 mL) and water (10 mL×3). The organic layer was dried over Na$_2$SO$_4$ and concentrated. The residue was purified by preparative TLC (PE:EtOAc=3:1) to give the title compound. MS: m/z=256 (M+1).

REACTION SCHEME FOR INTERMEDIATE A4

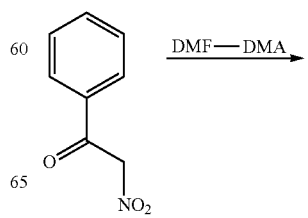

-continued

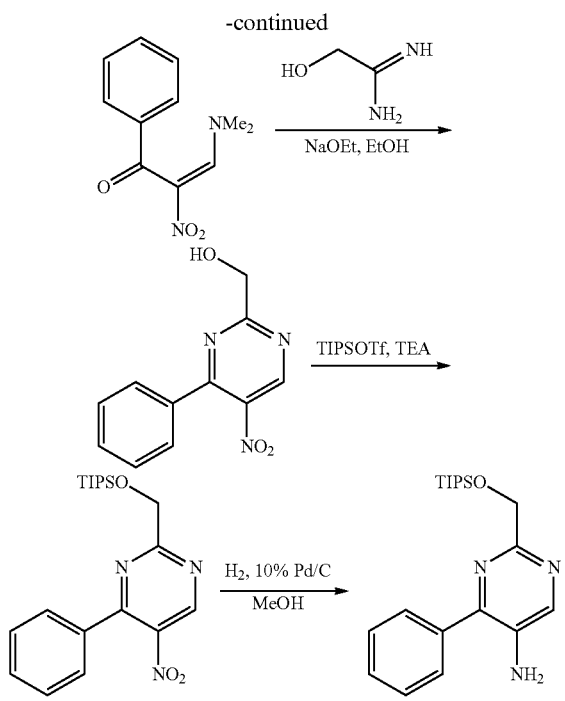

Intermediate A4

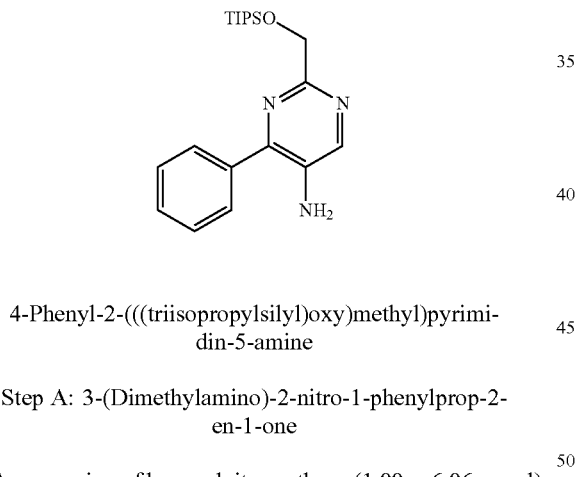

4-Phenyl-2-(((triisopropylsilyl)oxy)methyl)pyrimidin-5-amine

Step A: 3-(Dimethylamino)-2-nitro-1-phenylprop-2-en-1-one

A suspension of benzoylnitromethane (1.00 g, 6.06 mmol) and N,N-dimethylformamide dimethyl acetal (0.877 mL, 6.60 mmol) in DCM (12 mL) was stirred at ambient temperature for 5 days. The mixture was concentrated and the residue was purified by column chromatography on silica gel (EtOAc:hexanes=0:100 to 100:0) to yield the title compound. MS: m/z=221.2 (M+1).

Step B: (5-Nitro-4-phenylpyrimidin-2-yl)methanol

A mixture of 3-(dimethylamino)-2-nitro-1-phenylprop-2-en-1-one (2.99 g, 13.6 mmol), 2-hydroxyacetimidamide hydrochloride (1.95 g, 17.6 mmol), and sodium ethanolate (2.77 g, 40.7 mmol) in EtOH (27 mL) was stirred at ambient temperature for 3 h. The reaction mixture was partitioned between water (50 mL) and DCM (3×50 mL). The combined organic layers were dried over $Na_2SO_4$ and concentrated. The residue was purified by column chromatography on silica gel (EtOAc:hexanes=0:100 to 100:0) to yield the title compound. MS: m/z=232.1 (M+1).

Step C: 5-Nitro-4-phenyl-2-(((triisopropylsilyl)oxy)methyl)pyrimidine

TIPSOTf (1.29 mL, 4.76 mmol) was added to a solution of (5-nitro-4-phenylpyrimidin-2-yl)methanol (1.00 g, 4.33 mmol) and TEA (1.21 mL, 8.65 mmol) in DCM (10 mL), and the resulting mixture was stirred at ambient temperature for 0.5 h. The reaction mixture was purified directly by column chromatography on silica gel (EtOAc:hexanes=0:100 to 30:70) to yield the title compound. MS: m/z=388.3 (M+1).

Step D: 4-Phenyl-2-(((triisopropylsilyl)oxy)methyl)pyrimidin-5-amine

To a solution of 5-nitro-4-phenyl-2-(((triisopropylsilyl)oxy)methyl)pyrimidine (117 mg, 0.302 mmol) in MeOH (3 mL) was added a slurry of 10% Pd/C (10 mg, 10 wt %) in EtOAc (~0.2 mL), and the resulting mixture was stirred under $H_2$ at ambient temperature for 3 h. The suspension was filtered through Celite®, washing with MeOH (0.5 mL), and the filtrate was concentrated to yield the title compound. MS: m/z=358.3 (M+1).

REACTION SCHEME FOR INTERMEDIATE A5

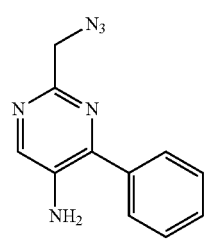 [SMILES: [N-]=[N+]=NCc1ncc(N)c(-c2ccccc2)n1]

Intermediate A5

2-(Azidomethyl)-4-phenylpyrimidin-5-amine

Step A: tert-Butyl (2-(azidomethyl)-4-phenylpyrimidin-5-yl)carbamate

DPPA (8.58 mL, 39.8 mmol) followed by DBU (6.00 mL, 39.8 mmol) were added to a solution of tert-butyl (2-(hydroxymethyl)-4-phenylpyrimidin-5-yl)carbamate (10.0 g, 33.2 mmol) mmol) in 2-methyltetrahydrofuran (100 mL) at 0° C. The resulting mixture was stirred at 0° C. for 30 min, then warmed to 23° C. and stirred for 4 h. The product mixture was partitioned between brine (200 mL) and EtOAc (2×100 mL). The combined organic layers were dried over sodium sulfate and concentrated. The residue was suspended in EtOAc (40 mL) and the resulting solid filtered. The filtrate was concentrated and the suspension/filtration sequence was repeated before the residue was purified by flash column chromatography (hexanes, grading to 50% EtOAc in hexanes) to provide the title compound. MS: m/z=327.2 (M+1).

Step B: 2-(Azidomethyl)-4-phenylpyrimidin-5-amine

A solution of tert-butyl (2-(azidomethyl)-4-phenylpyrimidin-5-yl)carbamate (6.00 g, 18.4 mmol) in EtOAc (200 mL) at 0° C. was saturated with HCl gas. The resulting solution was warmed to 23° C. and stirred for 1.5 h, then concentrated to afford the title compound as a hydrochloride salt. MS: m/z=227.3 (M+1).

Methyl 5-amino-6-phenylnicotinate

A deoxygenated mixture of methyl 5-amino-6-bromonicotinate (950 mg, 4.11 mmol), phenylboronic acid (752 mg, 6.27 mmol), PdCl$_2$(dppf).CH$_2$Cl$_2$ (336 mg, 0.411 mmol), and cesium carbonate (4.02 g, 12.3 mmol) in a 5:1 mixture of DMF and water (20 mL) was heated at 100° C. for 6 h. The mixture was cooled and partitioned between water (60 mL) and CH$_2$Cl$_2$ (3×80 mL). The combined organic layers were dried over Na$_2$SO$_4$ and concentrated. The residue was purified by column chromatography on silica gel (EtOAc: hexanes=0:100 to 100:0) to afford the title compound. MS: m/z=229.4 (M+1).

REACTION SCHEME FOR INTERMEDIATE A6

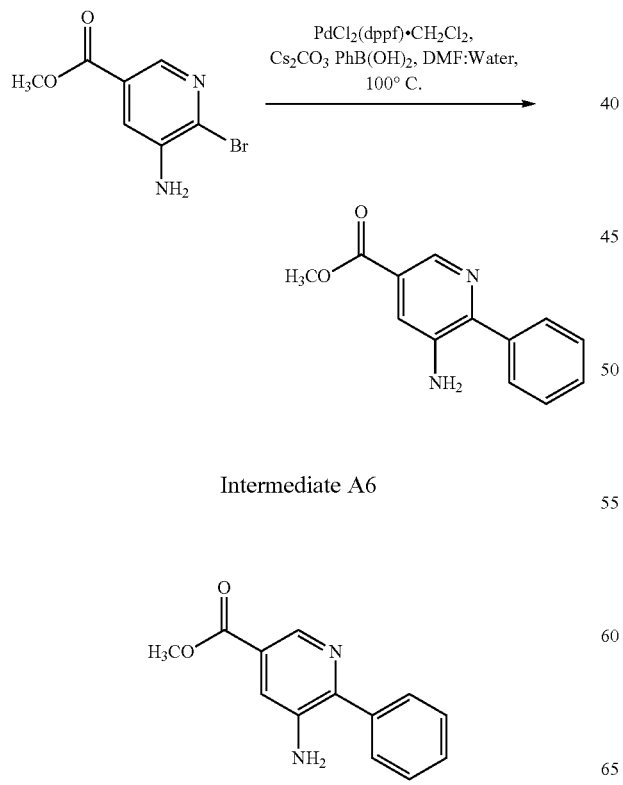

Intermediate A6

REACTION SCHEME FOR INTERMEDIATE A7

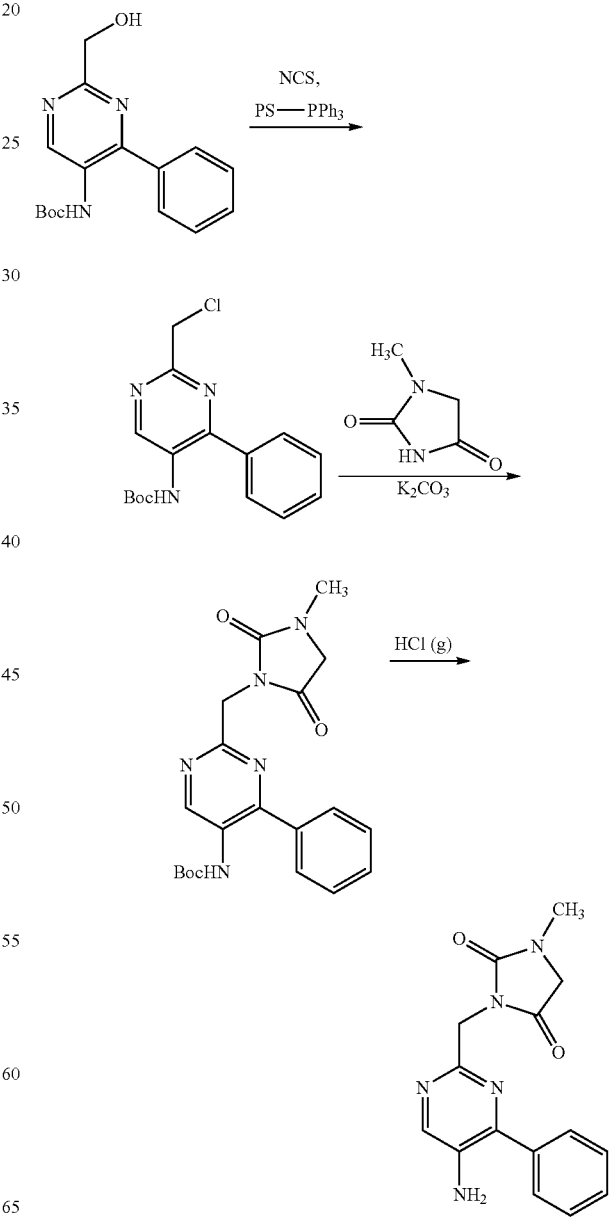

Intermediate A7

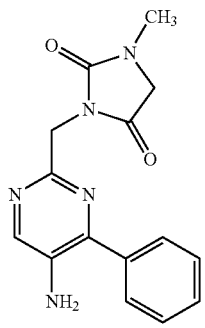 [SMILES: CN1CC(=O)N(Cc2ncc(N)c(-c3ccccc3)n2)C1=O]

3-((5-Amino-4-phenylpyrimidin-2-yl)methyl)-1-methylimidazolidine-2,4-dione

Step A: tert-Butyl (2-(chloromethyl)-4-phenylpyrimidin-5-yl)carbamate

NCS (576 mg, 4.31 mmol) was added to a suspension of tert-butyl (2-(hydroxymethyl)-4-phenylpyrimidin-5-yl)carbamate (1.00 g, 3.32 mmol) and PS-triphenylphosphine resin (3.11 g, 9.96 mmol) in DCM (20 mL) at 23° C. The resulting mixture was stirred gently for 20 min before additional NCS (300 mg, 2.25 mmol) was added. After 30 min, the resin was filtered and washed with DCM (2×50 mL). The combined filtrate was washed with saturated aqueous sodium bicarbonate solution (2×100 mL), dried over sodium sulfate and concentrated to provide the title compound. MS: m/z=320.2 (M+1).

Step B: tert-Butyl (2-((3-methyl-2,5-dioxoimidazolidin-1-yl)methyl)-4-phenylpyrimidin-5-yl)carbamate A solution of tert-butyl (2-(chloromethyl)-4-phenylpyrimidin-5-yl)carbamate (500 mg, 1.56 mmol), 1-methylimidazolidine-2,4-dione (357 mg, 3.13 mmol) and potassium carbonate (432 mg, 3.13 mmol) in a mixture of dioxane (5 mL) and water (2 mL) was stirred at 23° C. for 60 h. The product mixture was partitioned between brine (75 mL) and EtOAc (2×75 mL). The combined organic layers were dried over sodium sulfate and concentrated. The residue was purified by flash column chromatography (hexanes, grading to 100% EtOAc) to yield the title compound. MS: m/z=398.3 (M+1)

Step C: 3-((5-Amino-4-phenylpyrimidin-2-yl)methyl)-1-methylimidazolidine-2,4-dione A solution of tert-butyl (2-(3-methyl-2,5-dioxoimidazolidin-1-yl)methyl)-4-phenylpyrimidin-5-yl)carbamate (330 mg, 0.83 mmol) in EtOAc (30 mL) at 0° C. was saturated with HCl gas. The resulting solution was warmed to 23° C. and stirred for 1 h, then concentrated to afford the title compound as a hydrochloride salt. MS: m/z=298.2 (M+1).

REACTION SCHEME FOR INTERMEDIATE A8

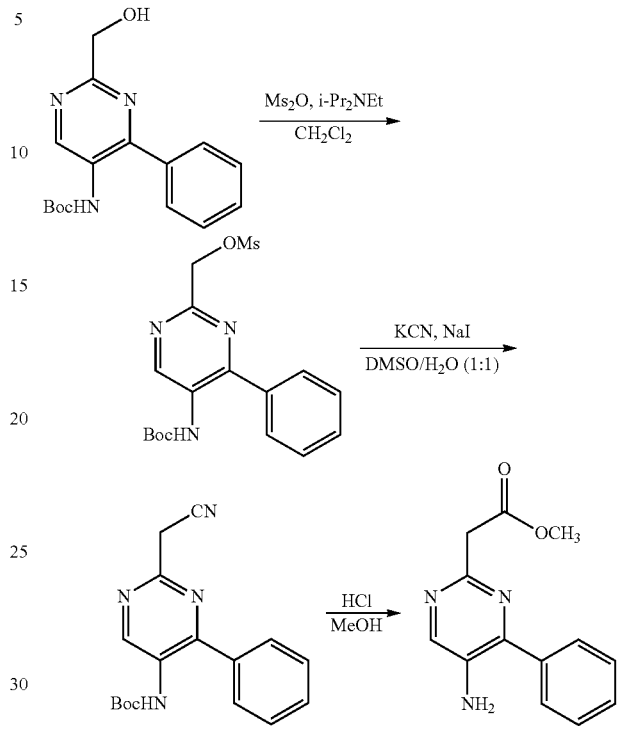

Intermediate A8

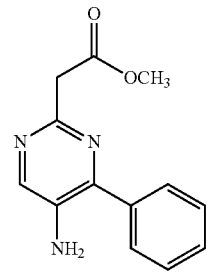 [SMILES: COC(=O)Cc1ncc(N)c(-c2ccccc2)n1]

Methyl 2-(5-amino-4-phenylpyrimidin-2-yl)acetate

Step A: (5-((tert-Butoxycarbonyl)amino)-4-phenylpyrimidin-2-yl)methyl methanesulfonate To a solution of tert-butyl (2-(hydroxymethyl)-4-phenylpyrimidin-5-yl)carbamate (2.00 g, 6.64 mmol) in CH$_2$Cl$_2$ (20 mL) at 23° C. were added methanesulfonic anhydride (2.54 g, 14.6 mmol) and N,N-diisopropylethylamine (1.73 mL, 9.96 mmol), and the resulting mixture was stirred for 1.5 h. The product mixture was poured into water (20 mL) and extracted with EtOAc (3×30 mL). The combined organic layers were dried over Na$_2$SO$_4$, filtered, and concentrated. The residue was purified by SiO$_2$ flash column chromatography (120 g cartridge), eluting with 0-100% EtOAc/hexanes, to give the title compound. MS: m/z=380.1 (M+1).

Step B: tert-Butyl (2-(cyanomethyl)-4-phenylpyrimidin-5-yl)carbamate (5-((tert-Butoxycarbonyl)amino)-4-phenylpyrimidin-2-yl)methyl methanesulfonate (8.46 g, 22.3 mmol) was dissolved in $CH_2Cl_2$ (20 mL). Sodium iodide (334 mg, 2.23 mmol) and potassium cyanide (1.9 g, 29 mmol) were added, followed by a 1:1 mixture of DMSO and $H_2O$ (500 mL). The resulting mixture was heated at 50° C. for 1 h. The product mixture was cooled and the organic layer separated. The aqueous layer was extracted with $CH_2Cl_2$ (3×100 mL). The combined organic layers were dried over $MgSO_4$, filtered, and concentrated. The residue was purified by $SiO_2$ flash column chromatography (80-gram Isco Gold cartridge), eluting with 0-50% EtOAc/hexanes, to give the title compound. MS: m/z=311.2 (M+1).

Step C: Methyl 2-(5-amino-4-phenylpyrimidin-2-yl)acetate

To tert-butyl (2-(cyanomethyl)-4-phenylpyrimidin-5-yl)carbamate (1.00 g, 3.22 mmol) was added a 3M solution of HCl in MeOH (80 mL, 240 mmol), and the resulting mixture was heated at 60° C. for 18 h. The reaction mixture was concentrated, and the residue was partitioned between saturated aqueous $NaHCO_3$ solution (100 mL) and $CH_2Cl_2$ (100 mL×3). The combined organic layers were dried over $MgSO_4$, filtered, and concentrated to give the title compound. MS: m/z=244.2 (M+1).

REACTION SCHEME FOR INTERMEDIATE A9

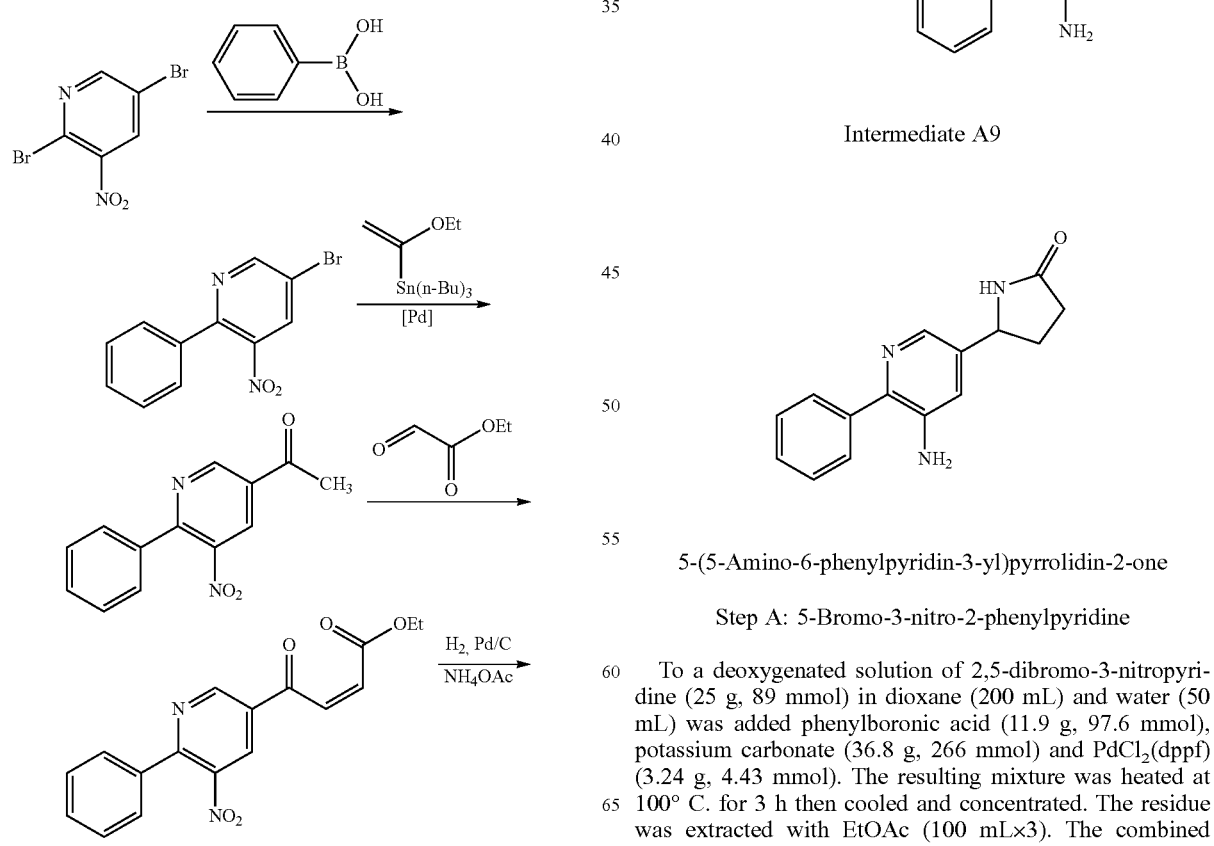

Intermediate A9

5-(5-Amino-6-phenylpyridin-3-yl)pyrrolidin-2-one

Step A: 5-Bromo-3-nitro-2-phenylpyridine

To a deoxygenated solution of 2,5-dibromo-3-nitropyridine (25 g, 89 mmol) in dioxane (200 mL) and water (50 mL) was added phenylboronic acid (11.9 g, 97.6 mmol), potassium carbonate (36.8 g, 266 mmol) and $PdCl_2$(dppf) (3.24 g, 4.43 mmol). The resulting mixture was heated at 100° C. for 3 h then cooled and concentrated. The residue was extracted with EtOAc (100 mL×3). The combined organic layers were washed with brine, dried over $Na_2SO_4$ and concentrated. The residue was purified by column chromatography (PE/EtOAc=50/1 to 40/1 to 30/1) to give the title compound. MS: m/z=278.9 (M+1).

Step B: 1-(5-Nitro-6-phenylpyridin-3-yl)ethanone

To a deoxygenated mixture of 5-bromo-3-nitro-2-phenylpyridine (10.0 g, 35.8 mmol) in dioxane (100 mL) were added tributyl(1-ethoxyvinyl)stannane (19.1 g, 53.7 mmol), copper(I) iodide (0.341 g, 1.79 mmol) and dichlorobis(tri-o-tolylphosphine)palladium (II) (2.82 g, 3.58 mmol), and the resulting mixture was heated at 100° C. for 3 h. Aqueous 2N HCl solution (30 mL) was added and the resulting mixture was stirred at 25° C. for 1 h. Saturated aqueous potassium fluoride (15 mL) solution was added and the product mixture was filtered. The filtrate was basified to pH 9 by addition of saturated aqueous $K_2CO_3$ solution and subsequently extracted with EtOAc (50 mL×3). The combined organic layers were dried over $Na_2SO_4$ and concentrated, and the residue was purified by preparative TLC (PE/EA=15/1, 10/1, 5/1) to give the title compound. MS: m/z=243.0 (M+1).

Step C: Ethyl 4-(5-nitro-6-phenylpyridin-3-yl)-4-oxobut-2-enoate

To a solution of 1-(5-nitro-6-phenylpyridin-3-yl)ethanone (0.500 g, 2.06 mmol) in AcOH (5 mL) was added ethyl 2-oxoacetate (1.05 g, 10.3 mmol), and the resulting mixture was stirred at 120° C. for 12 h. The product mixture was cooled and partitioned between water (10 mL) and EtOAc (20 mL×3). The combined organic layers were dried over $Na_2SO_4$ and concentrated. The residue was purified by preparative TLC (PE/EA=3/1) to give the title compound. MS: m/z=327.0 (M+1).

Step D: Ethyl 4-(5-amino-6-phenylpyridin-3-yl)-4-hydroxybutanoate

To a deoxygenated solution of ethyl 4-(5-nitro-6-phenylpyridin-3-yl)-4-oxobut-2-enoate (900 mg, 2.76 mmol) in MeOH (20 mL) was added 10% Pd/C (29.4 mg, 0.276 mmol) and $NH_4OAc$ (425 mg, 5.52 mmol), and the resulting mixture was heated under $H_2$ (50 psi) at 30° C. for 10 h. The mixture was filtered and the filtrate was concentrated. The residue was purified by column chromatography on silica gel (PE/EA=8/1, 5/1) to give the title compound. MS: m/z=301.1 (M+1).

Step E: Ethyl 4-(5-amino-6-phenylpyridin-3-yl)-4-oxobutanoate

To a solution of ethyl 4-(5-amino-6-phenylpyridin-3-yl)-4-hydroxybutanoate (0.600 g, 2.00 mmol) in $CH_2Cl_2$ (8 mL) was added PCC (1.72 g, 7.99 mmol), and the resulting mixture was stirred at 25° C. for 12 h. Water (5 mL) was added and the product mixture was filtered. The filtrate was extracted with EtOAc (5 mL×3), and the combined organic layers were concentrated to give the title compound. MS: m/z=299.0 (M+1).

Step F: Ethyl 4-(5-amino-6-phenylpyridin-3-yl)-4-(hydroxyimino)butanoate

To a solution of ethyl 4-(5-amino-6-phenylpyridin-3-yl)-4-oxobutanoate (380 mg, 1.27 mmol) in EtOH (4 mL) was added $NH_2OH \cdot HCl$ (133 mg, 1.91 mmol) and pyridine (0.308 mL, 3.82 mmol), and the resulting mixture was heated at 80° C. for 3 h. The mixture was partitioned between water (5 mL) and EtOAc (5 mL×3). The combined organics were concentrated, and the residue purified by preparative TLC (PE/EtOAc=1/1) to give the title compound. MS: m/z=314.0 (M+1).

Step G: 5-(5-Amino-6-phenylpyridin-3-yl)pyrrolidin-2-one

To a stirred solution of ethyl 4-(5-amino-6-phenylpyridin-3-yl)-4-(hydroxyimino)butanoate (150 mg, 0.479 mmol) in AcOH (4 mL) was added zinc powder (156 mg, 2.39 mmol), and the resulting mixture was heated at 80° C. for 6 h. The mixture was cooled and filtered, and the filtrate was concentrated. The residue was partitioned between saturated aqueous $NaHCO_3$ solution (10 mL) and EtOAc (15 mL×3). The combined organic layers were dried over $Na_2SO_4$ and concentrated. The residue was purified by preparative TLC (PE/EtOAc=1/2) to give the title compound. MS: m/z=254.3 (M+1). $^1$H NMR (400 MHz, $CDCl_3$) δ 7.95 (br s, 1H), 7.56 (d, J=7.0 Hz, 2H), 7.40 (t, J=7.2 Hz, 2H), 7.34 (d, J=7.0 Hz, 1H), 6.93 (br s, 1H), 6.65 (br s, 1H), 4.67 (t, J=6.7 Hz, 1H), 3.95 (br s, 2H), 2.57-2.49 (m, 1H), 2.46-2.32 (m, 2H), 1.99-1.91 (m, 1H).

REACTION SCHEME FOR INTERMEDIATE A10

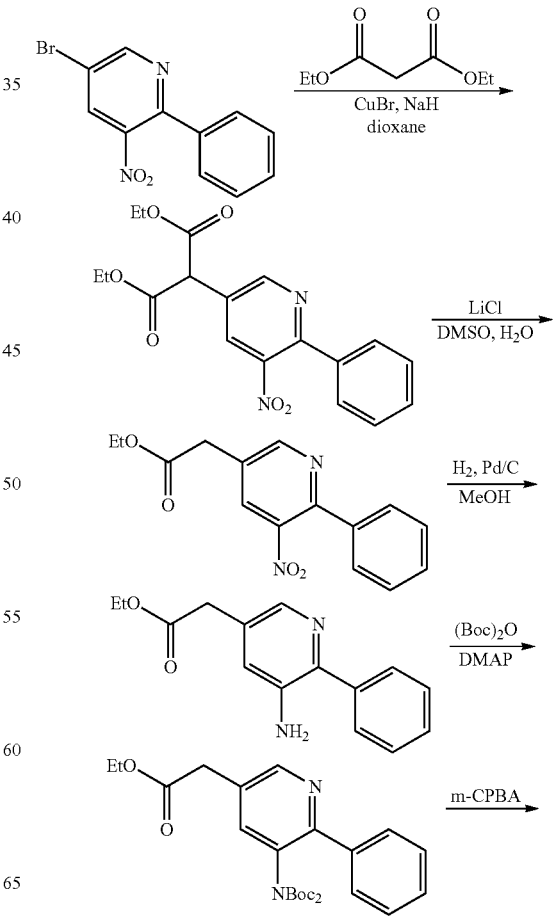

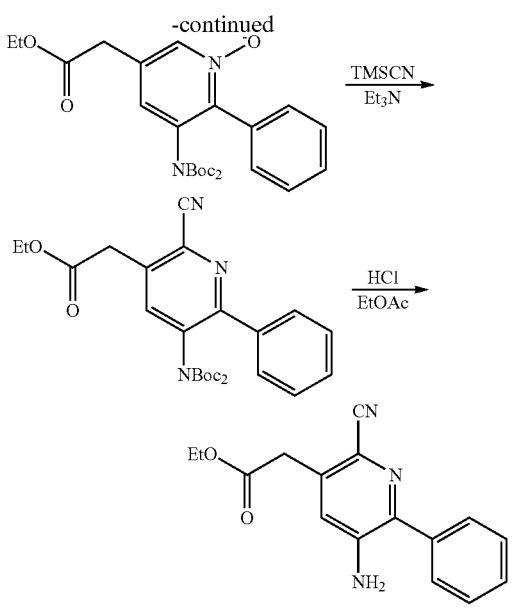

Intermediate A10

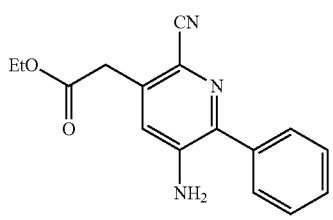 [SMILES: CCOC(=O)Cc1cc(N)c(-c2ccccc2)nc1C#N]

Ethyl 2-(5-amino-2-cyano-6-phenylpyridiN-3-yl)acetate

Step A: Diethyl 2-(5-nitro-6-phenylpyridin-3-yl)malonate

To a mixture of 5-bromo-3-nitro-2-phenylpyridine (5.00 g, 17.9 mmol), diethyl malonate (11.5 g, 71.7 mmol), and copper(I) bromide (10.3 g, 71.7 mmol) in dioxane (150 mL) was added NaH (60 wt. %, 3.15 g, 79.0 mmol) in portions at 25° C., and the resulting mixture was heated at 100° C. for 16 h. The reaction mixture was cooled and diluted with saturated aqueous NH$_4$Cl solution (100 mL). The aqueous mixture was extracted with EtOAc (100 mL×3), and the combined organic layers were dried over Na$_2$SO$_4$ and concentrated. The residue was purified by column chromatography on silica gel (PE/EtOAc=50/1, 30/1, 10/1) to give the title compound. MS: m/z=359.0 (M+1). $^1$H NMR (400 MHz, CDCl$_3$) δ 8.84 (s, 1H), 8.41 (s, 1H), 7.54-7.45 (m, 5H), 6.11 (s, 1H), 4.27-4.18 (m, 4H), 1.29-1.23 (m, 6H).

Step B: Ethyl 2-(5-nitro-6-phenylpyridin-3-yl)acetate

To a stirred solution of diethyl 2-(5-nitro-6-phenylpyridin-3-yl)malonate (5.80 g, 16.2 mmol) in DMSO (60 mL) and water (3 mL) was added lithium chloride (2.10 g, 48.6 mmol), and the resulting mixture was heated at 100° C. for 5 h. The mixture was cooled and partitioned between water (80 mL) and EtOAc (80 mL×3). The combined organic layers were dried over Na$_2$SO$_4$ and concentrated. The residue was purified by column chromatography on silica gel (PE/EtOAc=10/1, 5/1, 3/1) to give the title compound. MS: m/z=287.0 (M+1).

Step C: Ethyl 2-(5-amino-6-phenylpyridin-3-yl)acetate

A deoxygenated mixture of ethyl 2-(5-nitro-6-phenylpyridin-3-yl)acetate (5.50 g, 19.2 mmol) and 10% Pd/C (2.0 g, 1.9 mmol) in MeOH (50 mL) was stirred under H$_2$ (50 psi) at 30° C. for 5 h. The mixture was filtered and the filtrate was concentrated to give the title compound. MS: m/z=257.0 (M+1).

Step D: Ethyl 2-(5-(di-(tert-butoxycarbonyl)amino)-6-phenylpyridin-3-yl)acetate

A mixture of Boc$_2$O (7.80 mL, 33.6 mmol), triethylamine (5.10 g, 50.3 mmol), N,N-dimethylpyridin-4-amine (2.10 g, 16.8 mmol) and ethyl 2-(5-amino-6-phenylpyridin-3-yl)acetate (4.30 g, 16.8 mmol) in CH$_2$Cl$_2$ (50 mL) was stirred at 30° C. for 3 h. The mixture was concentrated, and the residue was purified by column chromatography on silica gel (PE/EtOAc=10/1, 5/1) to give the title compound. MS: m/z=457.3 (M+1).

Step E: 3-(Di-(tert-butoxycarbonyl)amino)-5-(2-ethoxy-2-oxoethyl)-2-phenylpyridine-1-oxide To a stirred solution of ethyl 2-(5-(di-(tert-butoxycarbonyl)amino)-6-phenylpyridin-3-yl)acetate (200 mg, 0.438 mmol) in CHCl$_3$ (4 mL) was added m-CPBA (267 mg, 1.31 mmol), and the resulting mixture was stirred at 25° C. for 2 h. The product mixture was partitioned between saturated aqueous NaHCO$_3$ solution (10 mL) and DCM (15 mL×3). The combined organic layers were dried over Na$_2$SO$_4$ and concentrated to give the title compound. MS: m/z=473.2 (M+1). $^1$H NMR (400 MHz, CDCl$_3$) δ 8.39 (s, 1H), 8.03 (d, J=14.1 Hz, 1H), 7.94 (dd, J$_1$=16.2 Hz, J$_2$=7.6 Hz, 1H), 7.64 (d, J=7.8 Hz, 1H), 7.43 (br s, 2H), 7.21 (s, 1H), 4.21 (d, J=6.7 Hz, 2H), 3.62 (s, 2H), 1.34 (s, 18H), 1.29-1.27 (m, 3H).

Step F: Ethyl 2-(5-(di-(tert-butoxycarbonyl)amino)-2-cyano-6-phenylpyridin-3-yl)acetate To a stirred solution of 3-(di-(tert-butoxycarbonyl)amino)-5-(2-ethoxy-2-oxoethyl)-2-phenylpyridine-1-oxide (2.0 g, 4.2 mmol) and Et$_3$N (1.8 mL, 13 mmol) in acetonitrile (30 mL) was added TMSCN (2.3 mL, 17 mmol), and the resulting mixture was heated at 80° C. for 5 h. The product mixture was partitioned between water (30 mL) and EtOAc (30 mL×3). The combined organic layers were dried over Na$_2$SO$_4$ and concentrated. The residue was purified by column chromatography on silica gel (PE/EtOAc=10/1, 5/1, 1/1) to give the title compound. MS: m/z=482.3 (M+1).

Step G: Ethyl 2-(5-amino-2-cyano-6-phenylpyridin-3-yl)acetate

A solution of ethyl 2-(5-(di-(tert-butoxycarbonyl)amino)-2-cyano-6-phenylpyridin-3-yl)acetate (500 mg, 1.00 mmol) in 4N HCl in EtOAc (10 mL, 40.0 mmol) was stirred at 20°

C. for 1 h. The mixture was concentrated to give the title compound as an HCl salt. MS: m/z=282.2 (M+1). ¹H NMR (400 MHz, CDCl₃) δ 7.62 (d, J=7.0 Hz, 2H), 7.53-7.44 (m, 3H), 7.04 (s, 1H), 4.38 (br s, 2H), 4.23 (q, J=7.0 Hz, 2H), 3.81 (s, 2H), 1.31 (t, J=7.2 Hz, 3H).

Intermediate A11

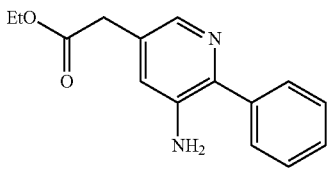 [SMILES: CCOC(=O)Cc1cnc(-c2ccccc2)c(N)c1]

Ethyl 2-(5-amino-6-phenylpyridin-3-yl)acetate

To a solution of ethyl 2-(5-nitro-6-phenylpyridin-3-yl)acetate (400 mg, 0.699 mmol) in THF (3 mL) and acetic acid (1 mL) was added zinc powder (137 mg, 2.10 mmol), and the resulting mixture was stirred at 25° C. for 2 h. The mixture was partitioned between water (20 mL) and ethyl acetate (10 mL×3). The combined organic layers were dried over Na₂SO₄ and concentrated. The residue was purified by preparative TLC (PE/EtOAc=1/1) to give the title compound. MS: m/z=257.1 (M+1).

REACTION SCHEME FOR INTERMEDIATE A12

5-(Methylsulfonyl)-2-phenylpyridin-3-amine

Step A: 5-Bromo-2-phenylpyridin-3-amine

To a solution of 5-bromo-3-nitro-2-phenylpyridine (7.00 g, 22.6 mmol) in ethanol (80 mL) was added stannous chloride (12.8 g, 67.7 mmol), and the resulting mixture was heated at 90° C. for 5 h. The mixture was partitioned between saturated aqueous sodium bicarbonate solution (200 mL) and ethyl acetate (200 mL×3). The combined organic layers were dried over Na₂SO₄ and concentrated to give the title compound. MS: m/z=249.1 (M+1).

Step B: 5-(Methylsulfonyl)-2-phenylpyridin-3-amine

To a solution of 5-bromo-2-phenylpyridin-3-amine (800 mg, 3.21 mmol) in dimethyl sulfoxide (8 mL) was added sodium methanesulfinate (393 mg, 3.85 mmol), copper(I) iodide (61.2 mg, 0.321 mmol), sodium hydroxide (25.7 mg, 0.642 mmol) and L-proline (73.9 mg, 0.642 mmol). The resulting mixture was heated at 70° C. for 6 h, then cooled and partitioned between saturated aqueous sodium bicarbonate solution (100 mL) and ethyl acetate (50 mL×3). The combined organic layers were dried over Na₂SO₄ and concentrated. The residue was purified by silica gel column chromatography (PE/EtOAc=10/1, 3/1) to afford the title compound. MS: m/z=249.1 (M+1). ¹H NMR (400 MHz, CDCl₃) δ 8.57 (d, J=1.57 Hz, 1H), 7.67 (d, J=7.04 Hz, 2H), 7.54-7.42 (m, 4H), 4.18 (s, 2H), 3.11 (s, 3H).

REACTION SCHEME FOR INTERMEDIATE A13

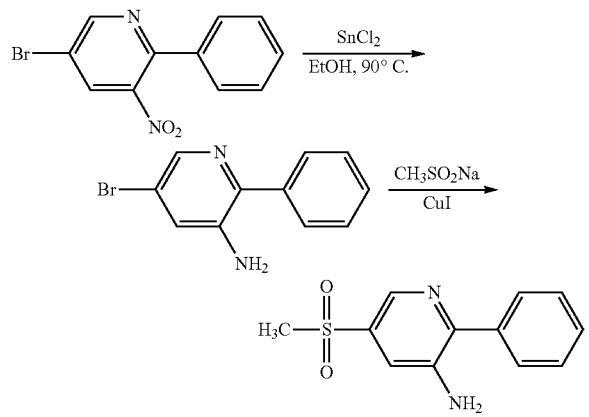

Intermediate A12

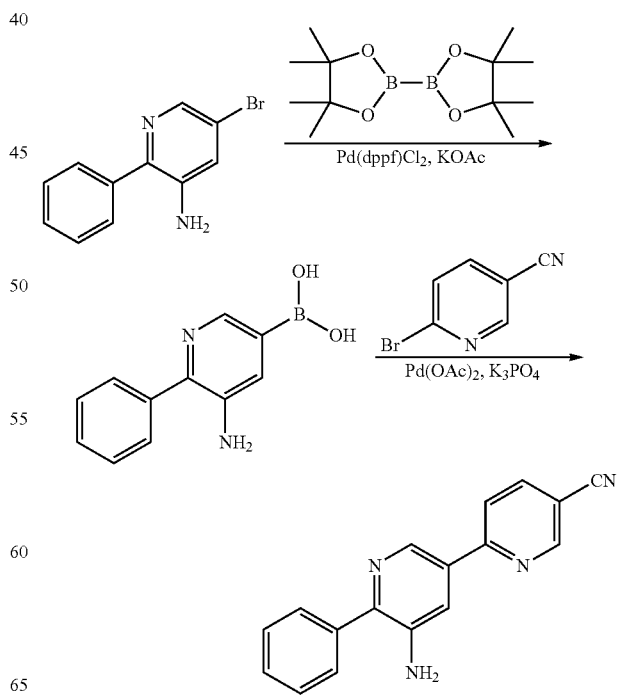

Intermediate A13

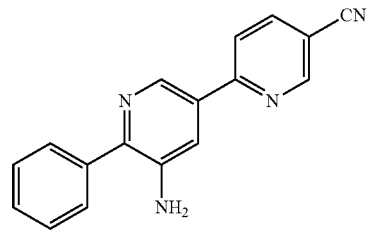 [SMILES: N#Cc1ccc(-c2cnc(-c3ccccc3)c(N)c2)nc1]

5'-Amino-6'-phenyl-[2,3'-bipyridine]-5-carbonitrile

Step A: (5-Amino-6-phenylpyridin-3-yl)boronic acid

A deoxygenated mixture of 5-bromo-2-phenylpyridin-3-amine (5.00 g, 20.1 mmol), PdCl$_2$(dppf) (1.47 g, 2.01 mmol), 4,4,4',4',5,5,5',5'-octamethyl-2,2'-bi(1,3,2-dioxaborolane) (5.10 g, 20.1 mmol) and KOAc (5.91 g, 60.2 mmol) in 1,4-dioxane (50 mL) was heated at 100° C. for 8 h. The mixture was cooled then partitioned between water (25 mL) and EtOAc (50 mL×3). The combined organic layers were dried over Na$_2$SO$_4$ and concentrated. The residue was purified by reverse-phase HPLC under acidic conditions (H$_2$O/CH$_3$CN gradient with 0.1% TFA present) to give the title compound. MS: m/z=215.2 (M+1).

Step B: 5'-Amino-6'-phenyl-[2,3'-bipyridine]-5-carbonitrile

A deoxygenated mixture of (5-amino-6-phenylpyridin-3-yl)boronic acid (500 mg, 2.34 mmol), 6-bromonicotinonitrile (428 mg, 2.34 mmol), K$_3$PO$_4$ (1020 mg, 5.84 mmol), Pd(OAc)$_2$ (105 mg, 0.467 mmol) and butyl di-1-adamantylphosphine (84 mg, 0.23 mmol) in THF (5 mL) and water (1 mL) was heated at 100° C. for 20 h. The mixture was partitioned between water (5 mL) and EtOAc (10 mL×3). The combined organic layers were dried over Na$_2$SO$_4$ and concentrated. The residue was purified by preparative TLC (PE/EtOAc=1/1) to give the title compound. MS: m/z=273.0 (M+1).

REACTION SCHEME FOR INTERMEDIATE A14

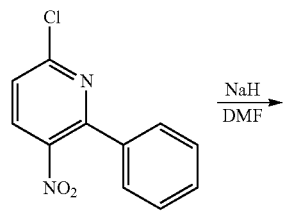

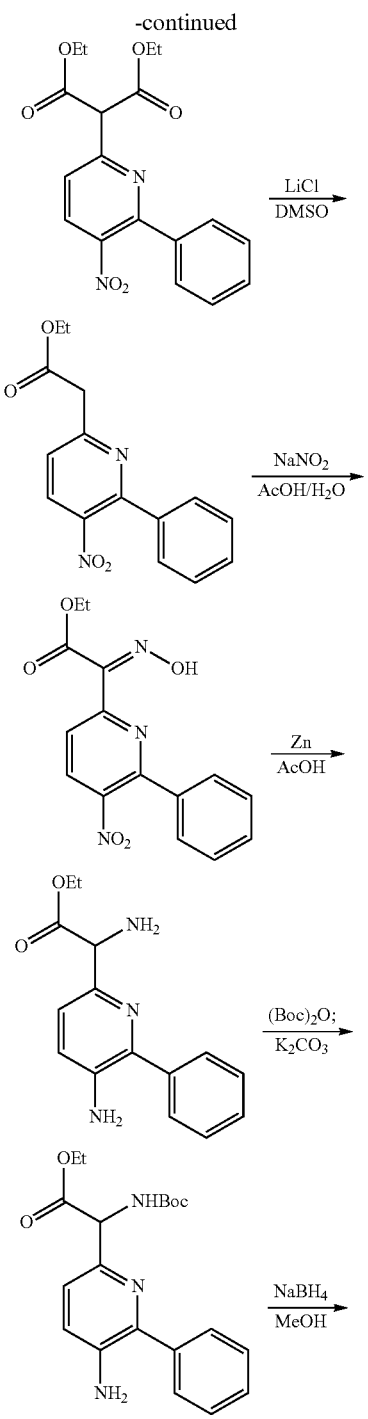

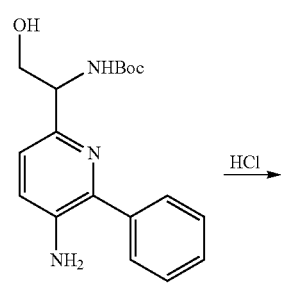

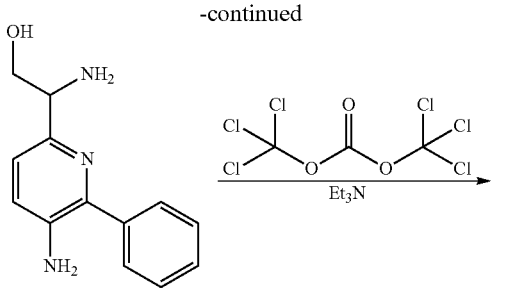

Intermediate A14

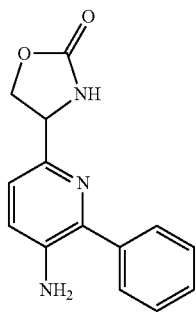 [SMILES: Nc1ccc(C2COC(=O)N2)nc1-c1ccccc1]

4-(5-Amino-6-phenylpyridin-2-yl)oxazolidin-2-one

Step A: Diethyl 2-(5-nitro-6-phenylpyridin-2-yl)malonate

To a solution of diethyl malonate (12.3 g, 76.8 mmol) in DMF (120 mL) at 0° C. was added NaH (60 wt. %, 3.84 g, 96 mmol), and the mixture was stirred for 10 min before 6-chloro-3-nitro-2-phenylpyridine (15.0 g, 63.9 mmol) was added. The resulting mixture was allowed to warm to 20° C. where it was stirred for 5 h. The product mixture was poured into ice water (600 mL) and extracted with EtOAc (200 mL×3). The combined organic layers were dried over $Na_2SO_4$ and concentrated. The residue was purified by silica gel column chromatography (PE/EtOAc=1/1) to afford title compound. MS: m/z=359.0 (M+1). $^1$H NMR (400 MHz, CDCl3) δ 8.17 (d, J=8.0 Hz, 1H), 7.70 (d, J=8.5 Hz, 1H), 7.61-7.52 (m, 2H), 7.51-7.42 (m, 3H), 5.09 (s, 1H), 4.35-4.21 (m, 4H), 1.30 (t, J=7.0 Hz, 6H).

Step B: Ethyl 2-(5-nitro-6-phenylpyridin-2-yl)acetate

To a solution of diethyl 2-(5-nitro-6-phenylpyridin-2-yl) malonate (15.0 g, 41.9 mmol) in DMSO (160 mL) was added lithium chloride (5.32 g, 126 mmol) and water (0.754 mL, 41.9 mmol), and the resulting mixture was heated at 100° C. for 18 h. The reaction was cooled and partitioned between water (500 mL) and EtOAc (300 mL×3). The combined organic layers were dried over $Na_2SO_4$ and concentrated. The residue was purified by reverse-phase HPLC under acidic conditions ($H_2O/CH_3CN$ gradient with 0.1% TFA present) to afford the title compound. MS: m/z=287.1 (M+1).

Step C: (E)-Ethyl 2-(hydroxyimino)-2-(5-nitro-6-phenylpyridin-2-yl)acetate

To a stirred solution of ethyl 2-(5-nitro-6-phenylpyridin-2-yl)acetate (1.00 g, 3.49 mmol) in AcOH (3 mL) was added dropwise a solution of $NaNO_2$ (0.265 g, 3.84 mmol) in water (1 mL), and the resulting mixture was stirred at 20° C. for 2 h. Water (3 mL) was added to the reaction mixture, and the precipitate was filtered, washed with water (20 mL), and air dried to give the title compound. MS: m/z=316.2 (M+1).

Step D: Ethyl 2-amino-2-(5-amino-6-phenylpyridin-2-yl)acetate

To a stirred solution of (E)-ethyl 2-(hydroxyimino)-2-(5-nitro-6-phenylpyridin-2-yl)acetate (720 mg, 2.28 mmol) in AcOH (3 mL) was added zinc powder (747 mg, 11.4 mmol), and the resulting mixture was heated at 80° C. for 5 h. The mixture was filtered and the filtrate concentrated to give the title compound. MS: m/z=272.2 (M+1).

Step E: Ethyl 2-(5-amino-6-phenylpyridin-2-yl)-2-((tert-butoxycarbonyl)amino)acetate To a stirred solution of ethyl 2-amino-2-(5-amino-6-phenylpyridin-2-yl)acetate (460 mg, 1.70 mmol) in THF (5 mL) and water (3 mL) was added solid $Na_2CO_3$ (539 mg, 5.09 mmol) followed by $Boc_2O$ (0.787 mL, 3.39 mmol). The resulting mixture was stirred at 25° C. for 1 h, then partitioned between water (20 mL) and EtOAc (20 mL×3). The combined organic layers were dried over $Na_2SO_4$ and concentrated. The residue was purified by column chromatography on silica gel (PE/EtOAc=5/1, 3/1) to give the title compound. MS: m/z=372.2 (M+1).

Step F: tert-Butyl (1-(5-amino-6-phenylpyridin-2-yl)-2-hydroxyethyl)carbamate

To a stirred solution of ethyl 2-(5-amino-6-phenylpyridin-2-yl)-2-((tert-butoxycarbonyl)amino)acetate (150 mg, 0.404 mmol) in MeOH (3 mL) was added $NaBH_4$ (76 mg, 2.0 mmol), and the resulting mixture was stirred at 25° C. for 4 h. The mixture was partitioned between water (20 mL) and EtOAc (20 mL×3). The combined organic layers were dried over $Na_2SO_4$ and concentrated. The residue was purified by preparative TLC (PE/EtOAc=1/1) to give the title compound. $^1$H NMR (400 MHz, CDCl$_3$) δ 7.67 (d, J=7.4 Hz, 2H), 7.50 (t, J=7.4 Hz, 2H), 7.45-7.40 (m, 1H), 7.19-7.15 (m, 1H), 7.10-7.06 (m, 1H), 5.83 (d, J=6.7 Hz, 1H), 4.78 (br s, 1H), 4.08 (d, J=8.2 Hz, 1H), 3.91 (d, J=3.9 Hz, 1H), 3.88 (d, J=3.9 Hz, 2H), 1.48-1.44 (m, 9H).

Step G: 2-Amino-2-(5-amino-6-phenylpyridin-2-yl)ethanol

A solution of tert-butyl (1-(5-amino-6-phenylpyridin-2-yl)-2-hydroxyethyl)carbamate (180 mg, 0.546 mmol) in 4N HCl in EtOAc (5 mL, 20 mmol) was stirred at 25° C. for 1 h. The mixture was concentrated to give the title compound as an HCl salt. MS: m/z=230.0 (M+1).

Step H:
4-(5-Amino-6-phenylpyridin-2-yl)oxazolidin-2-one

To a stirred solution of 2-amino-2-(5-amino-6-phenylpyridin-2-yl)ethanol (78 mg, 0.26 mmol) and Et$_3$N (0.108 mL, 0.774 mmol) in THF (3 mL) was added bis(trichloromethyl) carbonate (230 mg, 0.774 mmol). The resulting mixture was stirred at 25° C. for 2 h, then diluted with water (10 mL) and basified to pH 8 with solid Na$_2$CO$_3$. The aqueous product mixture was extracted with EtOAc (10 mL×3), and the combined organic layers were dried over Na$_2$SO$_4$ and concentrated. The residue was purified by preparative TLC (PE/EtOAc=1/1) to give the title compound. MS: m/z=256.3 (M+1). $^1$H NMR (400 MHz, CDCl$_3$) δ 7.58 (d, J=7.0 Hz, 2H), 7.48-7.40 (m, 3H), 7.36 (d, J=7.5 Hz, 1H), 7.13-7.09 (m, 1H), 7.07-7.02 (m, 1H), 6.00-5.92 (m, 1H), 4.75-4.68 (m, 1H), 4.40-4.32 (m, 1H).

REACTION SCHEME FOR INTERMEDIATE A15

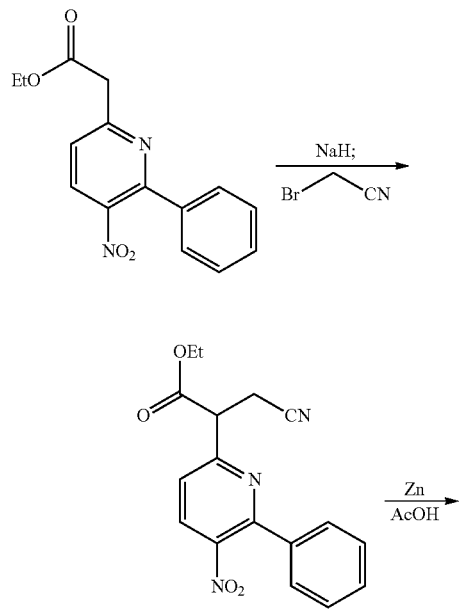

Intermediate A15

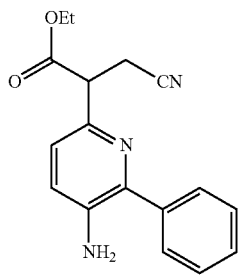 [SMILES: CCOC(=O)C(CC#N)c1ccc(N)c(-c2ccccc2)n1]

Ethyl 2-(5-amino-6-phenylpyridin-2-yl)-3-cyanopropanoate

Step A: Ethyl 3-cyano-2-(5-nitro-6-phenylpyridin-2-yl)propanoate

To a solution of ethyl 2-(5-nitro-6-phenylpyridin-2-yl)acetate (0.50 g, 1.7 mmol) in tetrahydrofuran (10 mL) at 0° C. was added sodium hydride (60 wt. %, 70 mg, 1.7 mmol). The mixture was stirred at 0° C. for 10 min before 2-bromoacetonitrile (210 mg, 1.7 mmol) was added. The resulting mixture was warmed to 25° C. and stirred for 1 h. The product mixture was partitioned between water (20 mL) and ethyl acetate (30 mL×2). The combined organic layers were dried over Na$_2$SO$_4$ and concentrated. The residue was purified by preparative TLC (PE/EtOAc=10/1) to give the title compound. $^1$H NMR (400 MHz, CD$_3$OD) δ 8.31 (d, J=8.2 Hz, 1H), 7.65 (d, J=8.2 Hz, 1H), 7.54 (d, J=7.0 Hz, 2H), 7.50-7.41 (m, 3H), 4.19 (q, J=6.8 Hz, 2H), 3.49 (br s, 1H), 3.20 (s, 2H), 1.19 (t, J=7.0 Hz, 3H).

Step B: Ethyl 2-(5-amino-6-phenylpyridin-2-yl)-3-cyanopropanoate

To a solution of ethyl 3-cyano-2-(5-nitro-6-phenylpyridin-2-yl)propanoate (0.40 g, 1.2 mmol) in ethanol (20 mL) was added ammonium chloride (658 mg, 12.3 mmol) and zinc powder (804 mg, 12.3 mmol). The resulting mixture was stirred at 0° C. for 10 min, then warmed to 25° C. and stirred for 1 h. The product mixture was filtered and concentrated, and the residue was partitioned between water (20 mL) and ethyl acetate (30 mL×3). The combined organic layers were dried over Na$_2$SO$_4$ and concentrated. The residue was purified by preparative TLC (PE/EtOAc=5/1) to give the title compound. $^1$H NMR (400 MHz, CD$_3$OD) δ 7.62 (d, J=7.0 Hz, 2H), 7.46 (t, J=7.4 Hz, 2H), 7.42-7.37 (m, 1H), 7.15-7.19 (m, 1H), 7.14-7.10 (m, 1H), 4.20-4.12 (m, 2H), 3.36 (d, J=3.1 Hz, 1H), 3.07 (dd, J$_1$=7.4 Hz, J$_2$=4.7 Hz, 2H), 1.19 (t, J=7.2 Hz, 3H).

REACTION SCHEME FOR INTERMEDIATE A16

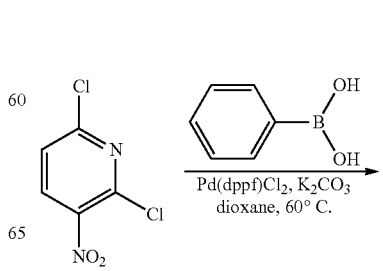

Intermediate A16

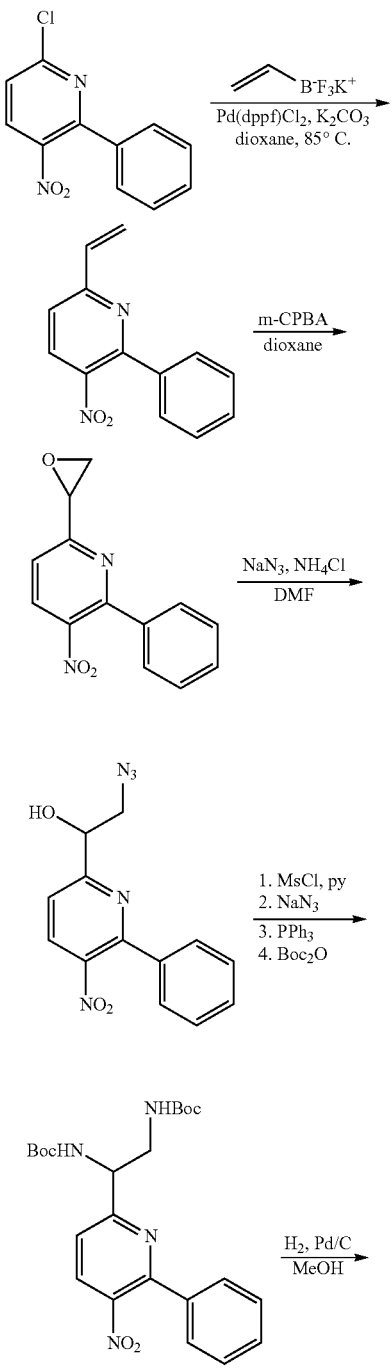

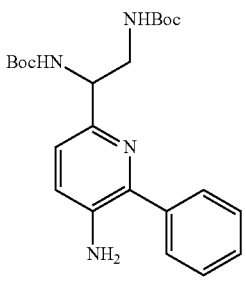 [SMILES: CC(C)(C)OC(=O)NCC(NC(=O)OC(C)(C)C)c1ccc(N)c(-c2ccccc2)n1]

Di-tert-butyl (1-(5-amino-6-phenylpyridin-2-yl)ethane-1,2-diyl)dicarbamate

Step A: 6-Chloro-3-nitro-2-phenylpyridine

A deoxygenated mixture of 2,6-dichloro-3-nitropyridine (45.0 g, 233 mmol) phenylboronic acid (31.3 g, 256 mmol), Pd(dppf)Cl$_2$ (3.41 g, 4.66 mmol) and potassium carbonate (97 g, 700 mmol) in dioxane (500 mL) and water (100 mL) was heated at 60° C. for 15 h. The mixture was filtered and concentrated, and the residue was partitioned between water (500 mL) and EtOAc (400 mL×3). The combined organic layers were dried over Na$_2$SO$_4$ and concentrated. The residue was purified by column chromatography on silica gel (PE/EtOAc=20/1, 10/1) to give the title compound. $^1$H NMR (CDCl$_3$, 400 MHz) δ 8.10 (d, J=8.6 Hz, 1H), 7.53-7.60 (m, 2H), 7.45-7.50 (m, 3H), 7.43 (d, J=8.2 Hz, 1H).

Step B: 3-Nitro-2-phenyl-6-vinylpyridine

A deoxygenated mixture of K$_2$CO$_3$ (4.42 g, 32.0 mmol), PdCl$_2$(dppf) (0.780 g, 1.06 mmol), potassium trifluoro(vinyl)borate (1.43 g, 10.6 mmol) and 6-chloro-3-nitro-2-phenylpyridine (2.50 g, 10.6 mmol) in 1,4-dioxane (25 mL) and water (5 mL) was heated at 85° C. for 5 h. The mixture was partitioned between water (30 mL) and EtOAc (30 mL×3). The combined organic layers were dried over Na$_2$SO$_4$ and concentrated, and the residue was purified by column chromatography on silica gel (PE/EtOAc=10/1, 5/1) to give the title compound. $^1$H NMR (CDCl$_3$, 400 MHz) δ 8.13 (d, J=8.2 Hz, 1H), 7.59-7.55 (m, 2H), 7.49-7.45 (m, 3H), 7.41 (d, J=8.2 Hz, 1H), 6.91 (dd, J$_1$=17.4 Hz, J$_2$=10.8 Hz, 1H), 6.42 (d, J=17.2 Hz, 1H), 5.70 (d, J=11.0 Hz, 1H).

Step C: 3-Nitro-6-(oxiran-2-yl)-2-phenylpyridine

To a stirred solution of 3-nitro-2-phenyl-6-vinylpyridine (10.0 g, 44.2 mmol) in 1,4-dioxane (120 mL) was added 3-chloroperbenzoic acid (18 g, 88 mmol), and the resulting mixture was heated at 80° C. for 5 h. The mixture was cooled, diluted with water (100 mL), and basified with Na$_2$CO$_3$ to pH 9. The aqueous layer was extracted with EtOAc (100 mL×3), and the combined organic layers were dried with Na$_2$SO$_4$ and concentrated. The residue was purified by column chromatography on silica gel (PE/EtOAc=10/1, 5/1, 3/1) to give the title compound. MS: m/z=243.0 (M+1).

Step D: 2-Azido-1-(5-nitro-6-phenylpyridin-2-yl)ethanol

A mixture of 3-nitro-6-(oxiran-2-yl)-2-phenylpyridine (6.00 g, 24.8 mmol), NH$_4$Cl (6.62 g, 124 mmol) and NaN$_3$ (4.83 g, 74.3 mmol) in DMF (80 mL) was heated at 80° C. for 5 h. The mixture was diluted with water (100 mL) and basified to pH 11 with K$_2$CO$_3$. The aqueous layer was extracted with EtOAc (100 mL×3), and the combined organic layers were dried over Na$_2$SO$_4$ and concentrated. The residue was purified by column chromatography on silica gel (PE/EtOAc=5/1, 3/1) to give the title compound. MS: m/z=286.1 (M+1).

Step E: Di-tert-butyl (1-(5-nitro-6-phenylpyridin-2-yl)ethane-1,2-diyl)dicarbamate To a stirred solution of 2-azido-1-(6-nitro-5-phenylpyridin-2-yl)ethanol (2.00 g, 7.01 mmol) and pyridine (4.09 mL, 50.6 mmol) in CH$_2$Cl$_2$ (25 mL) was added methanesulfonyl chloride (3.00 g, 26.2 mmol), and the resulting mixture was stirred at 20° C. for 5 h. The mixture was concentrated and the residue was dissolved in DMF (25 mL). The resulting solution was cooled to 0° C. and NaN$_3$ (4.00 g, 61.5 mmol) was added. After 3 h, PPh$_3$ (7.36 g, 28.0 mmol) was added and the resulting mixture was warmed to 20° C. and stirred for 2 h. The mixture was diluted with water (20 mL) and basified to pH 12 with K$_2$CO$_3$. The aqueous mixture was extracted with EtOAc (30 mL×3). To the aqueous layer was added Boc$_2$O (6.51 mL, 28.0 mmol), and the resulting mixture was stirred at 20° C. for 2 h. The mixture was extracted with EtOAc (30 mL×3), and the combined organic layers were dried over Na$_2$SO$_4$ and concentrated. The residue was purified by column chromatography on silica gel (PE/EtOAc=10/1, 8/1, 3/1) to give the title compound. MS: m/z=459.3 (M+1). $^1$H NMR (400 MHz, CDCl$_3$) δ 8.11 (d, J=8.2 Hz, 1H), 7.53 (br s, 3H), 7.49-7.42 (m, 5H), 3.58 (br s, 3H), 1.43 (br s, 18H).

Step F: Di-tert-butyl (1-(5-amino-6-phenylpyridin-2-yl)ethane-1,2-diyl)dicarbamate To a deoxygenated solution of di-tert-butyl (1-(6-nitro-5-phenylpyridin-2-yl)ethane-1,2-diyl)dicarbamate (350 mg, 0.763 mmol) in MeOH (10 mL) was added 10% Pd/C (16 mg, 0.15 mmol), and the resulting mixture was stirred under H$_2$ (50 psi) at 20° C. for 2 h. The mixture was filtered and the filtrate was concentrated to give the title compound. MS: m/z=429.2 (M+1).

REACTION SCHEME FOR INTERMEDIATE A17

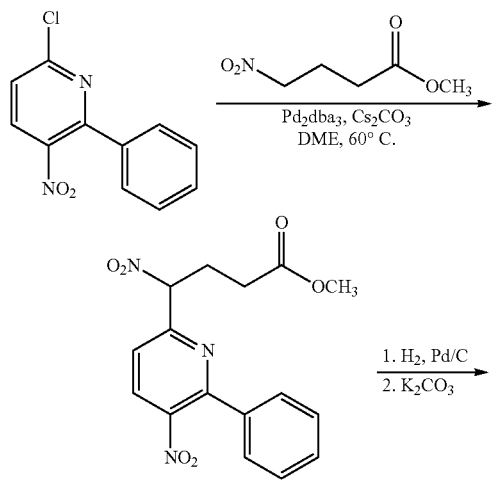

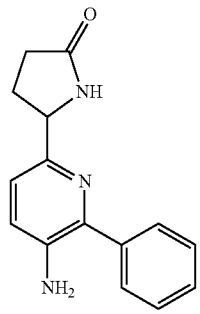

Intermediate A17

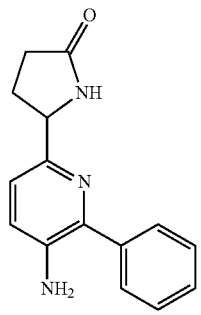 [SMILES: Nc1ccc(C2CCC(=O)N2)nc1-c1ccccc1]

5-(5-Amino-6-phenylpyridin-2-yl)pyrrolidin-2-one

Step A: Methyl 4-nitro-4-(5-nitro-6-phenylpyridin-2-yl)butanoate

To a deoxygenated mixture of 6-chloro-3-nitro-2-phenylpyridine (0.10 g, 0.43 mmol) in DME (1.5 mL) was added methyl 4-nitrobutanoate (0.13 g, 0.85 mmol), Cs$_2$CO$_3$ (0.28 g, 0.85 mmol), 2-(di-tert-butylphosphino)-2'-methylbiphenyl (53 mg, 0.17 mmol) and Pd$_2$(dba)$_3$ (0.04 g, 0.04 mmol). The resulting mixture was heated at 60° C. for 50 min under microwave irradiation. The reaction mixture was filtered and the filtrate was concentrated. The residue was purified by preparative TLC (PE/EtOAc=3/1) to give the title compound. MS: m/z=346.1 (M+1). $^1$H NMR (400 MHz, CD$_3$OD) δ 8.36 (d, J=8.4 Hz, 1H), 7.74 (d, J=8.4 Hz, 1H), 7.55-7.46 (m, 5H), 6.02 (t, J=7.2 Hz, 1H), 3.63 (s, 3H), 2.82-2.79 (m, 1H), 2.65-2.60 (m, 1H), 2.48-2.45 (m, 2H).

Step B: 5-(5-Amino-6-phenylpyridin-2-yl)pyrrolidin-2-one

To a deoxygenated solution of methyl 4-nitro-4-(5-nitro-6-phenylpyridin-2-yl)butanoate (80 mg, 0.23 mmol) in MeOH (8 mL) was added 10% Pd/C (49 mg, 0.046 mmol), and the resulting mixture was stirred under H$_2$ (30 psi) at 30° C. for 2 h. The reaction mixture was filtered and to the filtrate was added K$_2$CO$_3$ (64.0 mg, 0.46 mmol). The resulting mixture was heated at 60° C. for 30 min. After cooling, the mixture was filtered and the filtrate was concentrated. The residue was purified by preparative TLC (100% EtOAc) to give the title compound. $^1$H NMR (400 MHz, CD$_3$OD) δ

7.62-7.58 (m, 2H), 7.51-7.42 (m, 3H), 7.23-7.21 (m, 1H), 7.15-7.13 (m, 1H), 4.79-4.75 (m, 1H), 2.56-2.38 (m, 3H), 2.10-2.08 (m, 1H).

REACTION SCHEME FOR INTERMEDIATE A18

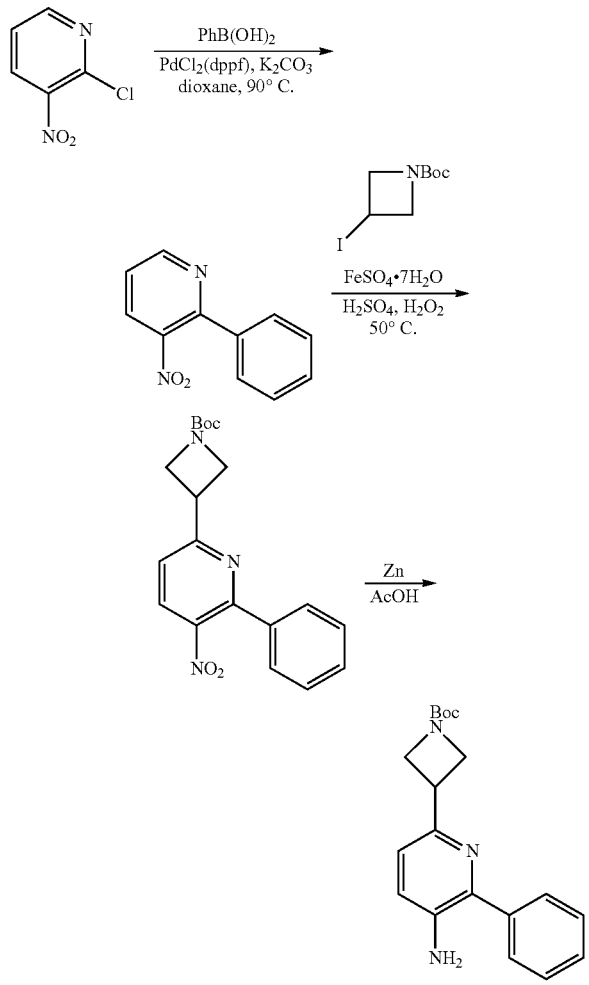

Intermediate A18

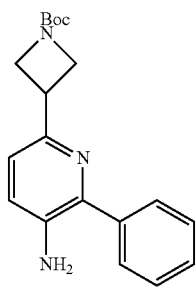 [SMILES: CC(C)(C)OC(=O)N1CC(c2ccc(N)c(-c3ccccc3)n2)C1]

tert-Butyl 3-(5-amino-6-phenylpyridin-2-yl)azetidine-1-carboxylate

Step A: 3-Nitro-2-phenylpyridine

To a deoxygenated mixture of 2-chloro-3-nitropyridine (10.0 g, 63.1 mmol) in dioxane (150 mL) and water (75 mL) was added $PdCl_2(dppf)$ (2.31 g, 3.15 mmol), phenylboronic acid (11.5 g, 95.0 mmol), $K_2CO_3$ (17.4 g, 126 mmol). The resulting mixture was heated at 90° C. for 16 h, then cooled, filtered and concentrated. The residue was partitioned with water (50 mL) and ethyl acetate (50 mL×2). The combined organic layers were dried over $Na_2SO_4$ and concentrated. The residue was purified by flash silica gel chromatography (ISCO, 120 g SepaFlash® Silica Flash Column, ethyl acetate in petroleum ether: 0-20%, dry loaded) to give the title compound. $^1$H NMR (400 MHz, $CDCl_3$) δ 8.92-8.82 (m, 1H), 8.19-8.11 (m, 1H), 7.61-7.54 (m, 2H), 7.52-7.42 (m, 4H).

Step B: tert-Butyl 3-(5-nitro-6-phenylpyridin-2-yl)azetidine-1-carboxylate

An aqueous solution of 30% $H_2O_2$ (1.31 mL, 15.0 mmol) was added to a stirred solution of 3-nitro-2-phenylpyridine (1.00 g, 5.00 mmol), concentrated aqueous $H_2SO_4$ solution (0.53 mL, 10 mmol), tert-butyl 3-iodoazetidine-1-carboxylate (2.83 g, 9.99 mmol) and iron(II) sulfate heptahydrate (0.42 g, 1.5 mmol) in DMSO (20 mL). The resulting mixture was stirred at 27° C. for 0.5 h before additional iron(II) sulfate heptahydrate (0.42 g, 1.5 mmol) and 30% $H_2O_2$ (1.31 mL, 15.0 mmol) were added. Stirring was continued for 0.5 h before the mixture was charged again with more 30% $H_2O_2$ (1.31 mL, 14.99 mmol) and iron (II) sulfate heptahydrate (0.42 g, 1.50 mmol). The resulting mixture was then heated at 50° C. for 60 h. The product mixture was poured into an ice-cold solution of aqueous 15% NaOH solution and the pH was adjusted to >10. The aqueous mixture was filtered, and the filtrate was extracted with ethyl acetate (150 mL×3). The combined organic extracts were dried over $Na_2SO_4$ and concentrated. The residue was purified by flash silica gel chromatography (ISCO; 40 g SepaFlash® Silica Flash Column, ethyl acetate in petroleum ether=0-30%, 40 mL/min, dry loaded) to give the title compound. MS: m/z=356.1 (M+1).

Step C: tert-Butyl 3-(5-amino-6-phenylpyridin-2-yl)azetidine-1-carboxylate

To a solution of tert-butyl 3-(5-nitro-2-phenylpyridin-4-yl)azetidine-1-carboxylate (48 mg, 0.14 mmol) in AcOH (2 mL) was added zinc powder (53 mg, 0.81 mmol), and the resulting mixture was stirred at 20° C. for 16 h. The mixture was partitioned between saturated aqueous $NaHCO_3$ solution (50 mL) and ethyl acetate (20 mL×3). The combined organic layers were washed with brine, dried over $Na_2SO_4$ and concentrated to give the title compound. MS: m/z=326.1 (M+1).

REACTION SCHEME FOR INTERMEDIATE A19

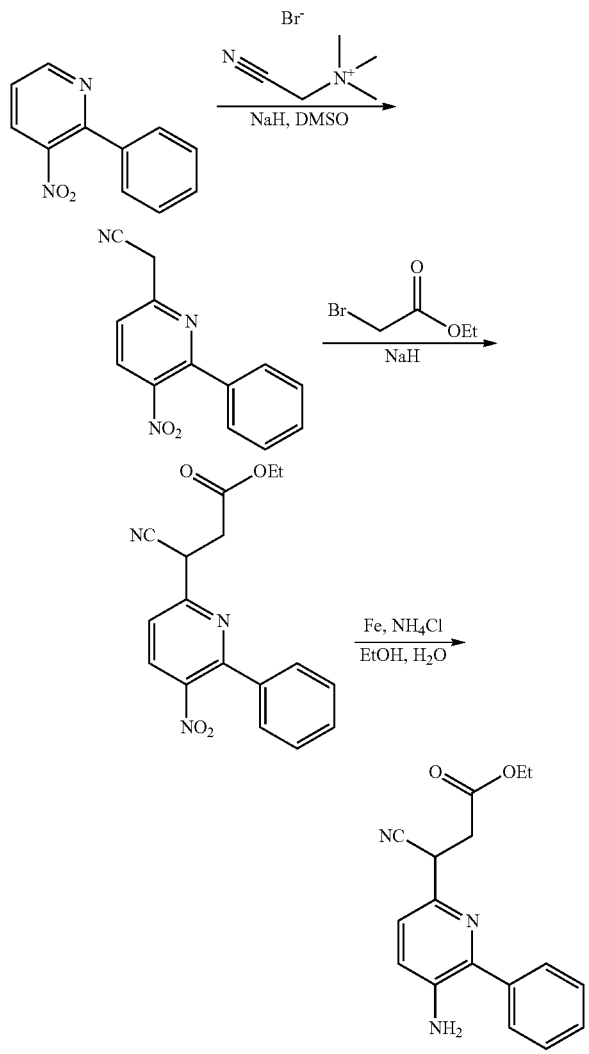

Intermediate A19

Ethyl 3-(5-amino-6-phenylpyridin-2-yl)-3-cyanopropanoate

Step A: 2-(5-Nitro-6-phenylpyridin-2-yl)acetonitrile

To a solution of 3-nitro-2-phenylpyridine (2.00 g, 9.99 mmol) in DMSO (20 mL) at 0° C. were added sodium hydride (60 wt. %, 3.6 g, 90 mmol) and 1-cyano-N,N,N-trimethylmethanaminium bromide (5.37 g, 30.0 mmol). The resulting mixture was stirred for 35 min, then partitioned between water (5 mL) and ethyl acetate (5 mL×3). The combined organic layers were dried over $Na_2SO_4$ and concentrated to give the title compound. MS: m/z=240.2 (M+1).

Step B: Ethyl 3-cyano-3-(5-nitro-6-phenylpyridin-2-yl)propanoate

To a deoxygenated solution of 2-(5-nitro-6-phenylpyridin-2-yl)acetonitrile (400 mg, 1.67 mmol) in THF (5 mL) at −78° C. was added sodium hydride (60 wt. %, 67 mg, 1.7 mmol). The mixture was stirred at −78° C. for 5 min before ethyl 2-bromoacetate (251 mg, 1.51 mmol) was added. The resulting mixture was warmed to 0° C. and stirred for 1 h. The mixture was diluted with water (10 mL) and extracted with ethyl acetate (10 mL×3). The combined organic layers were dried over $Na_2SO_4$ and concentrated. The residue was purified by preparative TLC (PE/EtOAc=2/1) to give the title compound. MS: m/z=325.9 (M+1). $^1$H NMR (400 MHz, $CD_3OD$) δ 8.18 (d, J=8.2 Hz, 1H), 7.69 (d, J=8.6 Hz, 1H), 7.58-7.42 (m, 5H), 4.58 (t, J=6.8 Hz, 1H), 4.17 (q, J=6.8 Hz, 2H), 3.33-3.25 (m, 1H), 3.19-3.10 (m, 1H), 1.23 (t, J=7.2 Hz, 3H).

Step C: Ethyl 3-(5-amino-6-phenylpyridin-2-yl)-3-cyanopropanoate

To a solution of ethyl 3-cyano-3-(5-nitro-6-phenylpyridin-2-yl)propanoate (200 mg, 0.541 mmol) in EtOH (3 mL) and water (1 mL) was added ammonium chloride (87 mg, 1.6 mmol) and iron powder (91 mg, 1.6 mmol). The resulting mixture was heated at 80° C. for 1 h, then cooled and filtered. The filtrate was partitioned between water (10 mL) and EtOAc (10 mL×3), and the combined organic layers was dried over $Na_2SO_4$ and concentrated. The residue was purified by preparative TLC (PE/EtOAc=1/1) to give the title compound. MS: m/z=296.1 (M+1).

REACTION SCHEME FOR INTERMEDIATE A20

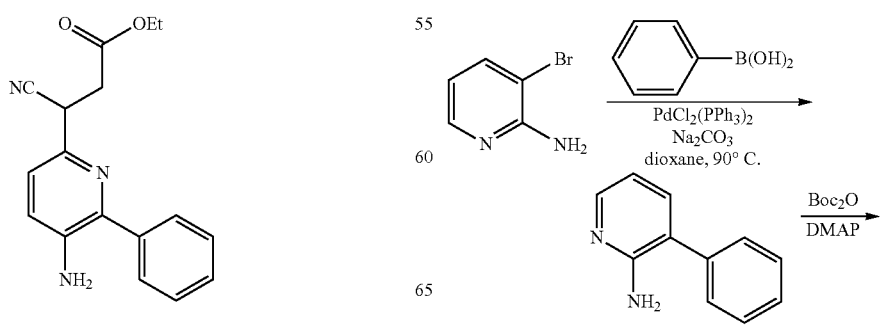

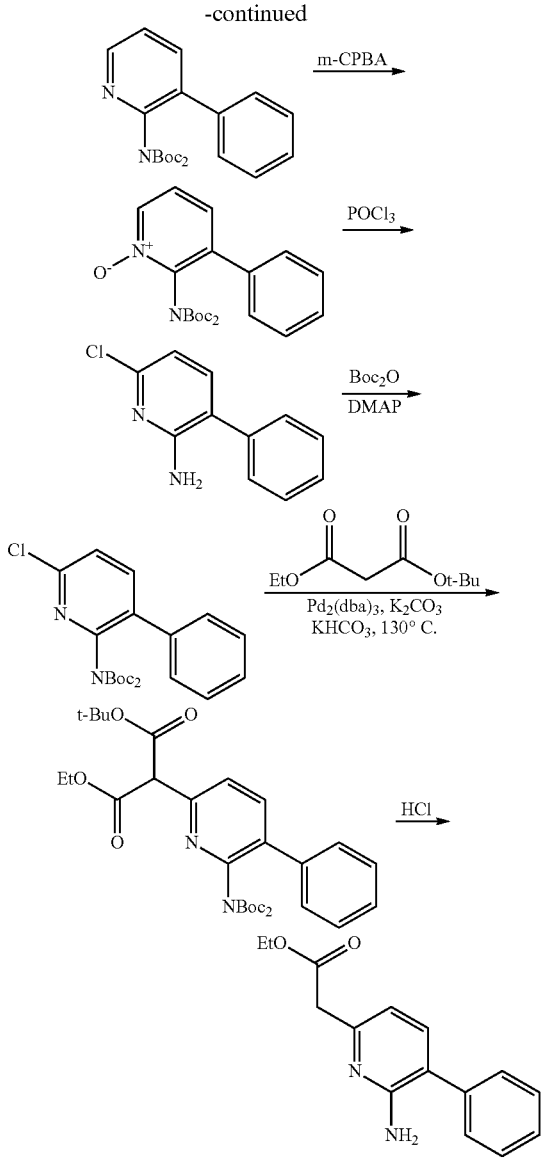

Intermediate A20

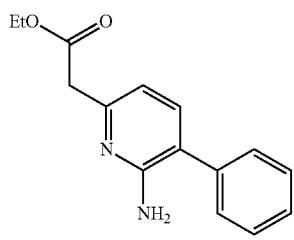 [SMILES: CCOC(=O)Cc1ccc(-c2ccccc2)c(N)n1]

Ethyl 2-(6-amino-5-phenylpyridin-2-yl)acetate

Step A: 3-Phenylpyridin-2-amine

To a deoxygenated solution of 3-bromopyridin-2-amine (5.00 g, 28.9 mmol), phenylboronic acid (4.23 g, 34.7 mmol) and sodium carbonate (9.2 g, 87 mmol) in 1,4-dioxane (60 mL) and water (30 mL) was added PdCl$_2$(PPh$_3$)$_2$ (1.01 g, 1.44 mmol). The resulting mixture was heated at reflux for 4 h, then cooled, filtered, and concentrated. The residue was partitioned between brine (50 mL) and ethyl acetate (30 mL×3). The combined organic layers were washed with brine, dried over Na$_2$SO$_4$, and concentrated. The residue was purified by silica gel column chromatography (ethyl acetate in petroleum ether: 20-50%) to give the title compound. $^1$H NMR (400 MHz, CDCl$_3$) δ 8.09 (d, J=3.5 Hz, 1H), 7.51-7.43 (m, 4H), 7.41-7.35 (m, 2H), 6.76 (dd, J=7.0, 5.1 Hz, 1H), 4.61 (br s, 2H).

Step B: 3-Phenylpyridin-2-(di-tert-butoxycarbonyl)amine

To a solution of 3-phenylpyridin-2-amine (10.0 g, 55.8 mmol) and di-tert-butyl dicarbonate (48.7 g, 223 mmol) in DCM (200 mL) was added DMAP (13.6 g, 112 mmol) in portions. The resulting mixture was stirred at 26° C. for 16 h, then washed with brine, dried over Na$_2$SO$_4$, and concentrated. The residue was purified by flash silica gel chromatography (ISCO; 120 g SepaFlash® Silica Flash Column, ethyl acetate in petroleum ether: 0-40%, 50 mL/min, dry loaded) to give the title compound. $^1$H NMR (400 MHz, CDCl$_3$) δ 8.52 (d, J=3.1 Hz, 1H), 7.75 (dd, J=7.4, 1.6 Hz, 1H), 7.45-7.34 (m, 6H), 1.30 (s, 18H).

Step C: 2-(Di-tert-butoxycarbonyl)amino-3-phenylpyridine 1-oxide

To a solution of 3-phenylpyridin-2-(di-tert-butoxycarbonyl)amine (17.5 g, 44.9 mmol) in DCM (100 mL) was added m-CPBA (48.4 g, 224 mmol), and the resulting mixture was stirred at 27° C. for 16 h. The mixture was diluted with saturated aqueous Na$_2$SO$_3$ solution (200 mL), stirred for 10 min, and partitioned between saturated aqueous NaHCO$_3$ solution (300 mL) and DCM (200 mL×3). The combined organic layers were washed with brine, dried over Na$_2$SO$_4$ and concentrated. The residue was purified by flash silica gel chromatography (ISCO; 120 g SepaFlash® Silica Flash Column, ethyl acetate in petroleum ether: 0-80%, 50 mL/min, dry loaded) to give the title compound. $^1$H NMR (400 MHz, CDCl$_3$) δ 8.29 (dd, J=6.1, 1.4 Hz, 1H), 7.47-7.39 (m, 5H), 7.27-7.22 (m, 2H), 1.33 (s, 18H).

Step D: 6-Chloro-3-phenylpyridin-2-amine

To a solution of 2-(di-tert-butoxycarbonyl)amino-3-phenylpyridine-1-oxide (10.0 g, 25.9 mmol) in DCM (80 mL) was added phosphorus oxychloride (20.8 mL, 223 mmol) and the resulting mixture was heated at 35° C. for 16 h. The mixture was concentrated, and the residue was carefully diluted with saturated aqueous NaHCO$_3$ solution (300 mL). The aqueous layer was extracted with ethyl acetate (100 mL×3). The combined organic layers were washed with saturated aqueous NaHCO$_3$ solution (100 mL×3), dried over Na$_2$SO$_4$ and concentrated. The residue was purified by flash silica gel chromatography (ISCO; 40 g SepaFlash® Silica Flash Column, ethyl acetate in petroleum ether: 0-20%, 40 mL/min, dry loaded) to give the title compound. $^1$H NMR (400 MHz, CDCl$_3$) δ 7.50-7.38 (m, 5H), 7.32 (d, J=7.4 Hz, 1H), 6.76 (d, J=7.8 Hz, 1H), 4.72 (br., 2H).

Step E: 6-Chloro-3-phenylpyridin-2-(di-tert-butoxycarbonyl)amine

To a solution of 6-chloro-3-phenylpyridin-2-amine (2.10 g, 9.75 mmol) and di-tert-butyl dicarbonate (8.51 g, 39.0 mmol) in DCM (30 mL) was added DMAP (2.38 g, 19.50 mmol) in batches, and the resulting mixture was stirred at 26° C. for 16 h. The resulting mixture was washed with brine (10 mL×3), dried over Na$_2$SO$_4$ and concentrated. The residue was purified by flash silica gel chromatography (ISCO; 40 g SepaFlash® Silica Flash Column, ethyl acetate in petroleum ether: 0-15%, 40 mL/min, dry loaded) to give the title compound. $^1$H NMR (400 MHz, CDCl$_3$) δ 7.71 (d, J=8.0 Hz, 1H), 7.45-7.37 (m, 6H), 1.30 (s, 18H).

Step F: 1-tert-Butyl 3-ethyl 2-(6-(di-tert-butoxycarbonyl)amino-5-phenylpyridin-2-yl)malonate A deoxygenated mixture of tri-tert-butylphosphonium tetrafluoroborate (0.34 g, 1.17 mmol), potassium hydrogencarbonate (0.88 g, 8.8 mmol), 6-chloro-3-phenylpyridin-2-(di-tert-butoxycarbonyl)amine (2.50 g, 5.87 mmol), tert-butyl ethyl malonate (3.33 mL, 17.6 mmol), Pd(dba)$_2$ (0.34 g, 0.59 mmol) and K$_2$CO$_3$ (1.22 g, 8.80 mmol) was heated at 130° C. for 1 h. The mixture was filtered and concentrated to give the title compound, which was used in the next step without purification. MS: m/z=557.2 (M+1).

Step G: Ethyl 2-(6-amino-5-phenylpyridin-2-yl)acetate

A mixture of 1-tert-butyl 3-ethyl 2-(6-(di-tert-butoxycarbonyl)amino-5-phenylpyridin-2-yl)malonate (39% purity, 5.20 g, 3.69 mmol) in a 4M solution of HCl in dioxane (12 mL) was stirred at 20° C. for 16 h. The mixture was partitioned between saturated aqueous NaHCO$_3$ solution (100 mL) and DCM (30 mL×3). The combined organic layers were washed with saturated aqueous NaHCO$_3$ solution (30 mL×3) then brine, dried over Na$_2$SO$_4$ and concentrated. The residue was purified by flash silica gel chromatography (ISCO; 12 g SepaFlash® Silica Flash Column, ethyl acetate in petroleum ether: 0-50%, 30 mL/min, dry loaded) to give the title compound. $^1$H NMR (400 MHz, CDCl$_3$) δ 7.48-7.41 (m, 4H), 7.40-7.32 (m, 2H), 6.74 (d, J=7.4 Hz, 1H), 4.61 (br., 2H), 4.21 (q, J=7.2 Hz, 2H), 3.69 (s, 2H), 1.31-1.26 (m, 3H).

REACTION SCHEME FOR INTERMEDIATE A21

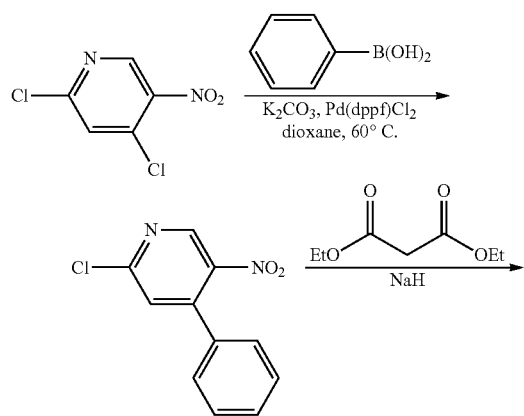

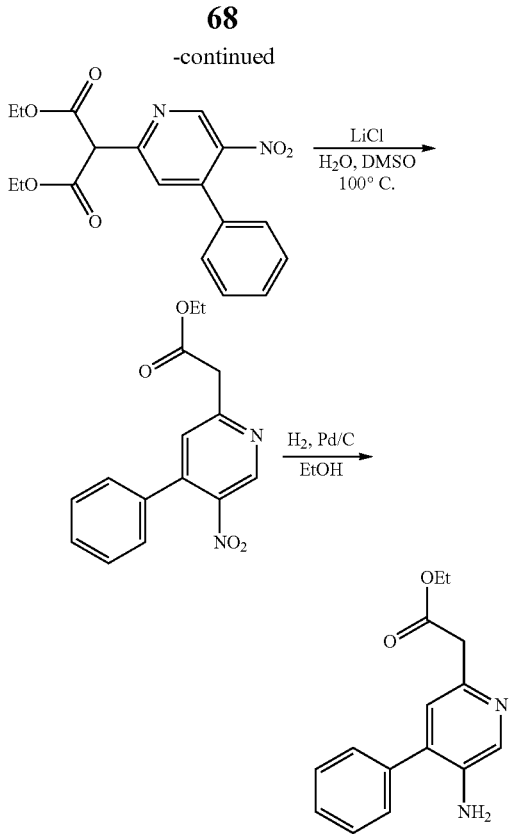

Intermediate A21

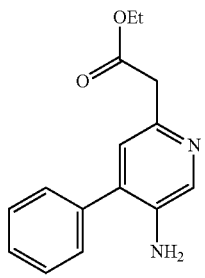 [SMILES: CCOC(=O)Cc1cc(-c2ccccc2)c(N)cn1]

Ethyl 2-(5-amino-4-phenylpyridin-2-yl)acetate

Step A: 2-Chloro-5-nitro-4-phenylpyridine

To a deoxygenated solution of 2,4-dichloro-5-nitropyridine (3.00 g, 15.6 mmol) in 1,4-dioxane (15 mL) and water (3 mL) was added phenylboronic acid (1.89 g, 15.6 mmol), potassium carbonate (4.30 g, 31.1 mmol) and PdCl$_2$(dppf) (0.57 g, 0.78 mmol). The resulting mixture was heated at 60° C. for 18 h. The mixture was cooled and partitioned between water (50 mL) and ethyl acetate (30 mL×3). The combined organic layers were dried over Na$_2$SO$_4$ and concentrated, and the residue was purified by silica gel column chromatography (PE/EtOAc=10/1) to give the title compound. MS: m/z=235.0 (M+1). $^1$H NMR (400 MHz, CDCl$_3$) δ 8.96 (s, 1H), 7.58-7.54 (m, 3H), 7.51 (s, 1H), 7.43-7.37 (m, 2H).

Step B: Diethyl 2-(5-nitro-4-phenylpyridin-2-yl)malonate

To a solution of diethyl malonate (2.40 g, 14.9 mmol) in DMF (20 mL) at 0° C. was added NaH (60 wt. %, 1.19 g, 29.8 mmol) portionwise. After the mixture was stirred for 10 min, 2-chloro-5-nitro-4-phenylpyridine (3.50 g, 14.9 mmol) was added. The resulting mixture was warmed to 23° C. and stirred for 2 h. The mixture was diluted with ice water (30 mL) and extracted with ethyl acetate (20 mL×3). The combined organic layers were dried over $Na_2SO_4$ and concentrated, and the residue was purified by silica gel column chromatography (PE/EtOAc=10/1) to give the title compound. MS: m/z=359.1 (M+1). $^1$H NMR (400 MHz, $CDCl_3$) δ 9.01 (s, 1H), 7.65 (s, 1H), 7.48 (dd, $J_1$=1.5, $J_1$=5.0 Hz, 3H), 7.40-7.33 (m, 2H), 5.05 (s, 1H), 4.33-4.22 (m, 4H), 1.30 (t, J=7.3 Hz, 6H).

Step C: Ethyl 2-(5-nitro-4-phenylpyridin-2-yl)acetate

To a solution of diethyl 2-(5-nitro-4-phenylpyridin-2-yl)malonate (2.5 g, 6.9 mmol) in dimethyl sulfoxide (5 mL) and water (0.5 mL) was added lithium chloride (0.30 g, 6.9 mmol). The resulting mixture was heated at 100° C. for 18 h, then cooled and partitioned between water (50 mL) and ethyl acetate (30 mL×3). The combined organic layers were dried over $Na_2SO_4$ and concentrated, and the residue was purified by silica gel column chromatography (PE/EtOAc=10/1) to give the title compound. MS: m/z=287.0 (M+1). $^1$H NMR (400 MHz, $CDCl_3$) δ 9.02 (s, 1H), 7.50-7.45 (m, 3H), 7.42 (s, 1H), 7.35 (d, J=3.5 Hz, 2H), 4.22 (q, J=7.0 Hz, 2H), 3.96 (s, 2H), 1.29 (t, J=7.0 Hz, 3H).

Step D: Ethyl 2-(5-amino-4-phenylpyridin-2-yl)acetate

To a deoxygenated solution of ethyl 2-(5-nitro-4-phenylpyridin-2-yl)acetate (135 mg, 0.50 mmol) in ethanol (10 mL) was added 10% Pd/C (50 mg, 0.05 mmol), and the resulting mixture was stirred under $H_2$ (50 psi) at 25-30° C. for 18 h. The mixture was filtered and the filtrate was concentrated to afford the title compound. MS: m/z=257.2 (M+1).

REACTION SCHEME FOR INTERMEDIATES A22 and A23

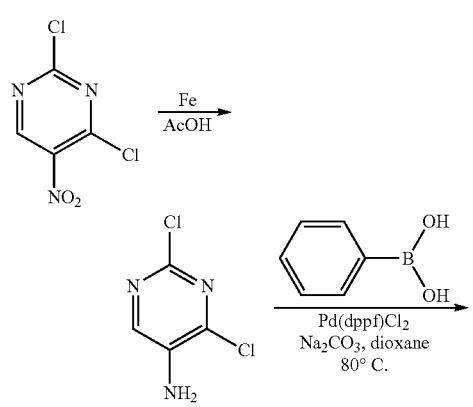

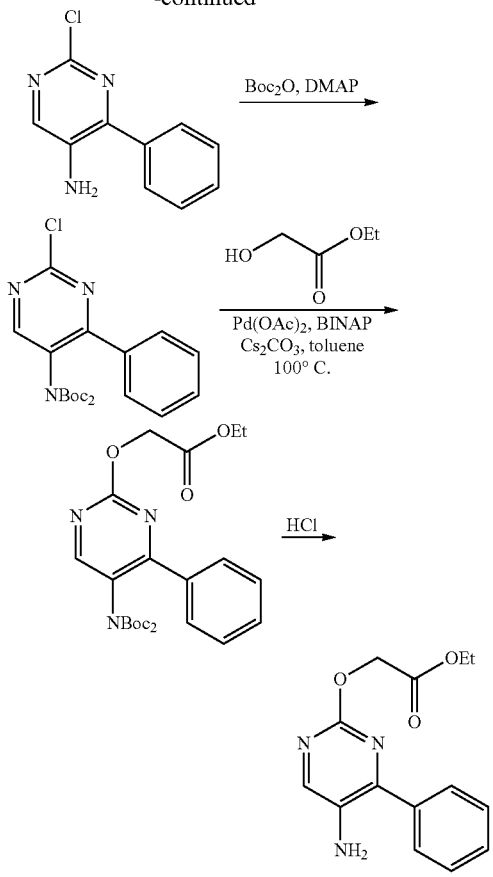

Intermediate A22

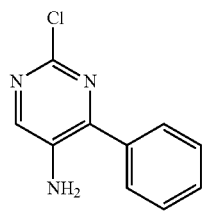

2-Chloro-4-phenylpyrimidin-5-amine

Step A: 2,4-Dichloropyrimidin-5-amine

To a stirred solution of 2,4-dichloro-5-nitropyrimidine (55.0 g, 284 mmol) in acetic acid (800 mL) was added iron powder (47.5 g, 851 mmol) in portions at 23° C. (exothermic reaction, the temperature of reaction solution reached 50° C.). The mixture was stirred for another 1 h without heating. The product mixture was filtered through Celite® and the cake was washed with ethyl acetate (400 mL). The filtrate was concentrated and the residue was suspended between ethyl acetate (400 mL) and water (40 mL). The mixture was stirred at 20° C. for 5 min and filtered. The organic layer was separated and the aqueous layer was extracted with ethyl acetate (200 mL). The combined organic layers were dried over sodium sulfate, filtered and concentrated. The residue was recrystallized (petroleum ether/ethyl acetate=10/1, 500 mL) to give the title compound. MS: m/z=163.9 (M+1). $^1$H NMR (400 MHz, CDCl$_3$) δ 8.02 (s, 1H), 4.08 (s, 2H).

Step B: 2-Chloro-4-phenylpyrimidin-5-amine

To a deoxygenated mixture of 2,4-dichloropyrimidin-5-amine (37.5 g, 229 mmol), phenylboronic acid (22.9 g, 188 mmol) and sodium carbonate (48.5 g, 457 mmol) in dioxane (400 mL) and water (200 mL) was added PdCl$_2$(dppf) (1.67 g, 2.29 mmol). The resulting mixture was heated at 80° C. for 10 h under nitrogen atmosphere. The product mixture was cooled and concentrated. The residue was partitioned between water (200 mL) and ethyl acetate (200 mL×3). The combined organic layers were dried over sodium sulfate, filtered and concentrated. The residue was purified by column chromatography on silica gel (PE/EtOAc=5/1) to give the title compound. MS: m/z=206.2 (M+1). $^1$H NMR (400 MHz, CDCl$_3$) δ 8.11 (s, 1H), 7.72 (d, J=6.3 Hz, 2H), 7.54-7.43 (m, 3H), 3.96 (s, 2H).

Intermediate A23

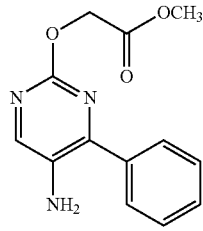 [SMILES: COC(=O)COc1ncc(N)c(-c2ccccc2)n1]

Methyl 2-((5-amino-4-phenylpyrimidin-2-yl)oxy)acetate

Step A: 2-Chloro-4-phenylpyrimidin-5-(tert-butoxycarbonyl))amine

To a mixture of 2-chloro-4-phenylpyrimidin-5-amine (19 g, 92 mmol), triethylamine (28 g, 280 mmol) and N,N-dimethylpyridin-4-amine (11 g, 92 mmol) was added dropwise a solution of di-tert-butyl dicarbonate (60.5 g, 280 mmol) in dichloromethane (20 mL). The resulting mixture was stirred at 20° C. for 1 h then concentrated. The residue was purified by column chromatography on silica gel (PE/EtOAc=10/1) to give the title compound. MS: m/z=406.0 (M+1). $^1$H NMR (400 MHz, CDCl$_3$) δ 8.39 (s, 1H), 7.72-7.64 (m, 2H), 7.53-7.43 (m, 3H), 1.26 (s, 18H).

Step B: Ethyl 2-((5-(bis(tert-butoxycarbonyl)amino)-4-phenylpyrimidin-2-yl)oxy)acetate To a deoxygenated solution of 2-chloro-4-phenylpyrimidin-5-(tert-butoxycarbonyl))amine (100 mg, 0.246 mmol), ethyl 2-hydroxyacetate (77 mg, 0.74 mmol) and cesium carbonate (161 mg, 0.493 mmol) in toluene (3 mL) was added Pd(OAc)$_2$ (5.5 mg, 0.025 mmol) and BINAP (31 mg, 0.049 mmol). The mixture was heated at 110° C. for 4 h. The product mixture was partitioned between water (5 mL) and ethyl acetate (5 mL×3). The combined organic layers were dried over sodium sulfate, filtered and concentrated to give the title compound. MS: m/z=474.3 (M+1).

Step C: Methyl 2-((5-amino-4-phenylpyrimidin-2-yl)oxy)acetate

To a stirred solution of ethyl 2-((5-(bis(tert-butoxycarbonyl)amino)-4-phenylpyrimidin-2-yl)oxy)acetate (110 mg, 0.232 mmol) in methanol (1 mL) was added a 4M solution of HCl in MeOH (4.0 mL, 16 mmol). The mixture was stirred at 15° C. for 30 min, then concentrated. The residue was basified with saturated sodium carbonate solution (10 mL) and extracted with ethyl acetate (10 mL×4). The combined organic layers were dried over sodium sulfate and concentrated, and the residue was purified by preparative TLC (PE/EtOAc=1/1) to afford the title compound. MS: m/z=260.2 (M+1).

REACTION SCHEME FOR INTERMEDIATE A24

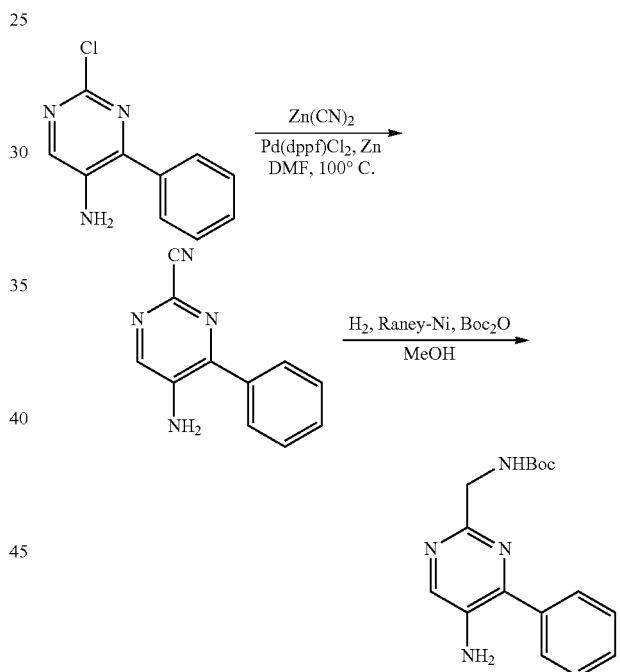

Intermediate A24

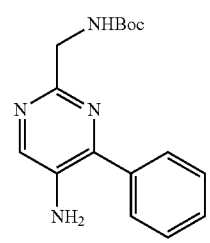 [SMILES: CC(C)(C)OC(=O)NCc1ncc(N)c(-c2ccccc2)n1]

tert-Butyl ((5-amino-4-phenylpyrimidin-2-yl)methyl)carbamate

Step A: 5-Amino-4-phenylpyrimidine-2-carbonitrile

To a solution of 2-chloro-4-phenylpyrimidin-5-amine (1.00 g, 4.86 mmol) in dimethyl formamide (20 mL) was added Zn(CN)$_2$ (1.14 g, 9.73 mmol), zinc powder (0.159 g, 2.43 mmol) and PdCl$_2$(dppf) (0.178 g, 0.243 mmol). The resulting mixture was heated at 145° C. for 18 h, then cooled and partitioned between water (50 mL) and EtOAc (20 mL×3). The combined organic layers were dried over Na$_2$SO$_4$ and concentrated, and the residue was purified by silica gel column chromatography (PE/EtOAc=1/1) to give the title compound. $^1$H NMR (400 MHz, CDCl$_3$) δ 8.24 (s, 1H), 7.72-7.71 (d, J=4 MHz, 2H), 7.54-7.50 (t, J=7.2 MHz, 3H) 4.53 (s, 2H).

Step B: tert-Butyl ((5-amino-4-phenylpyrimidin-2-yl)methyl)carbamate

To a deoxygenated mixture of 5-amino-4-phenylpyrimidine-2-carbonitrile (200 mg, 1.02 mmol) in MeOH (10 mL) was added Boc$_2$O (0.237 mL, 1.02 mmol) and Raney-Ni (598 mg, 1.02 mmol), and the resulting mixture was stirred under H$_2$ (50 psi) at 28-30° C. for 2 h. The product mixture was filtered and the filtrate was concentrated to give the title compound. MS: m/z=301.1 (M+1). $^1$H NMR (400 MHz, CDCl$_3$) δ 8.2 (s, 1H), 7.74-7.72 (d, J=8 MHz, 2H), 7.52-7.45 (t, J=2.8 MHz, 3H), 4.5 (s, 2H), 1.45 (s, 9H).

REACTION SCHEME FOR INTERMEDIATE A25

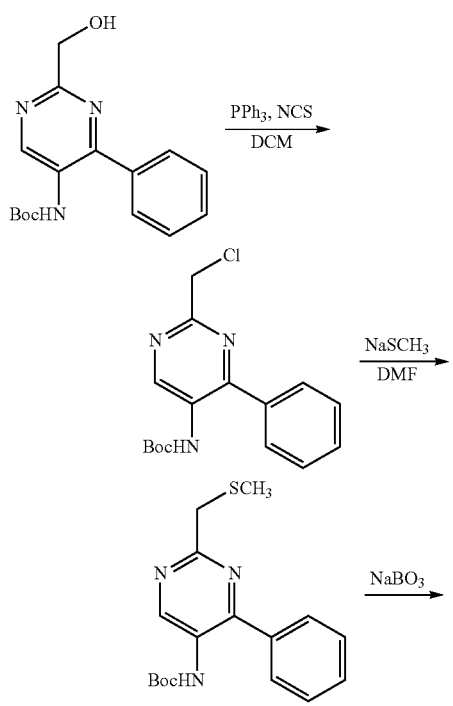

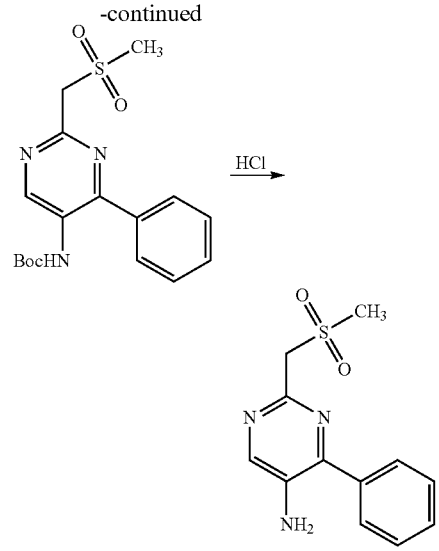

Intermediate A25

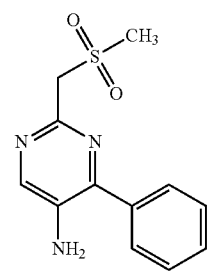 [SMILES: CS(=O)(=O)Cc1ncc(N)c(-c2ccccc2)n1]

2-((Methylsulfonyl)methyl)-4-phenylpyrimidin-5-amine

Step A: tert-Butyl (2-(chloromethyl)-4-phenylpyrimidin-5-yl)carbamate

To a mixture of tert-butyl (2-(hydroxymethyl)-4-phenylpyrimidin-5-yl)carbamate (300 mg, 0.996 mmol) in THF (5 mL) at 25° C. was added 1-chloropyrrolidine-2,5-dione (266 mg, 1.99 mmol) and triphenylphosphine (610 mg, 1.99 mmol). The mixture was stirred at 25° C. for 15 min, then partitioned between water (5 mL) and EtOAc (10 mL×2). The combined organic layers were dried over Na$_2$SO$_4$ and concentrated. The residue was purified by column chromatography on silica gel (PE/EtOAc=10/1) to give the title compound. MS: m/z=320.0 (M+1).

Step B: tert-Butyl (2-((methylthio)methyl)-4-phenylpyrimidin-5-yl)carbamate

To a mixture of tert-butyl (2-(chloromethyl)-4-phenylpyrimidin-5-yl)carbamate (250 mg, 0.782 mmol) in DMF (5 mL) was added sodium methanethiolate (82 mg, 1.2 mmol), and the resulting mixture was heated at 70° C. for 35 min. The product mixture was cooled and partitioned between water (5 mL) and EtOAc (5 mL×2). The combined organic layers were dried over Na$_2$SO$_4$ and concentrated to give the title compound. MS: m/z=322.1 (M+1).

Step C: tert-Butyl (2-((methylsulfonyl)methyl)-4-phenylpyrimidin-5-yl)carbamate

To a solution of tert-butyl (2-((methylthio)methyl)-4-phenylpyrimidin-5-yl)carbamate (100 mg, 0.302 mmol) in AcOH (5 mL) was added NaBO$_3$ (74.0 mg, 0.905 mmol), and the resulting mixture was heated at 70° C. for 25 min. The product mixture was cooled, then partitioned between water (5 mL) and DCM (5 mL×2). The combined organic layers were dried over Na$_2$SO$_4$ and concentrated to give the title compound. MS: m/z=364.1 (M+1).

Step D: 2-((Methylsulfonyl)methyl)-4-phenylpyrimidin-5-amine

To a solution of tert-butyl (2-((4-(methylsulfonyl)piperazin-1-yl)methyl)-4-phenylpyrimidin-5-yl)carbamate (115 mg, 0.257 mmol) in EtOAc (3 mL) was added a 4M solution of HCl in EtOAc (5.0 mL, 20 mmol). The resulting mixture was stirred at 25° C. for 30 min., then concentrated to give the title compound. MS: m/z=264.1 (M+1).

REACTION SCHEME FOR INTERMEDIATE A26

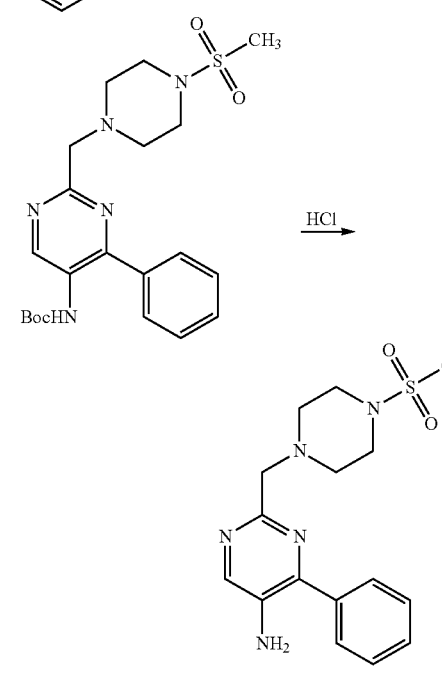

Intermediate A26

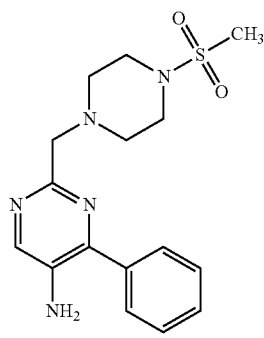 [SMILES: CS(=O)(=O)N1CCN(Cc2ncc(N)c(-c3ccccc3)n2)CC1]

2-((Methylsulfonyl)methyl)-4-phenylpyrimidin-5-amine

Step A: tert-Butyl (2-((4-(methylsulfonyl)piperazin-1-yl)methyl)-4-phenylpyrimidin-5-yl)carbamate To a solution of tert-butyl (2-(chloromethyl)-4-phenylpyrimidin-5-yl)carbamate (200 mg, 0.625 mmol) in acetonitrile (5 mL) was added potassium carbonate (173 mg, 1.25 mmol) and 1-(methylsulfonyl)piperazine (154 mg, 0.938 mmol). The resulting mixture was stirred at 25° C. for 30 min, then filtered and concentrated. The residue was purified by preparative TLC (PE/EtOAc=10/1) to give the title compound. MS: m/z=448.3 (M+1).

Step B: 2-((4-(Methylsulfonyl)piperazin-1-yl)methyl)-4-phenylpyrimidin-5-amine

To a solution of tert-butyl (2-((4-(methylsulfonyl)piperazin-1-yl)methyl)-4-phenylpyrimidin-5-yl)carbamate (115 mg, 0.257 mmol) in EtOAc (3 mL) was added a 4M solution of HCl in EtOAc (5.0 mL, 20 mmol). The resulting mixture was stirred at 25° C. for 30 min, then concentrated to give the title compound. MS: m/z=348.1 (M+1).

REACTION SCHEME FOR INTERMEDIATE A27

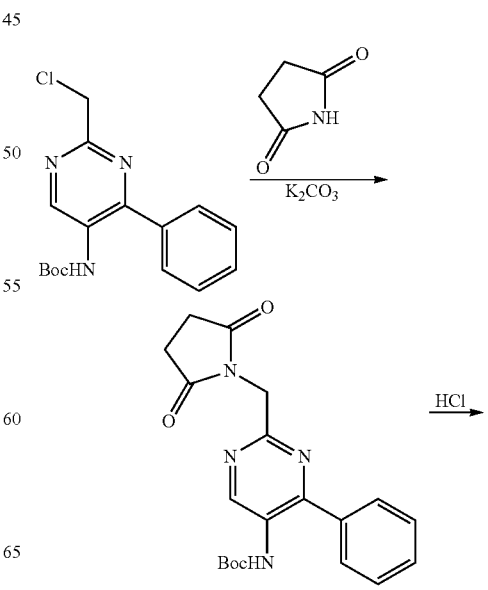

REACTION SCHEME FOR INTERMEDIATE A28

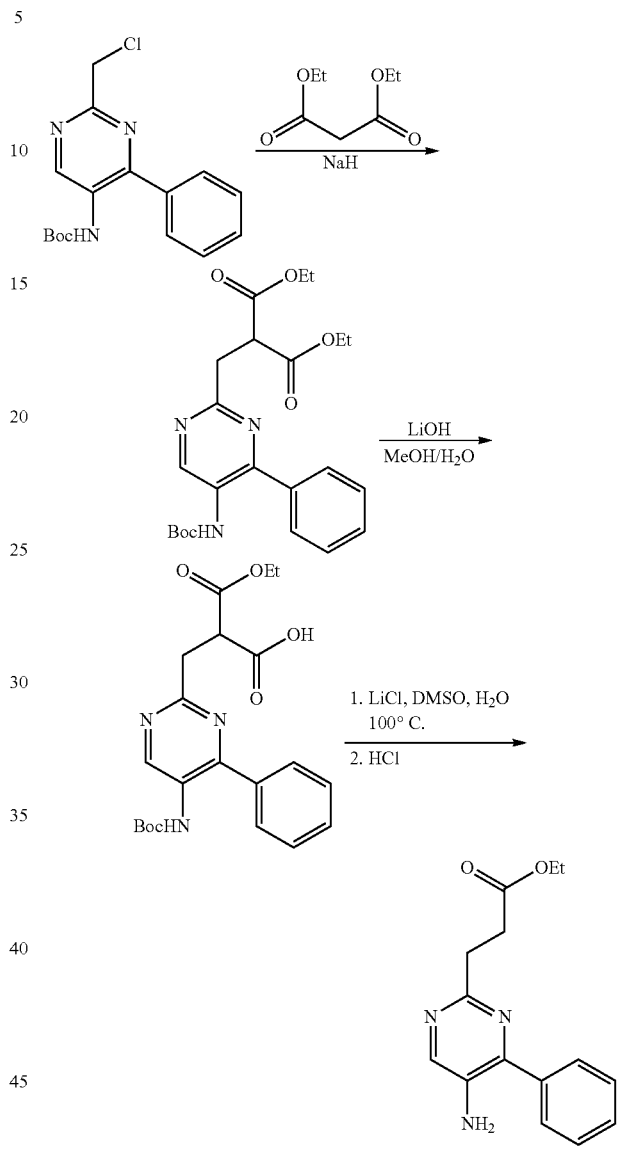

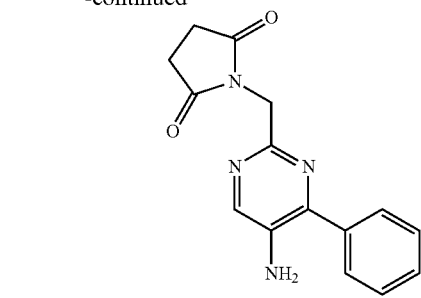

Intermediate A27

1-((5-Amino-4-phenylpyrimidin-2-yl)methyl)pyrrolidine-2,5-dione

Step A: tert-Butyl (2-(2,5-dioxopyrrolidin-1-yl)methyl)-4-phenylpyrimidin-5-yl)carbamate To a solution of tert-butyl (2-(chloromethyl)-4-phenylpyrimidin-5-yl)carbamate (180 mg, 0.56 mmol) in acetonitrile (3 mL) was added pyrrolidine-2,5-dione (112 mg, 1.12 mmol) and $K_2CO_3$ (233 mg, 1.68 mmol). The resulting mixture was stirred at 26° C. for 5 h then partitioned between water (5 mL) and EtOAc (10 mL×3). The combined organic layers were concentrated to give the title compound. MS: m/z=383.2 (M+1).

Step B: 1-((5-Amino-4-phenylpyrimidin-2-yl)methyl)pyrrolidine-2,5-dione

A mixture of tert-butyl (2-((2, 5-dioxopyrrolidin-1-yl)methyl)-4-phenylpyrimidin-5-yl) carbamate (180 mg, 0.47 mmol) in a 4M solution of HCl in EtOAc (5.0 mL, 20 mmol) was stirred at 26° C. for 1 h. The mixture was concentrated to afford the title compound as an HCl salt. MS: m/z=283.2 (M+1).

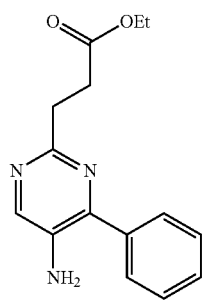 [SMILES: CCOC(=O)CCc1ncc(N)c(-c2ccccc2)n1]

Intermediate A28

Ethyl 3-(5-amino-4-phenylpyrimidin-2-yl)propanoate

Step A: Diethyl 2-((5-((tert-butoxycarbonyl)amino)-4-phenylpyrimidin-2-yl)methyl)malonate To a solution of diethyl malonate (120 mg, 0.75 mmol) in DMF (1 mL) at 0° C. was added sodium hydride (60 wt. %, 33 mg, 0.82 mmol) and the resulting mixture was stirred for 20 min. A solution of tert-butyl (2-(chloromethyl)-4-phenylpyrimidin-5-yl)carbamate (60 mg, 0.19 mmol) in DMF (1 mL) was added dropwise to the above mixture, and the mixture was stirred at 0° C. for 30 min. The reaction solution was diluted with water (2 mL) and the aqueous layer was extracted with EtOAc (5 mL×3). The combined organic layers were dried over $Na_2SO_4$ and concentrated to give the title compound. MS: m/z=444.2 (M+1).

Step B: 2-((5-((tert-Butoxycarbonyl)amino)-4-phenylpyrimidin-2-yl)methyl)-3-ethoxy-3-oxopropanoic acid To a solution of diethyl 2-((5-((tert-butoxycarbonyl)amino)-4-phenylpyrimidin-2-yl)methyl)malonate (92 mg, 0.21 mmol) in ethanol (2 mL) and water (0.1 mL) at 25° C. was added LiOH (9.9 mg, 0.41 mmol). The resulting mixture was stirred for 30 min, then diluted with water (2 mL) and acidified to pH 5 by addition of aqueous 3M HCl solution. The mixture was extracted with EtOAc (5 mL×3), and the combined organic layers were dried over $Na_2SO_4$ and concentrated to give the title compound. MS: m/z=416.4 (M+1).

Step C: Ethyl 3-(5-amino-4-phenylpyrimidin-2-yl)propanoate

To a solution of 2-((5-((tert-butoxycarbonyl)amino)-4-phenylpyrimidin-2-yl)methyl)-3-ethoxy-3-oxopropanoic acid (82 mg, 0.20 mmol) in DMSO (4 mL) and water (0.5 mL) was added LiCl (42 mg, 0.99 mmol). The resulting mixture was heated at 100° C. for 6 h, then cooled, diluted with water (5 mL), and extracted with EtOAc (5 mL×3). The combined organic layers were dried over $Na_2SO_4$, filtered and concentrated. The residue was dissolved in a 4M solution of HCl in dioxane (5 mL), and the resulting solution was heated at 50° C. for 30 min, then cooled and concentrated. The residue was partitioned between saturated aqueous $K_2CO_3$ solution (3 mL) and EtOAc (5 mL×3). The combined organic layers were dried over $Na_2SO_4$ and concentrated, and the residue was purified by preparative TLC (PE/EtOAc=1/1) to give the title compound. MS: m/z=272.2 (M+1). $^1$H NMR (400 MHz, $CDCl_3$) δ 8.21 (s, 1H), 7.74 (d, J=7.2 Hz, 2H), 7.52-7.44 (m, 3H), 4.12 (q, J=7.2 Hz, 2H), 3.55 (s, 2H), 3.25 (t, J=7.2 Hz, 2H), 2.85 (t, J=7.2 Hz, 2H), 1.22 (t, J=7.2 Hz, 3H).

REACTION SCHEME FOR INTERMEDIATE A29

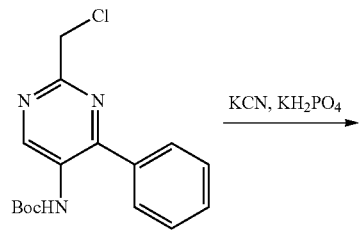

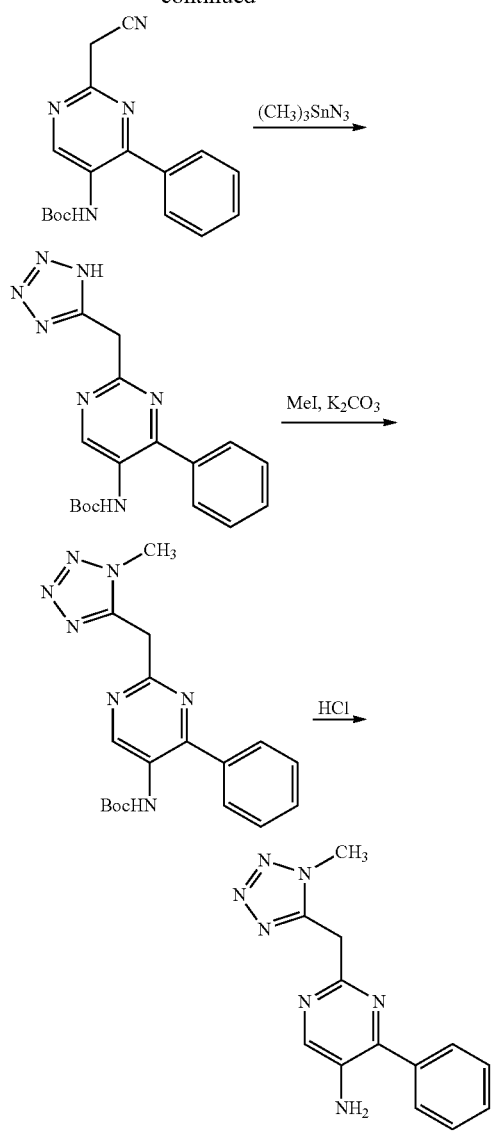

Intermediate A29

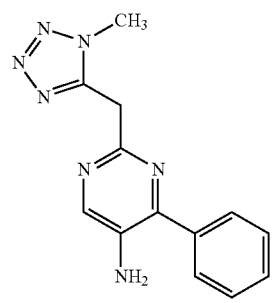 [SMILES: Cn1nnnc1Cc1ncc(N)c(-c2ccccc2)n1]

2-((1-Methyl-1H-tetrazol-5-yl)methyl)-4-phenylpyrimidin-5-amine

Step A: tert-Butyl (2-(cyanomethyl)-4-phenylpyrimidin-5-yl)carbamate

To a mixture of sodium cyanide (1.30 g, 26.6 mmol) and KH$_2$PO$_4$ (4.34 g, 31.9 mmol) in DMF (50 mL) was added tert-butyl (2-(chloromethyl)-4-phenylpyrimidin-5-yl)carbamate (1.70 g, 5.32 mmol), and the resulting mixture was stirred at 18° C. for 3 h. The product mixture was partitioned between water and EtOAc (50 mL×3). The combined organic layers were dried over Na$_2$SO$_4$ and concentrated. The residue was purified by column chromatography on silica gel (PE/EtOAc=5/1) to give the title compound. MS: m/z=311.0 (M+1).

Step B: tert-Butyl (2((2H-tetrazol-5-yl)methyl)-4-phenylpyrimidin-5-yl)carbamate To a solution of tert-butyl (2-(cyanomethyl)-4-phenylpyrimidin-5-yl)carbamate (200 mg, 0.644 mmol) in toluene (5 mL) was added azidotrimethylstannane (398 mg, 1.93 mmol). The resulting mixture was heated at 110° C. for 8 h under nitrogen atmosphere. The product mixture was cooled and KF (200 mg) was added. After stirring for 30 min, the mixture was filtered and the filtrate was concentrated. The residue was purified by reverse-phase HPLC to give the title compound. MS: m/z=354.0 (M+1).

Step C: tert-Butyl (2-((1-methyl-1H-tetrazol-5-yl)methyl)-4-phenylpyrimidin-5-yl)carbamate To a solution of tert-butyl (2-((2H-tetrazol-5-yl)methyl)-4-phenylpyrimidin-5-yl) carbamate (100 mg, 0.283 mmol) in acetonitrile (3 mL) was added K$_2$CO$_3$ (78 mg, 0.57 mmol) and CH$_3$I (0.027 mL, 0.42 mmol). The resulting mixture was stirred at 17° C. for 3 h, then partitioned between water and EtOAc (15 mL×3). The combined organic layers were dried over Na$_2$SO$_4$ and concentrated. The residue was purified by preparative TLC (PE/EtOAc=1/1) to give the title compound. MS: m/z=368.1 (M+1). $^1$H NMR (CDCl$_3$, 400 MHz) δ 7.47 (m, 5H), 6.61 (s, 1H), 4.56 (m, 2H), 4.01 (s, 3H), 1.40 (s, 9H).

Step D: 2-((1-Methyl-1H-tetrazol-5-yl)methyl)-4-phenylpyrimidin-5-amine

To a solution of tert-butyl (2-(2-methyl-2H-tetrazol-5-yl)methyl)-4-phenylpyrimidin-5-yl)carbamate (50 mg, 0.14 mmol) in EtOAc (2 mL) was added a 4 M solution of HCl in EtOAc (2 mL). The resulting mixture was stirred at 18° C. for 1 h and concentrated to give the title compound. MS: m/z=268.1 (M+1).

REACTION SCHEME FOR INTERMEDIATE A30

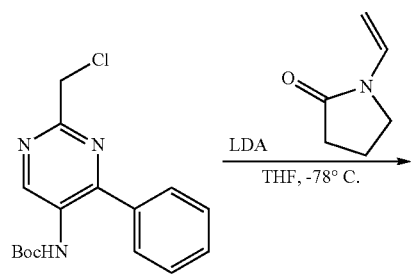

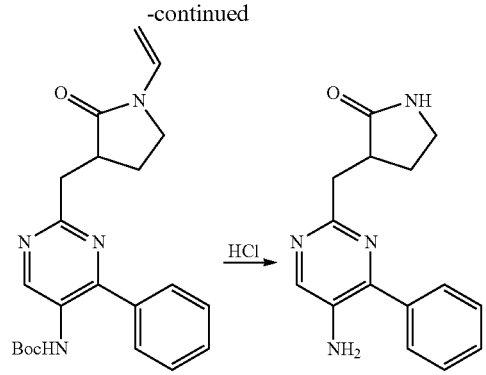

Intermediate A30

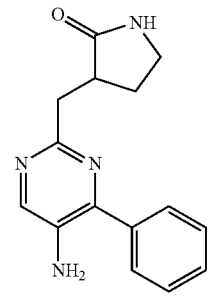 [SMILES: Nc1cnc(CC2CCNC2=O)nc1-c1ccccc1]

3-((5-Amino-4-phenylpyrimidin-2-yl)methyl)pyrrolidin-2-one

Step A: tert-Butyl (2-((2-oxo-1-vinylpyrrolidin-3-yl)methyl)-4-phenylpyrimidin-5-yl)carbamate To a solution of 1-vinylpyrrolidin-2-one (104 mg, 0.936 mmol) in THF (5 mL) at −78° C. was added LDA (134 mg, 1.25 mmol). The mixture was stirred at −78° C. for 10 min before tert-butyl (2-(chloromethyl)-4-phenyl pyrimidin-5-yl) carbamate (100 mg, 0.313 mmol) was added. The mixture was warmed to 26° C. and stirred for 1 h, then partitioned between water (5 mL) and EtOAc (5 mL×3). The combined organic layers were concentrated to give the title compound. MS: m/z=395.2 (M+1).

Step B: 3-((5-Amino-4-phenylpyrimidin-2-yl)methyl)pyrrolidin-2-one

A solution of tert-butyl (2-((2-oxo-1-vinylpyrrolidin-3-yl)-methyl)-4-phenylpyrimidin-5-yl)carbamate (100 mg, 0.254 mmol) in aqueous 6N HCl (2 mL, 12 mmol) was stirred at 26° C. for 5 h. The mixture was basified to pH 10 with saturated aqueous K$_2$CO$_3$ solution and extracted with EtOAc (5 mL×3). The combined organic layers were concentrated to give the title compound. MS: m/z=269.2 (M+1).

REACTION SCHEME FOR INTERMEDIATE A31

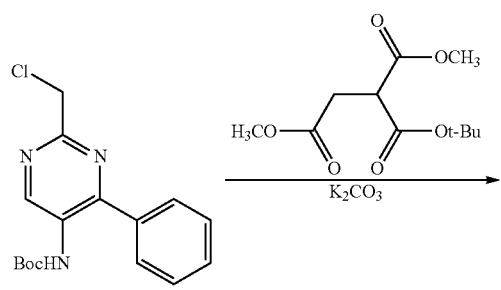

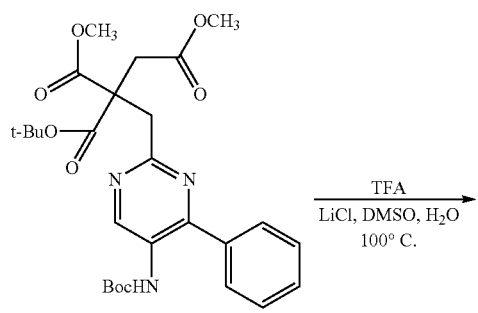

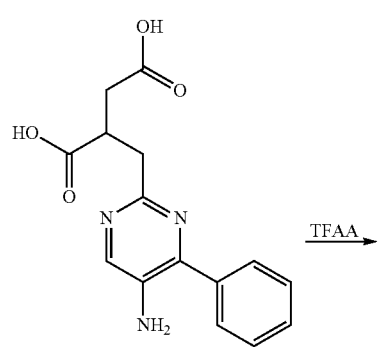

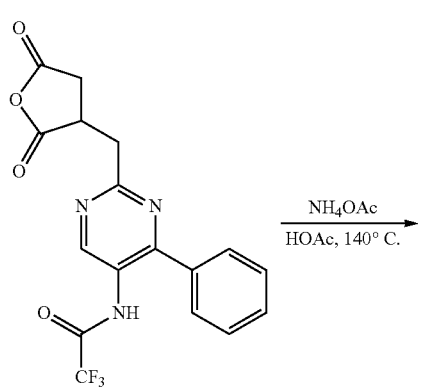

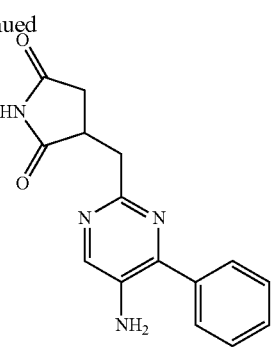

Intermediate A31

3-((5-Amino-4-phenylpyrimidin-2-yl)methyl)pyrrolidine-2,5-dione

Step A: 2-tert-Butyl 1,2-dimethyl 3-(5-((tert-butoxycarbonyl)amino)-4-phenylpyrimidin-2-yl)propane-1,2,2-tricarboxylate To a solution of tert-butyl (2-(chloromethyl)-4-phenylpyrimidin-5-yl)carbamate (350 mg, 1.09 mmol) in acetonitrile (10 mL) was added potassium carbonate (454 mg, 3.28 mmol) and 1-tert-butyl-1,2-dimethyl ethane-1,1,2-tricarboxylate (809 mg, 3.28 mmol). The resulting mixture was stirred at 20° C. for 5 h then partitioned between water (10 mL) and EtOAc (10 mL×2). The combined organic layers were dried over $Na_2SO_4$ and concentrated, and the residue was purified by column chromatography on silica gel (PE//EtOAc=7/1,5/1,3/1) to give the title compound. MS: m/z=530.3 (M+1).

Step B: 2-((5-Amino-4-phenylpyrimidin-2-yl)methyl)succinic acid

To a solution of 2-tert-butyl 1,2-dimethyl 3-(5-((tert-butoxycarbonyl)amino)-4-phenylpyrimidin-2-yl)propane-1,2,2-tricarboxylate (310 mg, 0.585 mmol) in DCM (1 mL) was added 2,2,2-trifluoroacetic acid (2.0 mL, 0.59 mmol). The resulting mixture was heated at 50° C. for 30 min then cooled and concentrated. The residue was dissolved in DMSO (2 mL) and lithium chloride (248 mg, 5.85 mmol) was added. The resulting mixture was heated at 100° C. for 5 h. The product mixture was filtered and the filtrate was concentrated. The residue was purified by reverse-phase HPLC under acidic condition (H₂O/CH₃CN gradient with 0.1% TFA present) to give the title compound. MS: m/z=302.0 (M+1).

Step C: N-(2-(2,5-Dioxotetrahydrofuran-3-yl)methyl)-4-phenylpyrimidin-5-yl)-2,2,2-trifluoroacetamide To a solution of 2-((5-amino-4-phenylpyrimidin-2-yl)methyl)succinic acid (60 mg, 0.20 mmol) in tetrahydrofuran (1 mL) was added 2,2,2-trifluoroacetic anhydride (418 mg, 1.99 mmol). The resulting mixture was stirred at 18° C. for 30 min then concentrated to give the title compound. MS: m/z=380.1 (M+1).

Step D: 3-((5-Amino-4-phenylpyrimidin-2-yl)methyl)pyrrolidine-2,5-dione

To a solution of N-(2-(2,5-dioxotetrahydrofuran-3-yl)methyl)-4-phenylpyrimidin-5-yl)-2,2,2-trifluoroacetamide (56 mg, 0.15 mmol) in DMF (0.5 mL) and AcOH (0.5 mL) was added NH₄OAc (57 mg, 0.74 mmol). The resulting mixture was heated at 140° C. for 2 h, then cooled and purified by reverse-phase HPLC under acidic condition (H₂O/CH₃CN gradient with 0.1% TFA present) to give the title compound. MS: m/z=283.3 (M+1).

REACTION SCHEME FOR INTERMEDIATE A32

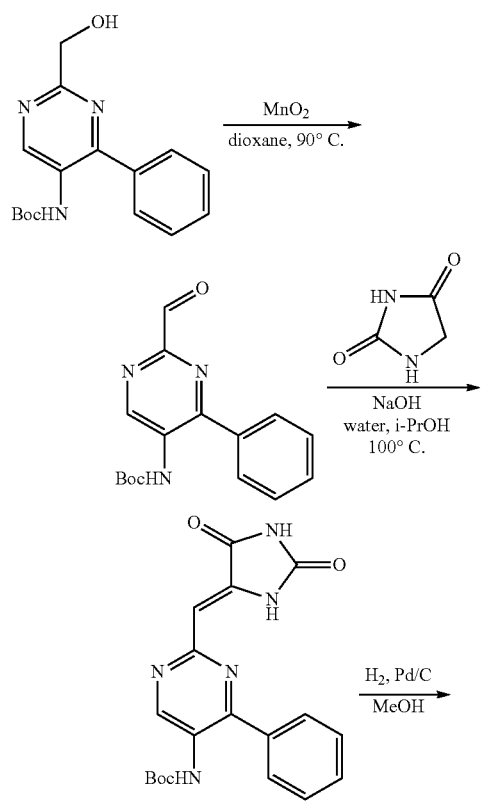

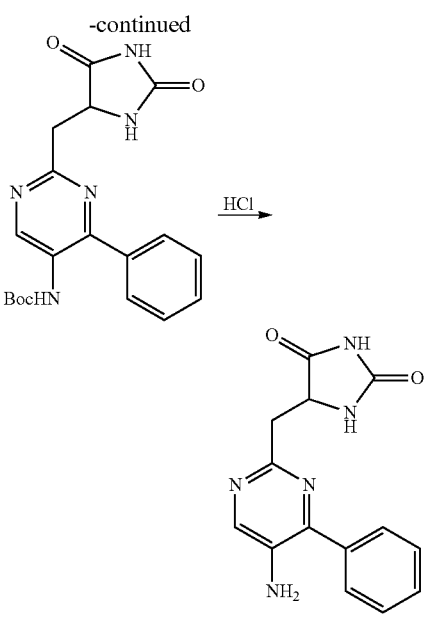

Intermediate A32

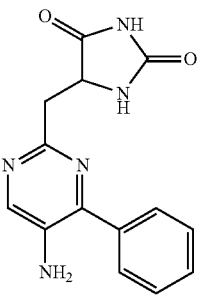 [SMILES: Nc1cnc(CC2NC(=O)NC2=O)nc1-c1ccccc1]

5-((5-Amino-4-phenylpyrimidin-2-yl)methyl)imidazolidine-2,4-dione

Step A: tert-Butyl (2-formyl-4-phenylpyrimidin-5-yl)carbamate

To a solution of tert-butyl (2-(hydroxymethyl)-4-phenylpyrimidin-5-yl)carbamate (700 mg, 2.32 mmol) in dioxane (8 mL) was added manganese dioxide (2.02 g, 23.2 mmol), and the resulting mixture was heated at 90° C. for 2 h. The product mixture was cooled and filtered, and the filtrate was concentrated. The residue was purified by column chromatography on silica gel (PE/EtOAc=3/1) to give the title compound. MS: m/z=299.2 (M+1).

Step B: tert-Butyl (2-(2,5-dioxoimidazolidin-4-ylidene)methyl)-4-phenylpyrimidin-5-yl)carbamate To a solution of tert-butyl (2-formyl-4-phenylpyrimidin-5-yl)carbamate (450 mg, 1.50 mmol) in water (5 mL) and isopropanol (2.5 mL) at 23° C. was added imidazolidine-2,4-dione (150 mg, 1.50 mmol) and sodium hydroxide (60 mg, 1.5 mmol). The resulting mixture was heated at 100° C. for 2 h, then cooled and acidified to pH 7 by addition of aqueous 3N HCl solution. The precipitate was filtered and dried to give the title compound. MS: m/z=382.2 (M+1). $^1$HNMR (400 MHz, CD$_3$OD) δ 10.16 (s, 1H), 9.08 (s, 1H), 8.73 (s, 1H), 7.75 (s, 2H), 7.46-7.53 (m, 4H), 6.29 (s, 1H), 1.24 (s, 9H).

Step C: tert-Butyl (2-(2,5-dioxoimidazolidin-4-yl) methyl)-4-phenylpyrimidin-5-yl)carbamate A mixture of tert-butyl (2-((2,5-dioxoimidazolidin-4-ylidene)methyl)-4-phenylpyrimidin-5-yl)carbamate (100 mg, 0.262 mmol) and 10% Pd/C (3 mg, 0.03 mmol) in methanol (20 mL) was stirred under hydrogen (50 psi) at 23° C. for 12 h. The mixture was filtered and the filtrate was concentrated to give the title compound. MS: m/z=384.1 (M+1).

Step D: 5-((5-Amino-4-phenylpyrimidin-2-yl) methyl)imidazolidine-2,4-dione

To a solution of tert-butyl (2-(2,5-dioxoimidazolidin-4-yl)methyl)-4-phenylpyrimidin-5-yl)carbamate (90 mg, 0.24 mmol) in dioxane (5 mL) was added a 4M solution of HCl in dioxane (5 mL). The mixture was stirred at 26° C. for 1 h then concentrated to give the title compound as an HCl salt. MS: m/z=284.0 (M+1).

REACTION SCHEME FOR INTERMEDIATE A33

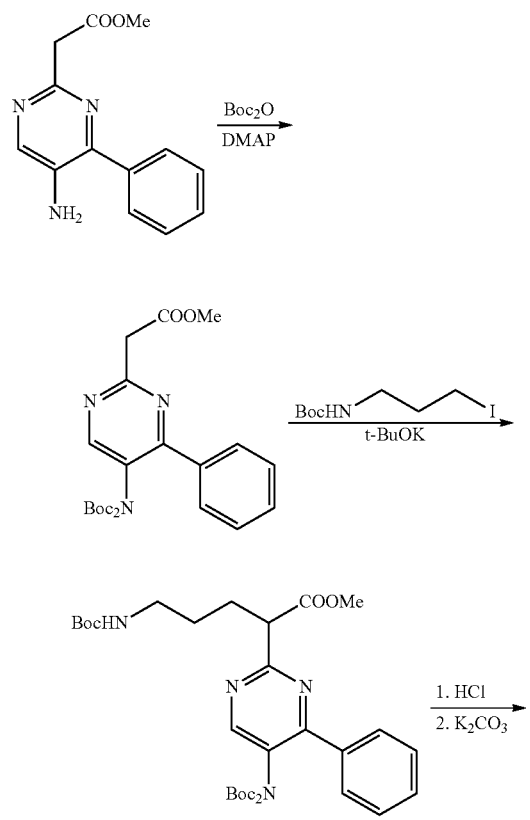

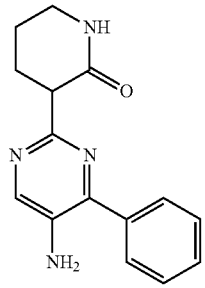 [SMILES: Nc1cnc(C2CCCNC2=O)nc1-c1ccccc1]

Intermediate A33

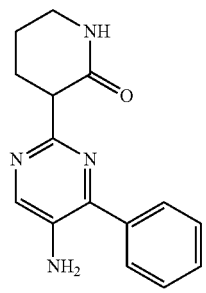

3-(5-Amino-4-phenylpyrimidin-2-yl)piperidin-2-one

Step A: 2-((5-(Di-tert-butoxycarbonyl)amino-4-phenylpyrimidin-2-yl)) acetate

To a mixture of methyl 2-(5-amino-4-phenylpyrimidin-2-yl) acetate (5.00 g, 20.6 mmol), Boc$_2$O (14.4 mL, 61.9 mmol), Et$_3$N (8.26 mL, 59.3 mmol) in DCM (30 mL) at 25° C. was added DMAP (2.70 g, 22.1 mmol). The resulting mixture was stirred for 1 h then partitioned between water (20 mL) and DCM (50 mL×3). The combined organic layer was dried over Na$_2$SO$_4$ and concentrated, and the residue was purified by column chromatography on silica gel (PE/EtOAc=10/1, 5/1) to give the title compound. MS: m/z=444.2 (M+1). $^1$H NMR (400 MHz, CDCl$_3$) δ 8.47 (s, 1H), 7.67 (dd, J=6.3, 2.7 Hz, 2H), 7.45 (d, J=2.3 Hz, 3H), 4.10 (s, 2H), 3.73 (s, 3H), 1.30 (s, 18H).

Step B: Methyl 2-(5-(bis(tert-butoxycarbonyl) amino)-4-phenylpyrimidin-2-yl)-5-((tert-butoxycarbonyl)amino)pentanoate To a mixture of 2-((5-(bis-tert-butoxycarbonyl)amino-4-phenylpyrimidin-2-yl)) acetate (300 mg, 0.676 mmol) and tert-butyl (3-iodopropyl) carbamate (231 mg, 0.812 mmol) in THF (6 mL) at 25° C. was added potassium 2-methylpropan-2-olate (1.35 mL, 1.35 mmol). The resulting mixture was stirred at 25° C. for 12 h then partitioned between water (30 mL) and EtOAc (30 mL×3). The combined organic layers were dried over Na$_2$SO$_4$ and concentrated to give the title compound. MS: m/z=601.4 (M+1).

Step C: 3-(5-Amino-4-phenylpyrimidin-2-yl)piperidin-2-one

A solution of methyl 2-(5-(bis(tert-butoxycarbonyl) amino)-4-phenylpyrimidin-2-yl)-5-((tert-butoxycarbonyl)

amino)pentanoate (240 mg, 0.400 mmol) in a 4M solution of HCl in dioxane (12 mL, 48.0 mmol) was stirred at 25° C. for 30 min, then concentrated. The residue was dissolved in MeOH (6 mL) and $K_2CO_3$ (442 mg, 3.20 mmol) was added. The resulting mixture was stirred at 25° C. for 12 h then filtered and concentrated. The residue was purified by column chromatography on silica gel (EtOAc/MeOH=10/1, 5/1) to give the title compound. MS: m/z=269.0 (M+1). $^1$H NMR (400 MHz, $CD_3OD$) δ 8.23 (s, 1H), 7.74 (d, J=6.7 Hz, 2H), 7.55-7.43 (m, 3H), 3.82 (dd, J=8.6, 7.0 Hz, 1H), 3.45-3.37 (m, 2H), 2.24-2.11 (m, 2H), 1.99-1.94 (m, 1H), 1.87-1.79 (m, 1H).

REACTION SCHEME FOR INTERMEDIATE A34

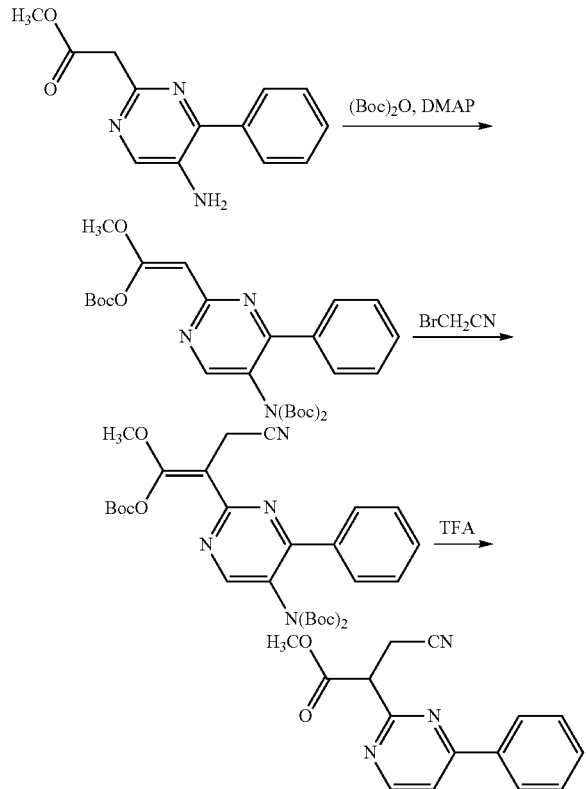

Intermediate A34

Methyl 2-(5-Amino-4-phenylpyrimidin-2-yl)-3-cyanopropanoate

Step A: tert-Butyl (2-(2-((bis-tert-butoxycarbonyl)oxy)-2-methoxyvinyl)-4-phenylpyrimidin-5-yl)carbamate To a mixture of methyl 2-(5-amino-4-phenylpyrimidin-2-yl)acetate (5.00 g, 20.6 mmol), $Boc_2O$ (14.4 mL, 61.9 mmol), $Et_3N$ (8.26 mL, 59.3 mmol) in $CH_2Cl_2$ (30 mL) at 25° C. was added DMAP (2.7 g, 22.10 mmol). The resulting mixture was stirred for 1 h then partitioned between water (20 mL) and $CH_2Cl_2$ (30 mL×3). The combined organic layers were dried over $Na_2SO_4$ and concentrated. The residue was purified by column chromatography on silica gel (PE/EtOAc=10/1, 5/1) to give the title compound. MS: m/z=544.3 (M+1).

Step B: Di-tert-butyl (2-(1-((tert-butoxycarbonyl)oxy)-3-cyano-1-methoxyprop-1-en-2-yl)-4-phenylpyrimidin-5-yl)carbamate To a solution of tert-butyl (2-(2-((di-tert-butoxycarbonyl)oxy)-2-methoxyvinyl)-4-phenylpyrimidin-5-yl)carbamate (2.50 g, 4.60 mmol) in dimethyl formamide (30 mL) at 25° C. were added $K_2CO_3$ (1.271 g, 9.20 mmol) and bromoacetonitrile (0.827 g, 6.90 mmol). The resulting mixture was stirred for 2 h then partitioned between water (50 mL) and EtOAc (30 mL×3). The combined organic layers were dried over $Na_2SO_4$ and concentrated. The residue was purified by silica gel column chromatography (PE/EtOAc=10/1, 5/1) to give the title compound. MS: m/z=583.4 (M+1). $^1$H NMR (400 MHz, $CDCl_3$) δ 8.48 (s, 1H), 7.81 (dd, $J_1$=6.53, $J_2$=3.01 Hz, 2H), 7.57-7.52 (m, 3H), 5.08 (s, 1H), 3.77 (s, 3H), 1.45 (s, 9H), 1.23 (d, J=6.02 Hz, 18H).

Step C: Methyl 2-(5-amino-4-phenylpyrimidin-2-yl)-3-cyanopropanoate

To a solution of di-tert-butyl (2-(1-((tert-butoxycarbonyl)oxy)-3-cyano-1-methoxyprop-1-en-2-yl)-4-phenylpyrimidin-5-yl)carbamate (2.00 g, 3.09 mmol) in acetonitrile (4 mL) at 25° C. was added TFA (5 mL). The mixture was stirred for 2 h then partitioned between saturated aqueous sodium bicarbonate solution (50 mL) and EtOAc (10 mL×3). The combined organic layers were dried over $Na_2SO_4$ and concentrated. The residue was purified by silica gel column chromatography (PE/EtOAc=10/1, 3/1) to afford the title compound. MS: m/z=282.9 (M+1).

REACTION SCHEME FOR INTERMEDIATE A35

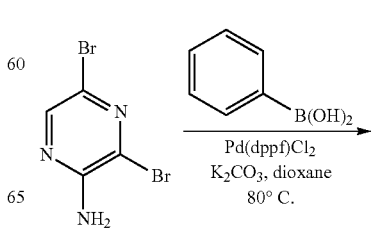

91

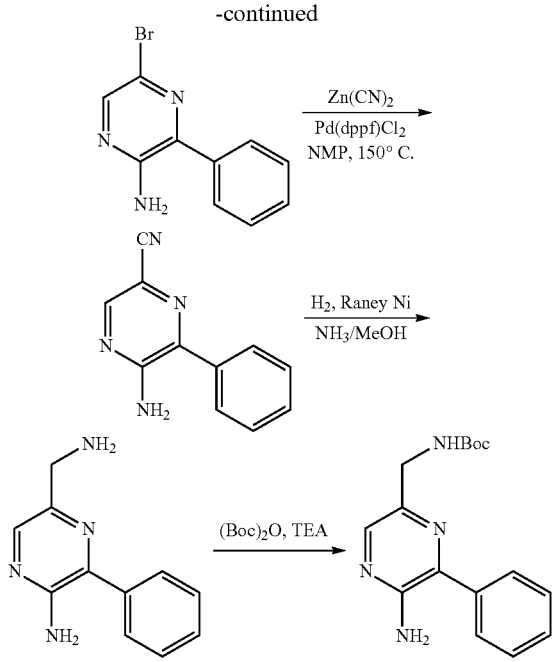

Intermediate A35 tert-Butyl ((5-amino-6-phenylpyrazin-2-yl)methyl)carbamate

Step A: 5-Bromo-3-phenylpyrazin-2-amine

To a deoxygenated solution of 3,5-dibromopyrazin-2-amine (5.00 g, 19.8 mmol) in 1,4-dioxane (100 mL) was added potassium carbonate (8.20 g, 59.3 mmol), phenylboronic acid (2.17 g, 17.8 mmol) and Pd(dppf)Cl$_2$ (1.45 g, 1.98 mmol). The resulting mixture was heated at 90° C. for 4 h, then cooled and partitioned between water (50 mL) and EtOAc (50 mL×2). The combined organic layers were dried over Na$_2$SO$_4$ and concentrated, and the residue was purified by column chromatography on silica gel (PE/EtOAc=15/1, 10/1, 5/1) to give the title compound. MS: m/z=249.9 (M+1).

Step B: 5-Amino-6-phenylpyrazine-2-carbonitrile

To a deoxygenated solution of 5-bromo-3-phenylpyrazin-2-amine (1.00 g, 3.20 mmol) in NMP (15 mL) was added dicyanozinc (1.13 g, 9.61 mmol) and Pd(dppf)Cl$_2$ (0.262 g, 0.320 mmol). The resulting mixture was heated at 150° C. for 3 h then cooled and partitioned between water (10 mL)

92 and EtOAc (15 mL×3). The combined organic layers were dried over Na$_2$SO$_4$ and concentrated, and the residue was purified by silica gel column chromatography (PE/EtOAc=10/1, 5/1, 2/1) to give the title compound. MS: m/z=196.9 (M+1).

Step C: 5-(Aminomethyl)-3-phenylpyrazin-2-amine

To a deoxygenated solution of 5-amino-6-phenylpyrazine-2-carbonitrile (270 mg, 0.90 mmol) in MeOH (15 mL) and a 4 M solution of NH$_3$ in MeOH (10 mL) was added Raney-Ni (5.3 mg, 0.090 mmol). The resulting mixture was stirred under H$_2$ (50 psi) at 20° C. for 30 min. The product mixture was filtered and the filtrate was concentrated to give the title compound. MS: m/z=201.0 (M+1).

Step D: tert-Butyl ((5-amino-6-phenylpyrazin-2-yl)methyl)carbamate

To a solution of 5-(aminomethyl)-3-phenylpyrazin-2-amine (260 mg, 1.30 mmol) in CH$_2$Cl$_2$ (5 mL) was added triethylamine (0.543 mL, 3.90 mmol) and Boc$_2$O (0.452 mL, 1.95 mmol). The resulting mixture was stirred for 30 min at 20° C. then partitioned between water (5 mL) and EtOAc (3 mL×3). The combined organic layers were dried over Na$_2$SO$_4$ and concentrated, and the residue was purified by silica gel column chromatography (PE/EtOAc=10/1, 5/1, 1/1) to give the title compound. MS: m/z=301.0 (M+1).

REACTION SCHEME FOR INTERMEDIATE A36

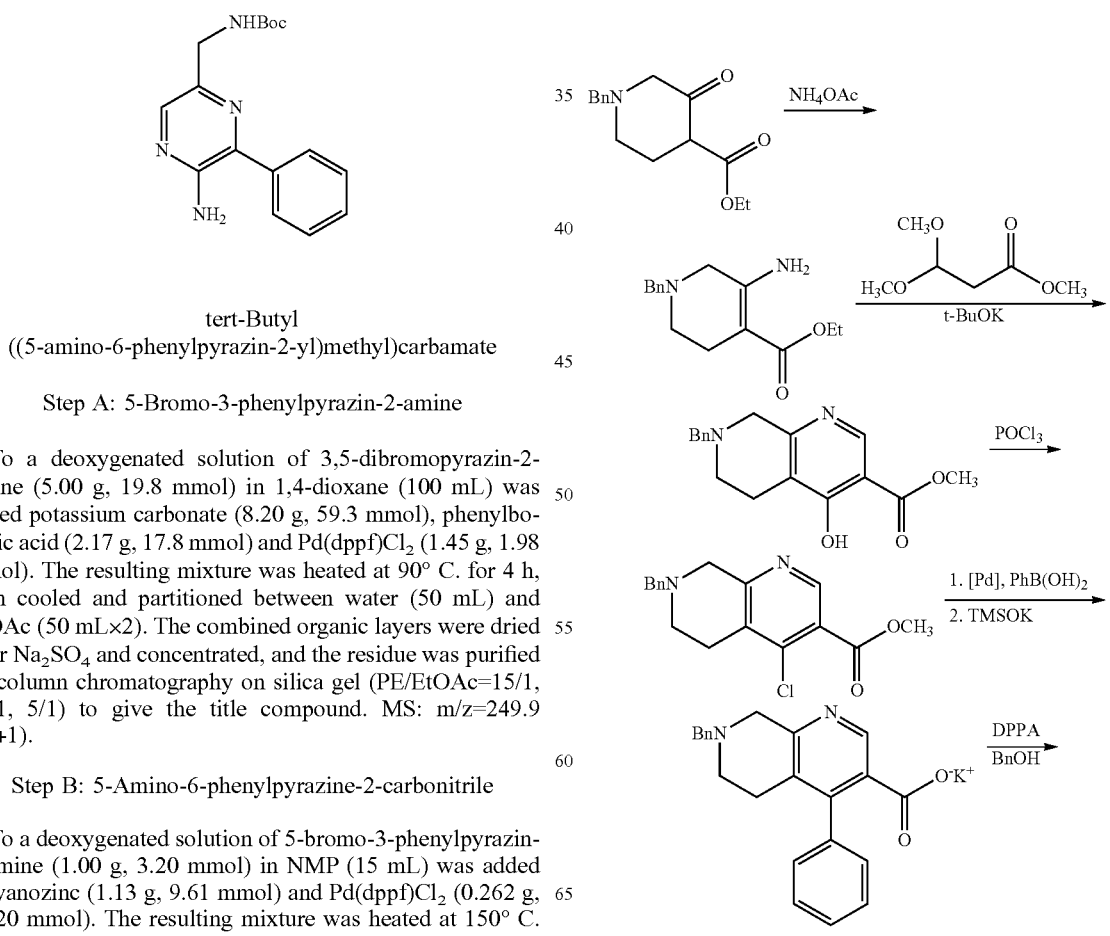

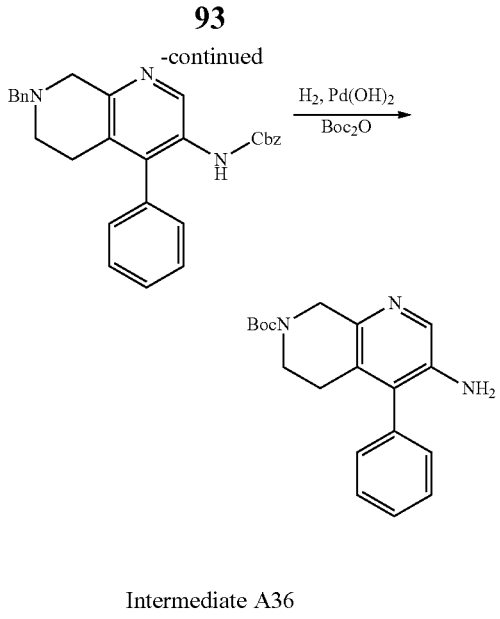

Intermediate A36 tert-Butyl 3-amino-4-phenyl-5,6-dihydro-1,7-naphthyridine-7(8H)-carboxylate

Step A: Ethyl 5-amino-1-benzyl-1,2,3,6-tetrahydropyridine-4-carboxylate

To a solution of ethyl 1-benzyl-3-oxopiperidine-4-carboxylate (30.0 g, 115 mmol) in methanol (200 mL) at 20° C. was added ammonium acetate (44.2 g, 574 mmol), and the resulting mixture was stirred for 18 h. The product mixture was concentrated, and the residue was partitioned between water (200 mL) and ethyl acetate (200 mL×2). The combined organic layer was dried over $Na_2SO_4$ and concentrated to afford the title compound. $^1$H NMR (400 MHz, $CD_3OD$) δ 7.47-7.21 (m, 5H), 4.09 (q, J=7.3 Hz, 2H), 3.79 (s, 2H), 3.33 (s, 2H), 2.75 (t, J=6.1 Hz, 2H), 2.44 (t, J=5.9 Hz, 2H), 1.21 (t, J=7.0 Hz, 3H).

Step B: Methyl 7-benzyl-4-hydroxy-5,6,7,8-tetrahydro-1,7-naphthyridine-3-carboxylate To a solution of potassium tert-butoxide (34.9 g, 311 mmol) in tetrahydrofuran (250 mL) at 20° C. was added ethyl 5-amino-1-benzyl-1,2,3,6-tetrahydropyridine-4-carboxylate (27.0 g, 104 mmol) and methyl 3,3-dimethoxypropanoate (46.1 g, 311 mmol). The resulting mixture was stirred for 18 h, then diluted with ice water (200 mL) and acidified to pH 5 by addition of aqueous 2M HCl solution. The resulting mixture was basified to pH 8 by addition of saturated aqueous sodium bicarbonate solution and extracted with ethyl acetate (200 mL×2). The combined organic layers were dried over $Na_2SO_4$ and concentrated, and the residue was purified by silica gel column chromatography (PE/EtOAc=1/1) to give the title compound. MS: m/z=299.1 (M+1).

Step C: Methyl 7-benzyl-4-chloro-5,6,7,8-tetrahydro-1,7-naphthyridine-3-carboxylate A solution of methyl 7-benzyl-4-hydroxy-5,6,7,8-tetrahydro-1,7-naphthyridine-3-carboxylate (20.0 g, 67.0 mmol) in phosphoryl trichloride (61.7 g, 402 mmol) was heated at 80° C. for 5 h. The mixture was cooled and carefully poured into water (200 mL), and the aqueous mixture was stirred at 20° C. for 1 h then basified to pH 8 with saturated aqueous potassium carbonate solution. The mixture was extracted with ethyl acetate (200 mL×2) and the combined organic layers were dried over $Na_2SO_4$ and concentrated. The residue was purified by silica gel column chromatography (PE/EtOAc=1/1) to give the title compound. MS: m/z=317.2 (M+1).

Step D: 7-Benzyl-4-phenyl-5,6,7,8-tetrahydro-1,7-naphthyridine-3-carboxylate

To a deoxygenated solution of methyl 7-benzyl-4-chloro-5,6,7,8-tetrahydro-1,7-naphthyridine-3-carboxylate (13.0 g, 41.0 mmol) in dioxane (150 mL) and water (15 mL) was added phenylboronic acid (5.00 g, 41.0 mmol), potassium carbonate (5.67 g, 41.0 mmol) and $PdCl_2(dppf)$ (30.0 g, 41.0 mmol). The resulting mixture was heated at 100° C. for 18 h, then cooled and partitioned between water (100 mL) and ethyl acetate (150 mL×2). The combined organic layers were dried over $Na_2SO_4$ and concentrated, and the residue was purified by silica gel column chromatography (PE/EtOAc=1/1) to afford methyl 7-benzyl-4-phenyl-5,6,7,8-tetrahydro-1,7-naphthyridine-3-carboxylate. To a solution of methyl 7-benzyl-4-phenyl-5,6,7,8-tetrahydro-1,7-naphthyridine-3-carboxylate (6.00 g, 16.74 mmol) in tetrahydrofuran (150 mL) at 20° C. was added potassium trimethylsilanolate (2.15 g, 16.7 mmol), and the resulting mixture was stirred for 5 h. The precipitate was filtered and dried to give the title compound. $^1$H NMR (400 MHz, $CD_3OD$) δ 8.30 (s, 1H), 7.30-7.16 (m, 10H), 3.64-3.59 (m, 4H), 2.62-2.55 (m, 2H), 2.48 (d, J=5.5 Hz, 2H).

Step E: Benzyl (7-benzyl-4-phenyl-5,6,7,8-tetrahydro-1,7-naphthyridin-3-yl)carbamate To a stirred solution of potassium 7-benzyl-4-phenyl-5,6,7,8-tetrahydro-1,7-naphthyridine-3-carboxylate (4.50 g, 11.8 mmol) in toluene (50 mL) was added diphenyl phosphoryl azide (4.21 g, 15.3 mmol) and benzyl alcohol (2.54 g, 23.5 mmol). The resulting mixture was heated at 100° C. for 18 h, then cooled and partitioned between water (50 mL) and ethyl acetate (50 mL×2). The combined organic layers were dried over $Na_2SO_4$ and concentrated, and the residue was purified by silica gel column chromatography (PE/EtOAc=5/1) to give the title compound. MS: m/z=450.2 (M+1). $^1$H NMR (400 MHz, $CD_3OD$) δ 8.53 (s, 1H), 7.47-7.36 (m, 5H), 7.34-7.26 (m, 6H), 7.22 (d, J=7.4 Hz, 2H), 7.15 (d, J=6.7 Hz, 2H), 5.02 (s, 2H), 3.70 (d, J=8.6 Hz, 4H), 2.71-2.64 (m, 2H), 2.56-2.50 (m, 2H).

Step F: tert-Butyl 3-amino-4-phenyl-5,6-dihydro-1,7-naphthyridine-7-(8H)-carboxylate To a deoxygenated solution of benzyl (7-benzyl-4-phenyl-5,6,7,8-tetrahydro-1,7-naphthyridin-3-yl) carbamate

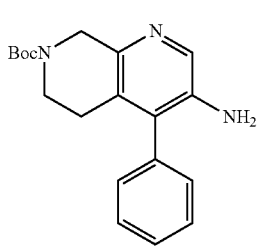 [SMILES: CC(C)(C)OC(=O)N1CCc2c(ncc(N)c2-c2ccccc2)C1]

(4.00 g, 8.90 mmol) in methanol (50 mL) was added 20% Pd(OH)$_2$ on carbon (0.63 g, 0.89 mmol). The resulting mixture was stirred under hydrogen (55 psi) at 20° C. for 3 h. The mixture was filtered and the filtrate was concentrated. The residue was dissolved in ethyl acetate (20 mL) and water (20 mL) at 20° C. and to this solution was added di-tert-butyl dicarbonate (2.09 g, 9.59 mmol) and sodium carbonate (1.69 g, 16.0 mmol). The resulting mixture was stirred for 18 h, then extracted with ethyl acetate (30 mL×2). The combined organic layers were dried over Na$_2$SO$_4$ and concentrated, and the residue was purified by silica gel column chromatography (PE/EtOAc=5/1) to give the title compound. MS: m/z=326.3 (M+1). $^1$H NMR (400 MHz, CD$_3$OD) δ 7.94 (s, 1H), 7.48-7.57 (m, 2H), 7.40-7.45 (m, 1H), 7.21 (d, J=7.0 Hz, 2H), 4.52 (s, 2H), 3.50 (s, 2H), 2.40 (t, J=5.5 Hz, 2H), 1.46 (s, 9H).

REACTION SCHEME FOR INTERMEDIATE A37

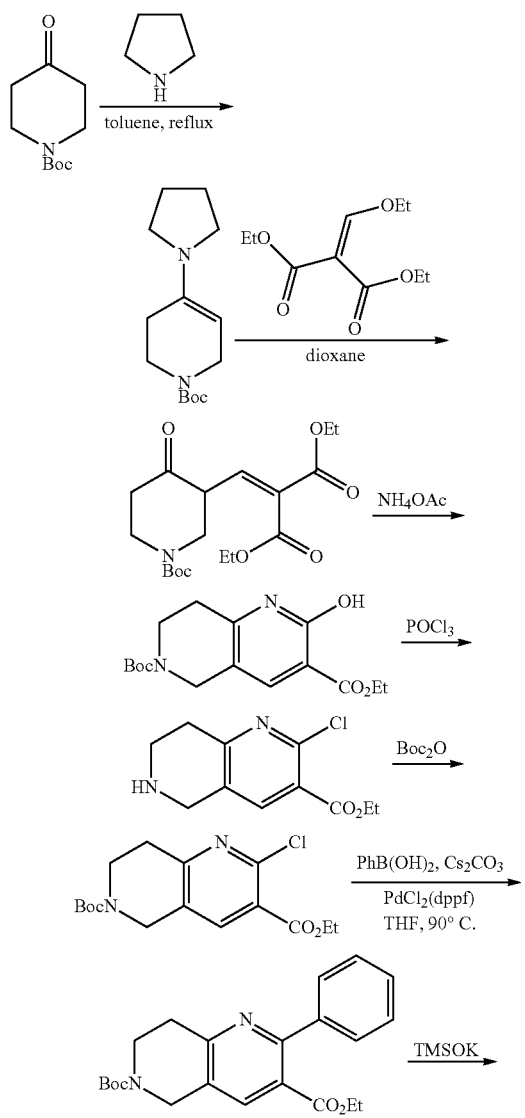

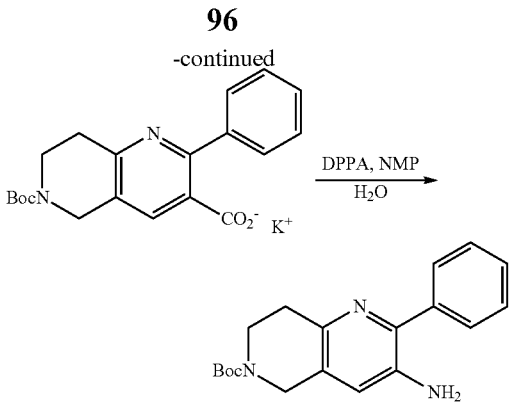

Intermediate A37 tert-Butyl 3-amino-2-phenyl-7,8-dihydro-1,6-naphthyridine-6(5H)-carboxylate

Step A: 6-tert-Butyl 3-ethyl 2-hydroxy-7,8-dihydro-1,6-naphthyridine-3,6(5H)-dicarboxylate A solution of tert-butyl 4-oxopiperidine-1-carboxylate (35.0 g, 176 mmol) and pyrrolidine (18.7 g, 263 mmol) in toluene (250 mL) was heated at reflux for 18 h using a Dean-Stark apparatus. The mixture was concentrated and the residue was dissolved in dioxane (250 mL). To this solution was added of diethyl 2-(ethoxymethylene)malonate (41.8 g, 193 mmol). The resulting mixture was heated at reflux for 6 h then cooled to 23° C. Ammonium acetate (23.0 g, 299 mmol) was added and the resulting mixture was heated at reflux for 1 h. The mixture was cooled and concentrated, and the residue was purified by column chromatography on silica gel (ethyl acetate) to give the title compound. MS: m/z=323.1 (M+1). $^1$H NMR (400 MHz, CD$_3$OD) δ 8.10 (s, 1H), 4.39 (s, 2H), 4.32 (q, J=7.2 Hz, 2H), 3.71 (t, J=5.0 Hz, 2H), 2.74 (t, J=5.5 Hz, 2H), 1.51 (s, 9H), 1.37 (t, J=7.0 Hz, 3H).

Step B: 6-tert-Butyl 3-ethyl 2-chloro-7,8-dihydro-1,6-naphthyridine-3,6(5H)-dicarboxylate To a suspension of 6-tert-butyl 3-ethyl 2-hydroxy-7,8-dihydro-1,6-naphthyridine-5,6(5H)-dicarboxylate (40.0 g, 124 mmol) in acetonitrile (200 mL) was added phosphorus oxychloride (34.7 mL, 372 mmol) dropwise, and the resulting mixture was heated at 90° C. for 12 h. The mixture was diluted with water (100 mL) and basified to pH 7 with saturated aqueous sodium bicarbonate solution. The mixture was extracted with ethyl acetate (100 mL×3) and the combined organic layers were dried over Na$_2$SO$_4$ and concentrated. The residue was dissolved in saturated aqueous sodium bicarbonate solution (100 mL) and THF (100 mL) and to this solution was added di-tert-butyl dicarbonate (57.6 mL, 248 mmol). The resulting mixture was stirred at 18° C. for 12 h then partitioned between water (50 mL) and ethyl acetate (100 mL×3). The combined organic layers were dried over Na$_2$SO$_4$ and concentrated, and the residue was purified by column chromatography on silica gel (PE/EtOAc=5/1) to afford the title compound. MS m/z=341.1 (M+1). $^1$H NMR (400 MHz, CDCl$_3$) δ 7.91 (s, 1H), 4.60 (s, 2H), 4.40 (q, J=7.0 Hz, 2H), 3.74 (t, J=5.5 Hz, 2H), 3.00 (s, 2H), 1.49 (s, 9H), 1.41 (t, J=7.24 Hz, 3H).

Step C: 6-tert-Butyl 3-ethyl 2-phenyl-7,8-dihydro-1,6-naphthyridine-3,6(5H)-dicarboxylate To a deoxygenated solution of 6-tert-butyl 3-ethyl 2-chloro-7,8-dihydro-1,6-naphthyridine-3,6(5H)-dicarboxylate (6.40 g, 18.8 mmol) and phenylboronic acid (3.43 g, 28.2 mmol) in THF (60 mL) and water (6 mL) was added cesium carbonate (18.4 g, 56.3 mmol) and PdCl$_2$(dppf) (0.687 g, 0.939 mmol). The resulting mixture was heated at 90° C. for 12 h. The mixture was cooled and filtered, and the filtrate was partitioned between water (20 mL) and ethyl acetate (50 mL×3). The combined organic layers were dried over Na$_2$SO$_4$ and concentrated, and the residue was purified by column chromatography on silica gel (PE/EtOAc=5/1) to afford the title compound. MS: m/z=323.1 (M+1). $^1$H NMR (400 MHz, CDCl$_3$) δ 7.80 (s, 1H), 7.41 (d, J=3.13 Hz, 2H), 7.34 (d, J=5.09 Hz, 3H), 4.61 (s, 2H), 4.06 (q, J=7.04 Hz, 2H), 3.72 (s, 2H), 3.02 (s, 2H), 1.44 (s, 9H) 0.96 (t, J=7.04 Hz, 3H).

Step D: Potassium 6-(tert-butoxycarbonyl)-2-phenyl-5,6,7,8-tetrahydro-1,6-naphthyridine-3-carboxylate To a solution of 6-tert-butyl 3-ethyl 2-phenyl-7,8-dihydro-1,6-naphthyridine-3,6(5H)-dicarboxylate (6.20 g, 16.2 mmol) in THF (100 mL) was added potassium trimethylsilanolate (3.12 g, 24.3 mmol), and the resulting mixture was stirred at 18° C. for 12 h. The product mixture was diluted with petroleum ether (100 mL) and the precipitate was filtered, washed with petroleum ether, and dried to give the title compound. MS: m/z=355.2 (M+1). $^1$H NMR (400 MHz, CD$_3$OD) δ 7.69 (d, J=6.6 Hz, 2H), 7.61 (s, 1H), 7.37 (m, 3H), 4.64 (s, 2H), 3.76 (s, 2H), 2.96 (t, J=5.7 Hz, 2H), 1.49 (s, 9H).

Step E: tert-Butyl 3-amino-2-phenyl-7,8-dihydro-1,6-naphthyridine-6(5H)-carboxylate To a solution of potassium 6-(tert-butoxycarbonyl)-2-phenyl-5,6,7,8-tetrahydro-1,6-naphthyridine-3-carboxylate (5.00 g, 12.7 mmol) in N-methyl-2-pyrrolidone (100 mL) at 20° C. was added diphenyl phosphoryl azide (4.57 g, 16.6 mmol). The resulting mixture was heated at 90° C. for 12 h under nitrogen atmosphere. Water (10 mL) was added and the mixture was heated at 90° C. for another 12 h. The mixture was cooled and partitioned between saturated aqueous sodium bicarbonate solution (30 mL) and ethyl acetate (30 mL×3). The combined organic layers were washed with water (30 mL×2) then brine (30 mL), dried over Na$_2$SO$_4$ and concentrated. The residue was purified by column chromatography on silica gel (PE/EtOAc=5/1) to afford the title compound. MS: m/z=326.1 (M+1). $^1$H NMR (400 MHz, CD$_3$OD) δ 7.47 (m, 5H), 6.98 (s, 1H), 4.52 (s, 2H), 3.71 (m, 2H), 2.80 (s, 2H), 1.48 (s, 9H).

REACTION SCHEME FOR INTERMEDIATE A38

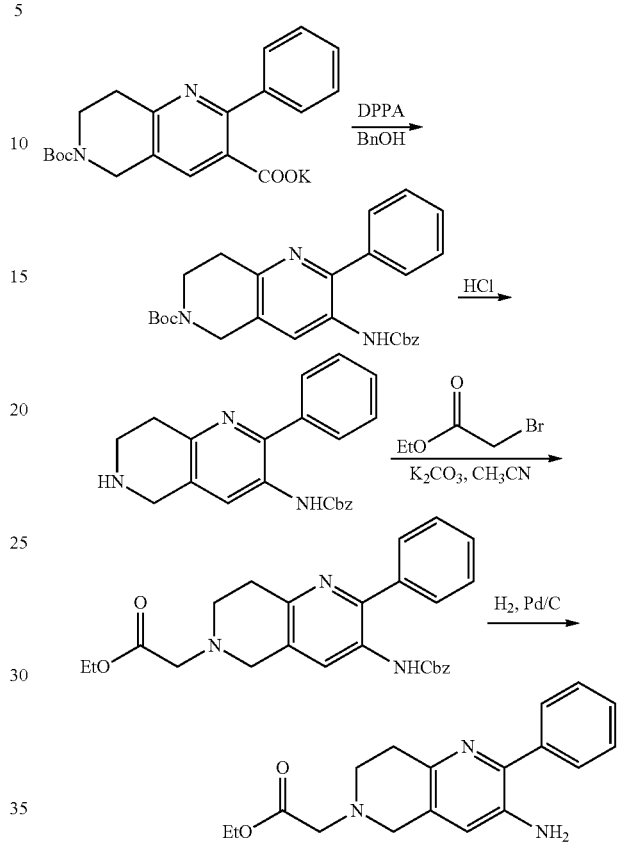

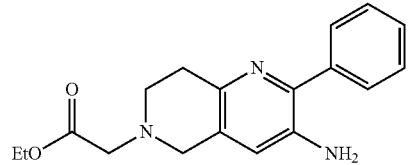 [SMILES: CCOC(=O)CN1CCc2nc(-c3ccccc3)c(N)cc2C1]

Intermediate A38

Ethyl 2-(3-amino-2-phenyl-7,8-dihydro-1,6-naphthyridin-6(5H)-yl)acetate

Step A: tert-Butyl 3-(((benzyloxy)carbonyl)amino)-2-phenyl-7,8-dihydro-1,6-naphthyridine-6(5H)-carboxylate To a stirred solution of potassium 6-(tert-butoxycarbonyl)-2-phenyl-5,6,7,8-tetrahydro-1,6-naphthyridine-3-carboxylate (6.50 g, 16.6 mmol) and benzyl alcohol (7.16 g, 66.2 mmol) in toluene (100 mL) at 20° C. was added DPPA (6.84 g, 24.8 mmol). The resulting mixture was heated at 110° C. for 16 h, then cooled and concentrated. The residue was partitioned between water (100 mL) and EtOAc (100 mL×3). The combined organic layers was dried over Na$_2$SO$_4$ and concentrated. The residue was purified by column chromatography on silica gel (PE/EtOAc=10/1, 5/1) to give the title compound. ¹H NMR (400 MHz, CDCl₃) δ 8.26 (br, 1H), 7.48-7.47 (m, 5H), 7.43-7.42 (m, 4H), 7.17-7.15 (m, 1H), 6.77 (br, 1H), 5.15 (s, 2H), 4.63 (s, 2H), 3.75 (br, 2H), 2.97 (br, 2H), 1.49 (s, 9H).

Step B: Benzyl (2-phenyl-5,6,7,8-tetrahydro-1,6-naphthyridin-3-yl)carbamate

A mixture of tert-butyl 3-(((benzyloxy) carbonyl) amino)-2-phenyl-7,8-dihydro-1,6-naphthyridine-6(5H)-carboxylate (4.00 g, 8.70 mmol) in a 4 M solution of HCl in EtOAc (50 mL, 200 mmol) was stirred at 20° C. for 1 h. The mixture was concentrated to give the title compound as an HCl salt. MS: m/z=360.2 (M+1).

Step C: Ethyl 2-(3-(((benzyloxy)carbonyl)amino)-2-phenyl-7,8-dihydro-1,6-naphthyridin-6(5H)-yl)acetate To a solution of benzyl (2-phenyl-5, 6, 7, 8-tetrahydro-1, 6-naphthyridin-3-yl) carbamate (2.80 g, 7.79 mmol) in acetonitrile (20 mL) was added K₂CO₃ (3.23 g, 23.4 mmol) and ethyl 2-bromoacetate (1.95 g, 11.7 mmol). The resulting mixture was stirred at 20° C. for 1 h, then partitioned between water (10 mL) and EtOAc (3×20 mL). The combined organic layers were dried over Na₂SO₄ and concentrated, and the residue was purified by column chromatography on silica gel (PE/EtOAc=5/1, 3/1, 2/1, 1/1) to give the title compound. MS: m/z=446.3 (M+1).

Step D: Ethyl 2-(3-amino-2-phenyl-7,8-dihydro-1,6-naphthyridin-6(5H)-yl)acetate

A mixture of ethyl 2-(3-(((benzyloxy)carbonyl)amino)-2-phenyl-7,8-dihydro-1,6-naphthyridin-6(5H)-yl)acetate (1.40 g, 3.14 mmol) and 10% Pd/C (0.33 g, 3.1 mmol) in EtOH (20 mL) was heated under H₂ (50 psi) at 50° C. for 6 h. The mixture was filtered and the filtrate concentrated to give the title compound. MS: m/z=312.1 (M+1).

REACTION SCHEME FOR INTERMEDIATE A39

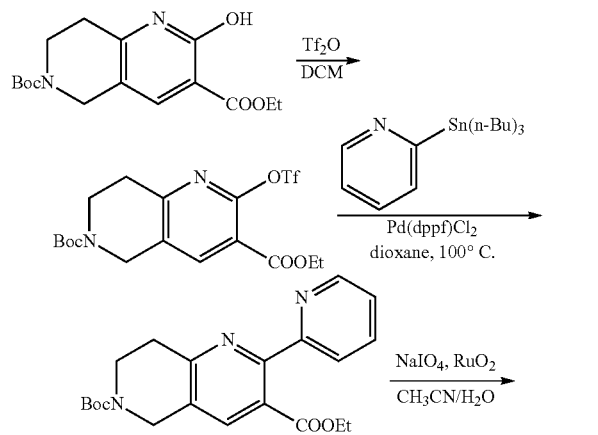

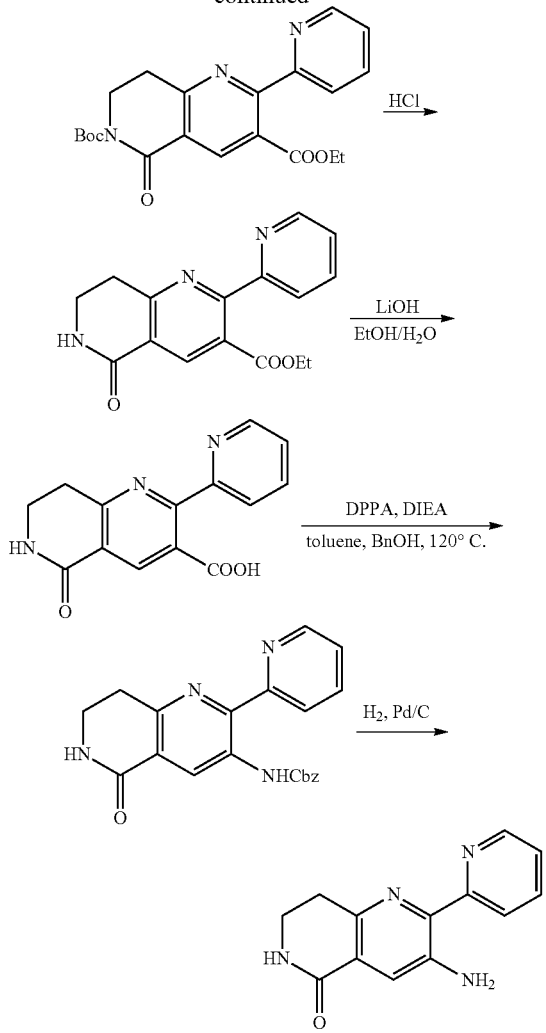

Intermediate A39

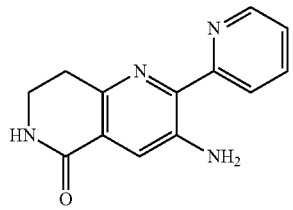 [SMILES: Nc1cc2c(nc1-c1ccccn1)CCNC2=O]

3-Amino-2-(pyridin-2-yl)-7,8-dihydro-1,6-naphthyridin-5(6H)-one

Step A: 6-tert-Butyl 3-ethyl 2-(((trifluoromethyl)sulfonyl)oxy)-7,8-dihydro-1,6-naphthyridine-3,6(5H)-dicarboxylate To a solution of 6-tert-butyl 3-ethyl 2-hydroxy-7,8-dihydro-1,6-naph thyridine-3,6(5H)-dicarboxylate (10.0 g, 31.0 mmol)) in CH₂Cl₂ (100 mL) at 25° C. was added triethylamine (9.42 g, 93.1 mmol) followed by trifluoromethanesulfonic anhydride (17.5 g, 62.0 mmol). The resulting mixture was stirred at 25° C. for 18 h, then partitioned between water (100 mL) and CH$_2$Cl$_2$ (200 mL×3). The combined organic layers were dried over MgSO$_4$ and concentrated, and the residue was purified by silica gel column chromatography (PE/EtOAc=10/1) to give the title compound. $^1$H NMR (400 MHz, CDCl$_3$) δ (s, 1H), 4.60 (s, 2H), 4.38 (q, J=7.2 Hz, 2H), 3.70 (t, J=5.5 Hz, 2H), 2.94 (d, J=5.1 Hz, 2H), 1.43 (s, 9H), 1.36 (t, J=7.0 Hz, 3H).

Step B: 6-tert-Butyl 3-ethyl 2-(pyridin-2-yl)-7,8-dihydro-1,6-naphthyridine-3,6(5H)-dicarboxylate To a deoxygenated solution of 6-tert-butyl 3-ethyl 2-(((trifluoromethyl) sulfonyl)oxy)-7,8-dihydro-1,6-naphthyridine-3,6(5H)-dicarboxylate (1.00 g, 2.20 mmol) in 1,4-dioxane (20 mL) was added 2-(tributylstannyl)pyridine (0.900 g, 2.60 mmol) and PdCl$_2$(dppf) (0.10 g, 0.20 mmol). The resulting mixture was heated at 100° C. for 15 h, then cooled and partitioned between water (30 mL) and ethyl acetate (20 mL×3). The combined organic layers were dried over Na$_2$SO$_4$ and concentrated, and the residue was purified by silica gel column chromatography (PE/EtOAc=10/1) to give the title compound. MS: m/z=384.1 (M+1). $^1$H NMR (400 MHz, CDCl$_3$) δ 8.53 (d, J=4.3 Hz, 1H), 7.93 (d, J=7.0 Hz, 1H), 7.75 (t, J=7.0 Hz, 1H), 7.70 (s, 1H), 7.21-7.26 (m, 1H), 4.60 (s, 2H), 4.16 (q, J=7.0 Hz, 2H), 3.72 (s, 2H), 3.02 (s, 2H), 1.42-1.46 (m, 9H), 1.06 (t, J=7.2 Hz, 3H).

Step C: 6-tert-Butyl 3-ethyl 5-oxo-2-(pyridin-2-yl)-7,8-dihydro-1,6-naphthyridine-3,6(5H)-dicarboxylate To a solution of 6-tert-butyl 3-ethyl 2-(pyridin-2-yl)-7,8-dihydro-1,6-naphthyridine-3,6(5H)-dicarboxylate (250 mg, 0.653 mmol) in acetonitrile (3 mL) and water (3 mL) at 27° C. was added sodium periodate (279 mg, 1.30 mmol) and ruthenium (IV) oxide (0.006 mL, 0.33 mmol). The resulting mixture was stirred for 1 h then partitioned between water (20 mL) and ethyl acetate (10 mL×3). The combined organic layers were dried over Na$_2$SO$_4$ and concentrated, and the residue was purified by silica gel column chromatography (PE/EtOAc=4/1) to give the title compound. MS: m/z=398.1 (M+1). $^1$H NMR (400 MHz, CDCl$_3$) δ 8.68 (s, 1H), 8.61 (d, J=4.3 Hz, 1H), 8.09 (d, J=7.8 Hz, 1H), 7.84 (t, J=7.0 Hz, 1H), 7.37-7.32 (m, 1H), 4.28 (q, J=7.0 Hz, 2H), 4.10 (t, J=6.3 Hz, 2H), 3.28 (t, J=6.3 Hz, 2H), 1.59 (s, 9H), 1.20 (t, J=7.2 Hz, 3H).

Step D: Ethyl 5-oxo-2-(pyridin-2-yl)-5,6,7,8-tetrahydro-1,6-naphthyridine-3-carboxylate A solution of 6-tert-butyl 3-ethyl 5-oxo-2-(pyridin-2-yl)-7,8-dihydro-1,6-naphthyridine-3,6(5H)-dicarboxylate (260 mg, 0.655 mmol) in a 4M solution of HCl in dioxane (5 mL) was stirred at 25° C. for 30 min. The mixture was concentrated to give the title compound as an HCl salt. MS: m/z=298.1 (M+1).

Step E: 5-Oxo-2-(pyridin-2-yl)-5,6,7,8-tetrahydro-1,6-naphthyridine-3-carboxylic acid To a solution of ethyl 5-oxo-2-(pyridin-2-yl)-5,6,7,8-tetrahydro-1,6-naphthyridine-3-carboxylate (180 mg, 0.606 mmol) in ethanol (2 mL) and water (0.50 mL) was added lithium hydroxide (29 mg, 1.2 mmol), and the resulting mixture was stirred 25° C. for 2 h. The mixture was acidified to pH 4 by addition of aqueous 2M HCl solution, then extracted with ethyl acetate (20 mL). The organic layer was dried over Na$_2$SO$_4$ and concentrated to give the title compound. $^1$H NMR (400 MHz, CD$_3$OD) δ 8.77 (s, 1H), 8.72 (d, J=4.7 Hz, 1H), 8.29-8.23 (m, 1H), 8.11 (d, J=7.8 Hz, 1H), 7.78-7.72 (m, 1H), 3.66 (t, J=6.8 Hz, 2H), 3.27-3.23 (m, 2H).

Step F: Benzyl (5-oxo-2-(pyridin-2-yl)-5,6,7,8-tetrahydro-1,6-naphthyridin-3-yl)carbamate To a solution of 5-oxo-2-(pyridin-2-yl)-5,6,7,8-tetrahydro-1,6-naphthyridine-3-carboxylic acid (150 mg, 0.557 mmol) in toluene (5 mL) was added N,N-diisopropylethylamine (0.29 mL, 1.7 mmol) and diphenyl phosphoryl azide (307 mg, 1.11 mmol), and the resulting mixture was heated at 80° C. for 1 h. Benzyl alcohol (0.12 mL, 1.1 mmol) was added and the mixture was heated at 100° C. for 15 h, then cooled and concentrated. The residue was purified by silica gel column chromatography (PE/EtOAc=1/1) to give the title compound. MS: m/z=375.2 (M+1).

Step G: 3-Amino-2-(pyridin-2-yl)-7,8-dihydro-1,6-naphthyridin-5(6H)-one

To a deoxygenated solution of benzyl (5-oxo-2-(pyridin-2-yl)-5,6,7,8-tetrahydro-1,6-naphthyridin-3-yl) carbamate (70 mg, 0.19 mmol) in methanol (10 mL) was added 10% Pd/C (199 mg, 0.188 mmol). The mixture was stirred under H$_2$ (50 psi) at 25° C. for 10 h, then filtered. The filtrate was concentrated and the residue was purified by preparative TLC (EtOAc/MeOH=10/1) to give the title compound. MS: m/z=241.0 (M+1). $^1$H NMR (400 MHz, CD$_3$OD) δ 8.62 (s, 1H), 8.48 (d, J=8.2 Hz, 1H), 7.93-7.87 (m, 1H), 7.67 (s, 1H), 7.35 (s, 1H), 3.57 (t, J=6.7 Hz, 2H), 3.06 (t, J=6.8 Hz, 2H).

REACTION SCHEME FOR INTERMEDIATE A40

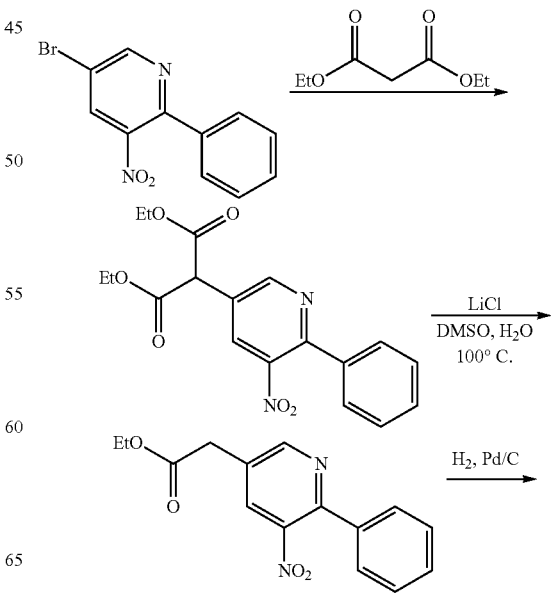

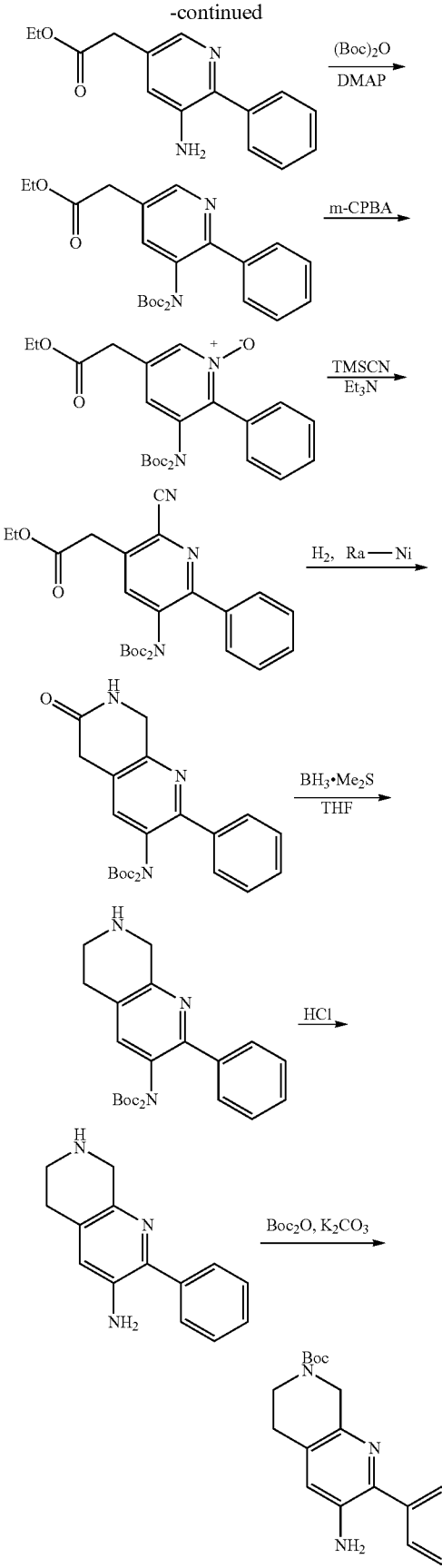

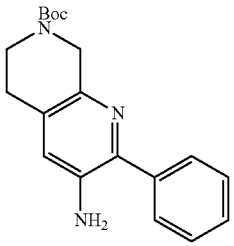 [SMILES: CC(C)(C)OC(=O)N1CCc2cc(N)c(-c3ccccc3)nc2C1]

Intermediate A40 tert-Butyl 3-amino-2-phenyl-5,6-dihydro-1,7-naphthyridine-7 (8H)-carboxylate

Step A: Diethyl 2-(5-nitro-6-phenylpyridin-3-yl)malonate

To a mixture of 5-bromo-3-nitro-2-phenylpyridine (10.0 g, 35.8 mmol), diethyl malonate (23.0 g, 143 mmol), copper (I) bromide (20.6 g, 143 mmol) in dioxane (60 mL) at 25° C. was added sodium hydride (6.30 g, 158 mmol) in portions. The resulting mixture was heated at 100° C. for 16 h, then cooled and diluted with saturated aqueous NH$_4$Cl solution (100 mL). The aqueous mixture was extracted with EtOAc (100 mL×3), and the combined organic layers were dried with Na$_2$SO$_4$ and concentrated. The residue was purified by chromatography on silica gel (PE/EtOAc=20/1, 10/1, 5/1) to give the title compound. MS: m/z=359.2 (M+1). $^1$H NMR (400 MHz, CDCl$_3$) δ 8.81 (d, J=1.2 Hz, 1H), 8.33 (d, J=1.6 Hz, 1H), 7.53-7.59 (m, 2H), 7.44-7.49 (m, 3H), 4.24 (m, 4H), 1.29 (d, J=5.1 Hz, 6H).

Step B: Ethyl 2-(5-nitro-6-phenylpyridin-3-yl)acetate

To a stirred solution of diethyl 2-(5-nitro-6-phenylpyridin-3-yl)malonate (5.80 g, 16.2 mmol) in DMSO (60 mL) and water (3 mL) was added lithium chloride (2.10 g, 48.6 mmol). The resulting mixture was heated at 100° C. for 5 h, then cooled and partitioned between water (80 mL) and EtOAc (80 mL×3). The combined organic layers were dried over Na$_2$SO$_4$ and concentrated. The residue was purified by chromatography on silica gel (PE/EtOAc=10/1, 5/1, 3/1) to give the title compound. MS: m/z=287.0 (M+1).

Step C: Ethyl 2-(5-((di-tert-butoxycarbonyl)amino)-6-phenylpyridin-3-yl)acetate

A deoxygenated mixture of ethyl 2-(5-nitro-6-phenylpyridin-3-yl)acetate (5.50 g, 19.2 mmol) and 10% Pd/C (2.0 g, 1.9 mmol) in MeOH (50 mL) was stirred under H$_2$ (50 psi) at 30° C. for 5 h. The mixture was filtered and the filtrate was concentrated. The residue was dissolved in CH$_2$Cl$_2$ (50 mL) and to this solution was added triethylamine (5.10 g, 50.3 mmol), DMAP (2.10 g, 16.8 mmol) and Boc$_2$O (7.80 mL, 33.6 mmol). The resulting mixture was stirred at 30° C. for 3 h, then concentrated. The residue was purified by column chromatography on silica gel (PE/EtOAc=10/1, 5/1) to give the title compound.

Step D: 3-((Di-tert-butoxycarbonyl)amino)-5-(2-ethoxy-2-oxoethyl)-2-Phenylpyridine-1-oxide To a stirred solution of ethyl 2-(5-((di-tert-butoxycarbonyl)amino)-6-phenylpyridin-3-yl)acetate (200 mg, 0.438 mmol) in CHCl₃ (4 mL) was added m-CPBA (267 mg, 1.32 mmol). The resulting mixture was stirred at 25° C. for 2 h, then partitioned between saturated aqueous Na₂SO₃ solution (10 mL) and CH₂Cl₂ (15 mL×3). The combined organic layers were washed with saturated aqueous NaHCO₃ solution (10 mL), dried over Na₂SO₄ and concentrated to give the title compound. MS: m/z=473.2 (M+1). ¹H NMR (400 MHz, CDCl₃) δ 8.39 (s, 1H), 8.03 (d, J=14.1 Hz, 1H), 7.94 (dd, J₁=16.2 Hz, J₂=7.6 Hz, 1H), 7.64 (d, J=7.8 Hz, 1H), 7.43 (br, 2H), 7.21 (s, 1H), 4.21 (d, J=6.7 Hz, 2H), 3.62 (s, 2H), 1.34 (s, 18H), 1.27-1.29 (m, 3H).

Step E: Ethyl 2-(5-((di-tert-butoxycarbonyl)amino)-2-cyano-6-phenylpyridin-3-yl)acetate To a stirred solution of 3-((di-tert-butoxycarbonyl)amino)-5-(2-ethoxy-2-oxoethyl)-2-phenylpyridine-1-oxide (2.0 g, 4.2 mmol) and Et₃N (1.8 mL, 13 mmol) in acetonitrile (30 mL) was added TMSCN (2.3 mL, 17 mmol). The resulting mixture was heated at 80° C. for 5 h, then cooled and partitioned between water (30 mL) and EtOAc (30 mL×3). The combined organic layers was dried over Na₂SO₄ and concentrated. The residue was purified by column chromatography on silica gel (PE/EtOAc=10/1, 5/1, 1/1) to give the title compound. MS: m/z=482.3 (M+1).

Step F: Di-tert-butyl (6-oxo-2-phenyl-5,6,7,8-tetrahydro-1,7-naphthyridin-3-yl)carbamate A deoxygenated mixture of ethyl 2-(5-((di-tert-butoxycarbonyl)amino)-2-cyano-6-phenylpyridin-3-yl)acetate (1.0 g, 2.1 mmol) and Raney-Ni (24 mg, 0.4 mmol) in MeOH (20 mL) was stirred under H₂ (50 psi) at 25° C. for 5 h. The mixture was filtered and the filtrate was concentrated to give the crude title compound. MS: m/z=440.2 (M+1). ¹H NMR (400 MHz, CDCl₃) δ 7.49 (d, J=6.7 Hz, 2H), 7.40-7.32 (m, 4H), 7.29 (s, 1H), 4.65 (br, 2H), 3.66 (br, 2H), 1.23 (s, 18H).

Step G: Di-tert-butyl (2-phenyl-5,6,7,8-tetrahydro-1,7-naphthyridin-3-yl)carbamate To a stirred solution of di-tert-butyl (6-oxo-2-phenyl-5,6,7,8-tetrahydro-1,7-naphthyridin-3-yl)carbamate (200 mg, 0.46 mmol) in THF (3 mL) at 25° C. was added BH₃.DMS (0.20 mL, 2.3 mmol), and the resulting mixture was stirred for 5 h. MeOH (1 mL) was added and mixture was concentrated. The residue was purified by preparative TLC (PE/EtOAc=1/1) to give the title compound. MS: m/z=467.3 (M+1+MeCN).

Step I: 2-Phenyl-5,6,7,8-tetrahydro-1,7-naphthyridin-3-amine

A mixture of di-tert-butyl (2-phenyl-5,6,7,8-tetrahydro-1,7-naphthyridin-3-yl)carbamate (100 mg, 0.24 mmol) in a 4 M solution of HCl in EtOAc (10 mL, 40.0 mmol) was stirred 25° C. for 2 h. The mixture was concentrated to give the title compound as HCl salt. MS: m/z=226.2 (M+1).

Step J: 2-Phenyl-5,6,7,8-tetrahydro-1,7-naphthyridin-3-amine

A mixture of 2-phenyl-5,6,7,8-tetrahydro-1,7-naphthyridin-3-amine (50 mg, 0.22 mmol), K₂CO₃ (92 mg, 0.67 mmol) and Boc₂O (0.10 mL, 0.44 mmol) in THF (3 mL) and water (1 mL) was stirred at 30° C. for 3 h. The product mixture was partitioned between water (20 mL) and EtOAc (20 mL×3). The combined organic layers was dried over Na₂SO₄ and concentrated. The residue was purified by preparative TLC (PE/EtOAc=2/1) to give the title compound. MS: m/z=326.2 (M+1).

REACTION SCHEME FOR INTERMEDIATE A41

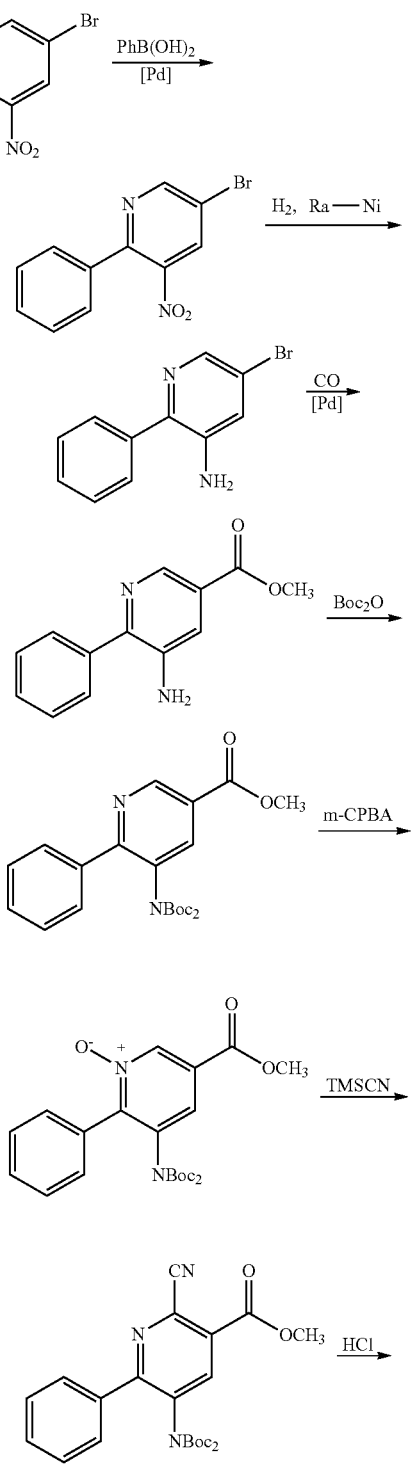

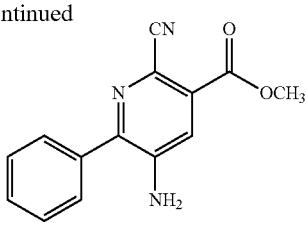

Intermediate A41

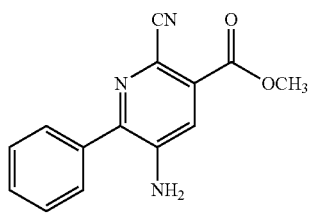 [SMILES: COC(=O)c1cc(N)c(-c2ccccc2)nc1C#N]

Methyl 5-amino-2-cyano-6-phenylnicotinate

Step A: 5-Bromo-3-nitro-2-phenylpyridine

To a deoxygenated solution of 2,5-dibromo-3-nitropyridine (50.0 g, 177 mmol) in DME (800 mL) and water (150 mL) was added phenylboronic acid (23.8 g, 195 mmol), K$_2$CO$_3$ (49.0 g, 355 mmol) and PdCl$_2$(dppf) (6.49 g, 8.87 mmol). The resulting mixture was heated at 100° C. for 18 h, then cooled and partitioned between water (1000 mL) and EtOAc (500 mL×3). The combined organic layers were dried over Na$_2$SO$_4$ and concentrated. The residue was purified by column chromatography on silica gel (100% PE, PE/EtOAc=50/1) to afford the title compound. MS: m/z=279.1, 281.1 (M+1). $^1$H NMR (400 MHz, CDCl$_3$) δ 8.91 (d, J=2.0 Hz, 1H), 8.28 (d, J=2.0 Hz, 1H), 7.53-7.55 (m, 2H), 7.45-7.48 (m, 3H).

Step B: 5-Bromo-2-phenylpyridin-3-amine

A mixture of 5-bromo-3-nitro-2-phenylpyridine (10.0 g, 35.8 mmol) and Raney-Ni (3.07 g, 35.8 mmol) in EtOAc (100 mL) was stirred under H$_2$ (50 psi) at 20° C. for 4 h. The mixture was filtered and the filtrate was concentrated to give the title compound. MS: m/z=249.1, 251.1 (M+1). $^1$H NMR (400 MHz, CDCl$_3$) δ 8.07 (d, J=2.0 Hz, 1H), 7.54-7.56 (m, 2H), 7.38-7.42 (m, 3H), 7.12 (s, 1H), 3.75 (br, 2H).

Step C: Methyl 5-amino-6-phenylnicotinate

To a solution of 5-bromo-2-phenylpyridin-3-amine (20 g, 80 mmol) in MeOH (200 mL) was added PdCl$_2$(dppf) (5.87 g, 8.03 mmol) and Et$_3$N (16.2 g, 161 mmol). The mixture was heated under CO (3 mbar) at 120° C. for 8 h. The product mixture was filtered and the filtrate was concentrated. The residue was purified by chromatography on silica gel (100% PE, PE/EA=20/1, 10/1) to give the title compound. $^1$H NMR (400 MHz, CD$_3$OD) δ 8.42 (d, J=2.0 Hz, 1H), 7.74 (d, J=2.0 Hz, 1H), 7.60-7.62 (m, 2H), 7.46-7.50 (m, 3H), 3.91 (s, 3H).

Step D: Methyl 5-((di-tert-butoxycarbonyl)amino)-6-phenylnicotinate

To a solution of methyl 5-amino-6-phenylnicotinate (12.0 g, 52.6 mmol) in DCM (150 mL) was added DMAP (12.8 g, 105 mmol), Et$_3$N (10.6 g, 105 mmol) and Boc$_2$O (45.9 g, 210 mmol). The resulting mixture was stirred at 15° C. for 1 h, then partitioned between water (100 mL) and DCM (100 mL×3). The combined organic layers were washed with citric acid, dried over Na$_2$SO$_4$ and concentrated. The residue was purified by chromatography on silica gel (PE, PE/EtOAc=50/1, 20/1) to give the title compound. MS: m/z=429.1 (M+1). $^1$H NMR (400 MHz, CDCl$_3$) δ 9.21 (d, J=1.6 Hz, 1H), 8.10 (d, J=2.0 Hz, 1H), 7.64-7.62 (m, 2H), 7.44-7.40 (m, 3H), 3.98 (s, 3H), 1.27 (s, 18 H).

Step E: 3-((Di-tert-butoxycarbonyl)amino)-5-(methoxycarbonyl)-2-phenylpyridine-1-oxide To a solution of methyl 5-((di-tert-butoxycarbonyl)amino)-6-phenylnicotinate (21.0 g, 49.0 mmol) in DCM (210 mL) was added m-CPBA (8.46 g, 49.0 mmol). The resulting mixture was stirred at 15° C. for 6 h, then partitioned between water (100 mL) and DCM (100 mL×3). The combined organic layers were dried over Na$_2$SO$_4$ and concentrated. The residue was purified by chromatography on silica gel (PE, PE/EtOAc=10/1, PE/EtOAc=5/1) to give the title compound. $^1$H NMR (400 MHz, CDCl$_3$) δ 8.05 (s, 1H), 7.95 (d, J=7.6 Hz, 1H), 7.64-7.45 (m, 5H), 3.99 (s, 3H), 1.41-1.25 (m, 18 H).

Step F: Methyl 5-((di-tert-butoxycarbonyl)amino)-2-cyano-6-phenylnicotinate

To a solution of 3-((di-tert-butoxycarbonyl)amino)-5-(methoxycarbonyl)-2-phenylpyridine-1-oxide (14.0 g, 31.5 mmol) in acetonitrile (150 mL) was added Et$_3$N (9.56 g, 945 mmol) and trimethylsilanecarbonitrile (6.25 g, 63.0 mmol). The resulting mixture was heated at 90° C. for 4 h. After cooling, the mixture was partitioned between water (100 mL) and EtOAc (100×3 mL). The combined organic layers were washed with citric acid, dried over Na$_2$SO$_4$ and concentrated. The residue was purified by chromatography on silica gel (PE, PE/EA=20/1, PE/EA=5/1) to give the title compound. MS: m/z=454.2 (M+1).

Step G: Methyl 5-amino-2-cyano-6-phenylnicotinate

To a solution of methyl 5-((di-tert-butoxycarbonyl)amino)-2-cyano-6-phenylnicotinate (200 mg, 0.44 mmol) in EtOAc (5 mL) was added a 4M solution of HCl in EtOAc (0.11 mL, 0.44 mmol), and the mixture was stirred at 20° C. for 30 min. The resulting slurry was concentrated to give the title compound. MS: m/z=254.2 (M+1).

REACTION SCHEME FOR INTERMEDIATE A42

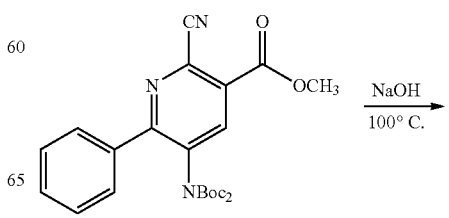

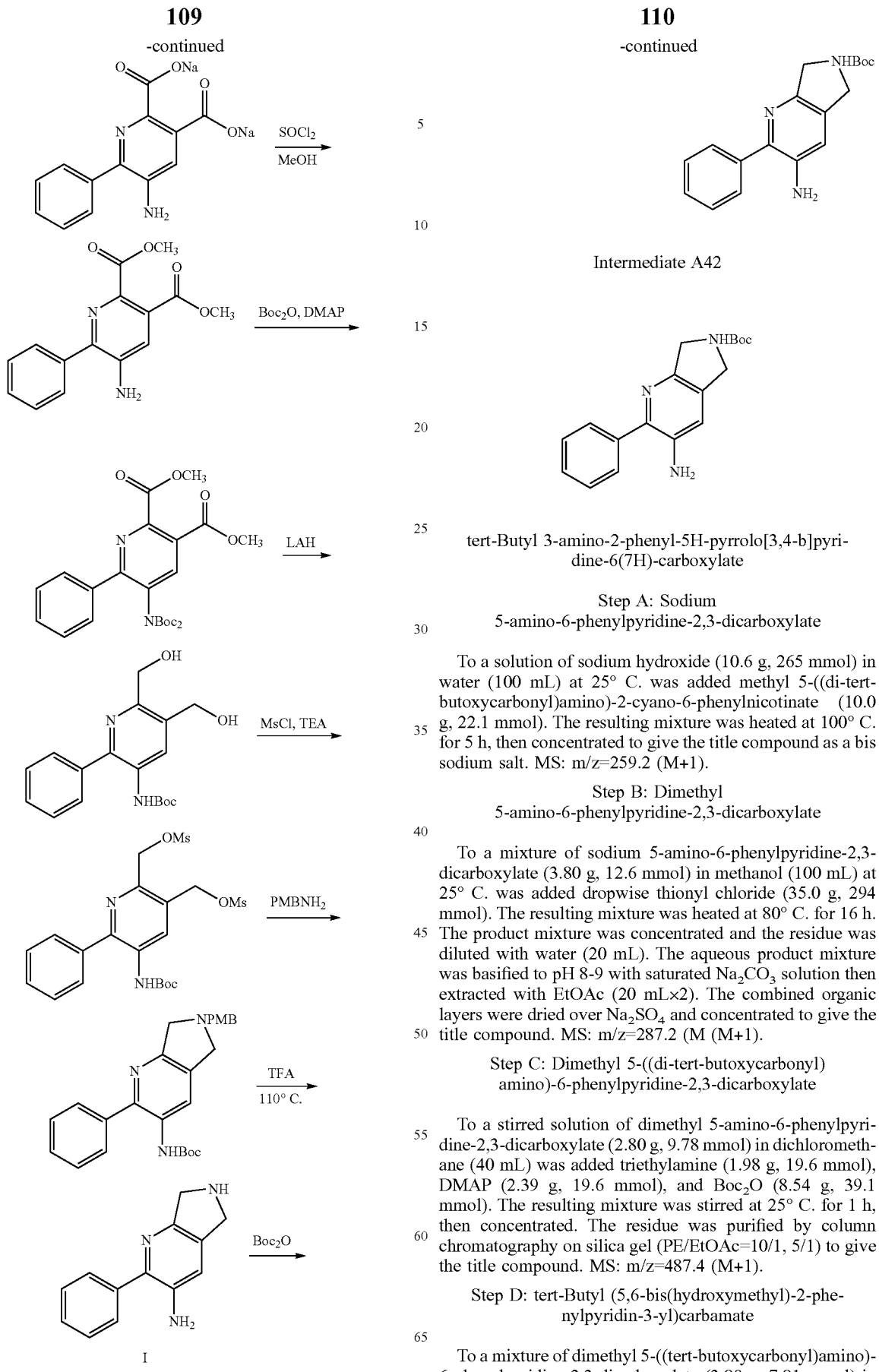

Intermediate A42 tert-Butyl 3-amino-2-phenyl-5H-pyrrolo[3,4-b]pyridine-6(7H)-carboxylate

Step A: Sodium 5-amino-6-phenylpyridine-2,3-dicarboxylate

To a solution of sodium hydroxide (10.6 g, 265 mmol) in water (100 mL) at 25° C. was added methyl 5-((di-tert-butoxycarbonyl)amino)-2-cyano-6-phenylnicotinate (10.0 g, 22.1 mmol). The resulting mixture was heated at 100° C. for 5 h, then concentrated to give the title compound as a bis sodium salt. MS: m/z=259.2 (M+1).

Step B: Dimethyl 5-amino-6-phenylpyridine-2,3-dicarboxylate

To a mixture of sodium 5-amino-6-phenylpyridine-2,3-dicarboxylate (3.80 g, 12.6 mmol) in methanol (100 mL) at 25° C. was added dropwise thionyl chloride (35.0 g, 294 mmol). The resulting mixture was heated at 80° C. for 16 h. The product mixture was concentrated and the residue was diluted with water (20 mL). The aqueous product mixture was basified to pH 8-9 with saturated $Na_2CO_3$ solution then extracted with EtOAc (20 mL×2). The combined organic layers were dried over $Na_2SO_4$ and concentrated to give the title compound. MS: m/z=287.2 (M (M+1).

Step C: Dimethyl 5-((di-tert-butoxycarbonyl)amino)-6-phenylpyridine-2,3-dicarboxylate To a stirred solution of dimethyl 5-amino-6-phenylpyridine-2,3-dicarboxylate (2.80 g, 9.78 mmol) in dichloromethane (40 mL) was added triethylamine (1.98 g, 19.6 mmol), DMAP (2.39 g, 19.6 mmol), and $Boc_2O$ (8.54 g, 39.1 mmol). The resulting mixture was stirred at 25° C. for 1 h, then concentrated. The residue was purified by column chromatography on silica gel (PE/EtOAc=10/1, 5/1) to give the title compound. MS: m/z=487.4 (M+1).

Step D: tert-Butyl (5,6-bis(hydroxymethyl)-2-phenylpyridin-3-yl)carbamate

To a mixture of dimethyl 5-((tert-butoxycarbonyl)amino)-6-phenylpyridine-2,3-dicarboxylate (3.80 g, 7.81 mmol) in THF (60 mL) at 0° C. was added LiAlH₄ (1.19 g, 31.2 mmol) in portions. The resulting mixture was stirred at 0° C. for 1 h and water (1.2 mL) and 15% aqueous sodium hydroxide solution (1.2 mL) were added sequentially. Mg₂SO₄ (5 g) was added and the mixture was filtered and the filtrate was concentrated to give the title compound. MS: m/z=331.1 (M+1).

Step E: tert-Butyl (6-(4-methoxybenzyl)-2-phenyl-6,7-dihydro-5H-pyrrolo[3,4-b]pyridin-3-yl)carbamate To a stirred solution of tert-butyl (5,6-bis(hydroxymethyl)-2-phenylpyridin-3-yl)carbamate (2.62 g, 7.93 mmol) and Et₃N (4.01 g, 39.7 mmol) in DCM (50 mL) at 0° C. was added dropwise MsCl (2.00 g, 17.5 mmol). The resulting mixture was stirred at 0° C. for 30 min before a solution of (4-methoxyphenyl)methanamine (1.31 g, 9.52 mmol) in DCM (0.5 mL) was added. The mixture was warmed to 25° C. where it was stirred for 16 h, then concentrated. The residue was purified by column chromatography on silica gel (PE/EtOAc=3/1) to give the title compound. MS: m/z=432.2 (M+1).

Step F: 2-Phenyl-6,7-dihydro-5H-pyrrolo[3,4-b]pyridin-3-amine

A mixture of tert-butyl (6-(4-methoxybenzyl)-2-phenyl-6,7-dihydro-5H-pyrrolo[3, 4-b]pyridin-3-yl) carbamate (200 mg, 0.463 mmol) in TFA (5 mL) was heated at 110° C. for 50 min under microwave irradiation. The reaction mixture was concentrated to give the title compound. MS: m/z=212.2 (M+1).

Step G: tert-Butyl 3-amino-2-phenyl-5H-pyrrolo[3,4-b]pyridine-6(7H)-carboxylate

A solution of 2-phenyl-6,7-dihydro-5H-pyrrolo[3,4-b]pyridin-3-amine (100 mg, 0.473 mmol) in DCM (2 mL) was added TEA (0.066 mL, 0.47 mmol) and Boc₂O (0.110 mL, 0.473 mmol). The resulting mixture was stirred at 25° C. for 1 h then concentrated. The residue was purified by preparative TLC (PE/EtOAc=1/1) to give the title compound. MS: m/z=312.2 (M+1).

REACTION SCHEME FOR INTERMEDIATE A43

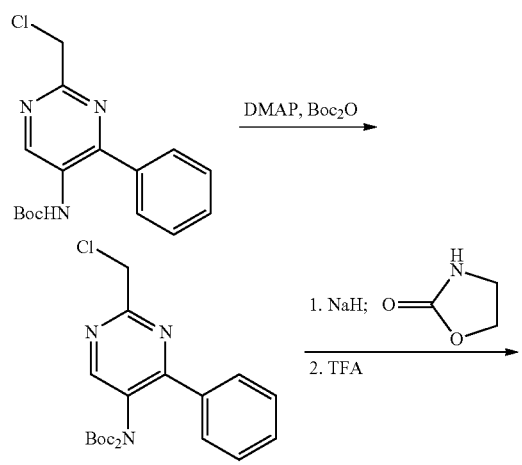

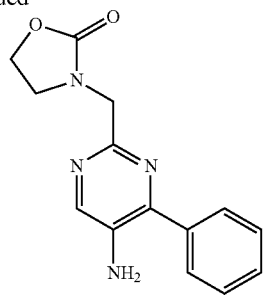

Intermediate A43

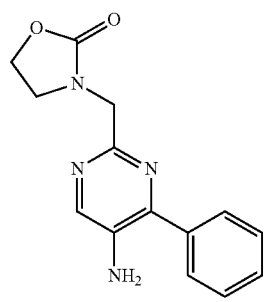 [SMILES: Nc1cnc(CN2CCOC2=O)nc1-c1ccccc1]

3-((5-Amino-4-phenylpyrimidin-2-yl)methyl)oxazolidin-2-one

Step A: Di-tert-butyl (2-(chloromethyl)-4-phenylpyrimidin-5-yl)carbamate

A solution of tert-butyl (2-(chloromethyl)-4-phenylpyrimidin-5-yl)carbamate (573 mg, 1.79 mmol), DMAP (438 mg, 3.58 mmol), and Boc₂O (0.832 ml, 3.58 mmol) in CH₂Cl₂ (18 mL) was stirred at 25° C. for 1 h. The product mixture was partitioned between water and 1,2-dichloroethane (2×). The combined organic extracts were dried over Na₂SO₄, filtered and concentrated. The residue was purified by flash chromatography (SiO₂, 120 g cartridge), eluting with EtOAc/hexanes (0% to 40%) to provide the title compound. MS: m/z=420 (M+1).

Step B: 3-((5-Amino-4-phenylpyrimidin-2-yl)methyl)oxazolidin-2-one

NaH (60 wt. %, 140 mg, 3.50 mmol) was added to a solution of di-tert-butyl (2-(chloromethyl)-4-phenylpyrimidin-5-yl)carbamate (147 mg, 0.350 mmol) and 2-oxazolidone (305 mg, 3.50 mmol) in DMF (4 mL) at 23° C. The resulting mixture was stirred 1 h and then partitioned between saturated aqueous NH₄Cl solution and ethyl acetate (2×). The combined extracts were dried over Na₂SO₄, filtered and concentrated. A mixture of the residue and TFA (0.027 mL, 0.35 mmol) in DCM (4 mL) was stirred at 23° C. for 1 h then concentrated. The residue was partitioned between saturated aqueous sodium bicarbonate solution and DCM (2×). The combined organic layers were dried over sodium sulfate and concentrated. This residue was purified by flash chromatography (SiO$_2$, 40 g cartridge), eluting with MeOH/CH$_2$Cl$_2$ (0% to 15%) to give the title compound. MS: m/z=271 (M+1).

REACTION SCHEME FOR INTERMEDIATE B1

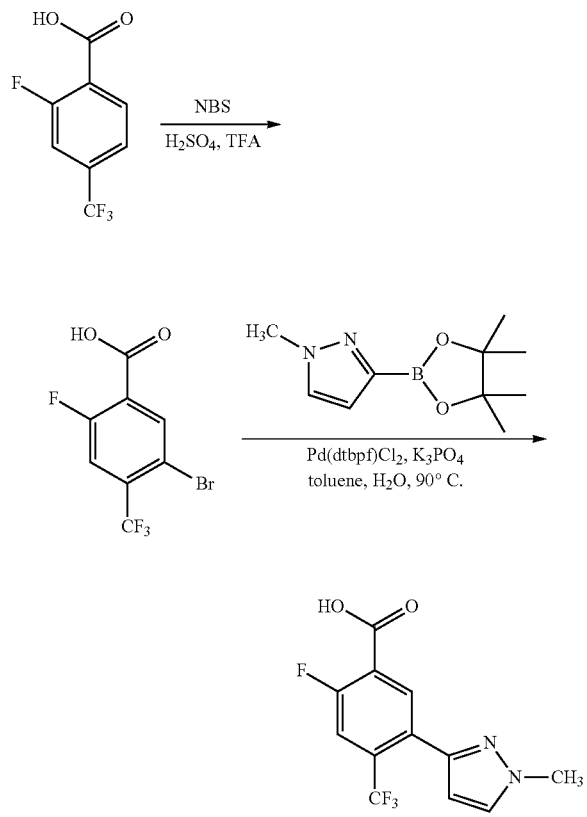

2-Fluoro-5-(1-methyl-1H-pyrazol-3-yl)-4-(trifluoromethyl)benzoic acid

Step A:
5-Bromo-2-fluoro-4-(trifluoromethyl)benzoic acid

N-Bromosuccinimide (23.1 g, 130 mmol) was added portionwise to a mixture of 2-fluoro-4-(trifluoromethyl) benzoic acid (15.0 g, 72.1 mmol), sulfuric acid (9.0 mL, 170 mmol, 18 M), and TFA (50.0 mL, 650 mmol) at 50° C. and the resulting mixture was stirred at 50° C. for 18 h. Additional N-bromosuccinimide (3.0 g, 16 mmol) was added and the mixture was stirred at 50° C. for 4 h. The reaction mixture was cooled and water (150 mL) was added. The resulting precipitate was collected and dried to give the title compound. $^1$H NMR (400 MHz, CDCl$_3$) δ 9.90 (s, 1H), 8.35 (d, J=6.3 Hz, 1H), 7.55 (d, J=10.3 Hz, 1H).

Step B: 2-Fluoro-5-(1-methyl-1H-pyrazol-3-yl)-4-(trifluoromethyl)benzoic acid

To a deoxygenated mixture of 5-bromo-2-fluoro-4-(trifluoromethyl)benzoic acid (5.0 g, 17 mmol), 1-(methyl)-3-(4,4,5,5-tetramethyl-1,3,2-dioxaborolan-2-yl)-1H-pyrazole (4.35 g, 20.9 mmol) and K$_3$PO$_4$ (11.1 g, 52.3 mmol) in toluene (55 mL) and H$_2$O (7 mL) was added 1,1'-bis(di-tert-butylphosphino)ferrocene palladium dichloride (1.14 g, 1.74 mmol). The resulting mixture was heated at 90° C. for 2 h, and then stirred at 50° C. for 18 h. The mixture was cooled and filtered. The filtrate was concentrated and the residue was partitioned between water (200 mL) and EtOAc (300 mL). The aqueous layer was acidified to pH 5 with aqueous HCl solution (1 N) and the resulting precipitate was collected and dried to give the title compound. MS: m/z=289 (M+1). $^1$H NMR (400 MHz, DMSO-d$_6$) δ 13.85 (s, 1H), 8.11 (d, 1H), 7.82 (m, 2H), 6.45 (s, 1H), 3.92 (s, 3H).

The following intermediate was prepared in similar fashion to the procedure described above.

| Compound Number | Structure | Compound Name | LCMS (M + 1) |
|---|---|---|---|
| B2 | 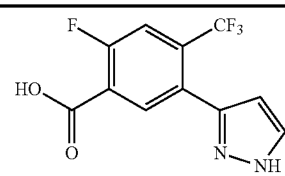 | 2-fluoro-5-(1H-pyrazol-3-yl)-4-(trifluoromethyl)benzoic acid | 275.5 |

Intermediate B1

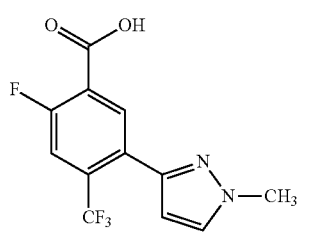 [SMILES: Cn1ccc(-c2cc(C(=O)O)c(F)cc2C(F)(F)F)n1]

Intermediate B3

3-Bromo-4-(trifluoromethyl)benzoic acid

Step A: Methyl 3-bromo-4-(trifluoromethyl)benzoate t-BuONO (79.0 g, 765 mmol) was added to a solution of methyl 3-amino-4-(trifluoromethyl)benzoate (67.0 g, 306 mmol) and CuBr (88.0 g, 612 mmol) in acetonitrile (1000 mL) at 0° C., and the resulting mixture was warmed to 25° C. and stirred for 12 h. The mixture was then poured into EtOAc (600 mL) and filtered. The filtrate was washed with an aqueous HCl solution (1 M, 200 mL×3), then brine (200 mL), dried over $Na_2SO_4$ and concentrated. The residue was purified by column chromatography on silica gel (PE: EA=200:1) to give the title compound. MS: m/z=283, 285 (M+1). $^1$H NMR (400 MHz, CDCl$_3$) δ 8.37 (s, 1H), 8.06 (d, J=8.0 Hz, 1H), 7.77 (d, J=8.0 Hz, 1H), 3.97 (s, 3H).

Step B: 3-Bromo-4-(trifluoromethyl)benzoic acid

A mixture of methyl 3-bromo-4-(trifluoromethyl)benzoate (5.0 g, 17.7 mmol) in aqueous NaOH solution (1 M, 100 mL) was stirred at 25° C. for 12 h. The mixture was acidified to pH 6 with aqueous HCl solution (1 M), and the resulting aqueous mixture was extracted with EtOAc (30 mL×3). The combined organic layers were dried over $Na_2SO_4$ and then concentrated to give the title compound. MS: m/z=270 (M+1). $^1$H NMR (400 MHz, CDCl$_3$) δ 8.44 (s, 1H), 8.14 (d, J=8.0 Hz, 1H), 7.83 (d, J=8.0 Hz, 1H).

REACTION SCHEME FOR INTERMEDIATE B4

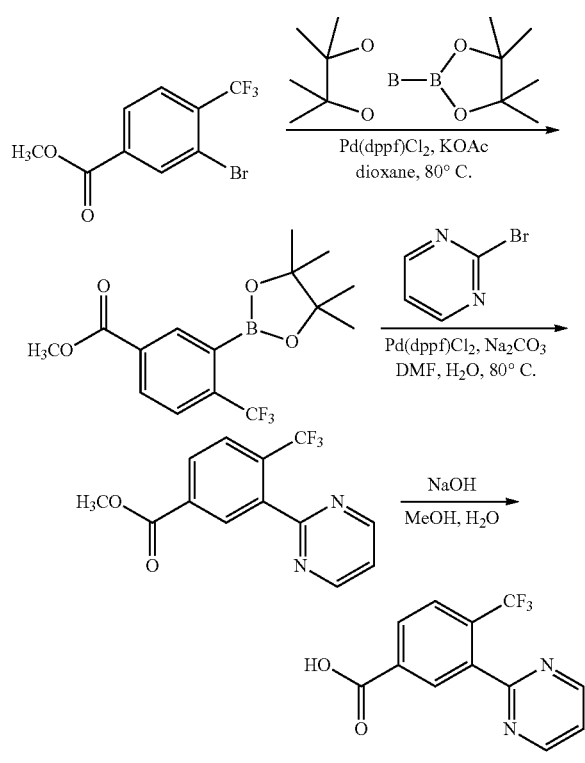

Intermediate B4

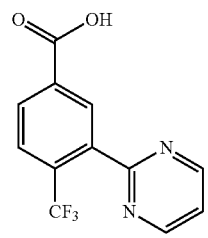 [SMILES: O=C(O)c1ccc(C(F)(F)F)c(-c2ncccn2)c1]

3-(Pyrimidin-2-yl)-4-(trifluoromethyl)benzoyl chloride

Step A: Methyl 3-(4,4,5,5-tetramethyl-1,3,2-dioxaborolan-2-yl)-4-(trifluoromethyl)benzoate To a deoxygenated mixture of methyl 3-bromo-4-(trifluoromethyl)benzoate (20.0 g, 70.7 mmol), 4,4,4',4',5,5,5',5'-octamethyl-2,2'-bi(1,3,2-dioxaborolane) (26.9 g, 106 mmol) and potassium acetate (20.8 g, 212 mmol) in dioxane (300 mL) was added PdCl$_2$(dppf) (2.59 g, 3.50 mmol), and the resulting mixture was heated at 80° C. for 5 h. The mixture was cooled and filtered. The filtrate was concentrated and the residue was partitioned between water (100 mL) and EtOAc (200 mL). The organic layer was washed with brine (100 mL), dried over $Na_2SO_4$ and concentrated. The residue was purified by column chromatography on silica gel (PE: EtOAc=15:1) to give the title compound. MS: m/z=331 (M+1).

Step B: Methyl 3-(pyrimidin-2-yl)-4-(trifluoromethyl)benzoate

To a deoxygenated mixture of methyl 3-(4,4,5,5-tetramethyl-1,3,2-dioxaborolan-2-yl)-4-(trifluoromethyl)benzoate (12.0 g, 36.4 mmol), 2-bromopyrimidine (8.67 g, 54.5 mmol) and sodium carbonate (11.6 g, 109 mmol) in DMF (450 mL) and water (60 mL) was added PdCl$_2$(dppf) (1.3 g, 1.8 mmol), and the resulting mixture was heated at 80° C. for 5 h. The mixture was cooled and filtered. The filtrate was concentrated and the residue was partitioned between water (100 mL) and EtOAc (200 mL). The combined organic layer was washed with brine (100 mL), dried over $Na_2SO_4$ and concentrated. The residue was purified by column chromatography on silica gel (PE:EtOAc=5:1) to give the title compound. MS: m/z=283 (M+1).

Step C: 3-(Pyrimidin-2-yl)-4-(trifluoromethyl)benzoic acid

A mixture of methyl 3-(pyrimidin-2-yl)-4-(trifluoromethyl)benzoate (7.0 g, 25 mmol) and NaOH (3.0 g, 74 mmol) in a 3:1 mixture of MeOH and H$_2$O (120 mL) was heated at 30° C. for 16 h. The reaction mixture was cooled and then partitioned between water (30 mL) and MTBE (2×60 mL). The aqueous layer was acidified to pH 4 with aqueous HCl solution (2 N). The precipitate was filtered, washed with water and dried to afford the title compound. MS: m/z=269 (M+1). $^1$H NMR (400 MHz, CD$_3$OD) δ 8.92 (d, J=5.0 Hz, 1H), 8.30 (m, 2H), 7.97 (d, J=8.0 Hz, 1H), 7.55 (t, J=4.9 Hz, 1H).

The following intermediates were prepared in similar fashion to the procedure described above.
| Compound Number | Structure | Compound Name | LCMS (M + 1) |
|---|---|---|---|
| B5 | 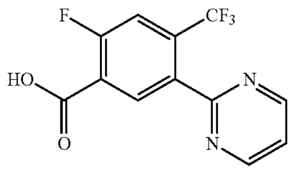 [SMILES: O=C(O)c1cc(-c2ncccn2)c(C(F)(F)F)cc1F] | 2-fluoro-5-(pyrimidin-2-yl)-4-(trifluoromethyl)benzoic acid | 301.1 |
| B6 | 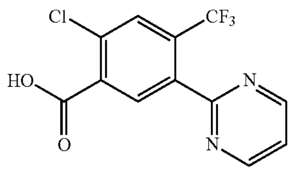 [SMILES: O=C(O)c1cc(-c2ncccn2)c(C(F)(F)F)cc1Cl] | 2-chloro-5-(pyrimidin-2-yl)-4-(trifluoromethyl)benzoic acid | 303.1 |
| B7 | 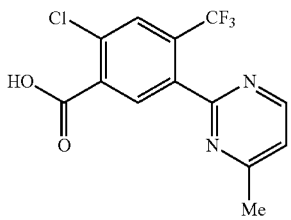 [SMILES: Cc1ccnc(-c2cc(C(=O)O)c(Cl)cc2C(F)(F)F)n1] | 2-chloro-5-(4-methylpyrimidin-2-yl)-4-(trifluoromethyl)benzoic acid | 317.1 |
REACTION SCHEME FOR INTERMEDIATE B8
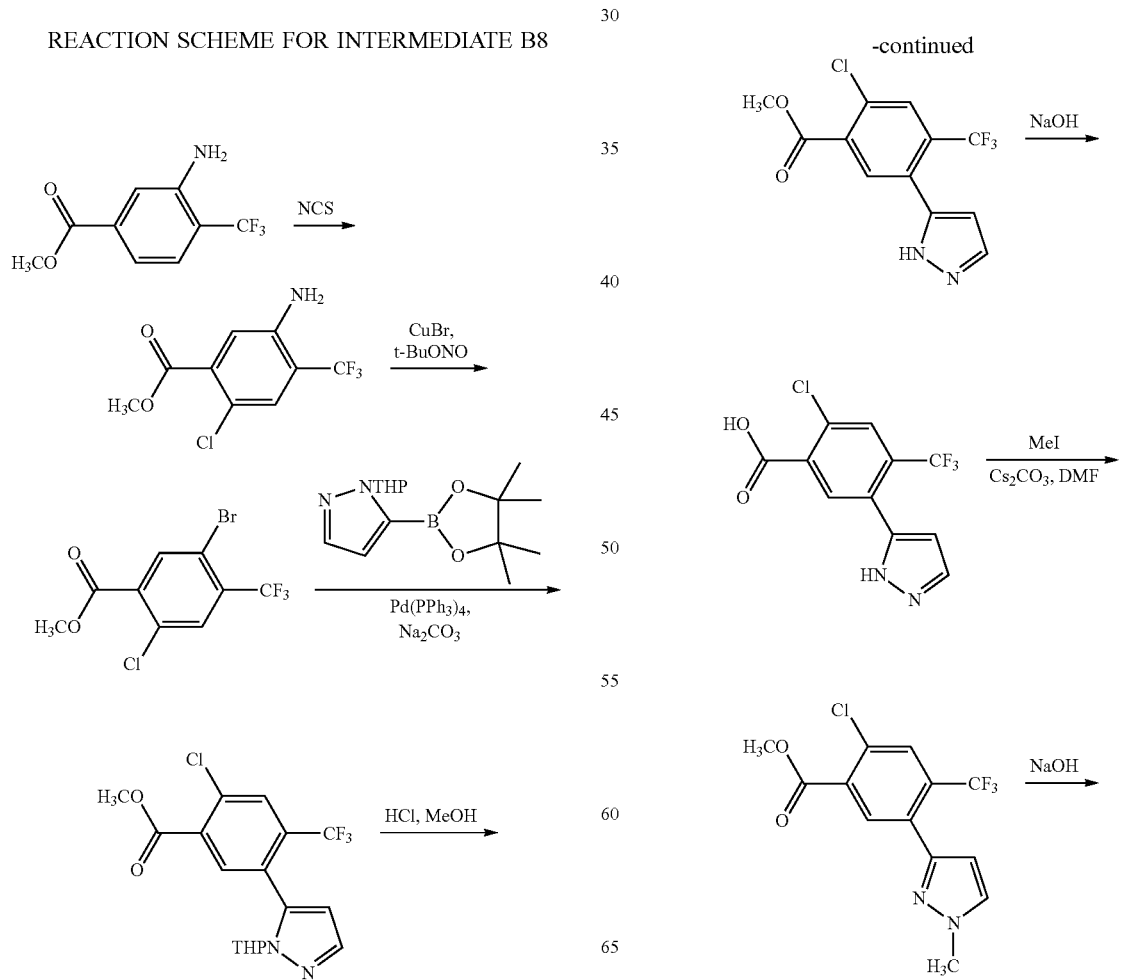

-continued

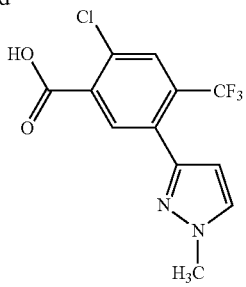

Intermediate B8

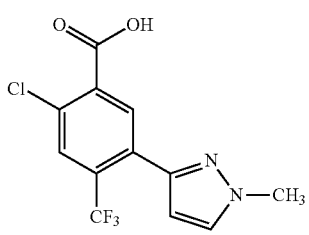 [SMILES: Cn1ccc(-c2cc(C(=O)O)c(Cl)cc2C(F)(F)F)n1]

2-Chloro-5-(1-methyl-1H-pyrazol-3-yl)-4-(trifluoromethyl)benzoic acid

Step A: Methyl 5-amino-2-chloro-4-(trifluoromethyl)benzoate

N-Chlorosuccinimide (8.2 g, 61 mmol) was added to a solution of methyl 3-amino-4-(trifluoromethyl)benzoate (13.2 g, 60.0 mmol) in acetonitrile (200 mL), and the resulting mixture was heated at 80° C. for 20 h. After cooling, the mixture was partitioned between water (500 mL) and EtOAc (2×300 mL). The combined organic layers were washed with brine (200 mL), dried over $Na_2SO_4$, and concentrated. The residue was purified by column chromatography on silica gel (PE:EtOAc=6:1) to afford the title compound. MS: m/z=254 (M+1). $^1H$ NMR (400 MHz, $CDCl_3$) δ 7.49 (s, 1H), 7.17 (s, 1H), 3.92 (s, 3H).

Step B: Methyl 5-bromo-2-chloro-4-(trifluoromethyl)benzoate t-Butyl nitrite (4.60 g, 44.5 mmol) and methyl 5-amino-2-chloro-4-(trifluoromethyl)benzoate (4.50 g, 17.8 mmol) were added portionwise to a suspension of copper(I) bromide (5.10 g, 35.6 mmol) in DCM (100 mL). The resulting mixture was heated at 60° C. for 2 h. After cooling, the mixture was diluted with water (50 mL) and aqueous HCl solution (2 M, 50 mL) and then extracted with EtOAc (80 mL×2). The combined organic layers were washed with water (100 mL), then brine (80 mL), dried over $Na_2SO_4$ and concentrated. The residue was purified by flash column chromatography on silica (PE:EtOAc from 50:1 to 30:1) to afford the title compound. MS: m/z=319 (M+1). $^1H$ NMR (400 MHz, $CDCl_3$) δ 8.15 (s, 1H), 7.77 (s, 1H), 3.97 (s, 3H).

Step C: Methyl-2-chloro-5-(1-(tetrahydro-2H-pyran-2-yl)-1H-pyrazol-5-yl)-4-(trifluoromethyl)benzoate To a deoxygenated mixture of methyl 5-bromo-2-chloro-4-(trifluoromethyl)benzoate (4.6 g, 14 mmol), 1-(tetrahydro-2H-pyran-2-yl)-5-(4,4,5,5-tetramethyl-1,3,2-dioxaborolan-2-yl)-1H-pyrazole (4.86 g, 17.5 mmol) and $Na_2CO_3$ (4.0 g, 44 mmol) in DMF (150 mL) and $H_2O$ (24 mL) was added $Pd(PPh_3)_4$ (686 mg, 0.58 mmol). The resulting mixture was heated at 80° C. for 5 h, then cooled and filtered. The filtrate was concentrated and the residue was partitioned between water (200 mL) and EtOAc (300 mL). The organic layer was washed with brine (100 mL), dried over $Na_2SO_4$ and concentrated. The residue was purified by column chromatography on silica gel (PE/EtOAc=10/1) to give the title compound. MS: m/z=389 (M+1).

Step D: Methyl 2-chloro-5-(1H-pyrazol-5-yl)-4-(trifluoromethyl)benzoate

A solution of methyl-2-chloro-5-(1-(tetrahydro-2H-pyran-2-yl)-1H-pyrazol-5-yl)-4-(trifluoromethyl)benzoate (2.5 g, 6.4 mmol) in a solution of HCl in MeOH (4M, 50 mL) was stirred at 15° C. for 1 h and then concentrated to give the title compound. MS: m/z=305 (M+1).

Step E: 2-Chloro-5-(1H-pyrazol-5-yl)-4-(trifluoromethyl)benzoic acid

A solution of NaOH (1.2 g, 0.030 mol) in $H_2O$ (15 mL) was added to a solution of methyl 2-chloro-5-(1H-pyrazol-5-yl)-4-(trifluoromethyl)benzoate (2.3 g, 7.6 mmol) in MeOH (45 mL), and the resulting mixture was stirred at 15° C. for 16 h. The majority of the MeOH was removed under reduced pressure and the remaining aqueous mixture was partitioned between MTBE (50 mL) and water (50 mL). The aqueous layer was acidified to pH 5 with aqueous HCl solution (3 N). The precipitate was filtered, washed with water (50 mL×2) and dried to give the title compound. MS: m/z=291 (M+1).

Step F: Methyl 2-chloro-5-(1-methyl-1H-pyrazol-3-yl)-4-(trifluoromethyl)benzoate and methyl 2-chloro-5-(1-methyl-1H-pyrazol-5-yl)-4-(trifluoromethyl)benzoate A mixture of 2-chloro-5-(1H-pyrazol-5-yl)-4-(trifluoromethyl)benzoic acid (500 mg, 1.72 mmol), $Cs_2CO_3$ (1.7 g, 5.2 mmol) and iodomethane (0.54 mL, 8.6 mmol) in DMF (15 mL) was heated at 80° C. for 2 h. The reaction mixture was cooled and filtered, and the filtrate was concentrated. The residue was partitioned between water (50 mL) and EtOAc (30 mL×3). The combined organic layers were washed with $H_2O$ (50 mL×3), then brine (50 mL), dried over $Na_2SO_4$ and concentrated to give the title compound. MS: m/z=319 (M+1).

Step G: 2-Chloro-5-(1-methyl-1H-pyrazol-3-yl)-4-(trifluoromethyl)benzoic acid

A solution of NaOH (414 mg, 10.4 mmol) in $H_2O$ (5 mL) was added to a mixture of methyl 2-chloro-5-(1-methyl-1H-pyrazol-3-yl)-4-(trifluoromethyl)benzoate and methyl 2-chloro-5-(1-methyl-1H-pyrazol-5-yl)-4-(trifluoromethyl) benzoate (550 mg, 3.5 mmol) in MeOH (15 mL). The resulting mixture was stirred at 15° C. for 16 h. The majority of the MeOH was removed under reduced pressure and the resulting aqueous solution was partitioned between MTBE (30 mL) and water (30 mL). The aqueous layer was acidified to pH 4 with an aqueous HCl solution (3 N). The resulting suspension was then extracted with EtOAc (50 mL×2). The combined organic layers were washed with brine (50 mL), dried over Na$_2$SO$_4$ and concentrated. The residue was recrystallized from MeOH (1 g/5 mL) to give the title compound. MS: m/z=305 (M+1). $^1$H NMR (400 MHz, CDCl$_3$) δ 8.36 (s, 1H), 7.86 (s, 1H), 7.48 (d, J=2.3 Hz, 1H), 6.59 (s, 1H), 4.15 (s, 3H).

The following intermediates were prepared in similar fashion using the corresponding tributylstannane reagent in the palladium catalyzed cross-coupling reaction.

| Compound Number | Structure | Compound Name | LCMS (M + 1) |
|---|---|---|---|
| B9 | 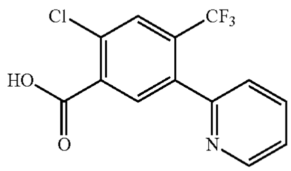 [SMILES: O=C(O)c1cc(-c2ccccn2)c(C(F)(F)F)cc1Cl] | 2-chloro-5-(pyridin-2-yl)-4-(trifluoromethyl)benzoic acid | 302 |
| B10 | 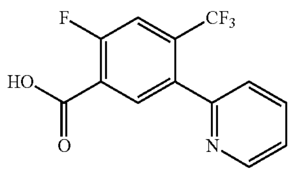 [SMILES: O=C(O)c1cc(-c2ccccn2)c(C(F)(F)F)cc1F] | 2-fluoro-5-(pyridin-2-yl)-4-(trifluoromethyl)benzoic acid | 286.0 |

Intermediate B11

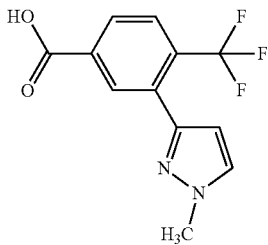 [SMILES: Cn1ccc(-c2cc(C(=O)O)ccc2C(F)(F)F)n1]

3-(1-Methyl-1H-pyrazol-3-yl)-4-(trifluoromethyl)benzoic acid

Step A: 4-Bromo-3-nitrobenzoic acid

4-Bromobenzoic acid (100 g, 0.5 mol) was added portionwise to aqueous HNO$_3$ solution (16 M, 200 mL), keeping the temperature between 0 and 25° C., followed by the dropwise addition of aqueous H$_2$SO$_4$ solution (18 M, 240 mL) at ambient temperature. The resulting mixture was stirred at ambient temperature for 4 h, and then carefully diluted with 1.5 L of water. The precipitate was filtered, washed with water, and dried to give the title compound. MS: m/z=246.0, 248.0 (M+1). $^1$H NMR (400 MHz, DMSO) δ 8.42 (s, 1H), 8.04 (s, 2H).

Step B: Methyl 4-bromo-3-nitrobenzoate

To a solution of 4-bromo-3-nitrobenzoic acid (115 g, 47.0 mmol) in MeOH (600 mL) was added aqueous H$_2$SO$_4$ solution (18 M, 200 mL) at ambient temperature. The mixture was heated at reflux for 2 h, and then cooled and filtered. The filtered solid was washed with water and dried to give the title compound. MS: m/z=260, 262 (M+1). $^1$H NMR (400 MHz, DMSO-d$_6$) δ 8.48 (s, 3H), 8.09 (s, 2H), 3.91 (s, 3H).

Step C: Methyl 3-nitro-4-(trifluoromethyl)benzoate

To a solution of methyl 4-bromo-3-nitrobenzoate (175 g, 0.670 mol) in anhydrous DMF (1.0 L) was added CuI (140 g, 0.73 mol) under N$_2$ atmosphere. After stirring at ambient temperature for 10 min, FSO$_2$CF$_2$CO$_2$CH$_3$ (185 mL, 0.730 mol) was added and the vented mixture was heated at 110° C. for 3 h until gas evolution ceased. The mixture was then cooled and filtered through Celite®, washing with EtOAc. The filtrate was concentrated and the residue was partitioned between water (400 mL) and MTBE. The organic layer was washed with water, then brine, dried over anhydrous Na$_2$SO$_4$ and concentrated. The residue was recrystallized from DCM/MeOH (5/1) to give the title compound. The mother liquor was concentrated and the residue purified by silica gel column chromatography (PE/EtOAc=20/1) to give additional title compound. MS: m/z=250.0 (M+1). $^1$H NMR (400 MHz, DMSO-d$_6$) δ 8.55 (br s, 1H), 8.39 (d, J=7.5 Hz, 1H), 8.19 (d, J=8.0 Hz, 1H), 3.88-3.99 (m, 3H).

Step D: Methyl 3-amino-4-(trifluoromethyl)benzoate

A solution of methyl 3-nitro-4-(trifluoromethyl)benzoate (102 g, 0.410 mol) and 10% Pd/C (10 g, 10 wt %) in MeOH (1.0 L) was stirred under H$_2$ (35 psi) at 30° C. for 12 h. The suspension was filtered through Celite®, washing with MeOH (30 mL×3). The filtrate was concentrated to give the title compound. MS: m/z=220.0 (M+1). $^1$H NMR (400 MHz, DMSO-d$_6$) δ 7.40-7.50 (m, 2H), 7.09-7.15 (m, 1H), 5.92 (s, 2H), 3.82 (s, 3H).

Step E: Methyl 3-bromo-4-(trifluoromethyl)benzoate

Methyl 3-amino-4-(trifluoromethyl)benzoate (40 g, 180 mmol) was added portionwise to a suspension of CuBr (53.0 g, 365 mmol) and t-BuONO (47 g, 460 mmol) in acetonitrile (600 mL) at 0° C. The resulting mixture was stirred at 0° C. for 2 h, and then warmed to 25° C. and stirred for 16 h. The mixture was partitioned between EtOAc and aqueous HCl solution (1 M, 200 mL×4). The organic layer was washed with brine (200 mL), dried over Na$_2$SO$_4$ and concentrated.

The residue was purified by column chromatography on silica gel (PE/EtOAc=200/1) to afford the title compound. MS: m/z=283, 285 (M+1). ¹H NMR (400 MHz, CDCl₃) δ 8.37 (s, 1H), 8.06 (d, J=8.0 Hz, 1H), 7.77 (d, J=8.0 Hz, 1H), 3.97 (s, 3H).

Step F: Methyl 3-(1-(tetrahydro-2H-pyran-2-yl)-1H-pyrazol-5-yl)-4-(trifluoromethyl) benzoate A deoxygenated mixture of methyl 3-bromo-4-(trifluoromethyl)benzoate (5.0 g, 17 mmol), 1-(tetrahydro-2H-pyran-2-yl)-5-(4,4,5,5-tetramethyl-1,3,2-dioxaborolan-2-yl)-1H-pyrazole (5.9 g, 21 mmol), Pd(PPh₃)₄ (0.80 g, 0.69 mmol), and aqueous Na₂CO₃ solution (2 M, 26 mL, 53 mmol) in DMF (150 mL) was heated at 70° C. under N₂ for 2 h. The mixture was concentrated and the residue was partitioned between EtOAc (200 mL) and water (100 mL). The organic layer was washed with brine (100 mL), then dried over Na₂SO₄ and concentrated. The residue was purified by column chromatography on silica gel (PE/EtOAc=10/1) to give the title compound. MS: m/z=355.0 (M+1). ¹H NMR (400 MHz, DMSO) δ 8.37 (s, 1H), 8.06 (d, J=8.0 Hz, 1H), 7.77 (d, J=8.0 Hz, 1H), 3.97 (s, 3H).

Step G: Methyl 3-(1H-pyrazol-5-yl)-4-(trifluoromethyl)benzoate

To a solution of methyl 3-(1-(tetrahydro-2H-pyran-2-yl)-1H-pyrazol-5-yl)-4-(trifluoromethyl)benzoate (5.0 g, 14 mmol) in MeOH (100 mL) was added a solution of HCl in MeOH (40 mL, 4 M). The mixture was stirred at 10° C. for 0.5 h then concentrated to give the title compound. MS: m/z=271.0 (M+1).

Step H: Methyl 3-(1-methyl-1H-pyrazol-3-yl)-4-(trifluoromethyl)benzoate and methyl 3-(1-methyl-1H-pyrazol-5-yl)-4-(trifluoromethyl)benzoate To a solution of methyl 3-(1H-pyrazol-5-yl)-4-(trifluoromethyl)benzoate (7.0 g, 26 mmol) in DMF (150 mL) was added Cs₂CO₃ (17 g, 52 mmol) and CH₃I (4.8 mL, 78 mmol). The reaction mixture was heated at 80° C. for 2 h, then cooled and concentrated. The residue was partitioned between water (150 mL) and EtOAc (100 mL×3). The combined organic layers were washed with brine (150 mL), dried over Na₂SO₄ and concentrated to give a mixture of methyl 3-(1-methyl-1H-pyrazol-3-yl)-4-(trifluoromethyl) benzoate and methyl 3-(1-methyl-1H-pyrazol-5-yl)-4-(trifluoromethyl)benzoate. MS: m/z=285.0 (M+1).

Step I: 3-(1-Methyl-1H-pyrazol-3-yl)-4-(trifluoromethyl)benzoic acid

To a solution of methyl 3-(1-methyl-1H-pyrazol-3-yl)-4-(trifluoromethyl)benzoate and methyl 3-(1-methyl-1H-pyrazol-5-yl)-4-(trifluoromethyl)benzoate (6.5 g, 23 mmol) in MeOH (100 mL) was added aqueous NaOH solution (35 mL, 2 M). The mixture was heated at 50° C. for 50 min then cooled. The majority of the MeOH was removed under reduced pressure and the resulting aqueous solution was partitioned between EtOAc (100 mL) and water (150 mL). The aqueous layer was acidified to pH 5 with aqueous HCl solution (1 N) and then further extracted with EtOAc (150 mL×2). The combined organic layers were washed with brine (150 mL), dried over anhydrous Na₂SO₄ and concentrated. The residue was purified by recrystallization from MeOH (1 g/5 mL) to provide the title compound. MS: m/z=271.0 (M+1). ¹H NMR (400 MHz, DMSO) δ 13.43-13.68 (m, 1H) 8.18-8.24 (m, 1H), 8.05-8.12 (m, 1H), 7.92-7.99 (m, 1H), 7.77-7.84 (m, 1H), 6.43-6.52 (m, 1H), 3.93 (s, 3H).

The following intermediate was prepared in similar fashion to the procedure described above.

| Compound Number | Structure | Compound Name | LCMS (M + 1) |
|---|---|---|---|
| B12 | 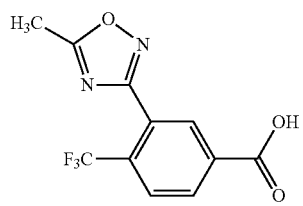 [SMILES: Cc1nc(-c2cc(C(=O)O)ccc2C(F)(F)F)no1] | 3-(1H-pyrazol-3-yl)-4-(trifluoromethyl) benzoic acid | 257.1 |

Intermediate B13

3-(5-Methyl-1,2,4-oxadiazol-3-yl)-4-(trifluoromethyl)benzoic acid

Step A: Methyl 3-cyano-4-(trifluoromethyl)benzoate

To a mixture of methyl 3-amino-4-(trifluoromethyl)benzoate (15 g, 0.073 mol) and aqueous HCl solution (12 M, 24 mL) in H₂O (100 mL) at 0° C. was added dropwise a solution of NaNO₂ (5.5 g, 0.080 mol) in H₂O (30 mL). The reaction was stirred at 0° C. for 30 min and then added dropwise to a slurry of CuCN (7.1 g, 0.080 mol) and KCN (8.4 g, 0.13 mol) in H₂O (200 mL), while maintaining the internal temperature between 5-10° C. After the addition was complete, the reaction was heated at 80° C. for 1 h. The mixture was cooled and the solution was extracted with EtOAc (200 mL×4). The combined organic layers were dried over anhydrous Na₂SO₄ and concentrated. The residue was purified by column chromatography on silica gel (2% EtOAc in PE) to afford the title compound. MS: m/z=230.0 (M+1). ¹H NMR (400 MHz, CDCl₃) δ 8.46-8.53 (m, 1H), 8.33-8.42 (m, 1H), 7.87-7.95 (m, 1H), 4.01 (s, 3H).

Step B: Methyl 3-(N'-hydroxycarbamimidoyl)-4-(trifluoromethyl)benzoate

To a mixture of methyl 3-cyano-4-(trifluoromethyl)benzoate (1.6 g, 7.0 mmol) and hydroxylamine hydrochloride (0.98 g, 14 mmol) in MeOH (20 mL) was added NaHCO₃ (2.3 g, 28 mmol). The resulting mixture was heated at 85° C. for 5 h, then cooled and concentrated. The residue was purified by column chromatography on silica gel (40% EtOAc in PE) to afford the title compound. MS: m/z=263.0 (M+1). ¹H NMR (400 MHz, CDCl₃) δ 8.26 (s, 1H), 8.18-

8.21 (d, J=8.4 Hz, 1H), 7.80-7.83 (d, J=8.0 Hz, 1H), 7.52 (s, 1H), 4.89 (s, 2H), 3.96 (s, 3H).

Step C: Methyl 3-(N-acetyl-N'-hydroxycarbamimidoyl)-4-(trifluoromethyl) benzoate To a solution of methyl 3-(N'-hydroxycarbamimidoyl)-4-(trifluoromethyl) benzoate (282 mg, 1.07 mmol) and TEA (0.30 mL, 2.14 mmol) in anhydrous DCM (20 mL) at 25° C. was added AcCl (0.083 mL, 1.18 mmol). The resulting mixture was heated at 30° C. for 20 min, then cooled and concentrated to give the title compound. MS: m/z=305.0 (M+1).

Step D: Methyl 3-(5-methyl-1,2,4-oxadiazol-3-yl)-4-(trifluoromethyl)benzoate

A solution of methyl 3-(N-acetyl-N'-hydroxycarbamimidoyl)-4-(trifluoromethyl) benzoate (0.28 g, 0.93 mmol) in toluene (10 mL) was heated at 110° C. for 2 h, then cooled and concentrated. The residue was purified by column chromatography on silica gel (30% EtOAc in PE) to afford the title compound. MS: m/z=287.0 (M+1). $^1$H NMR (400 MHz, CDCl$_3$) δ 8.37-8.49 (m, 1H), 8.22-8.32 (m, 1H), 7.87-7.99 (m, 1H), 3.96 (s, 3H), 2.70 (s, 3H).

Step E: 3-(5-Methyl-1,2,4-oxadiazol-3-yl)-4-(trifluoromethyl)benzoic acid

To a solution of methyl 3-(5-methyl-1,2,4-oxadiazol-3-yl)-4-(trifluoromethyl) benzoate (0.13 g, 0.45 mmol) in MeOH (2.0 mL) was added aqueous NaOH solution (2.0 mL, 1 M). The resulting mixture was heated at 50° C. for 1 h, and then cooled and acidified to pH 5 with aqueous HCl solution (1 M). The aqueous mixture was extracted with EtOAc (10 mL×3). The combined organic layers were dried over anhydrous Na$_2$SO$_4$ and concentrated to give the title compound. MS: m/z=273.0 (M+1). $^1$H NMR (400 MHz, CDCl$_3$) δ 8.47 (s, 1H), 8.27 (d, J=8.0 Hz, 1H), 7.91 (d, J=8.8 Hz, 1H), 2.69 (s, 3H).

Intermediate B14

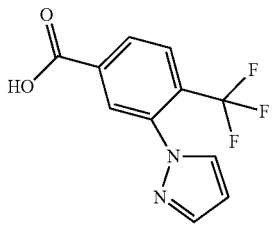 [SMILES: O=C(O)c1ccc(C(F)(F)F)c(-n2cccn2)c1]

3-(1H-Pyrazol-1-yl)-4-(trifluoromethyl)benzoic acid

Step A: Methyl 3-(1H-pyrazol-1-yl)-4-(trifluoromethyl)benzoate

A mixture of methyl 3-bromo-4-(trifluoromethyl)benzoate (0.50 g, 1.8 mmol), pyrazole (0.18 g, 2.6 mmol), Cs$_2$CO$_3$ (1.4 g, 4.4 mmol), CuI (670 mg, 3.52 mmol) and 1,10-phenanthroline (0.13 g, 0.70 mmol) in anhydrous toluene (15 mL) was heated at 140° C. for 1 h under microwave irradiation. After cooling, the reaction mixture was diluted with EtOAc (50 mL) and filtered. The filtrate was concentrated and the residue was purified by preparative TLC (PE/EA=5/1) to give the title compound. MS: m/z=271.0 (M+1).

Step B: 3-(1H-Pyrazol-1-yl)-4-(trifluoromethyl)benzoic acid

To a solution of methyl 3-(1H-pyrazol-1-yl)-4-(trifluoromethyl)benzoate (0.20 g, 0.74 mmol) in MeOH (15 mL) was added aqueous NaOH solution (3.0 mL, 2 M). The mixture was heated at 50° C. for 10 min. The majority of the MeOH was removed under reduced pressure and the resulting aqueous solution was partitioned between EtOAc (30 mL) and water (20 mL). The aqueous layer was acidified to pH 5 with aqueous HCl solution (1 M) and then extracted with EtOAc (30 mL×2). The combined organic layers were washed with brine (30 mL), dried over Na$_2$SO$_4$ and concentrated to give the title compound. MS: m/z=257.0 (M+1). $^1$H NMR (400 MHz, DMSO) δ 8.19 (m, 1H), 8.13 (m, 1H), 8.07 (m, 1H), 7.97 (m, 1H), 7.78 (m, 1H), 6.55 (m, 1H).

Intermediate B15

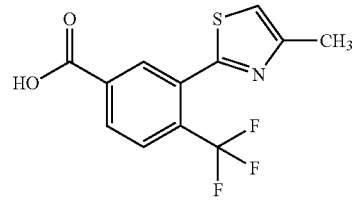 [SMILES: Cc1csc(-c2cc(C(=O)O)ccc2C(F)(F)F)n1]

3-(4-Methylthiazol-2-yl)-4-(trifluoromethyl)benzoic acid

Step A: 3-Amino-4-(trifluoromethyl)benzoic acid

A mixture of 3-nitro-4-(trifluoromethyl)benzoic acid (1.0 g, 4.3 mmol) and 10% Pd/C (0.20 g, 5% wt) in MeOH (20 mL) was stirred under H$_2$ atmosphere (15 psi) at ambient temperature for 12 h. The catalyst was filtered and the filtrate concentrated to afford the title compound. MS: m/z=206.0 (M+1). $^1$H NMR (400 MHz, DMSO) δ 7.46 (s, 1H), 7.38-7.45 (m, 1H), 7.13 (d, J=8.3 Hz, 1H), 5.84 (s, 2H).

Step B: Methyl 3-amino-4-(trifluoromethyl)benzoate

A mixture of 3-amino-4-(trifluoromethyl)benzoic acid (3.4 g, 16 mmol) and aqueous H$_2$SO$_4$ solution (18 M, 2.0 mL) in MeOH (20 mL) was heated at reflux until the starting material was consumed. The mixture was cooled then neutralized to pH 7 by the addition of aqueous NaOH solution (1N). The aqueous mixture was extracted with EtOAc (10 mL×3), and the combined organic combined layers were washed with brine, dried over Na$_2$SO$_4$ and concentrated to afford the title compound. MS: m/z=220.0 (M+1). $^1$H NMR (400 MHz, CDCl$_3$) δ 7.46-7.52 (m, 1H), 7.42 (s, 2H), 4.30 (br s, 2H), 3.92 (s, 3H).

Step C: Methyl 3-cyano-4-(trifluoromethyl)benzoate

To a mixture of methyl 3-amino-4-(trifluoromethyl)benzoate (3.2 g, 15 mmol) and aqueous HCl solution (12 M, 3.5 mL) in water (20 mL) was added dropwise a solution of NaNO$_2$ (1.2 g, 17 mmol) in water (7.0 mL) at 5° C. The resulting mixture was stirred for 30 min at 5° C. and then added dropwise to a slurry of CuCN (1.3 g, 15 mmol) and KCN (1.6 g, 25 mmol) in water (4 mL), while maintaining the internal temperature between 5-10° C. The mixture was stirred at 10° C. for 30 min and then heated at 80° C. for 1 h. After cooling, the mixture was extracted with DCM (30 mL×3). The combined organic layers were washed with brine, dried over Na$_2$SO$_4$ and concentrated to afford the title compound. MS: m/z=230 (M+1). $^1$H NMR (400 MHz, CDCl$_3$) δ 8.45-8.53 (m, 1H), 8.33-8.40 (m, 1H), 7.91 (d, 1H, J=8.5 Hz), 4.01 (s, 3H).

Step D: Methyl 3-carbamothioyl-4-(trifluoromethyl)benzoate

H$_2$S gas was bubbled through a solution of methyl 3-cyano-4-(trifluoromethyl)benzoate (0.10 g, 0.61 mmol) and TEA (0.20 mL, 1.4 mmol) in pyridine (10 mL) at ambient temperature for 30 min. The mixture was concentrated, and the residue was partitioned between water and EtOAc (10 mL×3). The combined organic layers were washed with brine, dried over Na$_2$SO$_4$ and concentrated. The residue was purified by column chromatography on silica gel (PE:EtOAc=5:1) to afford the title compound. MS: m/z=264.0 (M+1). $^1$H NMR (400 MHz, CDCl$_3$) δ 8.25-8.31 (m, 1H), 8.09-8.17 (m, 1H), 7.75 (d, J=8.0 Hz, 1H), 4.45-4.68 (m, 2H), 3.96 (s, 3H).

Step E: Methyl 3-(4-hydroxy-4-methyl-4,5-dihydrothiazol-2-yl)-4-(trifluoromethyl)benzoate A mixture of methyl 3-carbamothioyl-4-(trifluoromethyl)benzoate (100 mg, 0.38 mmol), TEA (0.20 mL, 1.4 mmol) and 1-chloropropan-2-one (0.033 mL, 0.42 mmol) in DMF (3.0 mL) was heated at 120° C. for 4 h, then concentrated. The residue was partitioned between water and EtOAc (10 mL×3). The combined organic layers were washed with brine, dried over Na$_2$SO$_4$ and concentrated. The residue was purified by column chromatography on silica gel (PE:EA=3:1) to afford the title compound. MS: m/z=320.0 (M+1).

Step F: 3-(4-Methylthiazol-2-yl)-4-(trifluoromethyl)benzoic acid

A solution of methyl 3-(4-hydroxy-4-methyl-4,5-dihydrothiazol-2-yl)-4-(trifluoromethyl)-benzoate in aqueous NaOH solution (1 M, 10 mL) was stirred at ambient temperature for 8 h. The mixture was acidified to pH 5 with aqueous HCl solution (1 M) then extracted with EtOAc (10 mL×3). The combined organic layers were washed with brine, dried over Na$_2$SO$_4$ and then concentrated to afford the title compound. MS: m/z=288.0 (M+1). $^1$H NMR (400 MHz, CDCl$_3$) δ 8.23-8.34 (m, 1H), 8.06-8.17 (m, 1H), 7.68-7.83 (m, 1H), 6.97-7.10 (m, 1H), 2.50 (s, 3H).

Intermediate B16

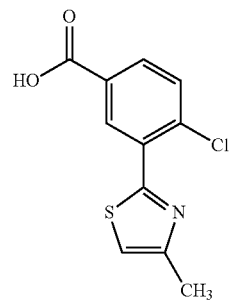 [SMILES: Cc1csc(-c2cc(C(=O)O)ccc2Cl)n1]

4-Chloro-3-(4-methylthiazol-2-yl)benzoic acid

Step A: Methyl 4-chloro-3-cyanobenzoate

To a mixture of methyl 3-amino-4-chlorobenzoate (10 g, 54 mmol) and aqueous HCl solution (12 M, 15 mL) in water (80 mL) at 0° C. was added dropwise a solution of NaNO$_2$ (4.5 g, 60 mmol) in water (18 mL) at 0° C. The reaction was stirred for 30 min at 0° C. and then added dropwise to a slurry of CuCN (4.9 g, 54 mmol) and KCN (6.0 g, 92 mmol) in water (40 mL), while maintaining the temperature between 5-10° C. The reaction mixture was stirred at 10° C. for 30 min and then heated at 80° C. for 1 h. After cooling, the mixture was extracted with DCM. The organic layer was washed with brine, dried over Na$_2$SO$_4$ and then concentrated to afford the title compound. MS: m/z=196.0 (M+1). $^1$H NMR (400 MHz, CDCl$_3$) δ 8.34 (d, J=2.0 Hz, 1H), 8.17-8.20 (m, 1H), 7.61 (d, J=8.4 Hz, 1H), 3.96 (s, 3H).

Step B: Methyl 3-carbamothioyl-4-chlorobenzoate

H$_2$S gas was bubbled through a solution of methyl 4-chloro-3-cyanobenzoate (3.0 g, 15 mmol) and TEA (2.13 mL, 15.3 mmol) in pyridine (15 mL) at ambient temperature for 1 h. The reaction mixture was concentrated and the residue was purified by column chromatography (PE:EtOAc=10:1) to give the title compound. MS: m/z=230.0 (M+1). $^1$H NMR (400 MHz, CDCl$_3$) δ 8.29 (d, J=1.6 Hz, 1H), 7.95-7.97 (m, 2H), 7.45 (d, J=8.4 Hz, 1H), 7.26 (s, 1H), 3.92 (s, 3H).

Step C: Methyl 4-chloro-3-(4-methylthiazol-2-yl)benzoate

A mixture of methyl 3-carbamothioyl-4-(trifluoromethyl)benzoate (1.0 g, 4.3 mmol), TEA (0.20 mL, 1.4 mmol) and 1-chloropropan-2-one (0.80 g, 8.6 mmol) in DMF (10 mL) was heated at 120° C. for 4 h, then concentrated. The residue was partitioned between water and EtOAc (10 mL×3). The combined organic layers were washed with brine, dried over Na$_2$SO$_4$ and concentrated. The residue was purified by column chromatography on silica gel (PE:EtOAc=3:1) to afford the title compound. MS: m/z=268.0 (M+1). $^1$H NMR (400 MHz, CDCl$_3$) δ 8.29 (d, J=2.0 Hz, 1H), 7.97-8.00 (m, 1H), 7.76 (d, J=8.0 Hz, 1H), 7.09 (s, 1H), 3.92 (s, 3H), 2.56 (s, 3H).

Step D: 4-Chloro-3-(4-methylthiazol-2-yl)benzoic acid

A mixture of methyl 4-chloro-3-(4-methylthiazol-2-yl)benzoate (0.40 g, 2.0 mmol) in aqueous NaOH solution (1M, 10 mL) was stirred at ambient temperature for 8 h. The mixture was acidified to pH 5 with aqueous HCl solution (2 M) and then extracted with EtOAc (10 mL×3). The combined organic layers were washed with brine, dried over Na₂SO₄ and then concentrated to afford the title compound. MS: m/z=254.0 (M+1).

Intermediate B17

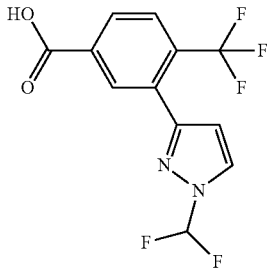 [SMILES: O=C(O)c1ccc(C(F)(F)F)c(-c2ccn(C(F)F)n2)c1]

3-(1-(Difluoromethyl)-1H-pyrazol-3-yl)-4-(trifluoromethyl)benzoic acid

A solution of methyl 3-(1H-pyrazol-5-yl)-4-(trifluoromethyl)benzoate (50 mg, 0.18 mmol), sodium chlorodifluoroacetate (34 mg, 0.22 mmol), and 18-crown-6 (9.8 mg, 0.037 mmol) in acetonitrile (1 mL) was heated at reflux for 40 h. Additional sodium chlorodifluoroacetate (34 mg, 0.22 mmol) was added after 18 and 22 h. The reaction mixture was cooled to ambient temperature and aqueous NaOH solution (10M, 0.056 mL, 0.55 mmol) was added. The resulting mixture was heated at 50° C. for 2 h. The mixture was cooled and then filtered, washing with acetonitrile (1 mL) and DMF (1 mL). The filtrate was purified by reverse-phase HPLC (5-95% acetonitrile+0.1% trifluoroacetic acid in water) to provide the title compound. MS: m/z=307.0 (M+1).

Intermediate B18

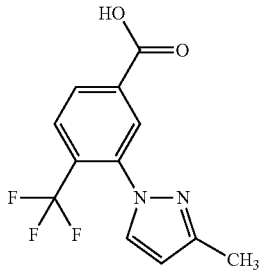 [SMILES: Cc1ccn(-c2cc(C(=O)O)ccc2C(F)(F)F)n1]

3-(3-Methyl-1H-pyrazol-1-yl)-4-(trifluoromethyl)benzoic acid

A deoxygenated solution of 3-methyl-1H-pyrazole (0.120 mL, 1.49 mmol), 3-bromo-4-(trifluoromethyl)benzoic acid (0.20 g, 0.74 mmol), copper(I) iodide (28 mg, 0.15 mmol), cesium carbonate (0.48 g, 1.5 mmol), and trans-N,N'-dimethylcyclohexane-1,2-diamine (0.023 mL, 0.15 mmol) in dioxane (1.0 mL) was heated at reflux for 18 h. The mixture was cooled and filtered, washing with DMF (1.5 mL). The filtrate was purified by reverse-phase HPLC (5-95% acetonitrile+0.1% trifluoroacetic acid in water) to afford the title compound. MS: m/z=271.0 (M+1).

Intermediate B19

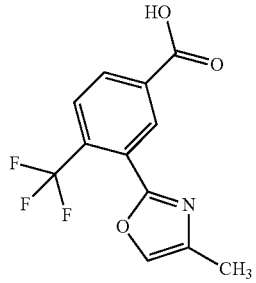 [SMILES: Cc1coc(-c2cc(C(=O)O)ccc2C(F)(F)F)n1]

3-(4-Methyloxazol-2-yl)-4-(trifluoromethyl)benzoic acid

A deoxygenated mixture of 3-bromo-4-(trifluoromethyl)benzoic acid (100 mg, 0.372 mmol), 4-methyloxazole (0.061 mL, 0.74 mmol), chloro(2-dicyclohexylphosphino-2',4',6'-tri-i-propyl-1,1'-biphenyl)[2-(2-aminoethyl)phenyl]palladium(II) methyl-t-butyl ether adduct (15.4 mg, 0.019 mmol), and sodium tert-butoxide (107 mg, 1.12 mmol) in DMA (1.5 mL) was heated under microwave irradiation at 110° C. for 18 h. The mixture was cooled and filtered, and the filtrate was purified by reverse-phase HPLC (C₁₈ column, H₂O: CH₃CN:CF₃CO₂H=95:5:0.1 to 5:95:0.1) to give the title compound. MS: m/z=272.0 (M+1).

Intermediate B20

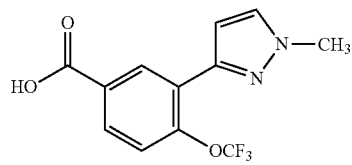 [SMILES: Cn1ccc(-c2cc(C(=O)O)ccc2OC(F)(F)F)n1]

3-(1-Methyl-1H-pyrazol-3-yl)-4-(trifluoromethoxy)benzoic acid

Step A: 3-Nitro-4-(trifluoromethoxy)benzoic acid 4-(Trifluoromethoxy)benzoic acid (37.4 g, 0.181 mol) was added portionwise to an aqueous HNO₃ solution (15 M, 75 mL) at 25° C. Aqueous H₂SO₄ solution (18 M, 90 mL) was added and the resulting mixture was stirred for 18 h. The reaction mixture was carefully diluted with water (300 mL) and the precipitate was filtered, washed with water, and dried to give the title compound. MS: m/z=252 (M+1). ¹H NMR (400 MHz, DMSO-d₆) δ 8.54 (s, 1H), 8.32 (d, J=8.0 Hz, 1H), 7.82 (d, J=8.0 Hz, 1H).

Step B: Methyl 3-nitro-4-(trifluoromethoxy)benzoate

Aqueous H₂SO₄ solution (18 M, 60 mL) was added dropwise to a solution of 3-nitro-4-(trifluoromethoxy)benzoic acid (33.5 g, 0.135 mol) in MeOH (400 mL) at 0° C. The resulting mixture was heated at 80° C. for 2 h, then cooled and concentrated. The residue was diluted with EtOAc, and washed with water (100 mL×3), aqueous NaHCO$_3$ solution (100 mL×3), and brine. The organic layer was dried over Na$_2$SO$_4$ and concentrated to give the title compound. MS: m/z: 266 (M+1). $^1$H NMR (400 MHz, DMSO-d$_6$) δ 8.54 (s, 1H), 8.32 (d, J=8.0 Hz, 1H), 7.82 (d, J=8.0 Hz, 1H), 3.90 (s, 3H).

Step C: Methyl 3-amino-4-(trifluoromethoxy)benzoate

A mixture of methyl 3-nitro-4-(trifluoromethoxy)benzoate (14 g, 0.053 mol) and 10% Pd/C (1.0 g, 10 wt %) in MeOH (200 mL) was stirred under H$_2$ (50 psi) at 15° C. for 24 h. The suspension was filtered and the filtrate was concentrated. The residue was purified by column chromatography on silica gel (PE:EtOAc=5:1) to give the title compound. MS: m/z=236 (M+1). $^1$H NMR (400 MHz, DMSO-d$_6$) δ 7.47 (d, J=2.0 Hz, 1H), 7.19-7.25 (m, 1H), 7.11-7.17 (m, 1H), 5.71 (s, 2H), 3.82 (s, 3H).

Step D: Methyl 3-bromo-4-(trifluoromethoxy)benzoate

A mixture of CuBr (5.0 g, 34 mmol) and t-BuONO (5.0 g, 43 mmol) in acetonitrile (60 mL) was stirred at 0° C. for 15 min, and then methyl 3-amino-4-(trifluoromethoxy)benzoate (4.0 g, 17 mmol) was added. The resulting mixture was stirred at 0° C. for 2 h, and then stirred at 15° C. for 16 h. The mixture was filtered and the filter cake was washed with EtOAc. The filtrate was washed with aqueous HCl solution (1N), water, and then brine. The organic layer was dried over Na$_2$SO$_4$ and concentrated. The residue was purified by column chromatography on silica gel (PE:EtOAc=20:1) to give the title compound. MS: m/z=298/300 (M+1). $^1$H NMR (400 MHz, DMSO-d$_6$) δ 8.14 (d, J=2.0 Hz, 1H), 7.96 (dd, J=8.7, 1.9 Hz, 1H), 7.55 (dd, J=8.7, 1.1 Hz, 1H), 3.84 (s, 3H).

Step E: Methyl 3-(1-(tetrahydro-2H-pyran-2-yl)-1H-pyrazol-5-yl)-4-(trifluoro-methoxy)benzoate A deoxygenated mixture of methyl 3-bromo-4-(trifluoromethoxy)benzoate (500 mg, 1.67 mmol), 1-(tetrahydro-2H-pyran-2-yl)-5-(4,4,5,5-tetramethyl-1,3,2-dioxaborolan-2-yl)-1H-pyrazole (510 mg, 1.84 mmol), Pd(PPh$_3$)$_4$ (50 mg, 0.05 mmol), and Na$_2$CO$_3$ (530 mg, 5.0 mmol) in DMF (5 mL) was heated at 100° C. under N$_2$ atmosphere for 16 h. The reaction mixture was cooled and then partitioned between water (15 mL) and EtOAc (15 mL×3). The combined organic layers were dried over Na$_2$SO$_4$ and concentrated. The residue was purified by preparative TLC (PE: EtOAc=3:1) to give the title compound. MS: m/z=371 (M+1).

Step F: Methyl 3-(1H-pyrazol-5-yl)-4-(trifluoromethoxy)benzoate

A solution of HCl in EtOAc (4 M, 10 mL, 40 mmol) was added to a solution of methyl 3-(1-(tetrahydro-2H-pyran-2-yl)-1H-pyrazol-5-yl)-4-(trifluoromethoxy)benzoate (300 mg, 1.1 mmol) in EtOAc (2 mL). The resulting mixture was stirred at 15° C. for 1 h and then concentrated to give the title compound. MS: m/z=287 (M+1).

Step G: Methyl 3-(1-methyl-1H-pyrazol-3-yl)-4-(trifluoromethoxy)benzoate

A mixture of methyl 3-(1H-pyrazol-5-yl)-4-(trifluoromethoxy)benzoate (220 mg, 0.81 mmol), CH$_3$I (0.292 mL, 4.00 mmol), and Cs$_2$CO$_3$ (780 mg, 2.4 mmol) in DMF (5 mL) was heated at 70° C. for 1 h. The mixture was cooled and then partitioned between water (10 mL) and EtOAc (10 mL×2). The combined organic layers were dried over Na$_2$SO$_4$ and concentrated. The residue was purified by preparative TLC (PE:EtOAc=2:1) to give the title compound. MS: m/z=301 (M+1).

Step H: 3-(1-Methyl-1H-pyrazol-3-yl)-4-(trifluoromethoxy)benzoic acid

A mixture of methyl 3-(1-methyl-1H-pyrazol-3-yl)-4-(trifluoromethoxy)benzoate (120 mg, 0.4 mmol) and aqueous NaOH solution (2M, 10 mmol, 5 mL) was heated at 50° C. for 30 min. The reaction mixture was cooled, acidified to pH 5 with aqueous HCl solution (1M), and then extracted with EtOAc (10 mL×2). The combined organic layers were dried over Na$_2$SO$_4$ and concentrated to give the title compound. MS: m/z=287 (M+1).

Intermediate C1

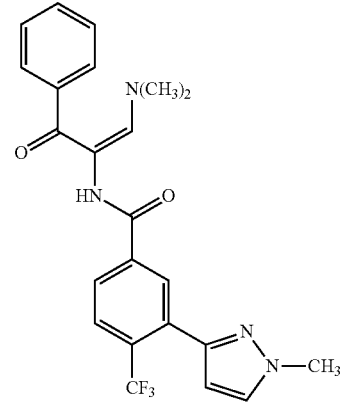 [SMILES: CN(C)/C=C(/NC(=O)c1ccc(C(F)(F)F)c(-c2ccn(C)n2)c1)C(=O)c1ccccc1]

N-(1-(Dimethylamino)-3-oxo-3-phenylprop-1-en-2-yl)-3-(1-methyl-1H-pyrazol-3-yl)-4-(trifluoromethyl)benzamide Step A: 3-(1-Methyl-1H-pyrazol-3-yl)-N-(2-oxo-2-phenylethyl)-4-(trifluoromethyl)benzamide A mixture of 3-(1-methyl-1H-pyrazol-3-yl)-4-(trifluoromethyl)benzoic acid (500 mg, 1.85 mmol), 2-aminoacetophenone hydrochloride (349 mg, 2.04 mmol), HATU (844 mg, 2.22 mmol), and DIEA (0.970 mL, 5.55 mmol) in DMF (4 mL) was stirred at ambient temperature for 2 h. The product mixture was purified directly by column chromatography on silica gel (EtOAc:hexanes=0:100 to 100:0) to yield the title compound. MS: m/z=388.2 (M+1).

Step B: N-(1-(Dimethylamino)-3-oxo-3-phenylprop-1-en-2-yl)-3-(1-methyl-1H-pyrazol-3-yl)-4-(trifluoromethyl)benzamide A mixture of 3-(1-methyl-1H-pyrazol-3-yl)-N-(2-oxo-2-phenylethyl)-4-(trifluoromethyl)benzamide (88.0 mg, 0.227 mmol) and N,N-dimethylformamide dimethyl acetal (0.036 mL, 0.27 mmol) in dioxane (1 mL) was stirred at ambient temperature for 16 h. The product mixture was purified directly by column chromatography on silica gel (DCM:MeOH:NH$_4$OH=100:0:0 to 90:10:1) to give the title compound. MS: m/z=443.2 (M+1).

Intermediate C$_2$

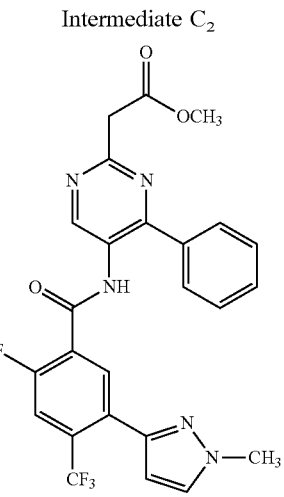

Methyl 2-(5-(2-fluoro-5-(1-methyl-1H-pyrazol-3-yl)-4-(trifluoromethyl)benzamido)-4-phenylpyrimidin-2-yl)acetate A mixture of methyl 2-(5-amino-4-phenylpyrimidin-2-yl) acetate (5.00 g, 20.6 mmol) and 2-fluoro-5-(1-methyl-1H-pyrazol-3-yl)-4-(trifluoromethyl)benzoic acid (5.92 g, 20.6 mmol) were dissolved in pyridine (68 mL), and the resulting solution was cooled to 0° C. Phosphorus oxychloride (2.10 mL, 22.6 mmol) was added dropwise. The resulting mixture was stirred for 3 h, then carefully diluted with saturated aqueous NaHCO$_3$ solution (60 mL). The aqueous mixture was partitioned between brine (250 mL) and EtOAc (200×3 mL). The combined organic layers were dried over MgSO$_4$, filtered, and concentrated. Heptane (100 mL×2) was added and the mixture concentrated to remove residual pyridine by azeotrope. The residue was purified by SiO$_2$ flash column chromatography (330 g cartridge), eluting with 0-100% EtOAc/hexanes to give the title compound. MS: m/z=514.3 (M+1).

Intermediate C$_3$

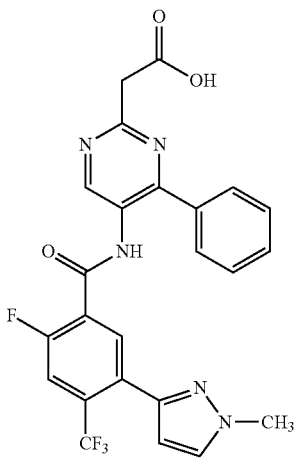 [SMILES: Cn1ccc(-c2cc(C(=O)Nc3cnc(CC(=O)O)nc3-c3ccccc3)c(F)cc2C(F)(F)F)n1]

2-(5-(2-Fluoro-5-(1-methyl-1H-pyrazol-3-yl)-4-(trifluoromethyl)benzamido)-4-phenylpyrimidin-2-yl) acetic acid Methyl 2-(5-(2-fluoro-5-(1-methyl-1H-pyrazol-3-yl)-4-(trifluoromethyl)benzamido)-4-phenylpyrimidin-2-yl)acetate (7.94 g, 15.5 mmol) was dissolved in dioxane (62 mL), and the resulting solution was cooled to 0° C. Saturated aqueous LiOH solution (46.3 mL, 247 mmol) was added, and the mixture was stirred at 23° C. for 75 min. The product mixture was diluted with water (100 mL) and washed with CH$_2$Cl$_2$ (2×100 mL). The basic aqueous layer was then acidified with dropwise addition of 12 N aqueous HCl solution (~20 mL). The resulting suspension was extracted with CH$_2$Cl$_2$ (3×100 mL), and the combined organic layers were dried over MgSO$_4$, filtered, and concentrated to give the title compound. MS: m/z=500.2 (M+1).

Intermediate C$_4$

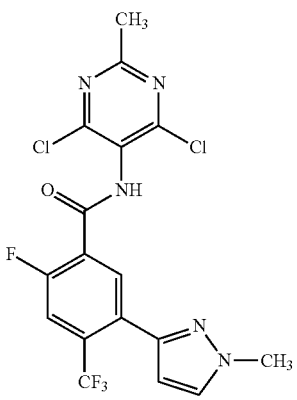 [SMILES: Cc1nc(Cl)c(NC(=O)c2cc(-c3ccn(C)n3)c(C(F)(F)F)cc2F)c(Cl)n1]

N-(4,6-Dichloro-2-methylpyrimidin-5-yl)-2-fluoro-5-(1-methyl-1H-pyrazol-3-yl)-4-(trifluoromethyl)benzamide To a solution of 5-amino-4,6-dichloro-2-methylpyrimidine (3.00 g, 16.8 mmol) in pyridine (140 mL) at −30° C. was added 2-fluoro-5-(1-methyl-1H-pyrazol-3-yl)-4-(trifluoromethyl)benzoic acid (4.86 g, 16.8 mmol) and phosphorus oxychloride (1.57 mL, 16.8 mmol). The mixture was stirred at 0° C. for 0.5 h, then at 23° C. for 0.5 h. Methanol (140 mL) was added followed by solid K$_2$CO$_3$ (20 g), and the resulting mixture was stirred for 10 min, then diluted with CH$_2$Cl$_2$ (600 mL) and filtered through a pad of silica gel, eluting with CH$_2$Cl$_2$. The filtrate was concentrated and the residue was purified by column chromatography on silica gel, eluting with 10-30% EtOAc in hexanes to give the title compound. MS: m/z=447.8 (M+1).

The following intermediate was prepared in similar fashion to the procedures described above.

| Compound Number | Structure | Compound Name | LCMS (M + 1) |
|---|---|---|---|
| C5 | 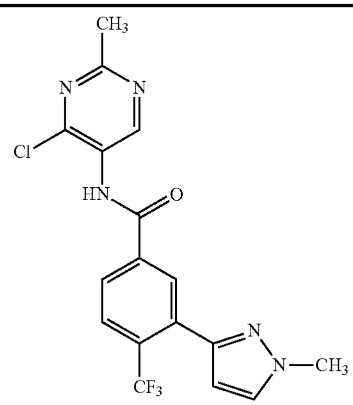 | N-(4-chloro-2-methylpyrimidin-5-yl)-3-(1-methyl-1H-pyrazol-3-yl)-4-(trifluoromethyl)benzamide | 396.1 |
REACTION SCHEME FOR INTERMEDIATE C$_6$
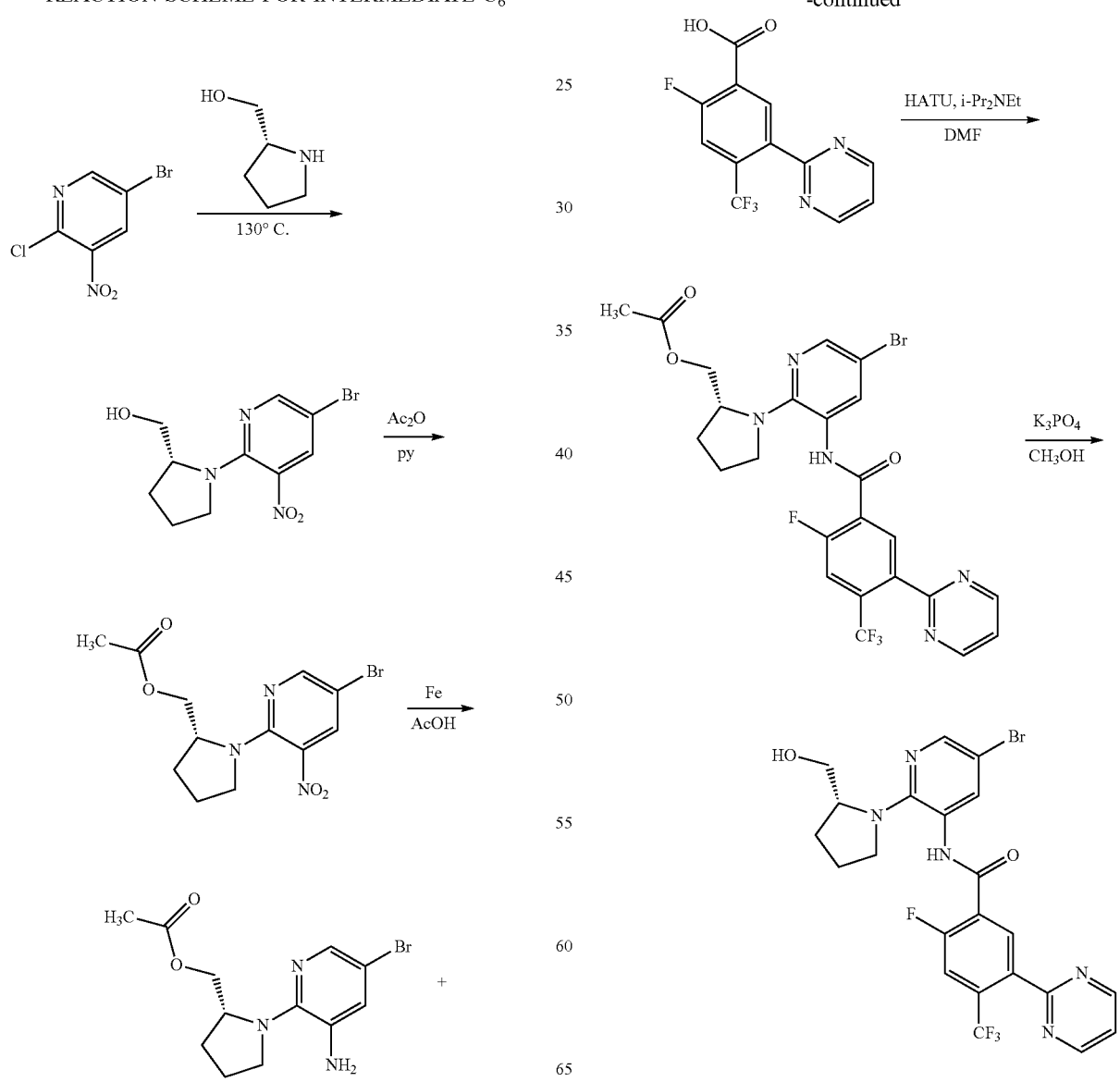

Intermediate C₆

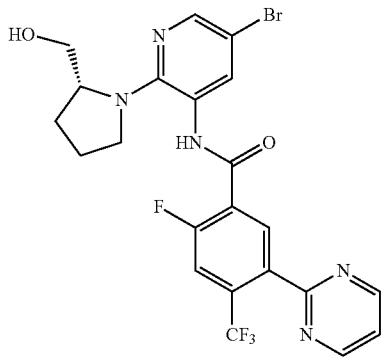 [SMILES: O=C(Nc1cc(Br)cnc1N1CCC[C@@H]1CO)c1cc(-c2ncccn2)c(C(F)(F)F)cc1F]

(R)—N-(5-Bromo-2-(2-(hydroxymethyl)pyrrolidin-1-yl)pyridin-3-yl)-2-fluoro-5-(pyrimidin-2-yl)-4-(trifluoromethyl)benzamide Step A: (R)-(1-(5-Bromo-3-nitropyridin-2-yl)pyrrolidin-2-yl)methanol To a flask containing 5-bromo-2-chloro-3-nitropyridine (2 g, 8 mmol) was added (R)-pyrrolidin-2-ylmethanol (1 g, 10 mmol), then 2-methyl-1-propanol (34 mL). The resulting solution was transferred in equal portions to three 20 mL microwave vials. Each vial was sealed and then heated in the microwave at 130° C. with stirring for 10 min. After cooling, the three individual reaction mixtures were combined and diluted with ethyl acetate (200 mL) then washed with water (200 mL). The aqueous fraction was extracted with ethyl acetate (50 mL×2). The combined organic layers were then washed with brine (100 mL) and dried over sodium sulfate, then filtered and concentrated to give the title compound.

Step B: (R)-(1-(5-Bromo-3-nitropyridin-2-yl)pyrrolidin-2-yl)methyl acetate

To a flask containing a solution of (R)-(1-(5-bromo-3-nitropyridin-2-yl)pyrrolidin-2-yl)methanol (2.4 g, 8 mmol) in pyridine (28 mL) was added acetic anhydride (1.6 mL, 17 mmol) and the resulting mixture was stirred at 23° C. overnight. The product mixture was then partitioned between ethyl acetate (200 mL) and water (200 mL). The aqueous layer was extracted with ethyl acetate (100 mL×2). The combined organic fractions were washed with brine (100 mL), then dried over magnesium sulfate, filtered and concentrated to give the title compound.

Step C: (R)-(1-(3-Amino-5-bromopyridin-2-yl)pyrrolidin-2-yl)methyl acetate

To (R)-(1-(5-bromo-3-nitropyridin-2-yl)pyrrolidin-2-yl)methyl acetate (2.9 g, 8 mmol) was added acetic acid (15 mL) followed by iron (2 g, 40 mmol), which was added in two portions. The resulting mixture was stirred at 23° C. for 20 h. The product mixture was diluted with ethyl acetate (100 mL) and water (100 mL) and the resulting mixture was filtered through a pad of Celite® (1 cm thick, 5 cm in diameter). Following this filtration, the organic and aqueous layers were separated. The aqueous layer was extracted with ethyl acetate (100 mL×2). All organic layers were combined, dried over sodium sulfate, filtered and concentrated. The residue was purified by flash chromatography (ISCO, redisep column 125 g, ethyl acetate in hexanes, 0-100% gradient over 10 minutes) to give the title compound. MS: m/z=314 (M+1). ¹H NMR (500 MHz, DMSO-d₆) δ 7.51 (d, J=2.2 Hz, 1H), 7.04 (d, J=2.2 Hz, 1H), 5.02 (s, 2H), 4.42-4.37 (m, 1H), 3.91-3.84 (m, 2H), 3.67-3.62 (m, 1H), 2.91-2.87 (m, 1H), 2.06-2.01 (m, 1H), 1.9 (s, 3H), 1.76-1.61 (m, 2H).

Step D: (R)-(1-(5-Bromo-3-(2-fluoro-5-(pyrimidin-2-yl)-4-(trifluoromethyl)benzamido)pyridin-2-yl)pyrrolidin-2-yl)methyl acetate To a flask containing (R)-(1-(3-amino-5-bromopyridin-2-yl)pyrrolidin-2-yl)methyl acetate (980 mg, 3.1 mmol) was added 2-fluoro-5-(pyrimidin-2-yl)-4-(trifluoromethyl)benzoic acid (930 mg, 3.3 mmol) and HATU (2300 mg, 6.2 mmol) followed by DMF (30 mL) and N,N-diisopropylethylamine (1.6 mL, 9.4 mmol). The resulting solution was stirred at 23° C. for 20 h. The product mixture was partitioned between ethyl acetate (200 mL) and water (200 mL). The aqueous layer was extracted with ethyl acetate (50 mL×2). The combined organic layers were washed with brine, then dried over magnesium sulfate, then filtered and concentrated. The residue was purified by flash chromatography (ISCO, redisep column 120 g, 0-100% (50/50, EtOH/EtOAc) in hexane, gradient over 15 minutes) to give the title compound as a the major component of a 4:1 mixture with (R)-(1-(3-amino-5-bromopyridin-2-yl)pyrrolidin-2-yl)methyl. MS: m/z=583 (M+1). ¹H NMR (500 MHz, DMSO-d₆) δ 10.31 (s, 1H), 8.99 (d, J=4.9 Hz, 2H), 8.17-8.15 (m, 2H), 8.02 (d, J=10.2 Hz, 1H), 7.90 (d, J=2.4 Hz, 1H), 7.62 (t, J=4.9 Hz, 1H), 4.07-4.01 (m, 2H), 3.96-3.91 (m, 1H), 3.70-3.64 (m, 2H), 2.04-1.90 (m, 2H), 1.95 (s, 3H), 1.80-1.70 (m, 2H).

Step E: (R)—N-(5-Bromo-2-(2-(hydroxymethyl)pyrrolidin-1-yl)pyridin-3-yl)-2-fluoro-5-(pyrimidin-2-yl)-4-(trifluoromethyl)benzamide To a solution of (R)-(1-(5-bromo-3-(2-fluoro-5-(pyrimidin-2-yl)-4-(trifluoromethyl)benzamido)pyridin-2-yl)pyrrolidin-2-yl)methyl acetate (775 mg, 1.06 mmol) and methanol (8 mL) was added potassium phosphate tribasic (3M, 0.710 mL, 2.13 mmol). The mixture was stirred at 23° C. for 1 h. The product mixture was concentrated and the residue was partitioned between water and EtOAc. The organic layer was washed with brine, dried over sodium sulfate, filtered and concentrated. The residue was purified by flash chromatography (ISCO, redisep column 120 g, 0-100% (50/50, EtOH/EtOAc) in hexane, gradient over 55 minutes) to give the title compound. MS: m/z=540 (M+1). ¹H NMR (500 MHz, DMSO-d₆) δ 10.35 (s, 1H), 8.99 (d, J=4.9 Hz, 2H), 8.16 (d, J=6.7 Hz, 1H), 8.12 (d, J=2.4 Hz, 1H), 8.02 (d, J=10.2 Hz, 1H), 7.91 (d, J=2.3 Hz, 1H), 7.61 (t, J=4.9 Hz, 1H), 5.15 (s, 1H), 4.55-4.49 (m, 2H), 4.34-4.29 (m, 1H), 3.60-3.55 (m, 1H), 3.48-3.44 (m, 1H), 1.93-1.84 (m, 2H), 1.79-1.69 (m, 2H).

REACTION SCHEME FOR INTERMEDIATE C7

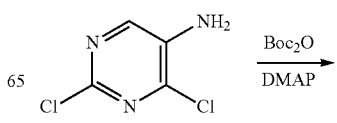

-continued

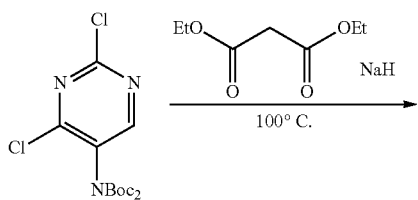

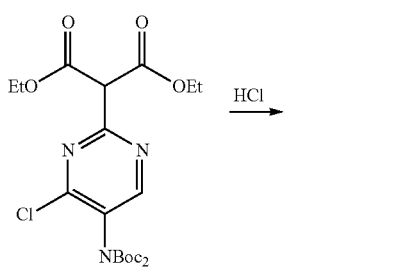

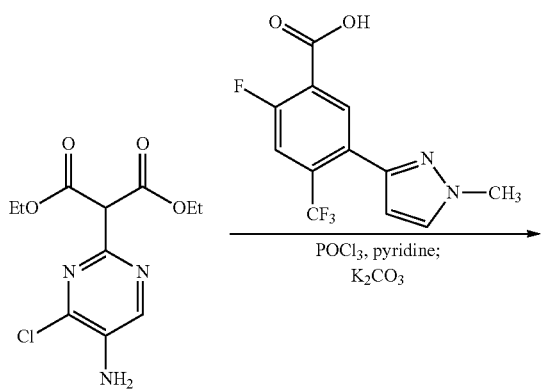

Intermediate C₇

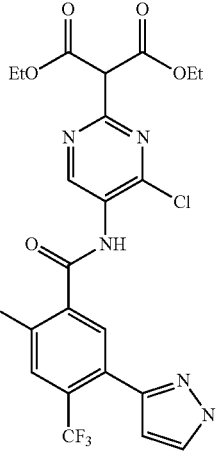

Diethyl 2-(4-chloro-5-(2-fluoro-5-(1-methyl-1H-pyrazol-3-yl)-4-(trifluoromethyl)benzamido)pyrimidin-2-yl)malonate

Step A: Di-tert-butyl (2,4-dichloropyrimidin-5-yl)carbamate

A mixture of 5-amino-2,4-dichloropyrimidine (6.50 g, 39.6 mmol), di-t-butyl dicarbonate (20.2 mL, 87.9 mmol) and DMAP (0.968 g, 7.93 mmol) in dichloromethane (250 mL) was stirred at 23° C. for 18 h, then concentrated. The residue was purified by column chromatography on silica gel, eluting with 10% EtOAc/hexanes, to give the title compound. MS: m/z=386.0 (M+Na). ¹H NMR (400 MHz, CDCl₃) δ 8.44 (s, 1H) 1.45 (s, 18H).

Step B: Diethyl 2-(5-((di-tert-butoxycarbonyl)amino)-4-chloropyrimidin-2-yl)malonate To a mixture of sodium hydride (60 wt. %, 99 mg, 2.5 mmol) in DMF (2 mL) at 23° C. was added dropwise diethyl malonate (0.38 mL, 2.5 mmol). The resulting mixture was stirring for 0.5 h before di-tert-butyl (2,4-dichloropyrimidin-5-yl)carbamate (300 mg, 0.824 mmol) in DMF (1 mL) was added. The mixture was heated at 100° C. for 3 h, then cooled and acidified with aqueous 1N HCl solution. The product mixture was partitioned between DCM and H₂O. The organic layer was dried over Na₂SO₄ and concentrated. The residue was purified by column chromatography on silica gel, eluting with 0-35% EtOAc/hexanes, to give the title compound. MS: m/z=488.1 (M+1).

Step C: Diethyl 2-(5-amino-4-chloropyrimidin-2-yl)malonate

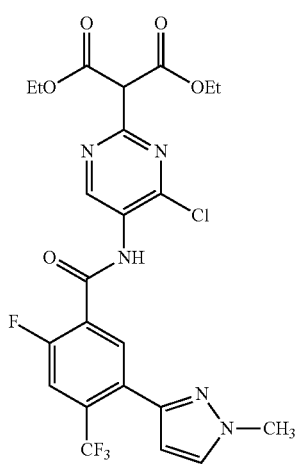 [SMILES: CCOC(=O)C(C(=O)OCC)c1ncc(NC(=O)c2cc(-c3ccn(C)n3)c(C(F)(F)F)cc2F)c(Cl)n1]

To diethyl 2-(5-((di-tert-butoxycarbonyl)amino)-4-chloropyrimidin-2-yl)malonate (280 mg, 0.574 mmol) was added a solution of 4N HCl in dioxane (1.43 mL, 5.74 mmol). The resulting mixture was stirred at 23° C. for 1 h, then concentrated to give the title compound as a hydrochloride salt. MS: m/z=288.1 (M+1).

Step D: Diethyl 2-(4-chloro-5-(2-fluoro-5-(1-methyl-1H-pyrazol-3-yl)-4-(trifluoromethyl)benzamido) pyrimidin-2-yl)malonate To a solution of diethyl 2-(5-amino-4-chloropyrimidin-2-yl)malonate (180 mg, 0.626 mmol) in pyridine (5.1 mL) at −30° C. was added 2-fluoro-5-(1-methyl-1H-pyrazol-3-yl)-4-(trifluoromethyl) benzoic acid (180 mg, 0.626 mmol) followed by phosphorus oxychloride (0.058 mL, 0.63 mmol). The resulting mixture was stirred at 0° C. for 0.5 h then carefully diluted with saturated aqueous sodium bicarbonate solution. The aqueous product mixture was extracted with DCM (2×). The combined organic layers were dried over $Na_2SO_4$ and concentrated. The residue was dissolved in methanol, and solid $K_2CO_3$ (excess) was added. The resulting mixture was stirred at 23° C. for 10 min. The product mixture was diluted with DCM (600 mL), and filtered through a pad of silica. The filtrate was concentrated and the residue purified by column chromatography on silica gel, eluting with 10-30% EtOAc/hexanes, to give the title compound. MS: m/z=544.0 (M+1).

REACTION SCHEME FOR INTERMEDIATE D1

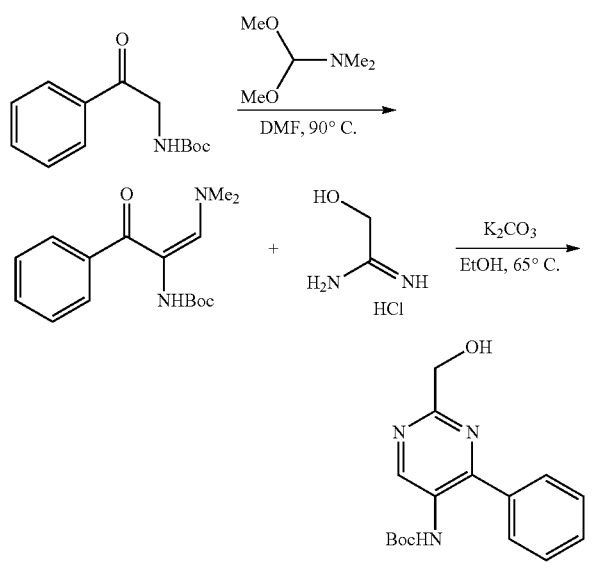

Intermediate D1 tert-Butyl (2-(hydroxymethyl)-4-phenylpyrimidin-5-yl)carbamate

Step A: (E)-tert-Butyl (1-(dimethylamino)-3-oxo-3-phenylprop-1-en-2-yl)carbamate A mixture of tert-butyl (2-oxo-2-phenylethyl)carbamate (1.00 g, 4.25 mmol) and 1,1-dimethoxy-N,N-dimethylmethanamine (0.598 mL, 4.46 mmol) in DMF (5 mL) was heated at 90° C. for 16 h. The product mixture was cooled and partitioned between EtOAc and water. The organic layer was washed with brine, dried over sodium sulfate and concentrated to give the title compound.

Step B: tert-Butyl (2-(hydroxymethyl)-4-phenylpyrimidin-5-yl)carbamate

Potassium carbonate (6.57 g, 47.5 mmol) was added to a mixture of (E)-tert-butyl (1-(dimethylamino)-3-oxo-3-phenylprop-1-en-2-yl)carbamate (4.60 g, 15.8 mmol) and 2-hydroxyacetimidamide hydrochloride (2.80 g, 25.3 mmol) in ethanol (25 mL) at 25° C. The resulting mixture was heated at 65° C. for 24 h then cooled and concentrated. The residue was partitioned between EtOAc (100 mL) and water (2×100 mL). The organic layer was washed with brine, dried over sodium sulfate and concentrated. The residue was purified by flash column chromatography on silica gel (10% EtOAc in hexanes, grading to 100% EtOAc) to provide the title compound. MS: m/z=302.6 (M+1).

REACTION SCHEME FOR EXAMPLE 1

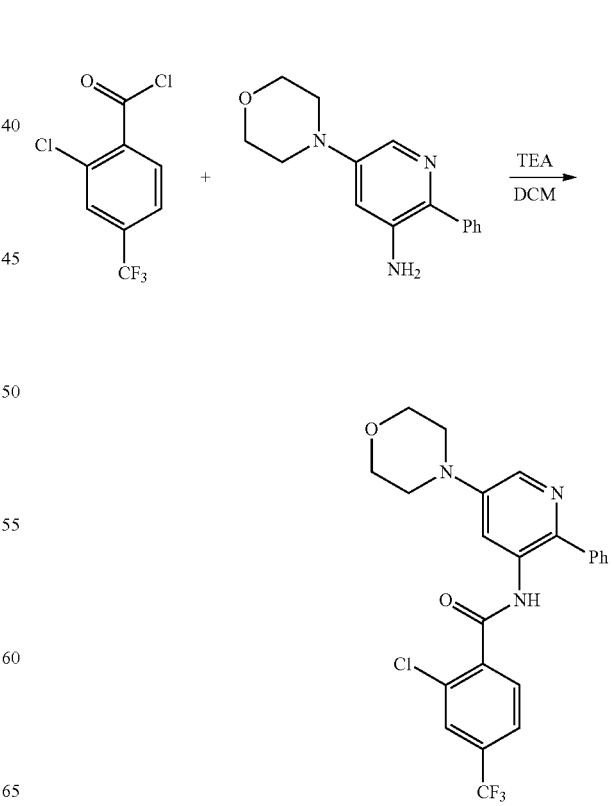

EXAMPLE 1

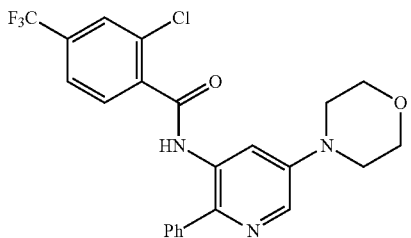 [SMILES: O=C(Nc1cc(N2CCOCC2)cnc1-c1ccccc1)c1ccc(C(F)(F)F)cc1Cl]

2-Chloro-N-(5-morpholino-2-phenylpyridin-3-yl)-4-(trifluoromethyl)benzamide

A mixture of 5-morpholino-2-phenylpyridin-3-amine (30 mg, 0.12 mmol), 2-chloro-4-(trifluoromethyl)benzoyl chloride (49 mg, 0.20 mol), and TEA (0.050 mL, 0.36 mmol) in DCM (2 mL) was stirred at 15° C. for 2 h. The reaction mixture was concentrated and the residue was partitioned between DCM (50 mL) and water (10 mL×3). The organic layer was dried over $Na_2SO_4$ and concentrated. The residue was purified by reverse-phase HPLC (10-40% acetonitrile+ 0.75% trifluoroacetic acid in water) to give the title compound. MS: m/z=462 (M+1). $^1$H NMR (400 MHz, $CD_3OD$) δ 8.30-8.25 (m, 2H), 7.82 (s, 1H), 7.74-7.70 (m, 1H), 7.69-7.63 (m, 3H), 7.59-7.54 (m, 3H), 3.92-3.88 (m, 4H), 3.47-3.42 (m, 4H).

EXAMPLE 2

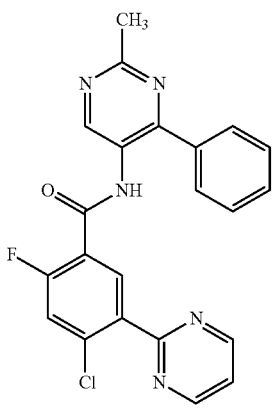 [SMILES: Cc1ncc(NC(=O)c2cc(-c3ncccn3)c(Cl)cc2F)c(-c2ccccc2)n1]

4-Chloro-2-fluoro-N-(2-methyl-4-phenylpyrimidin-5-yl)-5-(pyrimidin-2-yl)benzamide A mixture of 2-methyl-4-phenylpyrimidin-5-aminium chloride (95 mg, 0.43 mmol), pyridine (0.047 mL, 0.58 mmol), and 4-chloro-2-fluoro-5-(pyrimidin-2-yl)benzoyl chloride (78 mg, 0.29 mmol) in DMA (2.5 mL) was stirred at 23° C. for 16 h. The reaction mixture was filtered and then purified by reverse-phase HPLC (5-95% acetonitrile+0.1% trifluoroacetic acid in water) to give the title compound. MS: m/z=420.1 (M+1). $^1$H NMR (400 MHz, $CDCl_3$) δ 9.69 (s, 1H), 8.90 (d, J=4.9 Hz, 2H), 8.59 (d, J=8.4 Hz, 1H), 7.66 (dd, J=6.6, 2.3 Hz, 2H), 7.56-7.60 (m, 4H), 7.36 (t, J=4.9 Hz, 1H), 2.80 (s, 3H).

EXAMPLE 3

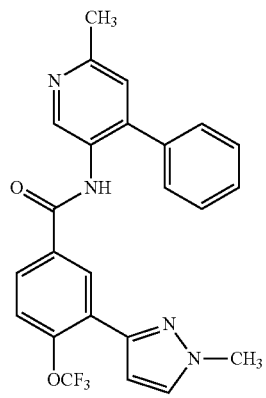 [SMILES: Cc1cc(-c2ccccc2)c(NC(=O)c2ccc(OC(F)(F)F)c(-c3ccn(C)n3)c2)cn1]

3-(1-Methyl-1H-pyrazol-3-yl)-N-(6-methyl-4-phenylpyridin-3-yl)-4-(trifluoromethoxy)benzamide Step A: 3-(1-Methyl-1H-pyrazol-3-yl)-4-(trifluoromethoxy)benzoyl chloride A mixture of 3-(1-methyl-1H-pyrazol-3-yl)-4-(trifluoromethoxy)benzoic acid (85 mg, 0.30 mmol) and oxalyl chloride (1.30 mL, 14.9 mmol) in DCM (10 mL) was heated at 50° C. for 1 h. The mixture was cooled and then concentrated to give the title compound. MS: m/z=301 (M+1, Me ester from reaction with MeOH).

Step B: 3-(1-Methyl-1H-pyrazol-3-yl)-N-(6-methyl-4-phenylpyridin-3-yl)-4-(trifluoromethoxy)benzamide A mixture of 3-(1-methyl-1H-pyrazol-3-yl)-4-(trifluoromethoxy)benzoyl chloride (88 mg, 0.29 mmol), 6-methyl-4-phenylpyridin-3-amine (82 mg, 0.32 mmol), and pyridine (0.047 mL, 0.58 mmol) in DCM (10 mL) was at heated at reflux for 18 h. The reaction mixture was cooled and then partitioned between saturated $NaHCO_3$ solution (30 mL) and DCM (20 mL×3). The combined organic layers were washed with water (30 mL) and brine (30 mL), then dried over $Na_2SO_4$ and concentrated. The residue was purified by reverse-phase HPLC to give the title compound. MS: m/z=453 (M+1). $^1$H NMR (400 MHz, $CD_3OD$) δ 9.13 (s, 1H), 8.42 (d, J=2.2 Hz, 1H), 7.90 (s, 1H), 7.83 (dd, J=8.6, 2.4 Hz, 1H), 7.67-7.64 (m, 3H), 7.61-7.53 (m, 3H), 7.48 (dd, J=8.6, 1.3 Hz, 1H), 6.64 (d, J=2.2 Hz, 1H), 3.97 (s, 3H), 2.79 (s, 3H).

EXAMPLE 4

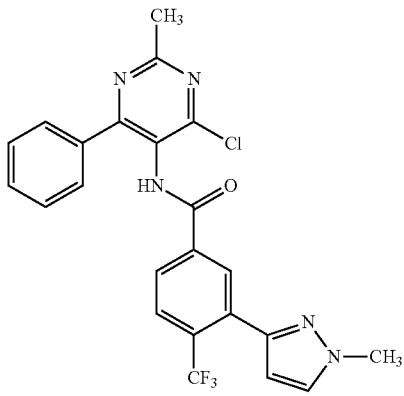 [SMILES: Cc1nc(Cl)c(NC(=O)c2ccc(C(F)(F)F)c(-c3ccn(C)n3)c2)c(-c2ccccc2)n1]

N-(4-Chloro-2-methyl-6-phenylpyrimidin-5-yl)-3-(1-methyl-1H-pyrazol-3-yl)-4-(trifluoromethyl)benzamide POCl$_3$ (0.205 mL, 2.20 mmol) was added to a mixture of 4-chloro-2-methyl-6-phenylpyrimidin-5-amine (322 mg, 1.47 mmol) and 3-(1-methyl-1H-pyrazol-3-yl)-4-(trifluoromethyl)benzoic acid (396 mg, 1.47 mmol) in pyridine (3 mL) at −15° C., and the resulting mixture was stirred for 2 h. The product mixture was purified directly by column chromatography on silica gel (EtOAc:hexanes=0:100 to 100:0) to yield the title compound. MS: m/z=472.2 (M+1). $^1$H NMR (400 MHz, CDCl$_3$) δ 8.05 (s, 1H), 7.84-7.78 (m, 2H), 7.68-7.63 (m, 3H), 7.40-7.36 (m, 4H), 6.48 (s, 1H), 3.93 (s, 3H), 2.77 (s, 3H).

REACTION SCHEME FOR EXAMPLE 5

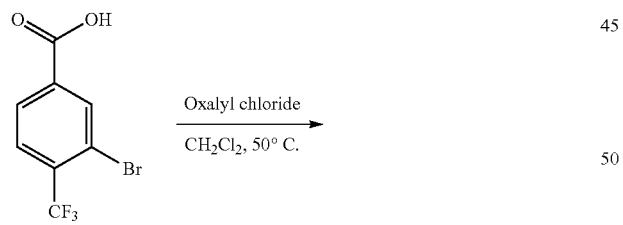

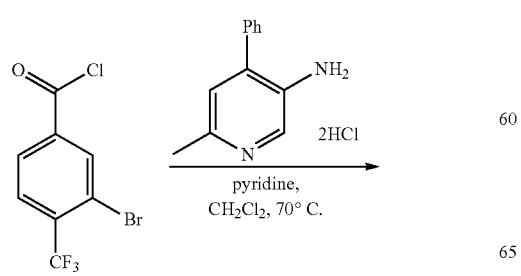

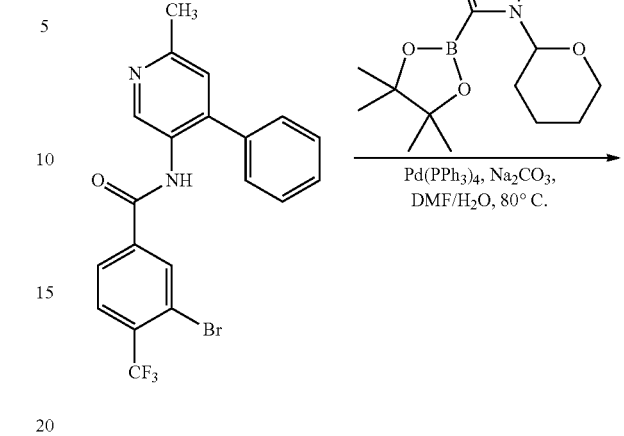

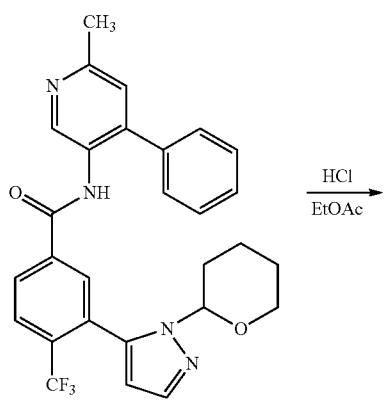

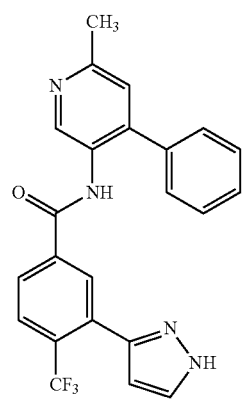 [SMILES: Cc1cc(-c2ccccc2)c(NC(=O)c2ccc(C(F)(F)F)c(-c3cc[nH]n3)c2)cn1]

EXAMPLE 5

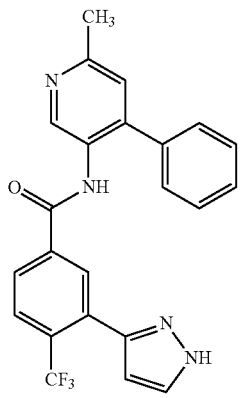

N-(6-Methyl-4-phenylpyridin-3-yl)-3-(1H-pyrazol-5-yl)-4-(trifluoromethyl)benzamide Step A: 3-Bromo-4-(trifluoromethyl)benzoyl chloride A mixture of 3-bromo-4-(trifluoromethyl)benzoic acid (400 mg, 1.49 mmol) and oxalyl chloride (1.30 mL, 14.9 mmol) in DCM (10 mL) was heated at 50° C. for 1 h and then concentrated to give the title compound. MS: m/z=283/285 (M+1, Me ester from reaction with MeOH).

Step B: 3-Bromo-N-(6-methyl-4-phenylpyridin-3-yl)-4-(trifluoromethyl)benzamide

A mixture of 3-bromo-4-(trifluoromethyl)benzoyl chloride (427 mg, 1.49 mmol), 6-methyl-4-phenylpyridin-3-amine (421 mg, 1.64 mmol), and pyridine (0.241 mL, 2.97 mmol) in DCM (10 mL) was heated at reflux for 18 h. The reaction mixture was cooled and then partitioned between a saturated aqueous NaHCO$_3$ solution (30 mL) and DCM (20 mL×3). The combined organic layers were washed with water (30 mL) and brine (30 mL), then dried over Na$_2$SO$_4$ and concentrated. The residue was purified by column chromatography on silica gel (PE:EtOAc:Et$_3$N=80:20:1, 70:30:1, then 50:50:1) to give the title compound. MS: m/z=435/437 (M+1). $^1$H NMR (400 MHz, CD$_3$OD) δ 8.54 (s, 1H), 8.14 (s, 1H), 7.89-7.84 (m, 2H), 7.48-7.38 (m, 6H), 2.60 (s, 3H).

Step C: N-(6-Methyl-4-phenylpyridin-3-yl)-3-(1-(tetrahydro-2H-pyran-2-yl)-1H-pyrazol-5-yl)-4-(trifluoromethyl)benzamide A deoxygenated mixture of 3-bromo-N-(6-methyl-4-phenylpyridin-3-yl)-4-(trifluoromethyl)-benzamide (200 mg, 0.460 mmol), 1-(tetrahydro-2H-pyran-2-yl)-5-(4,4,5,5-tetramethyl-1,3,2-dioxaborolan-2-yl)-1H-pyrazole (192 mg, 0.689 mmol), Pd(PPh$_3$)$_4$ (27 mg, 0.023 mmol), and Na$_2$CO$_3$ (122 mg, 1.15 mmol) in 4:1 DMF:water (7.5 mL) was heated at 80° C. for 18 h. The reaction mixture was cooled and then partitioned between water (30 mL) and EtOAc (30 mL×3). The combined organic layers were washed with water (50 mL) and brine (50 mL), dried over Na$_2$SO$_4$ and concentrated to give the title compound. MS: m/z=507 (M+1).

Step D: N-(6-Methyl-4-phenylpyridin-3-yl)-3-(1H-pyrazol-5-yl)-4-(trifluoromethyl)-benzamide A solution of HCl in EtOAc (4 M, 0.90 mL, 3.6 mmol) was added to a solution of N-(6-methyl-4-phenylpyridin-3-yl)-3-(1-(tetrahydro-2H-pyran-2-yl)-1H-pyrazol-5-yl)-4-(trifluoromethyl)benzamide (348 mg, 0.687 mmol) in THF (10 mL), and the resulting mixture was stirred at ambient temperature for 18 h. The mixture was concentrated and the residue was purified by reverse-phase HPLC to give the title compound. MS: m/z=423 (M+1). $^1$H NMR (400 MHz, CD$_3$OD) δ 9.09 (s, 1H), 8.02 (s, 1H), 7.91-7.98 (m, 2H), 7.88 (s, 1H), 7.73 (d, J=2.4 Hz, 1H), 7.61-7.64 (m, 2H), 7.50-7.57 (m, 3H), 6.50 (d, J=1.3 Hz, 1H), 2.79 (s, 3H).

The following examples were prepared in similar fashion to the procedures described above.

| Compound Number | Structure | Compound Name | LCMS (M + 1) |
|---|---|---|---|
| 6 | 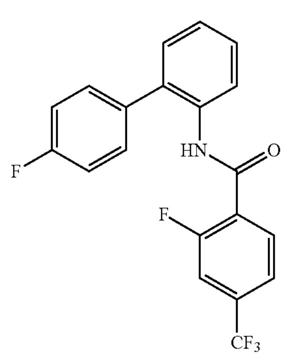 [SMILES: O=C(Nc1ccccc1-c1ccc(F)cc1)c1ccc(C(F)(F)F)cc1F] | 2-fluoro-N-(4'-fluorobiphenyl-2-yl)-4-(trifluoromethyl)benzamide | 378 |

| Compound Number | Structure | Compound Name | LCMS (M + 1) |
|---|---|---|---|
| 7 | 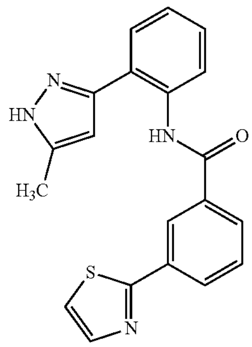 [SMILES: Cc1cc(-c2ccccc2NC(=O)c2cccc(-c3nccs3)c2)n[nH]1] | N-[2-(5-methyl-1H-pyrazol-3-yl)phenyl]-3-(1,3-thiazol-2-yl)benzamide | 361.1 |
| 8 | 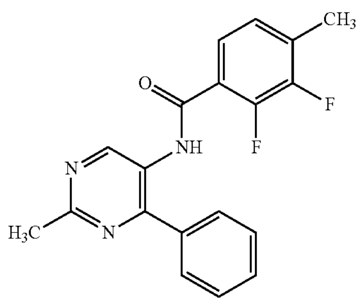 | 2,3-difluoro-4-methyl-N-(2-methyl-4-phenylpyrimidin-5-yl)benzamide | 340.1 |
| 9 | 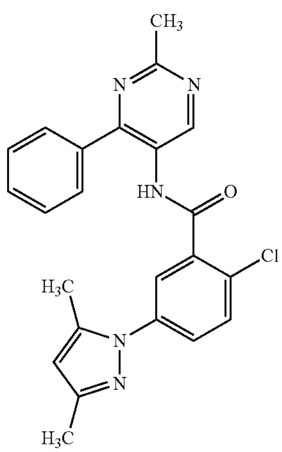 [SMILES: Cc1cc(C)n(-c2ccc(Cl)c(C(=O)Nc3cnc(C)nc3-c3ccccc3)c2)n1] | 2-chloro-5-(3,5-dimethyl-1H-pyrazol-1-yl)-N-(2-methyl-4-phenylpyrimidin-5-yl)benzamide | 418.1 |
| 10 | 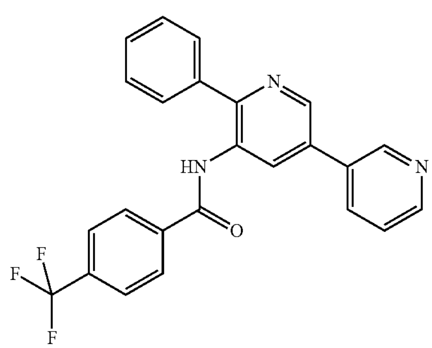 [SMILES: O=C(Nc1cc(-c2cccnc2)cnc1-c1ccccc1)c1ccc(C(F)(F)F)cc1] | N-(6-phenyl-3,3'-bipyridin-5-yl)-4-(trifluoromethyl)benzamide | 420 |

| Compound Number | Structure | Compound Name | LCMS (M + 1) |
|---|---|---|---|
| 11 | 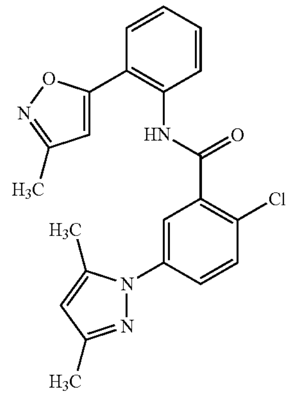 [SMILES: Cc1cc(-c2ccccc2NC(=O)c2cc(-n3nc(C)cc3C)ccc2Cl)on1] | 2-chloro-5-(3,5-dimethyl-1H-pyrazol-1-yl)-N-[2-(3-methylisoxazol-5-yl)phenyl]benzamide | 407.1 |
| 12 | 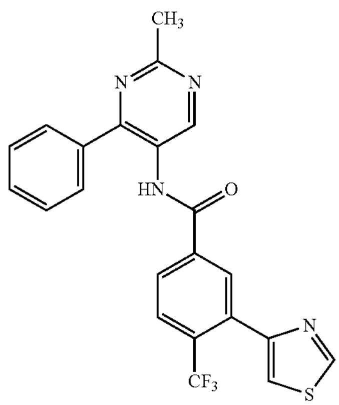 [SMILES: Cc1ncc(NC(=O)c2ccc(C(F)(F)F)c(-c3cscn3)c2)c(-c2ccccc2)n1] | N-(2-methyl-4-phenylpyrimidin-5-yl)-3-(1,3-thiazol-4-yl)-4-(trifluoromethyl)benzamide | 441.1 |
| 13 | 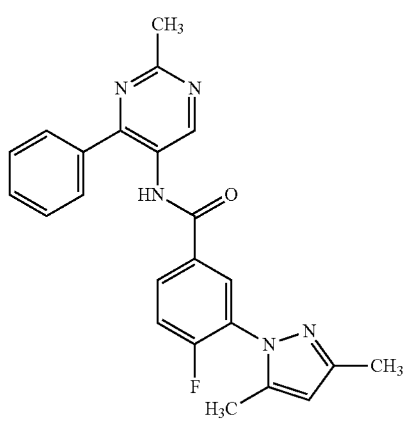 [SMILES: Cc1cc(C)n(-c2cc(C(=O)Nc3cnc(C)nc3-c3ccccc3)ccc2F)n1] | 3-(3,5-dimethyl-1H-pyrazol-1-yl)-4-fluoro-N-(2-methyl-4-phenylpyrimidin-5-yl)benzamide | 402.2 |

-continued

| Compound Number | Structure | Compound Name | LCMS (M + 1) |
|---|---|---|---|
| 14 | 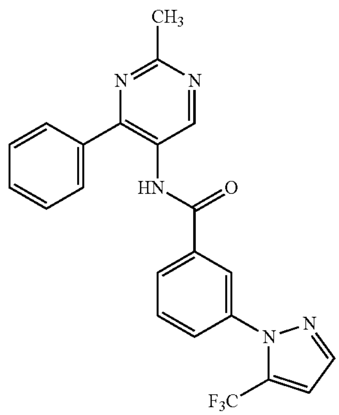 [SMILES: Cc1ncc(NC(=O)c2cccc(-n3nccc3C(F)(F)F)c2)c(-c2ccccc2)n1] | N-(2-methyl-4-phenylpyrimidin-5-yl)-3-[5-(trifluoromethyl)-1H-pyrazol-1-yl]benzamide | 424.1 |
| 15 | 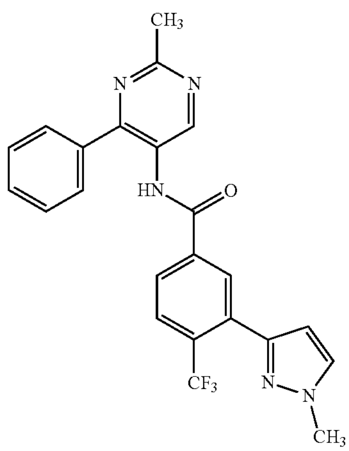 [SMILES: Cc1ncc(NC(=O)c2ccc(C(F)(F)F)c(-c3ccn(C)n3)c2)c(-c2ccccc2)n1] | N-(2-methyl-4-phenylpyrimidin-5-yl)-3-(1-methyl-1H-pyrazol-3-yl)-4-(trifluoromethyl)benzamide | 438.2 |
| 16 | 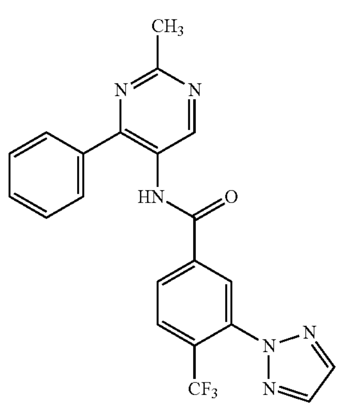 [SMILES: Cc1ncc(NC(=O)c2ccc(C(F)(F)F)c(-n3nccn3)c2)c(-c2ccccc2)n1] | N-(2-methyl-4-phenylpyrimidin-5-yl)-3-(2H-1,2,3-triazol-2-yl)-4-(trifluoromethyl)benzamide | 425.1 |

-continued

| Compound Number | Structure | Compound Name | LCMS (M + 1) |
|---|---|---|---|
| 17 | 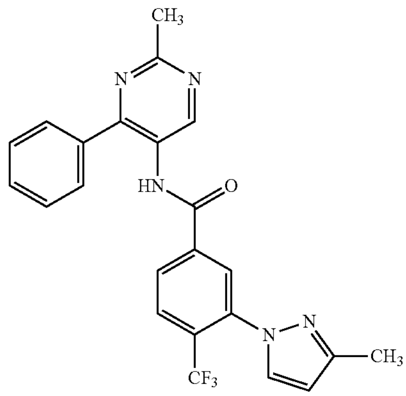 [SMILES: Cc1ccn(-c2cc(C(=O)Nc3cnc(C)nc3-c3ccccc3)ccc2C(F)(F)F)n1] | N-(2-methyl-4-phenylpyrimidin-5-yl)-3-(3-methyl-1H-pyrazol-1-yl)-4-(trifluoromethyl)benzamide | 438.2 |
| 18 | 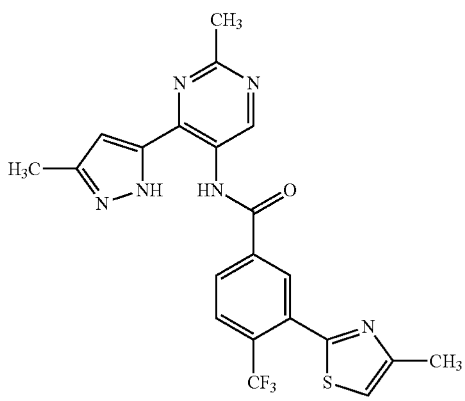 | N-[2-methyl-4-(3-methyl-1H-pyrazol-5-yl)pyrimidin-5-yl]-3-(4-methyl-1,3-thiazol-2-yl)-4-(trifluoromethyl)benzamide | 459 |
| 19 | 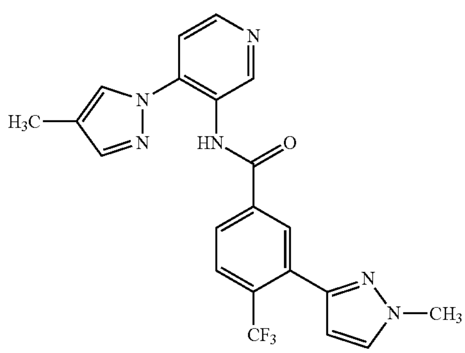 | 3-(1-methyl-1H-pyrazol-3-yl)-N-[4-(4-methyl-1H-pyrazol-1-yl)pyridin-3-yl]-4-(trifluoromethyl)benzamide | 427 |
| 20 | 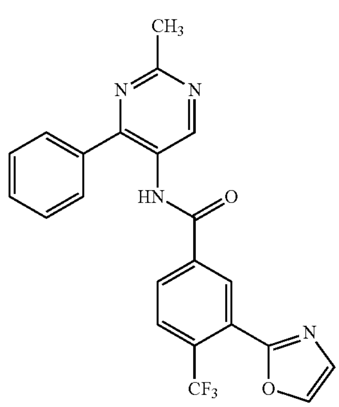 [SMILES: Cc1ncc(NC(=O)c2ccc(C(F)(F)F)c(-c3ncco3)c2)c(-c2ccccc2)n1] | N-(2-methyl-4-phenylpyrimidin-5-yl)-3-(1,3-oxazol-2-yl)-4-(trifluoromethyl)benzamide | 425 |

-continued

| Compound Number | Structure | Compound Name | LCMS (M + 1) |
|---|---|---|---|
| 21 | 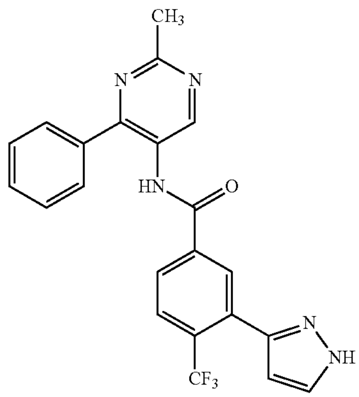 [SMILES: Cc1ncc(NC(=O)c2ccc(C(F)(F)F)c(-c3cc[nH]n3)c2)c(-c2ccccc2)n1] | N-(2-methyl-4-phenylpyrimidin-5-yl)-3-(1H-pyrazol-3-yl)-4-(trifluoromethyl)benzamide | 424 |
| 22 | 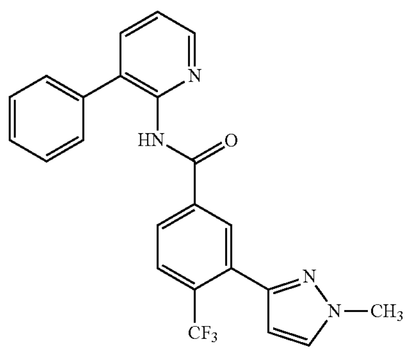 [SMILES: Cn1ccc(-c2cc(C(=O)Nc3ncccc3-c3ccccc3)ccc2C(F)(F)F)n1] | 3-(1-methyl-1H-pyrazol-3-yl)-N-(3-phenylpyridin-2-yl)-4-(trifluoromethyl)benzamide | 423 |
| 23 | 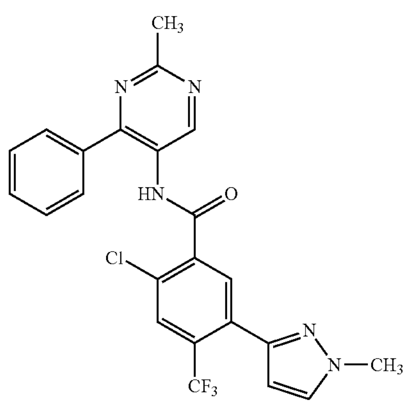 [SMILES: Cc1ncc(NC(=O)c2cc(-c3ccn(C)n3)c(C(F)(F)F)cc2Cl)c(-c2ccccc2)n1] | 2-chloro-N-(2-methyl-4-phenylpyrimidin-5-yl)-5-(1-methyl-1H-pyrazol-3-yl)-4-(trifluoromethyl)benzamide | 472.1 |
| 24 | 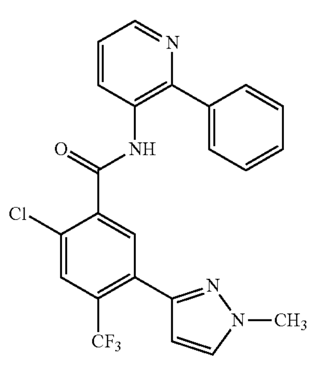 [SMILES: Cn1ccc(-c2cc(C(=O)Nc3cccnc3-c3ccccc3)c(Cl)cc2C(F)(F)F)n1] | 2-chloro-5-(1-methyl-1H-pyrazol-3-yl)-N-(2-phenylpyridin-3-yl)-4-(trifluoromethyl)benzamide | 457.1 |

-continued

| Compound Number | Structure | Compound Name | LCMS (M + 1) |
|---|---|---|---|
| 25 | 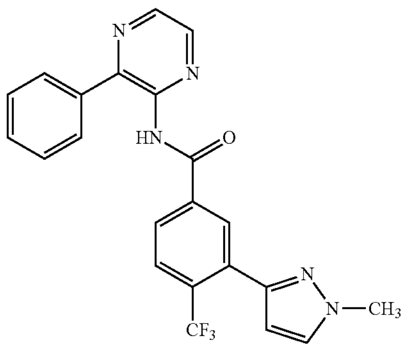 [SMILES: Cn1ccc(-c2cc(C(=O)Nc3nccnc3-c3ccccc3)ccc2C(F)(F)F)n1] | 3-(1-methyl-1H-pyrazol-3-yl)-N-(3-phenylpyrazin-2-yl)-4-(trifluoromethyl)benzamide | 424.2 |
| 26 | 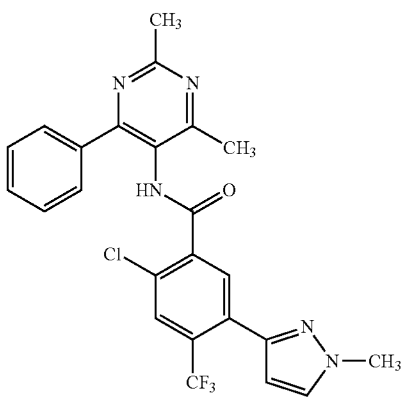 [SMILES: Cc1nc(C)c(NC(=O)c2cc(-c3ccn(C)n3)c(C(F)(F)F)cc2Cl)c(-c2ccccc2)n1] | N-(2,4-dimethyl-6-phenylpyrimidin-5-yl)-3-(1-methyl-1H-pyrazol-3-yl)-4-(trifluoromethyl)benzamide | 452.2 |
| 27 | 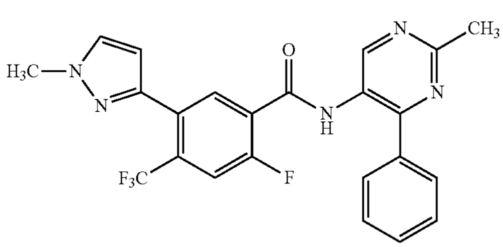 | 2-fluoro-N-(2-methyl-4-phenylpyrimidin-5-yl)-5-(1-methyl-1H-pyrazol-3-yl)-4-(trifluoromethyl)benzamide | 457.1 |
| 28 | 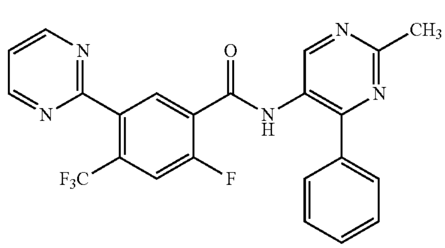 [SMILES: Cc1ncc(NC(=O)c2cc(-c3ncccn3)c(C(F)(F)F)cc2F)c(-c2ccccc2)n1] | 2-fluoro-N-(2-methyl-4-phenylpyrimidin-5-yl)-5-pyrimidin-2-yl-4-(trifluoromethyl)benzamide | 454.2 |

-continued

| Compound Number | Structure | Compound Name | LCMS (M + 1) |
|---|---|---|---|
| 29 | 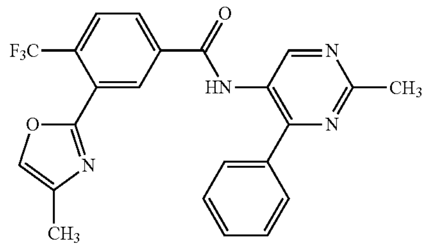 [SMILES: Cc1coc(-c2cc(C(=O)Nc3cnc(C)nc3-c3ccccc3)ccc2C(F)(F)F)n1] | 3-(4-methyl-1,3-oxazol-2-yl)-N-(2-methyl-4-phenylpyrimidin-5-yl)-4-(trifluoromethyl)benzamide | 439 |
| 30 | 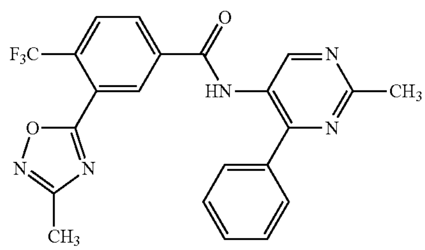 [SMILES: Cc1noc(-c2cc(C(=O)Nc3cnc(C)nc3-c3ccccc3)ccc2C(F)(F)F)n1] | 3-(3-methyl-1,2,4-oxadiazol-5-yl)-N-(2-methyl-4-phenylpyrimidin-5-yl)-4-(trifluoromethyl)benzamide | 440 |
| 31 | 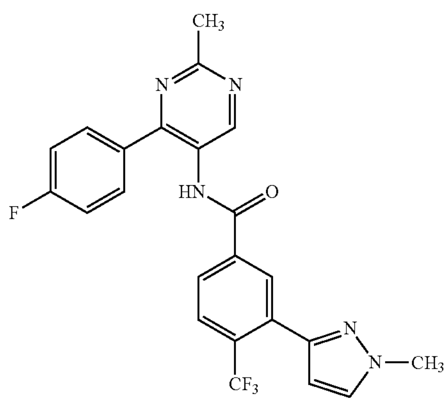 [SMILES: Cc1ncc(NC(=O)c2ccc(C(F)(F)F)c(-c3ccn(C)n3)c2)c(-c2ccc(F)cc2)n1] | N-[4-(4-fluorophenyl)-2-methylpyrimidin-5-yl]-3-(1-methyl-1H-pyrazol-3-yl)-4-(trifluoromethyl)benzamide | 456.2 |
| 32 | 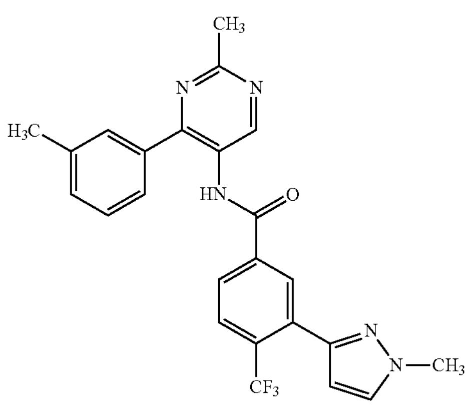 | N-[2-methyl-4-(3-methylphenyl)pyrimidin-5-yl]-3-(1-methyl-1H-pyrazol-3-yl)-4-(trifluoromethyl)benzamide | 452.3 |

| Compound Number | Structure | Compound Name | LCMS (M + 1) |
|---|---|---|---|
| 33 | 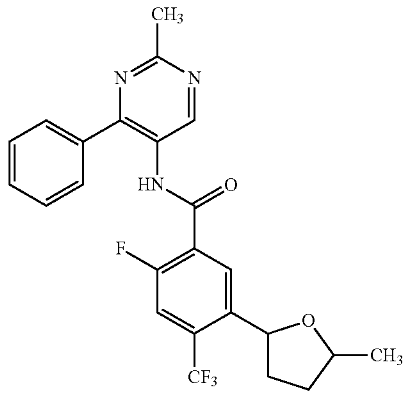 [SMILES: Cc1ncc(NC(=O)c2cc(C3CCC(C)O3)c(C(F)(F)F)cc2F)c(-c2ccccc2)n1] | 2-fluoro-N-(2-methyl-4-phenylpyrimidin-5-yl)-5-(5-methyltetrahydrofuran-2-yl)-4-(trifluoromethyl)benzamide | 460.2 |
| 34 | 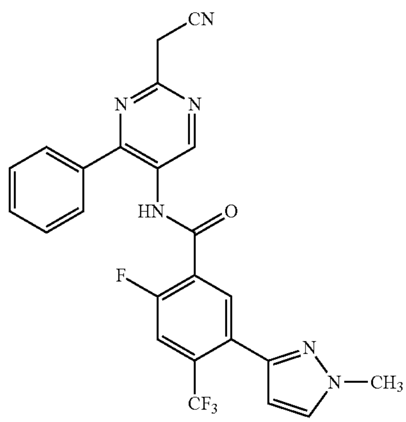 [SMILES: Cn1ccc(-c2cc(C(=O)Nc3cnc(CC#N)nc3-c3ccccc3)c(F)cc2C(F)(F)F)n1] | N-(2-(cyanomethyl)-4-phenylpyrimidin-5-yl)-2-fluoro-5-(1-methyl-1H-pyrazol-3-yl)-4-(trifluoromethyl)benzamide | 481.3 |
REACTION SCHEME FOR EXAMPLE 35
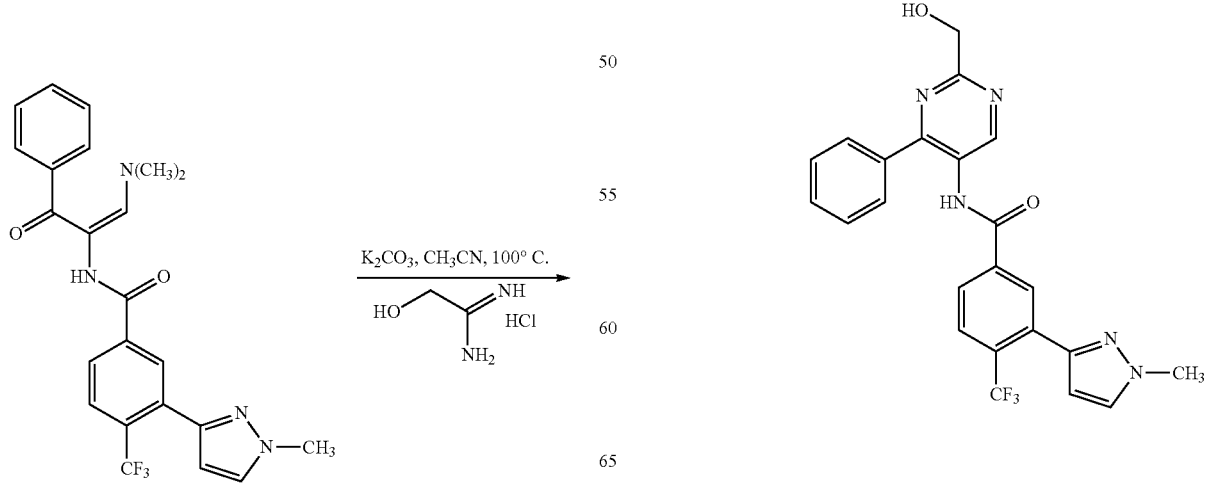

EXAMPLE 35

N-(2-(Hydroxymethyl)-4-phenylpyrimidin-5-yl)-3-(1-methyl-1H-pyrazol-3-yl)-4-(trifluoromethyl)benzamide

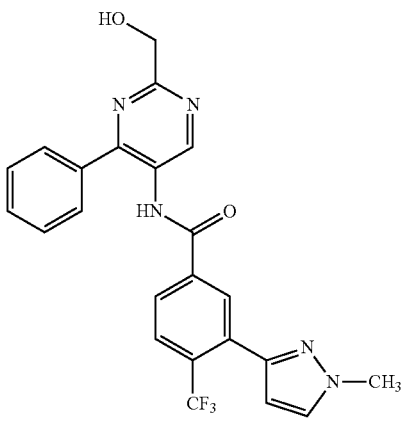 [SMILES: Cn1ccc(-c2cc(C(=O)Nc3cnc(CO)nc3-c3ccccc3)ccc2C(F)(F)F)n1]

A mixture of N-(1-(dimethylamino)-3-oxo-3-phenylprop-1-en-2-yl)-3-(1-methyl-1H-pyrazol-3-yl)-4-(trifluoromethyl)benzamide (2.04 g, 4.62 mmol), 2-hydroxyacetimidamide hydrochloride (0.818 g, 7.40 mmol), and potassium carbonate (1.92 g, 13.9 mmol) in EtOH (8 mL) was heated at 65° C. for 2 h and then at 80° C. for 18 h. The reaction mixture was cooled and then filtered, washing with EtOH and water. The filtrate was diluted with water (50 mL), and extracted with DCM (3×50 mL). The combined organic layers were dried over $Na_2SO_4$ and concentrated, and the residue was purified by column chromatography on silica gel (hexanes/EtOAc=97:3 to 0:100) to afford the title compound. MS: m/z=454.2 (M+1). $^1$H NMR (400 MHz, $CDCl_3$) δ 9.69 (s, 1H), 8.10 (s, 1H), 8.02 (s, 1H), 7.83-7.78 (m, 2H), 7.70-7.67 (m, 2H), 7.58-7.50 (m, 3H), 7.39 (d, J=2.3 Hz, 1H), 6.48 (s, 1H), 4.87 (d, J=4.8 Hz, 2H), 3.95 (s, 3H), 3.62 (t, J=4.8 Hz, 1H).

The following examples were prepared in similar fashion to the procedures described above.

| Compound Number | Structure | Compound Name | LCMS (M + 1) |
|---|---|---|---|
| 36 | 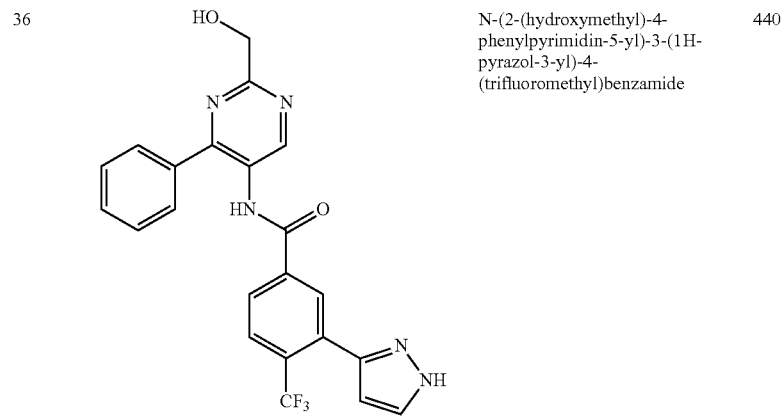 | N-(2-(hydroxymethyl)-4-phenylpyrimidin-5-yl)-3-(1H-pyrazol-3-yl)-4-(trifluoromethyl)benzamide | 440 |
| 37 | 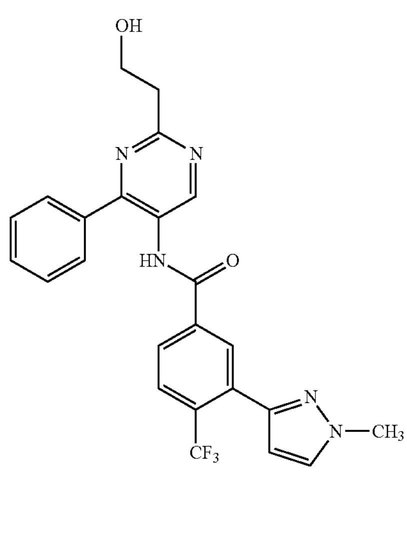 [SMILES: Cn1ccc(-c2cc(C(=O)Nc3cnc(CCO)nc3-c3ccccc3)ccc2C(F)(F)F)n1] | N-(2-(2-hydroxyethyl)-4-phenylpyrimidin-5-yl)-3-(1-methyl-1H-pyrazol-3-yl)-4-(trifluoromethyl)benzamide | 468.2 |

| Compound Number | Structure | Compound Name | LCMS (M + 1) |
|---|---|---|---|
| 38 | 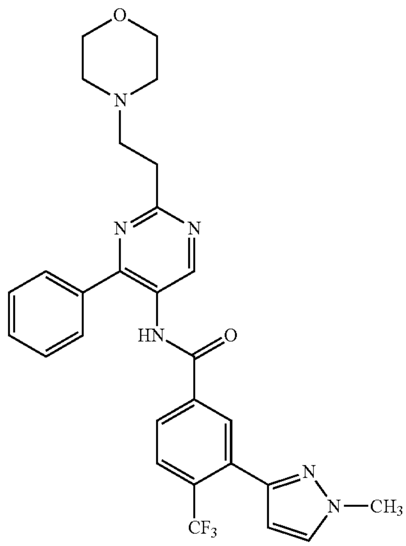 [SMILES: Cn1ccc(-c2cc(C(=O)Nc3cnc(CCN4CCOCC4)nc3-c3ccccc3)ccc2C(F)(F)F)n1] | 3-(1-methyl-1H-pyrazol-3-yl)-N-(2-(2-morpholinoethyl)-4-phenylpyrimidin-5-yl)-4-(trifluoromethyl)benzamide | 537.2 |

EXAMPLE 39

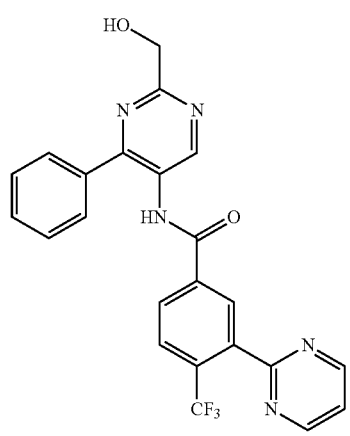 [SMILES: O=C(Nc1cnc(CO)nc1-c1ccccc1)c1ccc(C(F)(F)F)c(-c2ncccn2)c1]

N-(2-(Hydroxymethyl)-4-phenylpyrimidin-5-yl)-3-(pyrimidin-2-yl)-4-(trifluoromethyl)benzamide Step A: N-(4-Phenyl-2-(((triisopropylsilyl)oxy)methyl)pyrimidin-5-yl)-3-(pyrimidin-2-yl)-4-(trifluoromethyl)benzamide POCl$_3$ (0.023 mL, 0.25 mmol) was added to a solution of 4-phenyl-2-(((triisopropylsilyl)oxy)methyl)pyrimidin-5-amine (59 mg, 0.16 mmol), 3-(pyrimidin-2-yl)-4-(trifluoromethyl)benzoic acid (44 mg, 0.16 mmol), and pyridine (0.080 mL, 0.99 mmol) in DCM (1 mL) at −15° C., and the resulting mixture was stirred at ambient temperature for 4.5 h. The product mixture was purified directly by column chromatography on silica gel (EtOAc:hexanes=0:100 to 50:50) to give the title compound. MS: m/z=608.4 (M+1).

Step B: N-(2-(Hydroxymethyl)-4-phenylpyrimidin-5-yl)-3-(pyrimidin-2-yl)-4-(trifluoromethyl)benzamide A mixture of n-Bu$_4$NF (0.118 mL, 0.118 mmol, 1.0 M in THF) and N-(4-phenyl-2-(((triisopropylsilyl)oxy)methyl)pyrimidin-5-yl)-3-(pyrimidin-2-yl)-4-(trifluoromethyl)benzamide (36 mg, 0.059 mmol) in THF (1 mL) and was stirred at ambient temperature for 2.5 h. The product mixture was purified by column chromatography on silica gel (EtOAc:DCM=0:100 to 100:0) to yield the title compound. MS: m/z=452.2 (M+1). $^1$H NMR (400 MHz, DMSO-d$_6$) δ 10.7 (s, 1H), 8.94 (d, J=4.9 Hz, 2H), 8.86 (s, 1H), 8.21 (s, 1H), 8.15 (d, J=8.9 Hz, 1H), 8.02 (d, J=8.4 Hz, 1H), 7.80-7.75 (m, 2H), 7.56 (t, J=4.9 Hz, 1H), 7.42-7.40 (m, 3H), 5.30 (t, J=6.6 Hz, 1H), 4.64 (d, J=6.3 Hz, 2H).

The following example was prepared in similar fashion to the procedures described above.

| Compound Number | Structure | Compound Name | LCMS (M + 1) |
|---|---|---|---|
| 40 | 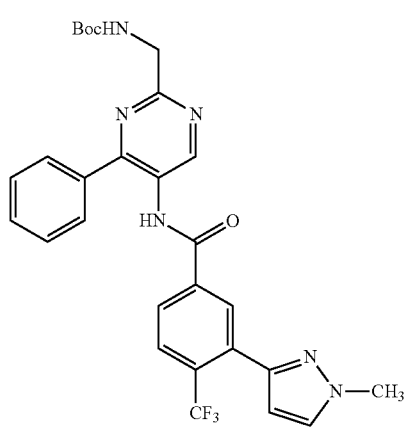 [SMILES: Cn1ccc(-c2cc(C(=O)Nc3cnc(CNC(=O)OC(C)(C)C)nc3-c3ccccc3)ccc2C(F)(F)F)n1] | N-(2-(hydroxymethyl)-4-phenylpyrimidin-5-yl)-3-(1H-pyrazol-3-yl)-4-(trifluoromethyl)benzamide | 440 |

EXAMPLE 41

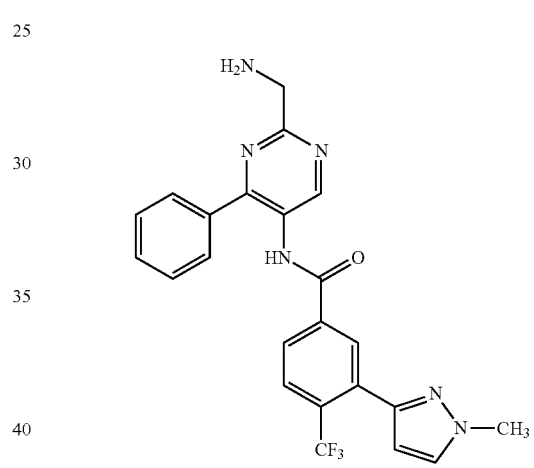

t-Butyl ((5-(3-(1-methyl-1H-pyrazol-3-yl)-4-(trifluoromethyl)benzamido)-4-phenylpyrimidin-2-yl)methyl)carbamate A mixture of N-(1-(dimethylamino)-3-oxo-3-phenylprop-1-en-2-yl)-3-(1-methyl-1H-pyrazol-3-yl)-4-(trifluoromethyl)benzamide (1.00 g, 2.26 mmol), tert-butyl (2-amino-2-iminoethyl)carbamate acetate (701 mg, 3.01 mmol), and potassium carbonate (0.937 g, 6.78 mmol) in acetonitrile (5 mL) was heated at 100° C. for 3.5 h. The reaction mixture was cooled and then filtered, washing with acetonitrile (3×10 mL). The filtrate was concentrated and the residue was purified by column chromatography on silica gel (hexanes:EtOAc=97:3 to 0:100) to give the title compound. MS: m/z=553.3 (M+1). $^1$H NMR (400 MHz, CDCl$_3$) δ 9.66 (s, 1H), 8.06 (s, 1H), 8.01 (s, 1H), 7.81-7.78 (m, 2H), 7.68 (dd, J=7.3, 1.6 Hz, 2H), 7.56-7.49 (m, 3H), 7.39 (d, J=2.2 Hz, 1H), 6.47 (s, 1H), 5.62 (s, 1H), 4.62 (d, J=5.5 Hz, 2H), 3.95 (s, 3H), 1.46 (s, 9H).

EXAMPLE 42

N-(2-(Aminomethyl)-4-phenylpyrimidin-5-yl)-3-(1-methyl-1H-pyrazol-3-yl)-4-(trifluoromethyl)benzamide A solution of t-butyl ((5-(3-(1-methyl-1H-pyrazol-3-yl)-4-(trifluoromethyl)benzamido)-4-phenylpyrimidin-2-yl)methyl)carbamate (615 mg, 1.11 mmol) in 4M HCl in dioxane (5.0 mL, 20 mmol) was stirred at ambient temperature for 5 h. The mixture was concentrated to yield the title compound as an HCl salt. MS: m/z=453.2 (M+1). $^1$H NMR (400 MHz, CDCl$_3$) δ 9.50 (s, 1H), 8.61 (s, 2H), 8.04 (d, J=8.4 Hz, 1H), 7.97 (s, 1H), 7.82-7.78 (m, 2H), 7.68-7.60 (m, 2H), 7.49-7.42 (m, 3H), 7.42 (d, J=2.3 Hz, 1H), 6.49 (s, 1H), 4.47 (s, 2H), 3.95 (s, 3H).

The following example was prepared in similar fashion to the procedures described above.

| Compound Number | Structure | Compound Name | LCMS (M + 1) |
|---|---|---|---|
| 43 | 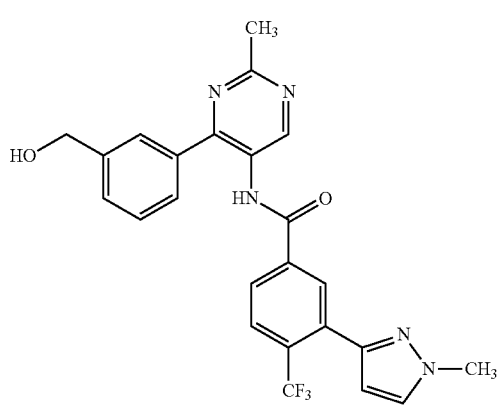 [SMILES: Cc1ncc(NC(=O)c2ccc(C(F)(F)F)c(-c3ccn(C)n3)c2)c(-c2cccc(CO)c2)n1] | N-(2-(aminomethyl)-4-phenylpyrimidin-5-yl)-3-(1-(difluoromethyl)-1H-pyrazol-3-yl)-4-(trifluoromethyl)benzamide | 489.2 |

EXAMPLE 44

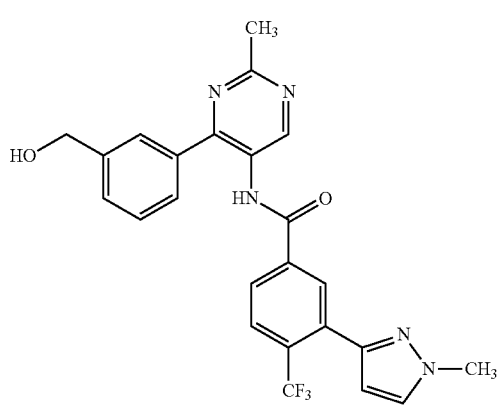 [SMILES: Cc1ncc(NC(=O)c2ccc(C(F)(F)F)c(-c3ccn(C)n3)c2)c(-c2cccc(CO)c2)n1]

N-(4-(3-(Hydroxymethyl)phenyl)-2-methylpyrimidin-5-yl)-3-(1-methyl-1H-pyrazol-3-yl)-4-(trifluoromethyl)benzamide A deoxygenated mixture of bis(tri-t-butylphosphine)palladium (0.78 mg, 1.5 μmol), N-(4-chloro-2-methylpyrimidin-5-yl)-3-(1-methyl-1H-pyrazol-3-yl)-4-(trifluoromethyl)benzamide (12 mg, 0.030 mmol), (3-(hydroxymethyl)phenyl)boronic acid (14 mg, 0.091 mmol), and aqueous cesium carbonate solution (0.030 mL, 0.061 mmol, 2M) in dioxane (0.4 mL) was heated at 100° C. under microwave irradiation for 0.5 h. The product mixture was purified by column chromatography on silica gel (DCM:MeOH:NH$_4$OH=100:0:0 to 90:10:1) to afford the title compound. MS: m/z=468.2 (M+1). $^1$H NMR (400 MHz, CD$_3$OD) δ 8.88 (s, 1H), 8.05 (s, 1H), 7.98 (d, J=8.2 Hz, 1H), 7.90 (d, J=8.2 Hz, 1H), 7.78 (s, 1H), 7.66-7.64 (m, 2H), 7.47-7.45 (m, 2H), 6.46 (s, 1H), 4.47 (d, J=1.2 Hz, 1H), 3.96 (s, 3H), 2.76 (s, 3H).

EXAMPLE 45

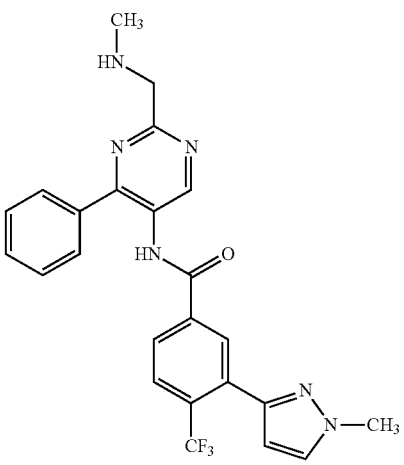 [SMILES: CNCc1ncc(NC(=O)c2ccc(C(F)(F)F)c(-c3ccn(C)n3)c2)c(-c2ccccc2)n1]

3-(1-Methyl-1H-pyrazol-3-O—N-(2-((methylamino)methyl)-4-phenylpyrimidin-5-yl)-4-(trifluoromethyl)benzamide Step A: N-(2-Formyl-4-phenylpyrimidin-5-yl)-3-(1-methyl-1H-pyrazol-3-yl)-4-(trifluoromethyl)benzamide A mixture of N-(2-(hydroxymethyl)-4-phenylpyrimidin-5-yl)-3-(1-methyl-1H-pyrazol-3-yl)-4-(trifluoromethyl)benzamide (452 mg, 0.997 mmol) and Dess-Martin periodinane (507 mg, 1.20 mmol) in DCM (5 mL) was stirred at ambient temperature for 18 h. Additional Dess-Martin Periodinane (200 mg, 0.47 mmol) was added and the mixture was stirred for 3 h. The reaction mixture was filtered, washing with DCM. The filtrate was concentrated and the residue was purified by column chromatography on silica gel (DCM:EtOAc=100:0 to 0:100) to yield the title compound. MS: m/z=452.2 (M+1).

Step B: 3-(1-Methyl-1H-pyrazol-3-yl)-N-(2-((methylamino)methyl)-4-phenylpyrimidin-5-yl)-4-(trifluoromethyl)benzamide A mixture of N-(2-formyl-4-phenylpyrimidin-5-yl)-3-(1-methyl-1H-pyrazol-3-yl)-4-(trifluoromethyl)benzamide (9 mg, 0.02 mmol), methylamine (0.030 mL, 0.060 mmol, 2M in THF), sodium triacetoxyborohydride (5 mg, 0.03 mmol), and acetic acid (0.057 mL, 0.10 mmol) in DCE (1 mL) was stirred at ambient temperature for 2 h. The reaction mixture was concentrated and the residue was purified by reverse-phase HPLC ($C_{18}$ column, $H_2O:CH_3CN:CF_3CO_2H$=95:5:0.1 to 5:95:0.1) to yield the title compound as the TFA salt. MS: m/z=467.3 (M+1). $^1$H NMR (400 MHz, $CDCl_3$) δ 9.57 (s, 1H), 8.57 (s, 1H), 7.98 (s, 1H), 7.87-7.82 (m, 2H), 7.69-7.66 (m, 2H), 7.50-7.47 (m, 3H), 7.44 (d, J=2.4 Hz, 1H), 6.51 (s, 1H), 4.48 (s, 2H), 3.98 (s, 3H), 2.92 (s, 3H).

EXAMPLE 46

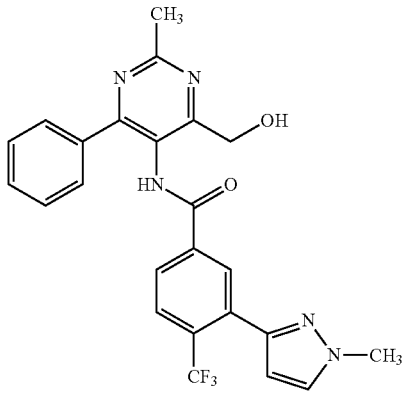 [SMILES: Cc1nc(CO)c(NC(=O)c2ccc(C(F)(F)F)c(-c3ccn(C)n3)c2)c(-c2ccccc2)n1]

N-(4-(Hydroxymethyl)-2-methyl-6-phenylpyrimidin-5-yl)-3-(1-methyl-1H-pyrazol-3-yl)-4-(trifluoromethyl)benzamide Step A: N-(4-(((t-Butyldimethylsilyl)oxy)methyl)-2-methyl-6-phenylpyrimidin-5-yl)-3-(1-methyl-1H-pyrazol-3-yl)-4-(trifluoromethyl)benzamide A deoxygenated mixture of N-(4-chloro-2-methyl-6-phenylpyrimidin-5-yl)-3-(1-methyl-1H-pyrazol-3-yl)-4-(trifluoromethyl)benzamide (50 mg, 0.11 mmol), t-butyldimethyl((tributylstannyl)methoxy)silane (69 mg, 0.16 mmol), and tetrakis(triphenylphosphine)palladium (12 mg, 0.011 mmol) in dioxane (0.6 mL) and was heated at 150° C. under microwave irradiation for 2 h. The reaction mixture was diluted with DMF (1 mL) and purified by reverse-phase HPLC ($C_{18}$ column, $H_2O:CH_3CN:CF_3CO_2H$=95:5:0.1 to 5:95:0.1). The desired fractions were neutralized by partitioning between saturated aqueous $NaHCO_3$ solution (10 mL) and DCM (3×10 mL). The combined organic layers were dried over $Na_2SO_4$ and concentrated to yield the title compound. MS: m/z=582.3 (M+1).

Step B: N-(4-(Hydroxymethyl)-2-methyl-6-phenylpyrimidin-5-yl)-3-(1-methyl-1H-pyrazol-3-yl)-4-(trifluoromethyl)benzamide A mixture of n-$Bu_4NF$ (0.108 mL, 0.108 mmol, 1M in THF) and N-(4-(((t-butyldimethylsilyl)oxy)methyl)-2-methyl-6-phenylpyrimidin-5-yl)-3-(1-methyl-1H-pyrazol-3-yl)-4-(trifluoromethyl)benzamide (21 mg, 0.036 mmol) in THF (1 mL) was stirred at ambient temperature for 1 h. The product mixture was purified by column chromatography on silica gel (DCM:EtOAc=97:3 to 0:100) to yield the title compound. MS: m/z=468.2 (M+1). $^1$H NMR (400 MHz, $CDCl_3$) δ 8.03 (s, 1H), 7.84-7.78 (m, 2H), 7.76-7.63 (s, 1H), 7.60-7.55 (m, 2H), 7.42-7.36 (m, 4H), 6.47 (s, 1H), 4.69 (s, 2H), 3.92 (s, 3H), 2.81 (s, 3H).

The following example was prepared in similar fashion to the procedures described above.

| Compound Number | Structure | Compound Name | LCMS (M + 1) |
|---|---|---|---|
| 47 | 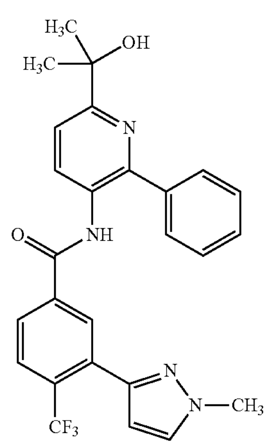 [SMILES: Cn1ccc(-c2cc(C(=O)Nc3ccc(C(C)(C)O)nc3-c3ccccc3)ccc2C(F)(F)F)n1] | N-(6-(2-hydroxypropan-2-yl)-2-phenylpyridin-3-yl)-3-(1-methyl-1H-pyrazol-3-yl)-4-(trifluoromethyl)benzamide | 481.2 |

REACTION SCHEME FOR EXAMPLE 48

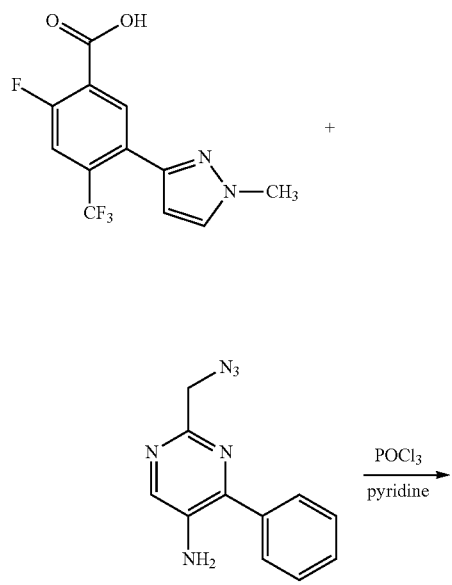

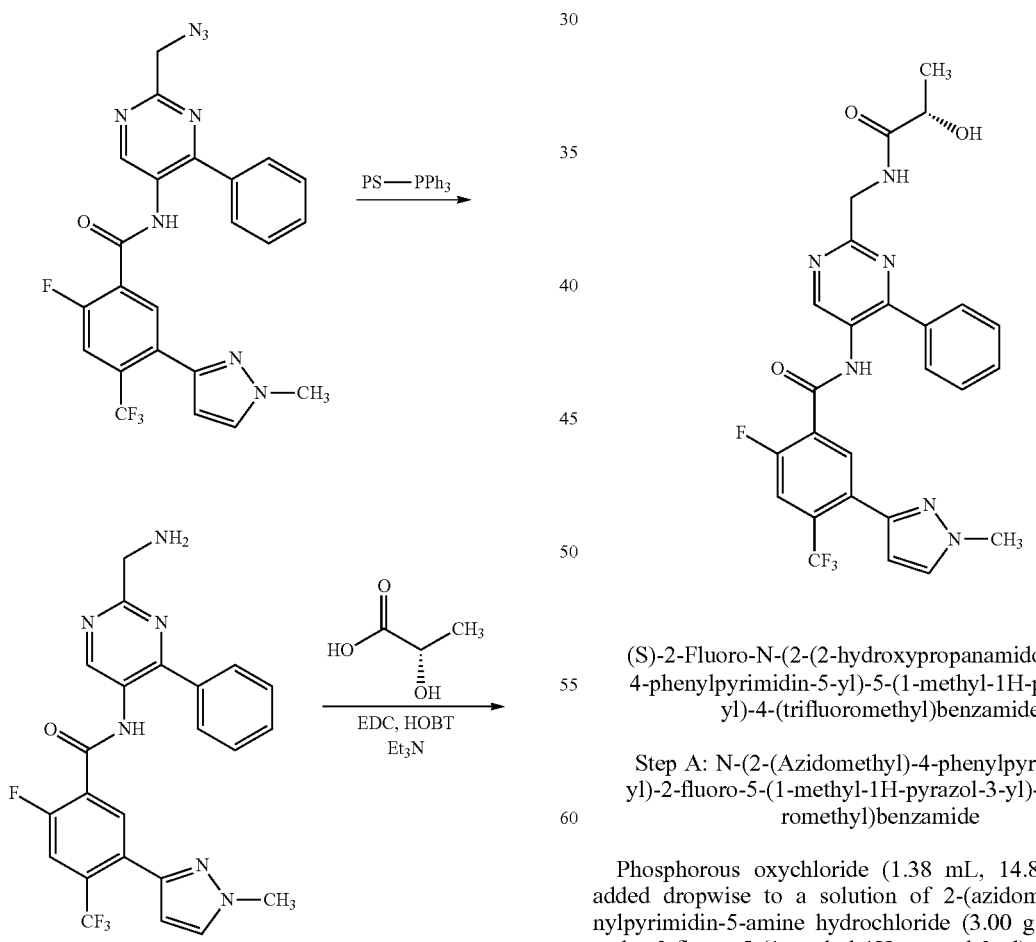

EXAMPLE 48

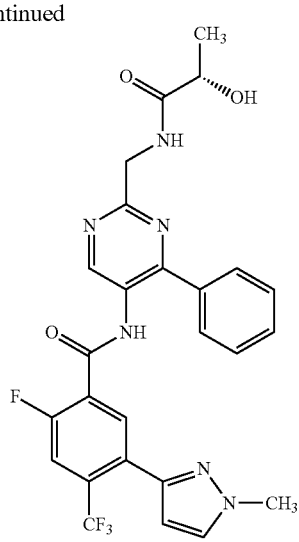

(S)-2-Fluoro-N-(2-(2-hydroxypropanamido)methyl)-4-phenylpyrimidin-5-yl)-5-(1-methyl-1H-pyrazol-3-yl)-4-(trifluoromethyl)benzamide Step A: N-(2-(Azidomethyl)-4-phenylpyrimidin-5-yl)-2-fluoro-5-(1-methyl-1H-pyrazol-3-yl)-4-(trifluoromethyl)benzamide Phosphorous oxychloride (1.38 mL, 14.8 mmol) was added dropwise to a solution of 2-(azidomethyl)-4-phenylpyrimidin-5-amine hydrochloride (3.00 g, 11.4 mmol) and 2-fluoro-5-(1-methyl-1H-pyrazol-3-yl)-4-(trifluoromethyl)benzoic acid (4.28 g, 14.8 mmol) in pyridine (30 mL) at 0° C. The resulting mixture was stirred for 30 min and then carefully diluted with saturated aqueous sodium bicarbonate solution (75 mL). A majority of the pyridine was removed under reduced pressure, and the remaining aqueous mixture was partitioned between water (100 mL) and EtOAc (2×100 mL). The combined organic layers were dried over sodium sulfate and concentrated. Potassium carbonate (3.16 g, 22.8 mmol) was added to a solution of the residue in MeOH (50 mL) and the resulting suspension was stirred for 20 min then concentrated. The residue was partitioned between water (100 mL) and EtOAc (2×100 mL). The combined organic layers were dried over sodium sulfate and concentrated. The residue was purified by flash column chromatography (hexanes, grading to 100% EtOAc) to provide the title compound. MS: m/z=497.3 (M+1).

Step B: N-(2-(Aminomethyl)-4-phenylpyrimidin-5-yl)-2-fluoro-5-(1-methyl-1H-pyrazol-3-yl)-4-(trifluoromethyl)benzamide A suspension of N-(2-(azidomethyl)-4-phenylpyrimidin-5-yl)-2-fluoro-5-(1-methyl-1H-pyrazol-3-yl)-4-(trifluoromethyl)benzamide (5.05 g, 10.2 mmol) and PS-triphenylphosphine resin (3.51 g, 30.5 mmol) in 2-methyltetrahydrofuran (100 mL) was gently agitated for 2 h before water (1.83 mL, 102 mmol) was added. The mixture was then heated at 40° C. for 60 h then filtered. The resin was washed with 2-methyltetrahydrofuran (2×50 mL) followed by DCM (2×50 mL). The combined filtrate was concentrated to provide the title compound. MS: m/z=471.3 (M+1).

Step C: (S)-2-Fluoro-N-(2-(2-hydroxypropanamido)methyl)-4-phenylpyrimidin-5-yl)-5-(1-methyl-1H-pyrazol-3-yl)-4-(trifluoromethyl)benzamide A mixture of N-(2-(aminomethyl)-4-phenylpyrimidin-5-yl)-2-fluoro-5-(1-methyl-1H-pyrazol-3-yl)-4-(trifluoromethyl)benzamide (1.00 g, 2.13 mmol), (S)-2-hydroxypropanoic acid (0.319 mL, 4.25 mmol), EDC (0.815 g, 4.25 mmol), HOBT (0.651 g, 4.25 mmol) and Et₃N (0.889 mL, 6.38 mmol) in DMF (5 mL) was stirred at 23° C. for 1 h. The product mixture was partitioned between saturated aqueous sodium bicarbonate solution (100 mL) and EtOAc (2×100 mL). The combined organic layers were dried over sodium sulfate and concentrated. Potassium carbonate (250 mg, 1.81 mmol) was added to a solution of the residue in MeOH (30 mL), and the resulting suspension was stirred for 30 min then concentrated. The residue was partitioned between brine and EtOAc (2×50 mL). The combined organic layers were dried over sodium sulfate and concentrated. The residue was purified by preparative reverse-phase HPLC (water/CH₃CN gradient with 0.1% TFA as a modifier) to give the title compound. MS: m/z=543.3 (M+1). $^1$H NMR (400 MHz, DMSO-d$_6$) δ 10.63 (s, 1H), 8.94 (s, 1H), 8.27 (m, 1H), 7.92 (d, J=6.8 Hz, 1H), 7.88 (d, J=10.3 Hz, 1H), 7.84-7.81 (m, 3H), 7.51 (br m, 3H), 6.45 (s, 1H), 5.64 (d, J=5.1 Hz, 1H), 4.57 (d, J=5.6 Hz, 2H), 4.07 (m, 1H), 3.92 (s, 3H), 1.27 (d, J=6.6 Hz, 3H).

The following examples were prepared in similar fashion to the procedures described above.

| Compound Number | Structure | Compound Name | LCMS (M + 1) |
|---|---|---|---|
| 49 | 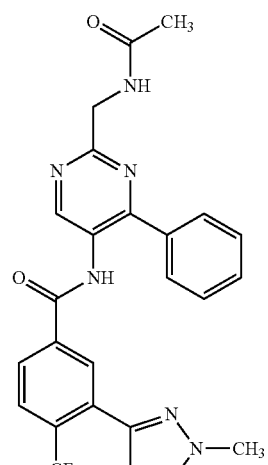 | N-(2-(acetamidomethyl)-4-phenylpyrimidin-5-yl)-3-(1-methyl-1H-pyrazol-3-yl)-4-(trifluoromethyl)benzamide | 495.2 |

| Compound Number | Structure | Compound Name | LCMS (M + 1) |
|---|---|---|---|
| 50 | 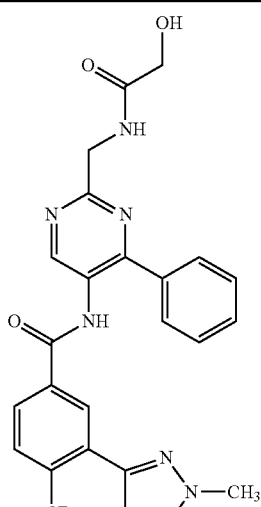 | N-(2-((2-hydroxyacetamido)methyl)-4-phenylpyrimidin-5-yl)-3-(1-methyl-1H-pyrazol-3-yl)-4-(trifluoromethyl)benzamide | 511.2 |
| 51 | 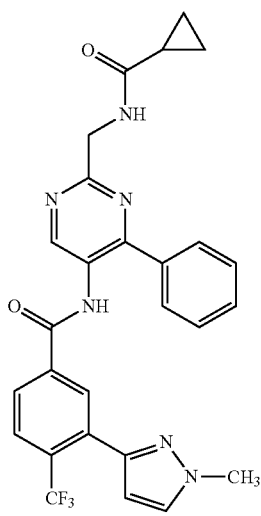 [SMILES: Cn1ccc(-c2cc(C(=O)Nc3cnc(CNC(=O)C4CC4)nc3-c3ccccc3)ccc2C(F)(F)F)n1] | N-(2-(cyclopropanecarboxamidomethyl)-4-phenylpyrimidin-5-yl)-3-(1-methyl-1H-pyrazol-3-yl)-4-(trifluoromethyl)benzamide | 521.3 |
| 52 | 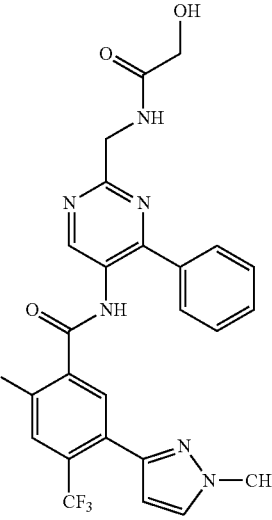 | 2-fluoro-N-(2-((2-hydroxyacetamido)methyl)-4-phenylpyrimidin-5-yl)-5-(1-methyl-1H-pyrazol-3-yl)-4-(trifluoromethyl)benzamide | 529.2 |

-continued

| Compound Number | Structure | Compound Name | LCMS (M + 1) |
|---|---|---|---|
| 53 | 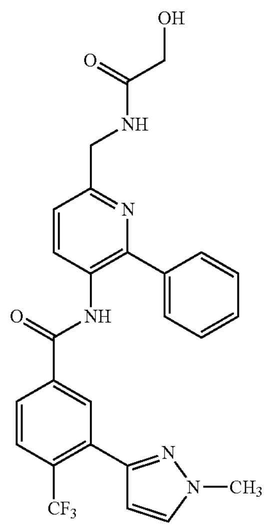 [SMILES: Cn1ccc(-c2cc(C(=O)Nc3ccc(CNC(=O)CO)nc3-c3ccccc3)ccc2C(F)(F)F)n1] | N-(6-((2-hydroxyacetamido)methyl)-2-phenylpyridin-3-yl)-3-(1-methyl-1H-pyrazol-3-yl)-4-(trifluoromethyl)benzamide | 510.2 |
| 54 | 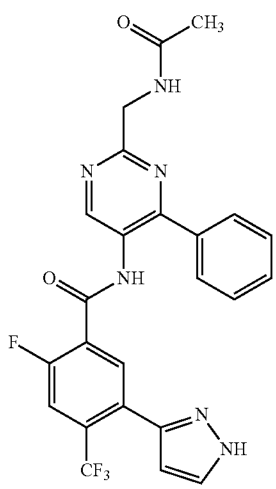 [SMILES: CC(=O)NCc1ncc(NC(=O)c2cc(-c3cc[nH]n3)c(C(F)(F)F)cc2F)c(-c2ccccc2)n1] | N-(2-(acetamidomethyl)-4-phenylpyrimidin-5-yl)-2-fluoro-5-(1H-pyrazol-3-yl)-4-(trifluoromethyl)benzamide | 499.4 |
| 55 | 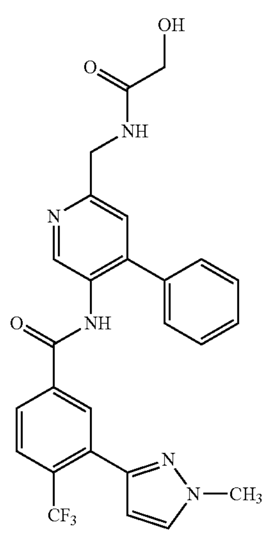 [SMILES: Cn1ccc(-c2cc(C(=O)Nc3cnc(CNC(=O)CO)cc3-c3ccccc3)ccc2C(F)(F)F)n1] | N-(6-((2-hydroxyacetamido)methyl)-4-phenylpyridin-3-yl)-3-(1-methyl-1H-pyrazol-3-yl)-4-(trifluoromethyl)benzamide | 510.1 |

| Compound Number | Structure | Compound Name | LCMS (M + 1) |
|---|---|---|---|
| 56 | 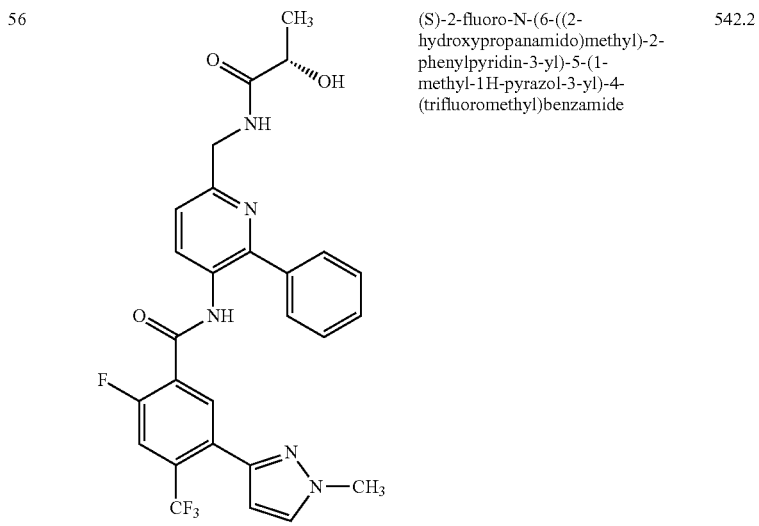 | (S)-2-fluoro-N-(6-((2-hydroxypropanamido)methyl)-2-phenylpyridin-3-yl)-5-(1-methyl-1H-pyrazol-3-yl)-4-(trifluoromethyl)benzamide | 542.2 |
| 57 | 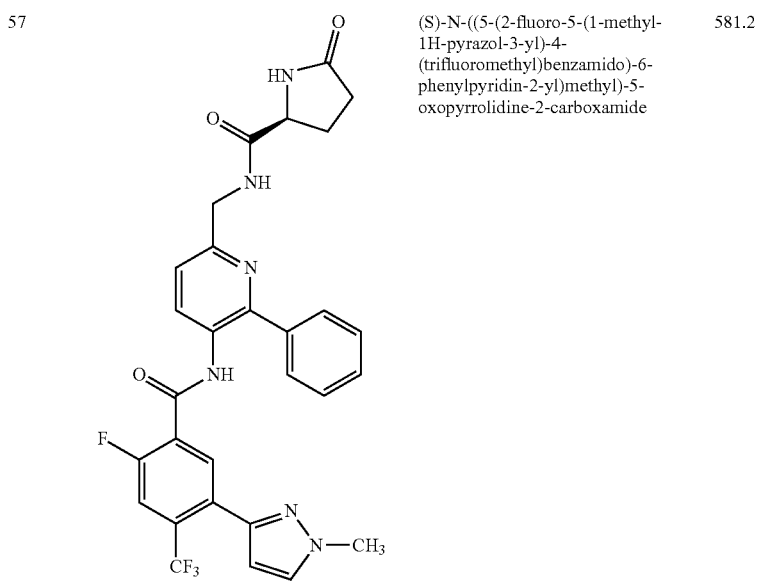 | (S)-N-((5-(2-fluoro-5-(1-methyl-1H-pyrazol-3-yl)-4-(trifluoromethyl)benzamido)-6-phenylpyridin-2-yl)methyl)-5-oxopyrrolidine-2-carboxamide | 581.2 |

-continued

| Compound Number | Structure | Compound Name | LCMS (M + 1) |
|---|---|---|---|
| 58 | 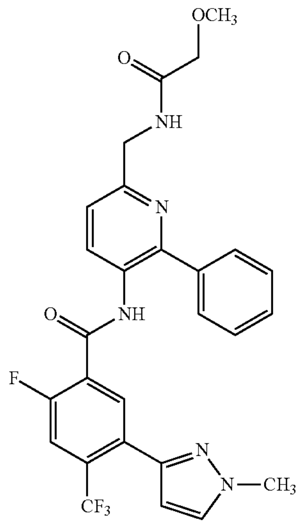 [SMILES: COCC(=O)NCc1ccc(NC(=O)c2cc(-c3ccn(C)n3)c(C(F)(F)F)cc2F)c(-c2ccccc2)n1] | 2-fluoro-N-(6-((2-methoxyacetamido)methyl)-2-phenylpyridin-3-yl)-5-(1-methyl-1H-pyrazol-3-yl)-4-(trifluoromethyl)benzamide | 542.2 |
| 59 | 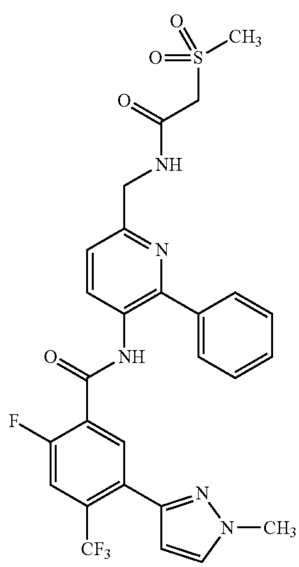 [SMILES: Cn1ccc(-c2cc(C(=O)Nc3ccc(CNC(=O)CS(C)(=O)=O)nc3-c3ccccc3)c(F)cc2C(F)(F)F)n1] | 2-fluoro-5-(1-methyl-1H-pyrazol-3-yl)-N-(6-((2-(methylsulfonyl)acetamido)methyl)-2-phenylpyridin-3-yl)-4-(trifluoromethyl)benzamide | 590.3 |
| 60 | 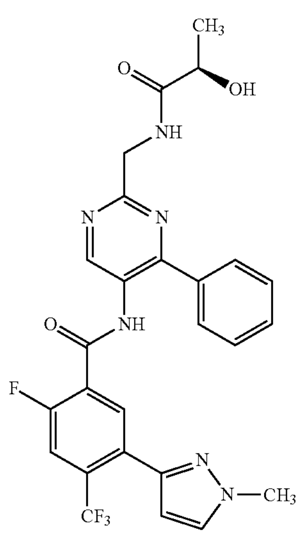 [SMILES: C[C@@H](O)C(=O)NCc1ncc(NC(=O)c2cc(-c3ccn(C)n3)c(C(F)(F)F)cc2F)c(-c2ccccc2)n1] | (R)-2-fluoro-N-(2-((2-hydroxypropanamido)methyl)-4-phenylpyrimidin-5-yl)-5-(1-methyl-1H-pyrazol-3-yl)-4-(trifluoromethyl)benzamide | 543.1 |

| Compound Number | Structure | Compound Name | LCMS (M + 1) |
|---|---|---|---|
| 61 | 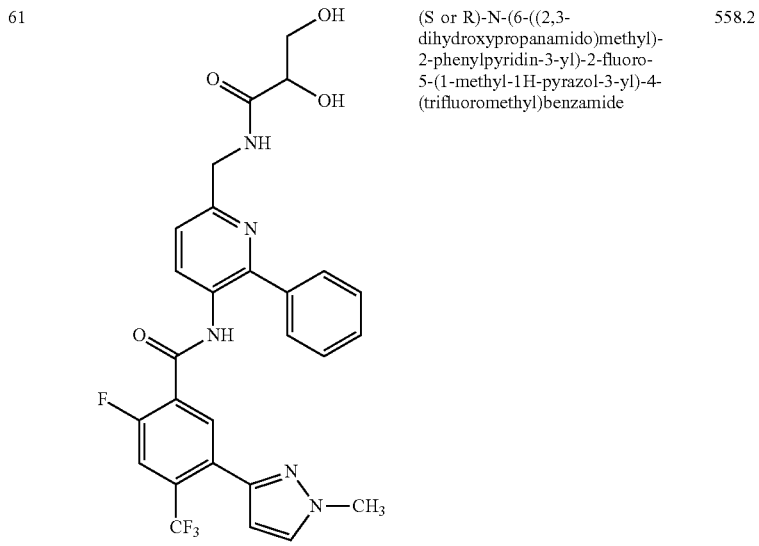 | (S or R)-N-(6-((2,3-dihydroxypropanamido)methyl)-2-phenylpyridin-3-yl)-2-fluoro-5-(1-methyl-1H-pyrazol-3-yl)-4-(trifluoromethyl)benzamide | 558.2 |
| 62 | 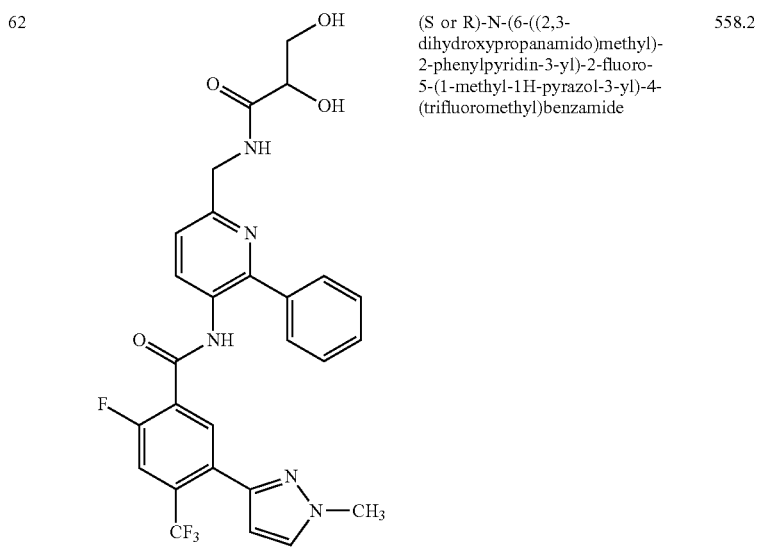 | (S or R)-N-(6-((2,3-dihydroxypropanamido)methyl)-2-phenylpyridin-3-yl)-2-fluoro-5-(1-methyl-1H-pyrazol-3-yl)-4-(trifluoromethyl)benzamide | 558.2 |

| Compound Number | Structure | Compound Name | LCMS (M + 1) |
|---|---|---|---|
| 63 | 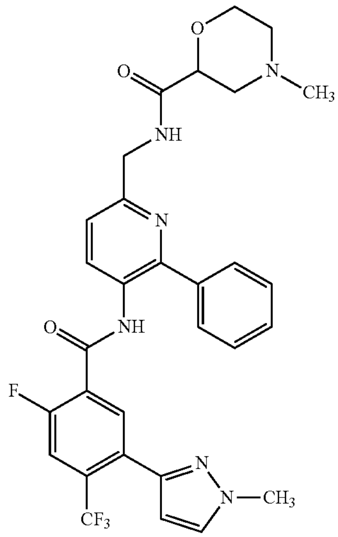 [SMILES: CN1CCOC(C(=O)NCc2ccc(NC(=O)c3cc(-c4ccn(C)n4)c(C(F)(F)F)cc3F)c(-c3ccccc3)n2)C1] | (S or R)-N-((5-(2-fluoro-5-(1-methyl-1H-pyrazol-3-yl)-4-(trifluoromethyl)benzamido)-6-phenylpyridin-2-yl)methyl)-4-methylmorpholine-2-carboxamide | 597.2 |
| 64 | 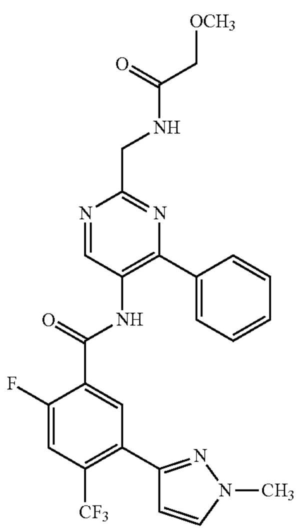 [SMILES: COCC(=O)NCc1ncc(NC(=O)c2cc(-c3ccn(C)n3)c(C(F)(F)F)cc2F)c(-c2ccccc2)n1] | 2-fluoro-N-(2-((2-methoxyacetamido)methyl)-4-phenylpyrimidin-5-yl)-5-(1-methyl-1H-pyrazol-3-yl)-4-(trifluoromethyl)benzamide | 543.1 |
| 65 | 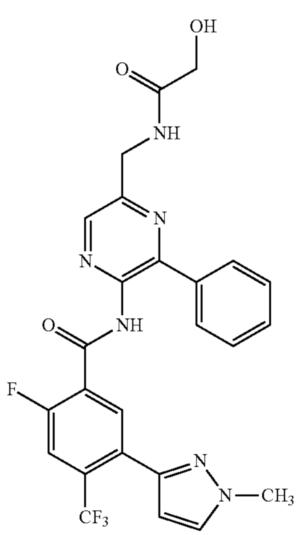 [SMILES: Cn1ccc(-c2cc(C(=O)Nc3ncc(CNC(=O)CO)nc3-c3ccccc3)c(F)cc2C(F)(F)F)n1] | 2-fluoro-N-(5-((2-hydroxyacetamido)methyl)-3-phenylpyrazin-2-yl)-5-(1-methyl-1H-pyrazol-3-yl)-4-(trifluoromethyl)benzamide | 529.2 |

-continued
| Compound Number | Structure | Compound Name | LCMS (M + 1) |
|---|---|---|---|
| 66 | 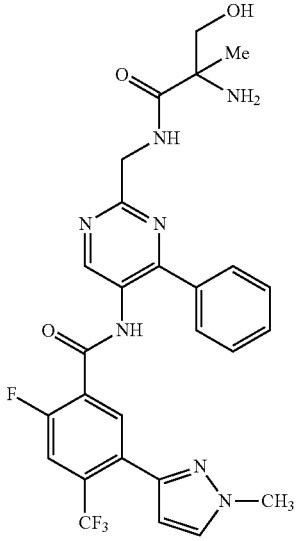 [SMILES: Cn1ccc(-c2cc(C(=O)Nc3cnc(CNC(=O)C(C)(N)CO)nc3-c3ccccc3)c(F)cc2C(F)(F)F)n1] | (S or R)-N-(2-((2-amino-3-hydroxy-2-methylpropanamido)methyl)-4-phenylpyrimidin-5-yl)-2-fluoro-5-(1-methyl-1H-pyrazol-3-yl)-4-(trifluoromethyl)benzamide | 572.2 |
| 67 | 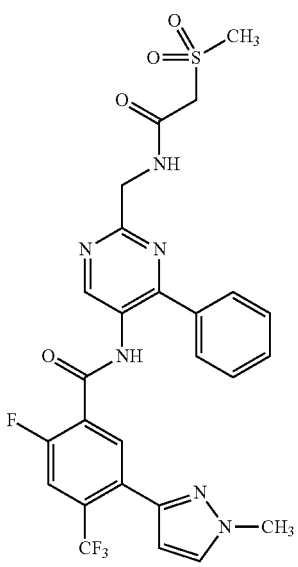 [SMILES: Cn1ccc(-c2cc(C(=O)Nc3cnc(CNC(=O)CS(C)(=O)=O)nc3-c3ccccc3)c(F)cc2C(F)(F)F)n1] | 2-fluoro-5-(1-methyl-1H-pyrazol-3-yl)-N-(2-((2-(methylsulfonyl)acetamido)methyl)-4-phenylpyrimidin-5-yl)-4-(trifluoromethyl)benzamide | 591.1 |

-continued
| Compound Number | Structure | Compound Name | LCMS (M + 1) |
|---|---|---|---|
| 68 | 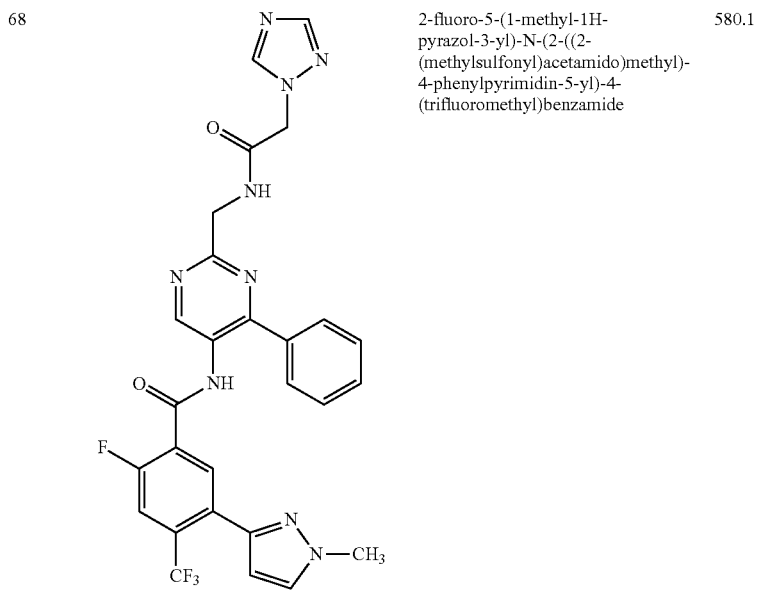 | 2-fluoro-5-(1-methyl-1H-pyrazol-3-yl)-N-(2-((2-(methylsulfonyl)acetamido)methyl)-4-phenylpyrimidin-5-yl)-4-(trifluoromethyl)benzamide | 580.1 |
| 69 | 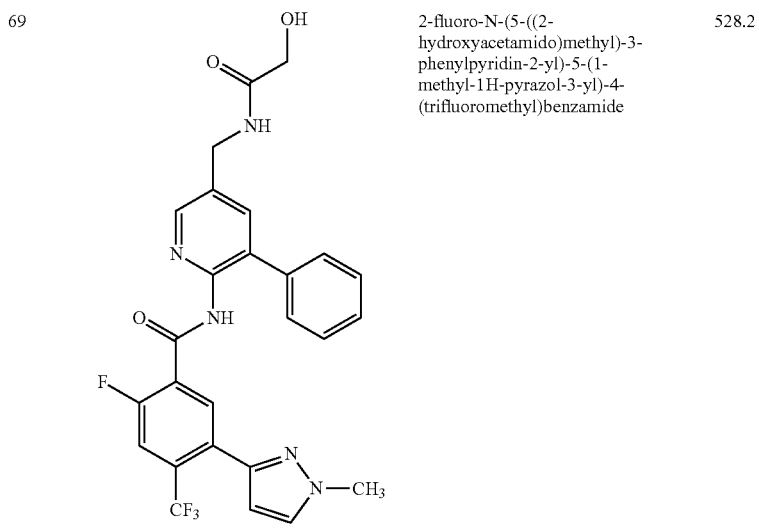 | 2-fluoro-N-(5-((2-hydroxyacetamido)methyl)-3-phenylpyridin-2-yl)-5-(1-methyl-1H-pyrazol-3-yl)-4-(trifluoromethyl)benzamide | 528.2 |

-continued
| Compound Number | Structure | Compound Name | LCMS (M + 1) |
|---|---|---|---|
| 70 | 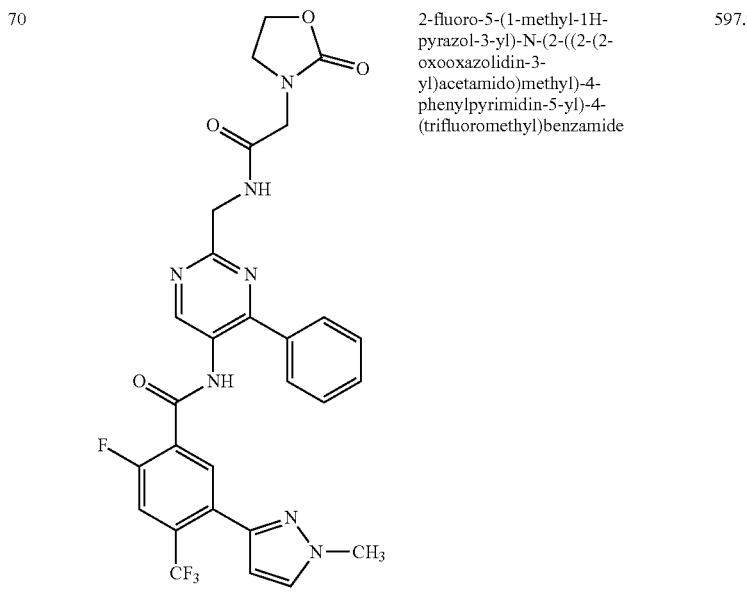 | 2-fluoro-5-(1-methyl-1H-pyrazol-3-yl)-N-(2-((2-(2-oxooxazolidin-3-yl)acetamido)methyl)-4-phenylpyrimidin-5-yl)-4-(trifluoromethyl)benzamide | 597.9 |
| 71 | 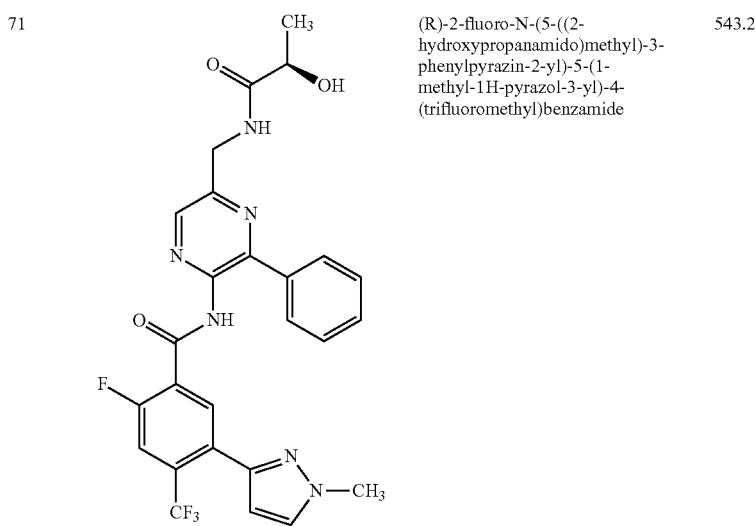 | (R)-2-fluoro-N-(5-((2-hydroxypropanamido)methyl)-3-phenylpyrazin-2-yl)-5-(1-methyl-1H-pyrazol-3-yl)-4-(trifluoromethyl)benzamide | 543.2 |

-continued
| Compound Number | Structure | Compound Name | LCMS (M + 1) |
|---|---|---|---|
| 72 | 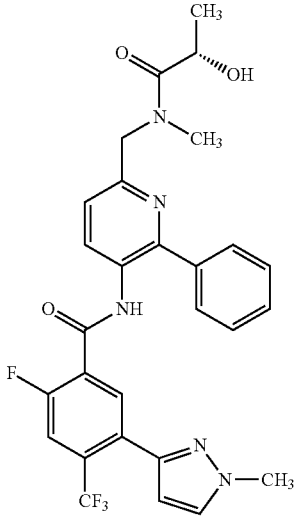 [SMILES: C[C@H](O)C(=O)N(C)Cc1ccc(NC(=O)c2cc(-c3ccn(C)n3)c(C(F)(F)F)cc2F)c(-c2ccccc2)n1] | (S)-2-fluoro-N-(6-((2-hydroxy-N-methylpropanamido)methyl)-2-phenylpyridin-3-yl)-5-(1-methyl-1H-pyrazol-3-yl)-4-(trifluoromethyl)benzamide | 556.2 |
| 73 | 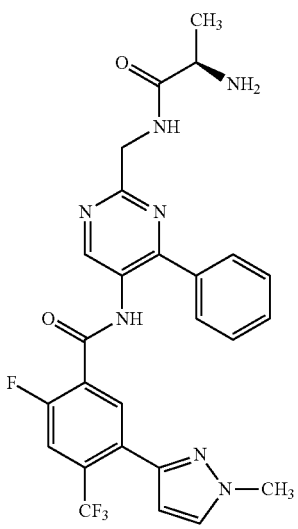 [SMILES: C[C@@H](N)C(=O)NCc1ncc(NC(=O)c2cc(-c3ccn(C)n3)c(C(F)(F)F)cc2F)c(-c2ccccc2)n1] | (R)-N-(2-((2-aminopropanamido)methyl)-4-phenylpyrimidin-5-yl)-2-fluoro-5-(1-methyl-1H-pyrazol-3-yl)-4-(trifluoromethyl)benzamide | 542.1 |

| Compound Number | Structure | Compound Name | LCMS (M + 1) |
|---|---|---|---|
| 74 | 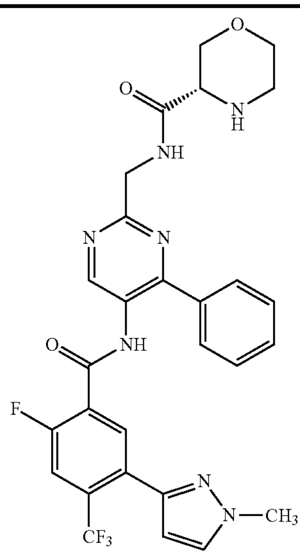 | (S)-N-((5-(2-fluoro-5-(1-methyl-1H-pyrazol-3-yl)-4-(trifluoromethyl)benzamido)-4-phenylpyrimidin-2-yl)methyl)morpholine-3-carboxamide | 584.2 |
| 75 | 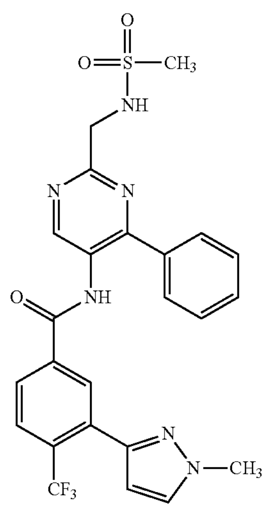 [SMILES: Cn1ccc(-c2cc(C(=O)Nc3cnc(CNS(C)(=O)=O)nc3-c3ccccc3)ccc2C(F)(F)F)n1] | 3-(1-methyl-1H-pyrazol-3-yl)-N-(2-(methylsulfonamidomethyl)-4-phenylpyrimidin-5-yl)-4-(trifluoromethyl)benzamide | 531.2 |

EXAMPLE 76

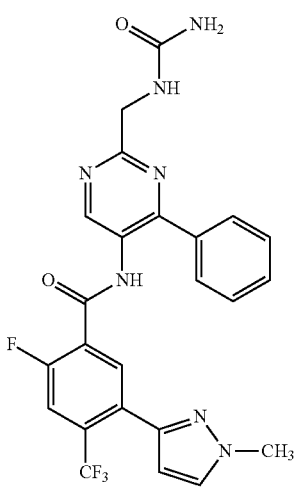 [SMILES: Cn1ccc(-c2cc(C(=O)Nc3cnc(CNC(N)=O)nc3-c3ccccc3)c(F)cc2C(F)(F)F)n1]

2-Fluoro-5-(1-methyl-1H-pyrazol-3-yl)-N-(4-phenyl-2-(ureidomethyl)pyrimidin-5-yl)-4-(trifluoromethyl)benzamide Trimethylsilylisocyanate (0.022 mL, 0.17 mmol) was added to a solution of N-(2-(aminomethyl)-4-phenylpyrimidin-5-yl)-2-fluoro-5-(1-methyl-1H-pyrazol-3-yl)-4-(trifluoromethyl)benzamide (130 mg, 0.17 mmol) in DMF (1.5 mL). The resulting mixture was stirred for 30 min and then purified by preparative reverse-phase HPLC (water/CH$_3$CN gradient with 0.1% TFA as a modifier) to give the title compound. MS: m/z=514.3 (M+1). $^1$H NMR (400 MHz, DMSO-d$_6$) δ 10.61 (s, 1H), 8.93 (s, 1H), 7.92 (d, J=6.6 Hz, 1H), 7.88 (d, J=10.5 Hz, 1H), 7.84-7.81 (m, 3H), 7.51 (br m, 3H), 6.50 (br m, 1H), 6.45 (s, 1H), 5.70 (br s, 2H), 4.46 (d, J=5.9 Hz, 2H), 3.92 (s, 3H).

The following examples were prepared in similar fashion to the procedures described above.

| Compound Number | Structure | Compound Name | LCMS (M + 1) |
|---|---|---|---|
| 77 | 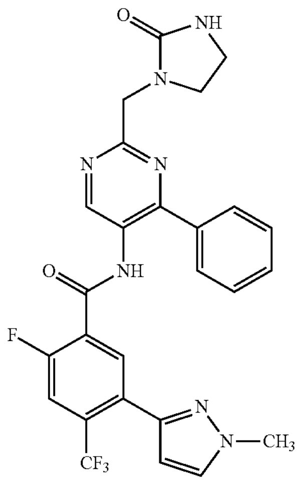 [SMILES: Cn1ccc(-c2cc(C(=O)Nc3cnc(CN4CCNC4=O)nc3-c3ccccc3)c(F)cc2C(F)(F)F)n1] | 2-fluoro-5-(1-methyl-1H-pyrazol-3-yl)-N-(2-((2-oxoimidazolidin-1-yl)methyl)-4-phenylpyrimidin-5-yl)-4-(trifluoromethyl)benzamide | 540.3 |
| 78 | 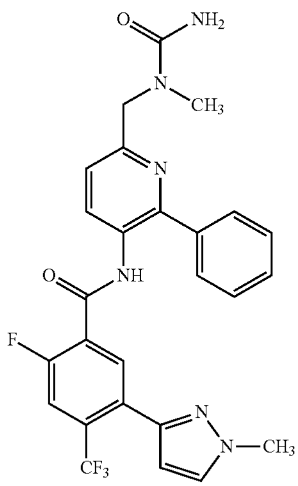 [SMILES: CN(Cc1ccc(NC(=O)c2cc(-c3ccn(C)n3)c(C(F)(F)F)cc2F)c(-c2ccccc2)n1)C(N)=O] | 2-fluoro-5-(1-methyl-1H-pyrazol-3-yl)-N-(6-((1-methylureido)methyl)-2-phenylpyridin-3-yl)-4-(trifluoromethyl)benzamide | 527.2 |
| 79 | 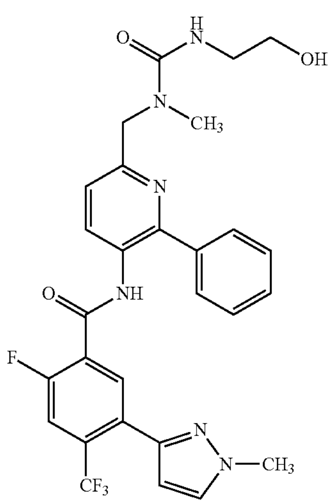 [SMILES: CN(Cc1ccc(NC(=O)c2cc(-c3ccn(C)n3)c(C(F)(F)F)cc2F)c(-c2ccccc2)n1)C(=O)NCCO] | 2-fluoro-N-(6-((3-(2-hydroxyethyl)-1-methylureido)methyl)-2-phenylpyridin-3-yl)-5-(1-methyl-1H-pyrazol-3-yl)-4-(trifluoromethyl)benzamide | 571.2 |

EXAMPLE 80

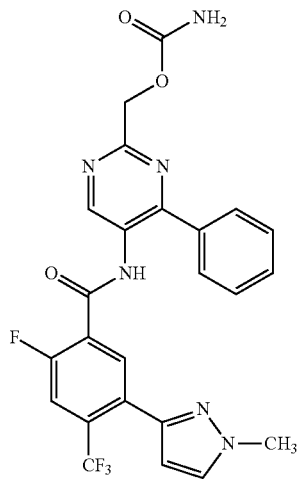 [SMILES: Cn1ccc(-c2cc(C(=O)Nc3cnc(COC(N)=O)nc3-c3ccccc3)c(F)cc2C(F)(F)F)n1]

(5-(2-Fluoro-5-(1-methyl-1H-pyrazol-3-yl)-4-(trifluoromethyl)benzamido)-4-phenylpyrimidin-2-yl) methyl carbamate Trichloroacetylisocyanate (0.177 mL, 1.48 mmol) was added to a solution of 2-fluoro-N-(2-(hydroxymethyl)-4-phenylpyrimidin-5-yl)-5-(1-methyl-1H-pyrazol-3-yl)-4-(trifluoromethyl)benzamide (500 mg, 1.06 mmol) in chloroform (10 mL) at 23° C., and the resulting mixture was stirred for 1 h. Basic alumina (Brockmann activity I, 5 grams) was added and the suspension was stirred for 1 h, then filtered and washed with a solution of 20% MeOH in DCM (3×50 mL). The combined filtrate was washed with brine, dried over sodium sulfate and concentrated. The residue was crystallized from EtOAc (5 mL) to give the title compound. MS: m/z=515.3 (M+1). $^1$H NMR (400 MHz, CD$_3$OD) δ 9.11 (s, 1H), 7.97 (d, J=6.8 Hz, 1H), 7.82 (m, 2H), 7.69 (d, J=10.7 Hz, 1H), 7.66 (d, J=2.5 Hz, 1H), 7.51 (m, 3H), 6.44 (s, 1H), 5.28 (s, 2H), 3.96 (s, 3H).

REACTION SCHEME FOR EXAMPLE 81

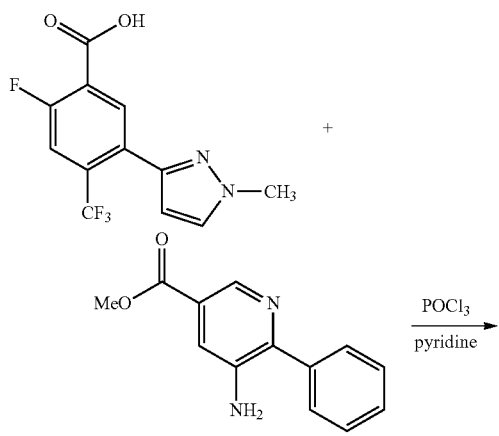

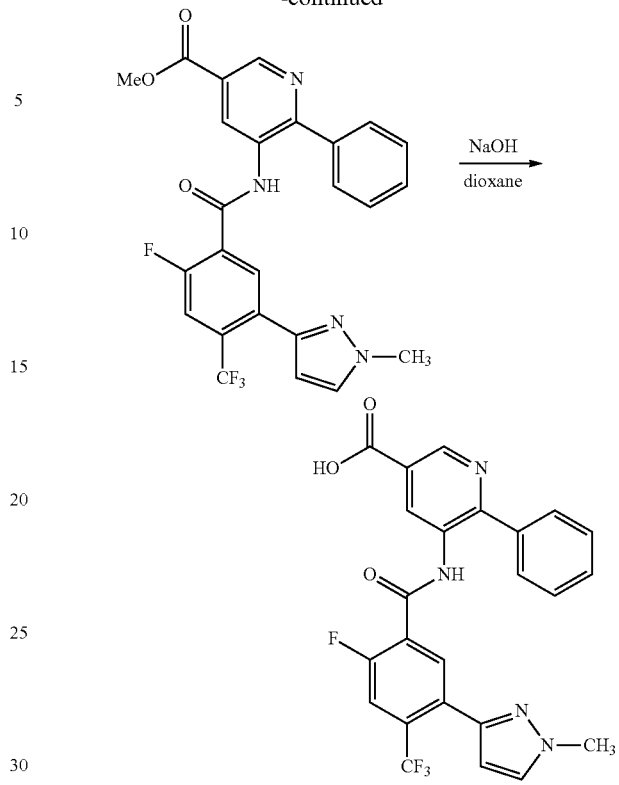

EXAMPLE 81

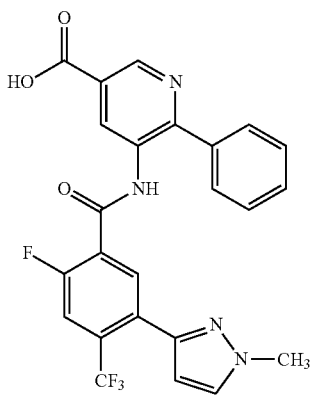 [SMILES: Cn1ccc(-c2cc(C(=O)Nc3cc(C(=O)O)cnc3-c3ccccc3)c(F)cc2C(F)(F)F)n1]

5-(2-Fluoro-5-(1-methyl-1H-pyrazol-3-yl)-4-(trifluoromethyl)benzamido)-6-phenylnicotinic acid Step A: Methyl 5-(2-fluoro-5-(1-methyl-1H-pyrazol-3-yl)-4-(trifluoromethyl)benzamido)-6-phenylnicotinate Phosphorous oxychloride (0.19 mL, 1.3 mmol) was added dropwise to a solution of methyl 5-amino-6-phenylnicotinate (195 mg, 0.854 mmol) and 2-fluoro-5-(1-methyl-1H-pyrazol-3-yl)-4-(trifluoromethyl)benzoic acid (271 mg, 0.940 mmol) in pyridine (2.9 mL) at −10° C. The resulting mixture was stirred at 0° C. for 2 h and then carefully diluted with saturated aqueous sodium bicarbonate solution (10 mL). The mixture was diluted with EtOAc (100 mL) and washed with aqueous sodium bicarbonate solution (10 mL×3). The organic layer was washed with brine (3 mL), dried over Na$_2$SO$_4$ and concentrated. The residue was purified by column chromatography on silica gel (EtOAc:hexanes=0:100 to 80:20) to give the title compound. MS: m/z=499.1 (M+1).

Step B: 5-(2-Fluoro-5-(1-methyl-1H-pyrazol-3-yl)-4-(trifluoromethyl)benzamido)-6-phenylnicotinic acid A mixture of methyl 5-(2-fluoro-5-(1-methyl-1H-pyrazol-3-yl)-4-(trifluoromethyl)benzamido)-6-phenylnicotinate (390 mg, 0.78 mmol) and aqueous NaOH solution (1 M, 0.78 mmol, 0.78 mL) in 1,4-dioxane (2.5 mL) was stirred at ambient temperature for 2 h. The reaction mixture was acidified to pH 5 with aqueous HCl solution (1 M), and then extracted with EtOAc (50 mL×3). The combined organic layers were dried over $Na_2SO_4$ and concentrated to give the title compound. MS: m/z=485.2 (M+1).

EXAMPLE 82

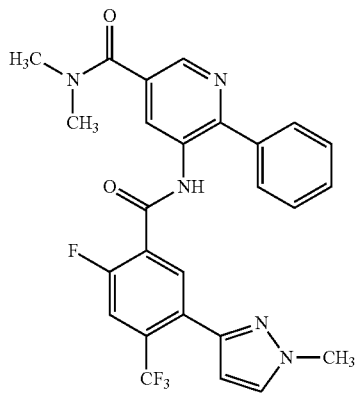 [SMILES: CN(C)C(=O)c1cnc(-c2ccccc2)c(NC(=O)c2cc(-c3ccn(C)n3)c(C(F)(F)F)cc2F)c1]

5-(2-Fluoro-5-(1-methyl-1H-pyrazol-3-yl)-4-(trifluoromethyl)benzamido)-N,N-dimethyl-6-phenylnicotinamide HOBt (25 mg, 0.16 mmol) was added to a solution of 5-(2-fluoro-5-(1-methyl-1H-pyrazol-3-yl)-4-(trifluoromethyl)benzamido)-6-phenylnicotinic acid (65 mg, 0.13 mmol), EDC (31 mg, 0.16 mmol), dimethylamine (1M in THF, 0.16 mL, 0.20 mmol) and DIPEA (0.071 mL, 0.40 mmol) in DMF (0.5 mL), and the resulting mixture was stirred at 25° C. for 12 h. The reaction mixture was diluted with EtOAc (30 mL) and washed with aqueous sodium bicarbonate solution (3 mL×2). The organic layer was washed with brine (3 mL), dried over $Na_2SO_4$ and concentrated. The residue was purified by reverse-phase HPLC (5-80% acetonitrile+0.75% trifluoroacetic acid in water) to give the title compound. MS: m/z=512.2 (M+1). $^1$H NMR (500 MHz, $CDCl_3$) δ 9.22 (s, 1H), 8.81 (d, J=7.6 Hz, 1H), 8.68 (s, 1H), 8.38 (d, J=7.6 Hz, 1H), 7.61-7.51 (m, 5H), 7.48 (d, J=11.9 Hz, 1H), 7.43 (s, 1H), 6.46 (s, 1H), 4.00 (s, 3H), 3.20 (s, 3H), 3.17 (s, 3H).

The following examples were prepared in similar fashion to the procedures described above.

| Compound Number | Structure | Compound Name | LCMS (M + 1) |
| --- | --- | --- | --- |
| 83 | 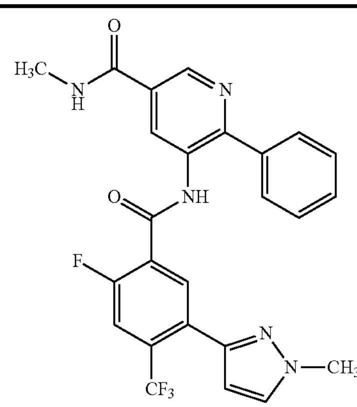 | 5-(2-fluoro-5-(1-methyl-1H-pyrazol-3-yl)-4-(trifluoromethyl)benzamido)-N-methyl-6-phenylnicotinamide | 498.2 |
| 84 | 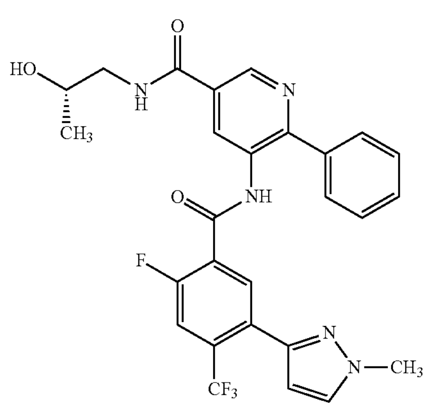 [SMILES: C[C@H](O)CNC(=O)c1cnc(-c2ccccc2)c(NC(=O)c2cc(-c3ccn(C)n3)c(C(F)(F)F)cc2F)c1] | (S)-5-(2-fluoro-5-(1-methyl-1H-pyrazol-3-yl)-4-(trifluoromethyl)benzamido)-N-(2-hydroxypropyl)-6-phenylnicotinamide | 542.2 |

-continued

| Compound Number | Structure | Compound Name | LCMS (M + 1) |
|---|---|---|---|
| 85 | 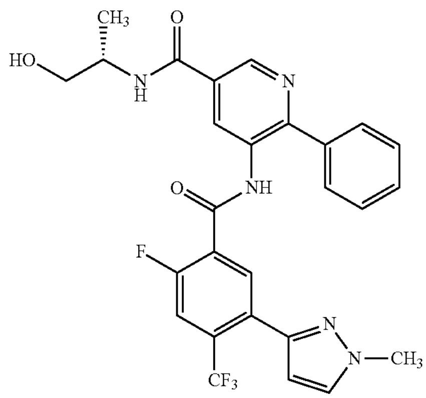 [SMILES: C[C@@H](CO)NC(=O)c1cnc(-c2ccccc2)c(NC(=O)c2cc(-c3ccn(C)n3)c(C(F)(F)F)cc2F)c1] | (S)-5-(2-fluoro-5-(1-methyl-1H-pyrazol-3-yl)-4-(trifluoromethyl)benzamido)-N-(1-hydroxypropan-2-yl)-6-phenylnicotinamide | 542.2 |
| 86 | 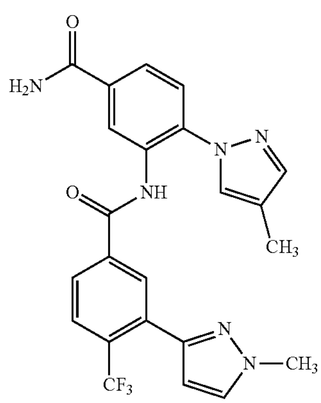 [SMILES: Cc1cnn(-c2ccc(C(N)=O)cc2NC(=O)c2ccc(C(F)(F)F)c(-c3ccn(C)n3)c2)c1] | N-(5-carbamoyl-2-(4-methyl-1H-pyrazol-1-yl)phenyl)-3-(1-methyl-1H-pyrazol-3-yl)-4-(trifluoromethyl)benzamide | 469 |
| 87 | 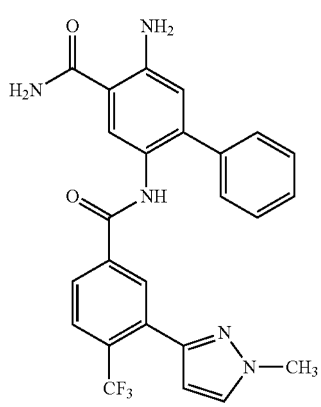 [SMILES: Cn1ccc(-c2cc(C(=O)Nc3cc(C(N)=O)c(N)cc3-c3ccccc3)ccc2C(F)(F)F)n1] | 2-amino-5-(3-(1-methyl-1H-pyrazol-3-yl)-4-(trifluoromethyl)benzamido)-6-phenylnicotinamide | 481.2 |

-continued

| Compound Number | Structure | Compound Name | LCMS (M + 1) |
|---|---|---|---|
| 88 | 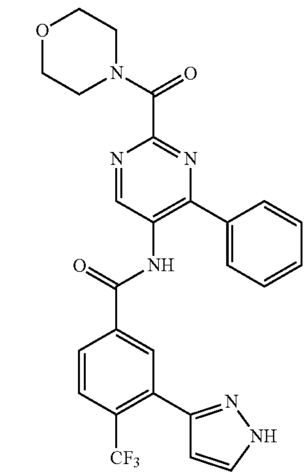 [SMILES: O=C(Nc1cnc(C(=O)N2CCOCC2)nc1-c1ccccc1)c1ccc(C(F)(F)F)c(-c2cc[nH]n2)c1] | N-(2-(morpholine-4-carbonyl)-4-phenylpyrimidin-5-yl)-3-(1H-pyrazol-3-yl)-4-(trifluoromethyl)benzamide | 523.2 |
| 89 | 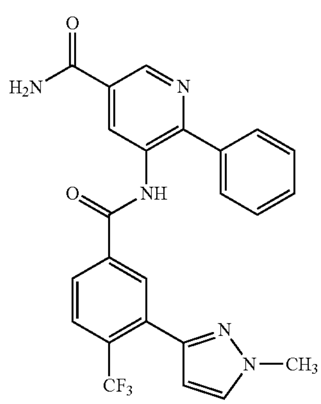 [SMILES: Cn1ccc(-c2cc(C(=O)Nc3cc(C(N)=O)cnc3-c3ccccc3)ccc2C(F)(F)F)n1] | 5-(3-(1-methyl-1H-pyrazol-3-yl)-4-(trifluoromethyl)benzamido)-6-phenylnicotinamide | 466.2 |
| 90 | 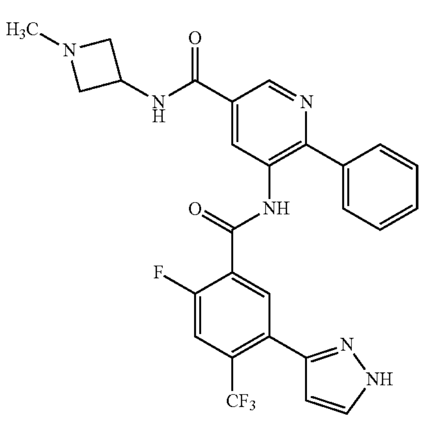 [SMILES: CN1CC(NC(=O)c2cnc(-c3ccccc3)c(NC(=O)c3cc(-c4cc[nH]n4)c(C(F)(F)F)cc3F)c2)C1] | 5-(2-fluoro-5-(1H-pyrazol-3-yl)-4-(trifluoromethyl)benzamido)-N-(1-methylazetidin-3-yl)-6-phenylnicotinamide | 539.2 |

| Compound Number | Structure | Compound Name | LCMS (M + 1) |
|---|---|---|---|
| 91 | 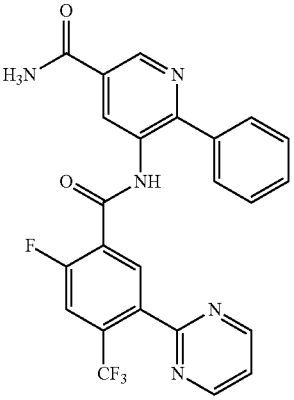 [SMILES: NC(=O)c1cnc(-c2ccccc2)c(NC(=O)c2cc(-c3ncccn3)c(C(F)(F)F)cc2F)c1] | 5-(2-fluoro-5-(pyrimidin-2-yl)-4-(trifluoromethyl)benzamido)-6-phenylnicotinamide | 482.2 |
| 92 | 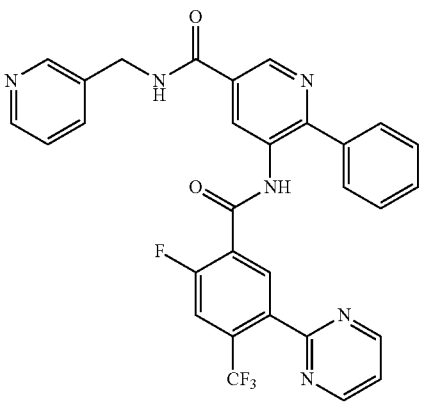 [SMILES: O=C(NCc1cccnc1)c1cnc(-c2ccccc2)c(NC(=O)c2cc(-c3ncccn3)c(C(F)(F)F)cc2F)c1] | 5-(2-fluoro-5-(pyrimidin-2-yl)-4-(trifluoromethyl)benzamido)-6-phenyl-N-(pyridin-3-ylmethyl)nicotinamide | 573.2 |
| 93 | 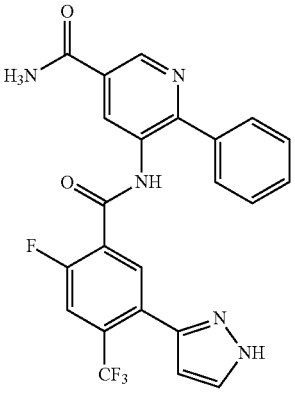 [SMILES: NC(=O)c1cnc(-c2ccccc2)c(NC(=O)c2cc(-c3cc[nH]n3)c(C(F)(F)F)cc2F)c1] | 5-(2-fluoro-5-(1H-pyrazol-3-yl)-4-(trifluoromethyl)benzamido)-6-phenylnicotinamide | 470.2 |

| Compound Number | Structure | Compound Name | LCMS (M + 1) |
|---|---|---|---|
| 94 | 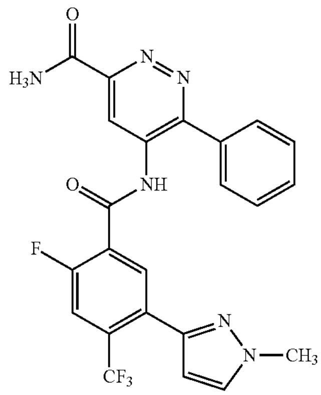 [SMILES: Cn1ccc(-c2cc(C(=O)Nc3cc(C(N)=O)nnc3-c3ccccc3)c(F)cc2C(F)(F)F)n1] | 5-(2-fluoro-5-(1-methyl-1H-pyrazol-3-yl)-4-(trifluoromethyl)benzamido)-6-phenylpyridazine-3-carboxamide | 485.1 |

EXAMPLE 95

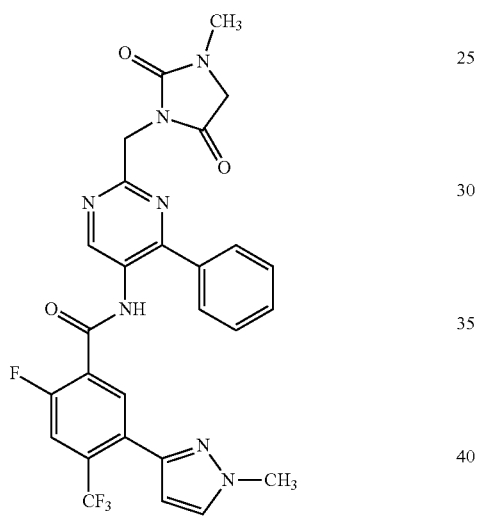

2-Fluoro-5-(1-methyl-1H-pyrazol-3-yl)-N-(2-((3-methyl-2,5-dioxoimidazolidin-1-yl)methyl)-4-phenylpyrimidin-5-yl)-4-(trifluoromethyl)benzamide Phosphorous oxychloride (0.040 mL, 0.43 mmol) was added dropwise to a solution of 3-((5-amino-4-phenylpyrimidin-2-yl)methyl)-1-methylimidazolidine-2,4-dione hydrochloride (130 mg, 0.39 mmol) and 2-fluoro-5-(1-methyl-1H-pyrazol-3-yl)-4-(trifluoromethyl)benzoic acid (112 mg, 0.39 mmol) in pyridine (5 mL) at 0° C. The resulting mixture was stirred for 30 min and then carefully diluted with saturated aqueous sodium bicarbonate solution (50 mL). A majority of the pyridine was removed under reduced pressure, and the remaining aqueous mixture was extracted with EtOAc (2×100 mL). The combined organic layers were dried over sodium sulfate and concentrated. The residue was purified by flash column chromatography (hexanes, grading to 100% EtOAc) followed by preparative reverse-phase HPLC (water/CH$_3$CN gradient with 0.1% TFA as a modifier) to provide the title compound. MS: m/z=568.3 (M+1). $^1$H NMR (400 MHz, CDCl$_3$) δ 9.76 (s, 1H), 8.62 (d, J=13.9 Hz, 1H), 8.44 (d, J=7.6 Hz, 1H), 7.64 (m, 2H), 7.56 (m, 3H), 7.47 (d, J=12.0 Hz, 1H), 7.40 (s, 1H), 7.51 (m, 3H), 6.44 (s, 1H), 5.01 (s, 2H), 4.01 (s, 2H), 3.96 (s, 3H), 3.06 (s, 3H).

The following examples were prepared in similar fashion to the procedures described above.

| Compound Number | Structure | Compound Name | LCMS (M + 1) |
|---|---|---|---|
| 96 | 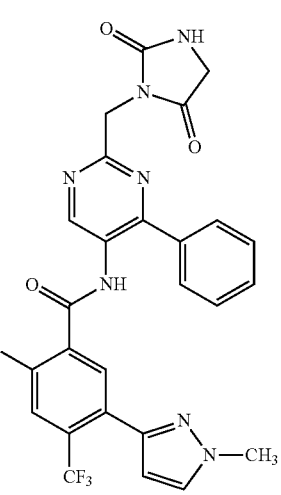 | N-(2-((2,5-dioxoimidazolidin-1-yl)methyl)-4-phenylpyrimidin-5-yl)-2-fluoro-5-(1-methyl-1H-pyrazol-3-yl)-4-(trifluoromethyl)benzamide | 554.2 |
| 97 | 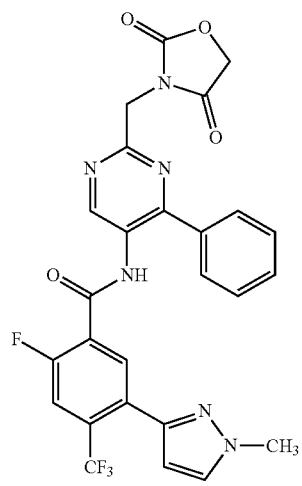 [SMILES: Cn1ccc(-c2cc(C(=O)Nc3cnc(CN4C(=O)COC4=O)nc3-c3ccccc3)c(F)cc2C(F)(F)F)n1] | N-(2-((2,4-dioxooxazolidin-3-yl)methyl)-4-phenylpyrimidin-5-yl)-2-fluoro-5-(1-methyl-1H-pyrazol-3-yl)-4-(trifluoromethyl)benzamide | 555.1 |
| 98 | 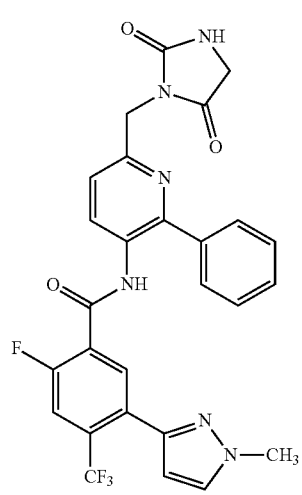 [SMILES: Cn1ccc(-c2cc(C(=O)Nc3ccc(CN4C(=O)CNC4=O)nc3-c3ccccc3)c(F)cc2C(F)(F)F)n1] | N-(6-((2,5-dioxoimidazolidin-1-yl)methyl)-2-phenylpyridin-3-yl)-2-fluoro-5-(1-methyl-1H-pyrazol-3-yl)-4-(trifluoromethyl)benzamide | 553.1 |

EXAMPLE 99

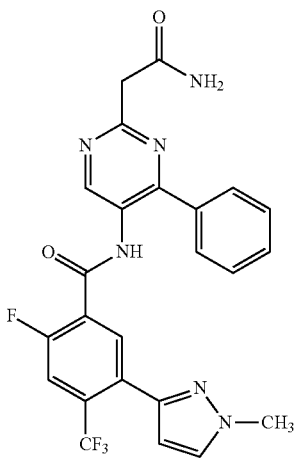 [SMILES: Cn1ccc(-c2cc(C(=O)Nc3cnc(CC(N)=O)nc3-c3ccccc3)c(F)cc2C(F)(F)F)n1]

N-(2-(2-Amino-2-oxoethyl)-4-phenylpyrimidin-5-yl)-2-fluoro-5-(1-methyl-1H-pyrazol-3-yl)-4-(trifluoromethyl)benzamide A solution of 2-(5-(2-fluoro-5-(1-methyl-1H-pyrazol-3-yl)-4-(trifluoromethyl)benzamido)-4-phenylpyrimidin-2-yl)acetic acid (439 mg, 0.879) in 1,4-dioxane (30 mL) was saturated with ammonia gas. BOP (408 mg, 0.923 mmol) was added, and ammonia gas was bubbled through the mixture with rapid stirring. After 20 min, the mixture was partitioned between brine (75 mL) and EtOAc (75 mL×2). The combined organic layers were dried over Na$_2$SO$_4$, filtered and concentrated. The residue was suspended in EtOAc with sonication, then filtered, and the filtered solid was washed with EtOAc to give the title compound. The combined filtrate was concentrated and the residue purified by SiO$_2$ flash column chromatography (hexanes, grading to 100% 3:1 EtOAc/EtOH) to give additional title compound. MS: m/z=499.3 (M+1). $^1$H NMR (500 MHz, DMSO-d$_6$): δ 10.60 (s, 1H), 8.92 (s, 1H), 7.92 (d, J=6.8 Hz, 1H), 7.89 (d, J=10.4 Hz, 1H), 7.81 (m, 3H), 7.60 (s, 1H), 7.52 (m, 3H), 7.07 (s, 1H), 6.45 (s, 1H), 3.93 (s, 3H), 3.83 (s, 2H).

EXAMPLE 100

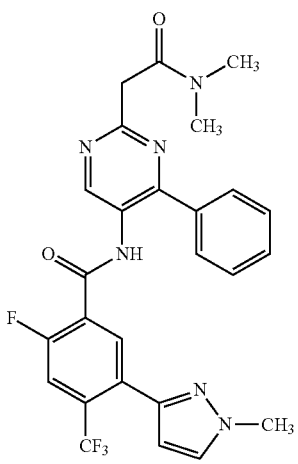 [SMILES: CN(C)C(=O)Cc1ncc(NC(=O)c2cc(-c3ccn(C)n3)c(C(F)(F)F)cc2F)c(-c2ccccc2)n1]

N-(2-(2-(Dimethylamino)-2-oxoethyl)-4-phenylpyrimidin-5-yl)-2-fluoro-5-(1-methyl-1H-pyrazol-3-yl)-4-(trifluoromethyl)benzamide A solution of dimethylamine was prepared by bubbling dimethylamine gas into 5 mL of 1,2-dichloroethane for 1 min. 2-(5-(2-fluoro-5-(1-methyl-1H-pyrazol-3-yl)-4-(trifluoromethyl)benzamido)-4-phenylpyrimidin-2-yl)acetic acid (25 mg, 0.050 mmol) and HATU (20.9 mg, 0.055 mmol) were placed in a vial with stirring, and the prepared solution of dimethylamine (0.5 mL) was added. After 10 min, the mixture was diluted with water (10 mL) and extracted with CH$_2$Cl$_2$ (3×10 mL). The combined organic layers were dried over MgSO$_4$, filtered and concentrated. The residue was purified by SiO$_2$ flash column chromatography, eluting with 0-40% (3:1 EtOAc/EtOH)/CH$_2$Cl$_2$ to give the title compound. MS: m/z=527.3 (M+1). $^1$H NMR (500 MHz, DMSO-d$_6$): δ 10.62 (s, 1H), 8.95 (s, 1H), 7.92 (d, J=6.6 Hz, 1H), 7.88 (d, J=10.2 Hz, 1H), 7.80 (m, 3H), 7.51 (m, 3H), 6.45 (s, 1H), 3.97 (s, 2H), 3.92 (s, 3H) 3.09 (s, 3H), 2.87 (s, 3H).

EXAMPLE 101

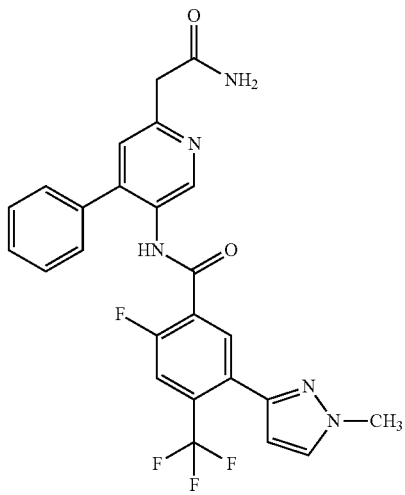 [SMILES: Cn1ccc(-c2cc(C(=O)Nc3cnc(CC(N)=O)cc3-c3ccccc3)c(F)cc2C(F)(F)F)n1]

N-(6-(2-Amino-2-oxo ethyl)-4-phenylpyridin-3-yl)-2-fluoro-5-(1-methyl-1H-pyrazol-3-yl)-4-(trifluoromethyl)benzamide Step A: Ethyl 2-(5-(2-fluoro-5-(pyrimidin-2-yl)-4-(trifluoromethyl)benzamido)-4-phenyl pyridine-2-yl) acetate To a solution of 2-fluoro-5-(1-methyl-1H-pyrazol-3-yl)-4-(trifluoromethyl)benzoic acid (169 mg, 0.585 mmol) and ethyl 2-(5-amino-4-phenylpyridin-2-yl)acetate (150 mg, 0.585 mmol) in pyridine (3 mL) at 25° C. was added dropwise POCl$_3$ (0.109 mL, 1.17 mmol). The resulting mixture was stirred for 10 min then diluted with ice water (20 mL) and extracted with EtOAc (10 mL×3). The combined organic layers were dried over Na$_2$SO$_4$ and concentrated. The residue was purified by preparative TLC (PE/EtOAc=1/1) to give the title compound. MS: m/z=527.7 (M+1).

Step B: N-(6-(2-Amino-2-oxoethyl)-4-phenylpyridin-3-yl)-2-fluoro-5-(1-methyl-1H-pyrazol-3-yl)-4-(trifluoromethyl)benzamide A solution of ethyl 2-(5-(2-fluoro-5-(1-methyl-1H-pyrazol-3-yl)-4-(trifluoromethyl) benzamido)-4-phenylpyridin-2-yl)acetate (50 mg, 0.095 mmol) in a 4M solution of $NH_3$ in EtOH (8 mL) was stirred at 25° C. for 36 h. The product mixture was concentrated, and the residue was purified by reverse-phase HPLC under basic condition ($H_2O/CH_3CN$ gradient with 0.05% $NH_4OH$ present) to give the title compound. MS: m/z=498.1 (M+1). $^1$H NMR (400 MHz, $CDCl_3$) δ 9.66 (s, 1H), 8.51-8.39 (m, 2H), 7.56-7.49 (m, 3H), 7.46-7.31 (m, 5H), 7.23 (s, 1H), 6.42 (s, 1H), 5.42 (s, 1H), 3.95 (s, 3H), 3.76 (s, 2H).

EXAMPLE 102

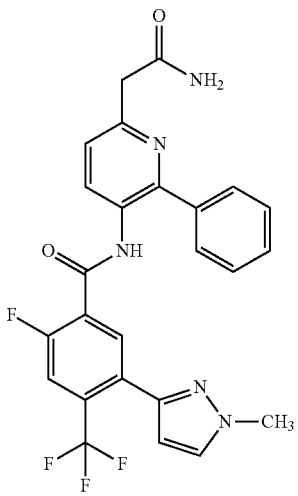 [SMILES: Cn1ccc(-c2cc(C(=O)Nc3ccc(CC(N)=O)nc3-c3ccccc3)c(F)cc2C(F)(F)F)n1]

N-(6-(2-Amino-2-oxoethyl)-2-phenylpyridin-3-yl)-2-fluoro-5-(1-methyl-1H-pyrazol-3-yl)-4-(trifluoromethyl)benzamide Step A: Ethyl 2-(5-(2-fluoro-5-(1-methyl-1H-pyrazol-3-yl)-4-(trifluoromethyl)benzamido)-6-phenylpyridin-2-yl)acetate To a solution of 2-fluoro-5-(1-methyl-1H-pyrazol-3-yl)-4-(trifluoromethyl)benzoic acid (225 mg, 0.780 mmol) and ethyl 2-(5-amino-6-phenylpyridin-2-yl)acetate (200 mg, 0.780 mmol) in pyridine (3 mL) at 32° C. was added dropwise $POCl_3$ (0.073 mL, 0.780 mmol). The resulting mixture was stirred for 10 min then diluted with water (20 mL) and extracted with EtOAc (15 mL×3). The combined organic layers were dried over $Na_2SO_4$ and concentrated, and the residue was purified by preparative TLC (PE/EtOAc=2/1) to give the title compound. MS: m/z=507.2 (M+1). $^1$H NMR (400 MHz, $CDCl_3$) δ 8.85 (d, J=8.2 Hz, 1H), 8.63 (d, J=13.3 Hz, 1H), 8.41 (d, J=7.4 Hz, 1H), 7.61-7.36 (m, 8H), 6.44 (s, 1H), 4.20 (q, J=7.0 Hz, 2H), 3.96 (s, 3H), 3.90 (s, 2H), 1.30-1.26 (m, 3H).

Step B: N-(6-(2-Amino-2-oxoethyl)-2-phenylpyridin-3-yl)-2-fluoro-5-(1-methyl-1H-pyrazol-3-yl)-4-(trifluoromethyl)benzamide To a solution of ethyl 2-(5-(2-fluoro-5-(1-methyl-1H-pyrazol-3-yl)-4-(trifluoromethyl) benzamido)-6-phenylpyridin-2-yl) acetate (50 mg, 0.095 mmol) in MeOH (2 mL) at 25° C. was added a 3M solution of $NH_3$ in MeOH (5 mL). The resulting mixture was stirred for 24 h. The product mixture was concentrated, and the residue was purified by reverse-phase HPLC under basic conditions ($H_2O/CH_3CN$ gradient with 0.05% $NH_4OH$ present) to give the title compound. MS: m/z=498.1 (M+1). $^1$H NMR (400 MHz, $CDCl_3$) δ 8.86 (d, J=8.2 Hz, 1H), 8.63 (d, J=13.7 Hz, 1H), 8.42 (d, J=7.8 Hz, 1H), 7.63-7.49 (m, 5H), 7.45 (d, J=11.7 Hz, 1H), 7.40 (d, J=2.0 Hz, 1H), 7.35 (d, J=8.6 Hz, 1H), 6.44 (s, 1H), 5.39 (s, 1H), 3.96 (s, 3H), 3.80 (s, 2H).

The following examples were prepared in similar fashion to the procedures described above.

| Compound Number | Structure | Compound Name | LCMS (M + 1) |
|---|---|---|---|
| 103 | 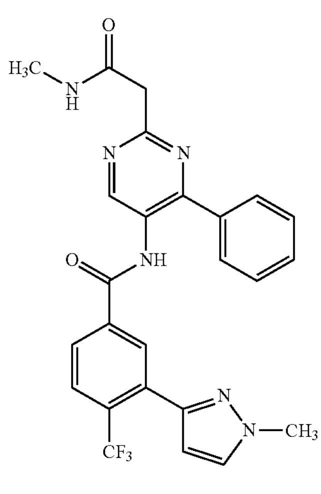 [SMILES: CNC(=O)Cc1ncc(NC(=O)c2ccc(C(F)(F)F)c(-c3ccn(C)n3)c2)c(-c2ccccc2)n1] | 3-(1-methyl-1H-pyrazol-3-yl)-N-(2-(2-(methylamino)-2-oxoethyl)-4-phenylpyrimidin-5-yl)-4-(trifluoromethyl)benzamide | 495.2 |

-continued

| Compound Number | Structure | Compound Name | LCMS (M + 1) |
|---|---|---|---|
| 104 | 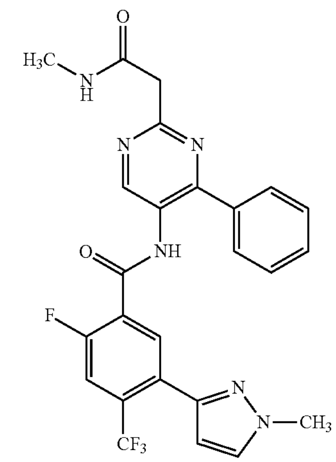 [SMILES: CNC(=O)Cc1ncc(NC(=O)c2cc(-c3ccn(C)n3)c(C(F)(F)F)cc2F)c(-c2ccccc2)n1] | 2-fluoro-5-(1-methyl-1H-pyrazol-3-yl)-N-(2-(2-(methylamino)-2-oxoethyl)-4-phenylpyrimidin-5-yl)-4-(trifluoromethyl)benzamide | 513.3 |
| 105 | 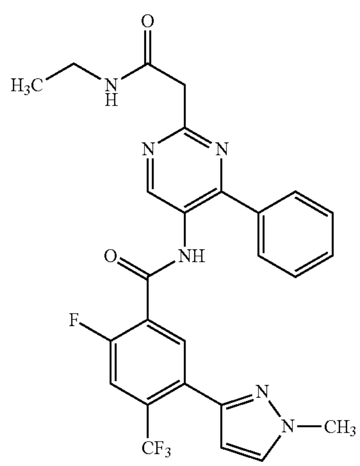 [SMILES: CCNC(=O)Cc1ncc(NC(=O)c2cc(-c3ccn(C)n3)c(C(F)(F)F)cc2F)c(-c2ccccc2)n1] | N-(2-(2-(ethylamino)-2-oxoethyl)-4-phenylpyrimidin-5-yl)-2-fluoro-5-(1-methyl-1H-pyrazol-3-yl)-4-(trifluoromethyl)benzamide | 527.3 |
| 106 | 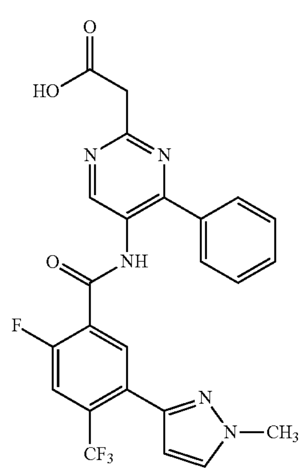 [SMILES: Cn1ccc(-c2cc(C(=O)Nc3cnc(CC(=O)O)nc3-c3ccccc3)c(F)cc2C(F)(F)F)n1] | 2-(5-(2-fluoro-5-(1-methyl-1H-pyrazol-3-yl)-4-(trifluoromethyl)benzamido)-4-phenylpyrimidin-2-yl)acetic acid | 500.2 |

| Compound Number | Structure | Compound Name | LCMS (M + 1) |
|---|---|---|---|
| 107 | 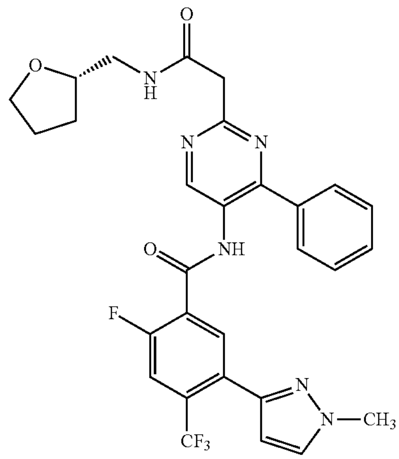 [SMILES: Cn1ccc(-c2cc(C(=O)Nc3cnc(CC(=O)NC[C@@H]4CCCO4)nc3-c3ccccc3)c(F)cc2C(F)(F)F)n1] | (S)-2-fluoro-5-(1-methyl-1H-pyrazol-3-yl)-N-(2-(2-oxo-2-(((tetrahydrofuran-2-yl)methyl)amino)ethyl)-4-phenylpyrimidin-5-yl)-4-(trifluoromethyl)benzamide | 583.4 |
| 108 | 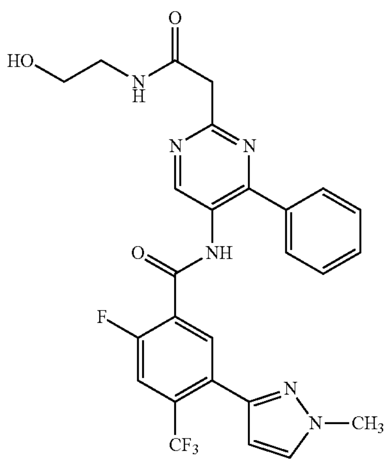 [SMILES: Cn1ccc(-c2cc(C(=O)Nc3cnc(CC(=O)NCCO)nc3-c3ccccc3)c(F)cc2C(F)(F)F)n1] | 2-fluoro-N-(2-(2-((2-hydroxyethyl)amino)-2-oxoethyl)-4-phenylpyrimidin-5-yl)-5-(1-methyl-1H-pyrazol-3-yl)-4-(trifluoromethyl)benzamide | 543.3 |
| 109 | 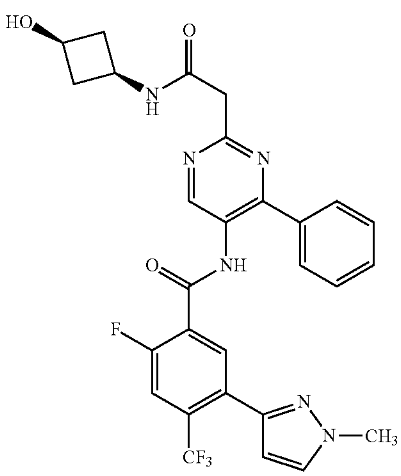 [SMILES: Cn1ccc(-c2cc(C(=O)Nc3cnc(CC(=O)N[C@H]4C[C@@H](O)C4)nc3-c3ccccc3)c(F)cc2C(F)(F)F)n1] | 2-fluoro-N-(2-(2-(((1s,3s)-3-hydroxycyclobutyl)amino)-2-oxoethyl)-4-phenylpyrimidin-5-yl)-5-(1-methyl-1H-pyrazol-3-yl)-4-(trifluoromethyl)benzamide | 569.4 |

-continued

| Compound Number | Structure | Compound Name | LCMS (M + 1) |
|---|---|---|---|
| 110 | 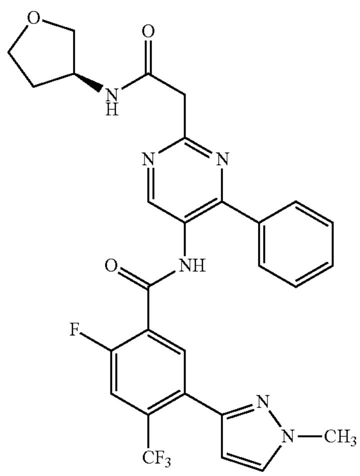 [SMILES: Cn1ccc(-c2cc(C(=O)Nc3cnc(CC(=O)N[C@H]4CCOC4)nc3-c3ccccc3)c(F)cc2C(F)(F)F)n1] | (S)-2-fluoro-5-(1-methyl-1H-pyrazol-3-yl)-N-(2-(2-oxo-2-(((tetrahydrofuran-3-yl)amino)ethyl)-4-phenylpyrimidin-5-yl)-4-(trifluoromethyl)benzamide | 569.3 |
| 111 | 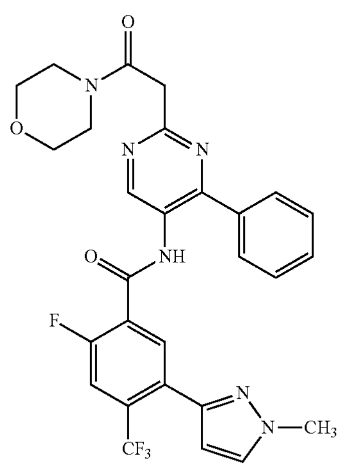 [SMILES: Cn1ccc(-c2cc(C(=O)Nc3cnc(CC(=O)N4CCOCC4)nc3-c3ccccc3)c(F)cc2C(F)(F)F)n1] | 2-fluoro-5-(1-methyl-1H-pyrazol-3-yl)-N-(2-(2-morpholino-2-oxoethyl)-4-phenylpyrimidin-5-yl)-4-(trifluoromethyl)benzamide | 569.2 |
| 112 | 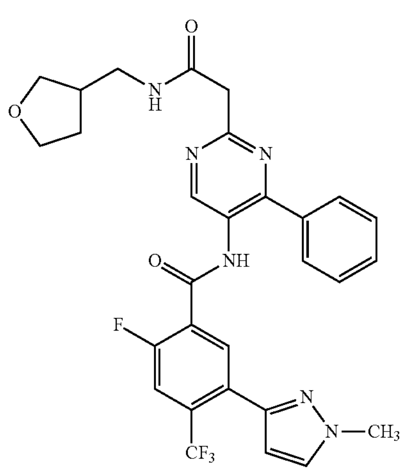 [SMILES: Cn1ccc(-c2cc(C(=O)Nc3cnc(CC(=O)NCC4CCOC4)nc3-c3ccccc3)c(F)cc2C(F)(F)F)n1] | 2-fluoro-5-(1-methyl-1H-pyrazol-3-yl)-N-(2-(2-oxo-2-(((tetrahydrofuran-3-yl)methyl)amino)ethyl)-4-phenylpyrimidin-5-yl)-4-(trifluoromethyl)benzamide | 583.3 |

-continued

| Compound Number | Structure | Compound Name | LCMS (M + 1) |
|---|---|---|---|
| 113 | 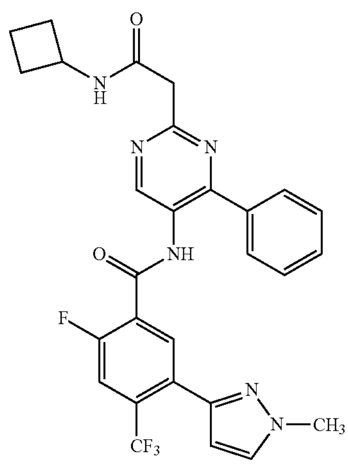 [SMILES: Cn1ccc(-c2cc(C(=O)Nc3cnc(CC(=O)NC4CCC4)nc3-c3ccccc3)c(F)cc2C(F)(F)F)n1] | N-(2-(2-(cyclobutylamino)-2-oxoethyl)-4-phenylpyrimidin-5-yl)-2-fluoro-5-(1-methyl-1H-pyrazol-3-yl)-4-(trifluoromethyl)benzamide | 553.2 |
| 114 | 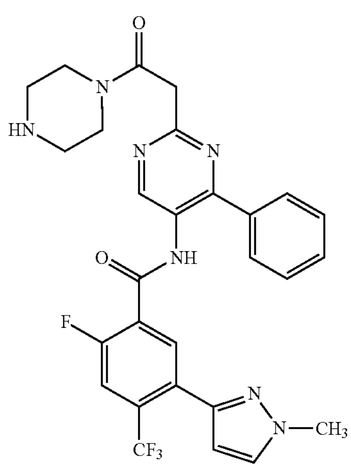 [SMILES: Cn1ccc(-c2cc(C(=O)Nc3cnc(CC(=O)N4CCNCC4)nc3-c3ccccc3)c(F)cc2C(F)(F)F)n1] | 2-fluoro-5-(1-methyl-1H-pyrazol-3-yl)-N-(2-(2-oxo-2-(piperazin-1-yl)ethyl)-4-phenylpyrimidin-5-yl)-4-(trifluoromethyl)benzamide | 568.2 |
| 115 | 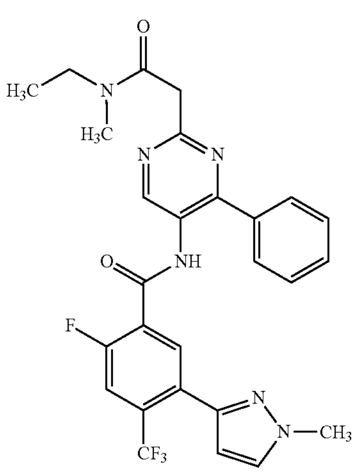 [SMILES: CCN(C)C(=O)Cc1ncc(NC(=O)c2cc(-c3ccn(C)n3)c(C(F)(F)F)cc2F)c(-c2ccccc2)n1] | N-(2-(2-(ethyl(methyl)amino)-2-oxoethyl)-4-phenylpyrimidin-5-yl)-2-fluoro-5-(1-methyl-1H-pyrazol-3-yl)-4-(trifluoromethyl)benzamide | 541.2 |

-continued

| Compound Number | Structure | Compound Name | LCMS (M + 1) |
|---|---|---|---|
| 116 | 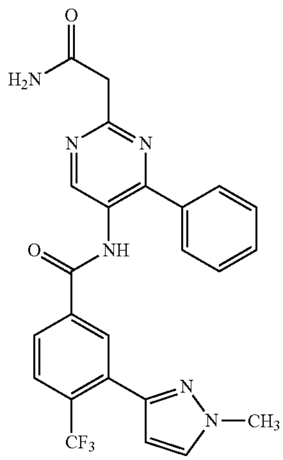 [SMILES: Cn1ccc(-c2cc(C(=O)Nc3cnc(CC(N)=O)nc3-c3ccccc3)ccc2C(F)(F)F)n1] | N-(2-(2-amino-2-oxoethyl)-4-phenylpyrimidin-5-yl)-3-(1-methyl-1H-pyrazol-3-yl)-4-(trifluoromethyl)benzamide | 481.2 |
| 117 | 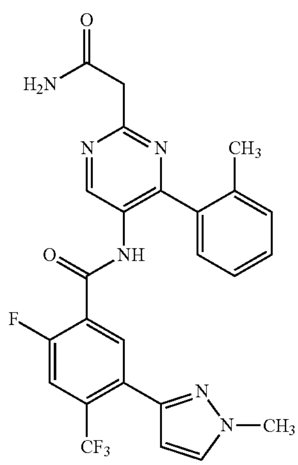 [SMILES: Cc1ccccc1-c1nc(CC(N)=O)ncc1NC(=O)c1cc(-c2ccn(C)n2)c(C(F)(F)F)cc1F] | N-(2-(2-amino-2-oxoethyl)-4-(o-tolyl)pyrimidin-5-yl)-2-fluoro-5-(1-methyl-1H-pyrazol-3-yl)-4-(trifluoromethyl)benzamide | 513.0 |
| 118 | 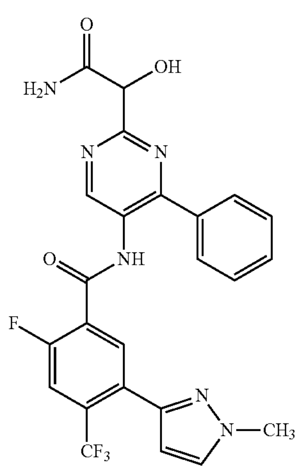 [SMILES: Cn1ccc(-c2cc(C(=O)Nc3cnc(C(O)C(N)=O)nc3-c3ccccc3)c(F)cc2C(F)(F)F)n1] | N-(2-(2-amino-1-hydroxy-2-oxoethyl)-4-phenylpyrimidin-5-yl)-2-fluoro-5-(1-methyl-1H-pyrazol-3-yl)-4-(trifluoromethyl)benzamide | 514.9 |

-continued

| Compound Number | Structure | Compound Name | LCMS (M + 1) |
|---|---|---|---|
| 119 | 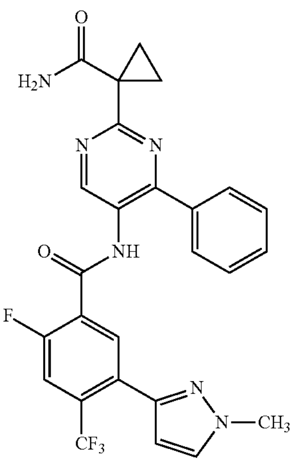 [SMILES: Cn1ccc(-c2cc(C(=O)Nc3cnc(C4(C(N)=O)CC4)nc3-c3ccccc3)c(F)cc2C(F)(F)F)n1] | N-(2-(1-carbamoylcyclopropyl)-4-phenylpyrimidin-5-yl)-2-fluoro-5-(1-methyl-1H-pyrazol-3-yl)-4-(trifluoromethyl)benzamide | 525.1 |
| 120 | 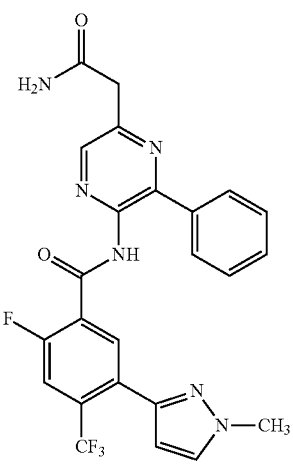 [SMILES: Cn1ccc(-c2cc(C(=O)Nc3ncc(CC(N)=O)nc3-c3ccccc3)c(F)cc2C(F)(F)F)n1] | N-(5-(2-amino-2-oxoethyl)-3-phenylpyrazin-2-yl)-2-fluoro-5-(1-methyl-1H-pyrazol-3-yl)-4-(trifluoromethyl)benzamide | 499.1 |
| 121 | 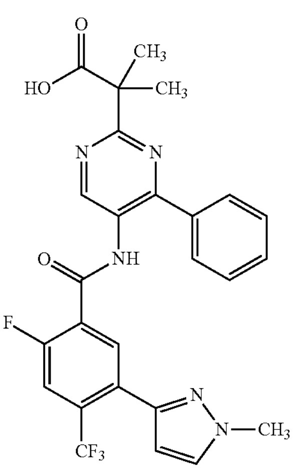 [SMILES: Cn1ccc(-c2cc(C(=O)Nc3cnc(C(C)(C)C(=O)O)nc3-c3ccccc3)c(F)cc2C(F)(F)F)n1] | 2-(5-(2-fluoro-5-(1-methyl-1H-pyrazol-3-yl)-4-(trifluoromethyl)benzamido)-4-phenylpyrimidin-2-yl)-2-methylpropanoic acid | 528.2 |

-continued

| Compound Number | Structure | Compound Name | LCMS (M + 1) |
|---|---|---|---|
| 122 | 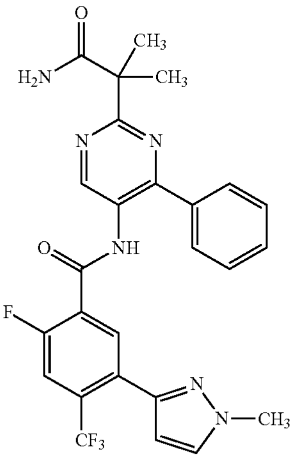 [SMILES: Cn1ccc(-c2cc(C(=O)Nc3cnc(C(C)(C)C(N)=O)nc3-c3ccccc3)c(F)cc2C(F)(F)F)n1] | N-(2-(1-amino-2-methyl-1-oxopropan-2-yl)-4-phenylpyrimidin-5-yl)-2-fluoro-5-(1-methyl-1H-pyrazol-3-yl)-4-(trifluoromethyl)benzamide | 527.1 |
| 123 | 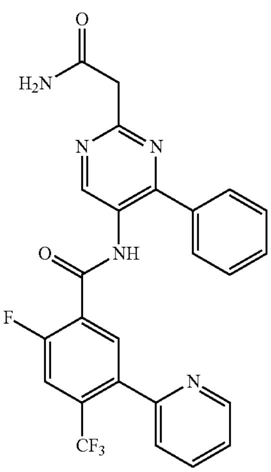 | N-(2-(2-amino-2-oxoethyl)-4-phenylpyrimidin-5-yl)-2-fluoro-5-(pyridin-2-yl)-4-(trifluoromethyl)benzamide | 496.1 |
| 124 | 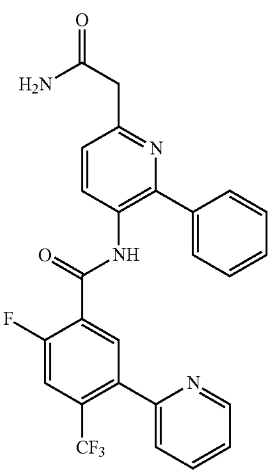 [SMILES: NC(=O)Cc1ccc(NC(=O)c2cc(-c3ccccn3)c(C(F)(F)F)cc2F)c(-c2ccccc2)n1] | N-(6-(2-amino-2-oxoethyl)-2-phenylpyridin-3-yl)-2-fluoro-5-(pyridin-2-yl)-4-(trifluoromethyl)benzamide | 495.1 |

-continued

| Compound Number | Structure | Compound Name | LCMS (M + 1) |
|---|---|---|---|
| 125 | 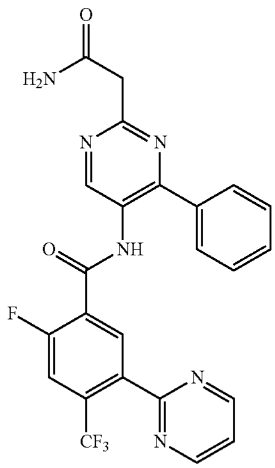 [SMILES: NC(=O)Cc1ncc(NC(=O)c2cc(-c3ncccn3)c(C(F)(F)F)cc2F)c(-c2ccccc2)n1] | N-(2-(2-amino-2-oxoethyl)-4-phenylpyrimidin-5-yl)-2-fluoro-5-(pyrimidin-2-yl)-4-(trifluoromethyl)benzamide | 497.1 |
| 126 | 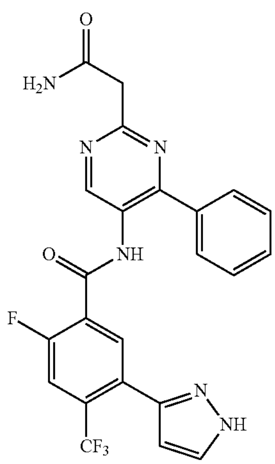 [SMILES: NC(=O)Cc1ncc(NC(=O)c2cc(-c3cc[nH]n3)c(C(F)(F)F)cc2F)c(-c2ccccc2)n1] | N-(2-(2-amino-2-oxoethyl)-4-phenylpyrimidin-5-yl)-2-fluoro-5-(1H-pyrazol-3-yl)-4-(trifluoromethyl)benzamide | 485.1 |
| 127 | 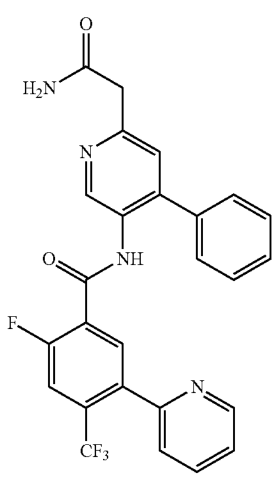 [SMILES: NC(=O)Cc1cc(-c2ccccc2)c(NC(=O)c2cc(-c3ccccn3)c(C(F)(F)F)cc2F)cn1] | N-(6-(2-amino-2-oxoethyl)-4-phenylpyridin-3-yl)-2-fluoro-5-(pyridin-2-yl)-4-(trifluoromethyl)benzamide | 495.1 |

EXAMPLE 128

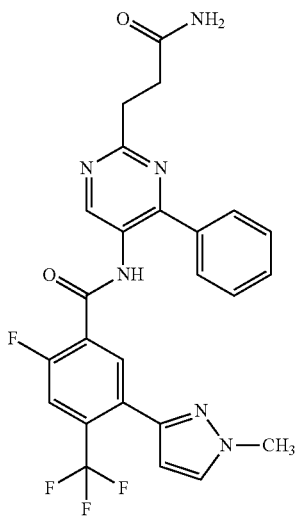 [SMILES: Cn1ccc(-c2cc(C(=O)Nc3cnc(CCC(N)=O)nc3-c3ccccc3)c(F)cc2C(F)(F)F)n1]

N-(2-(3-Amino-3-oxopropyl)-4-phenylpyrimidin-5-yl)-2-fluoro-5-(1-methyl-1H-pyrazol-3-yl)-4-(trifluoromethyl)benzamide Step A: Ethyl 3-(5-(2-fluoro-5-(1-methyl-1H-pyrazol-3-yl)-4-(trifluoromethyl)benzamido)-4-phenylpyrimidin-2-yl)propanoate To a solution of 2-fluoro-5-(1-methyl-1H-pyrazol-3-yl)-4-(trifluoromethyl)benzoic acid (51 mg, 0.18 mmol) in pyridine (1 mL) at 25° C. was added POCl$_3$ (0.020 mL, 0.21 mmol). After the mixture was stirred for 15 min, ethyl 3-(5-amino-4-phenylpyrimidin-2-yl)propanoate (40 mg, 0.15 mmol) in pyridine (1 mL) was added dropwise. The resulting mixture was stirred for 10 min then partitioned between water (5 mL) and EtOAc (5 mL×3). The combined organic layers were dried over Na$_2$SO$_4$ and concentrated. The residue was purified by preparative TLC (PE/EtOAc=1/1) to give the title compound. MS: m/z=542.3 (M+1). $^1$H NMR (400 MHz, CDCl$_3$) δ 9.72 (s, 1H), 8.61-8.58 (m, 1H), 8.46 (d, J=8.0 Hz, 1H), 7.67-7.66 (m, 2H), 7.57-7.56 (m, 3H), 7.41 (s, 1H), 7.40 (s, 1H), 6.45 (s, 1H), 4.15 (q, J=7.6 Hz, 2H), 3.97 (s, 3H), 3.37 (t, J=7.2 Hz, 2H), 2.93 (t, J=7.2 Hz, 2H), 1.24 (t, J=7.2 Hz, 3H).

Step B: N-(2-(3-Amino-3-oxopropyl)-4-phenylpyrimidin-5-yl)-2-fluoro-5-(1-methyl-1H-pyrazol-3-yl)-4-(trifluoromethyl)benzamide To a solution of ethyl 3-(5-(2-fluoro-5-(1-methyl-1H-pyrazol-3-yl)-4-(trifluoromethyl)benzamido)-4-phenylpyrimidin-2-yl)propanoate (30 mg, 0.055 mmol) in ethanol (0.5 mL) was added concentrated aqueous NH$_4$OH solution (5 mL, 0.05 mmol). The resulting mixture was stirred at 25° C. for 16 h then filtered and purified by reverse-phase HPLC under basic conditions (H$_2$O/CH$_3$CN gradient with 0.05% NH$_4$OH present) to give the title compound. MS: m/z=513.1 (M+1). $^1$H NMR (400 MHz, CD$_3$OD) δ 9.02 (s, 1H), 7.96 (d, J=6.4 Hz, 1H), 7.82-7.81 (m, 2H), 7.71-7.66 (m, 2H), 7.51-7.50 (m, 3H), 6.45 (s, 1H), 3.97 (s, 3H), 3.34 (t, J=7.2 Hz, 2H), 2.83 (t, J=7.2 Hz, 2H).

REACTION SCHEME FOR EXAMPLE 129

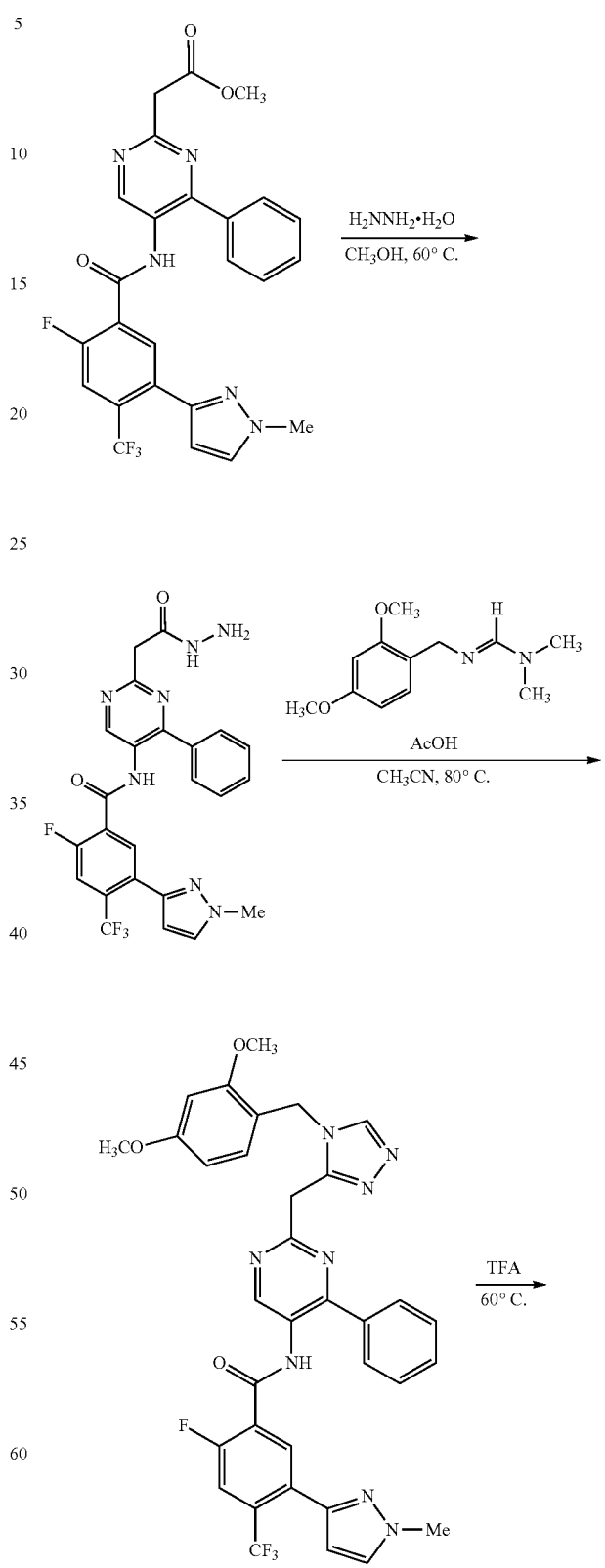

-continued

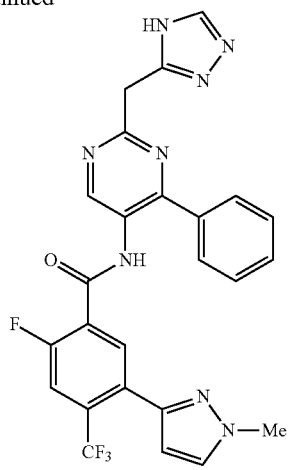

EXAMPLE 129

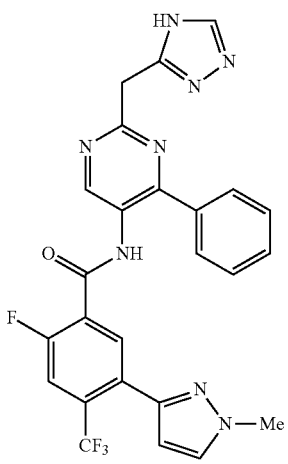 [SMILES: Cn1ccc(-c2cc(C(=O)Nc3cnc(Cc4nnc[nH]4)nc3-c3ccccc3)c(F)cc2C(F)(F)F)n1]

N-(2-((4H-1,2,4-Triazol-3-yl)methyl)-4-phenylpyrimidin-5-yl)-2-fluoro-5-(1-methyl-1H-pyrazol-3-yl)-4-(trifluoromethyl)benzamide Step A: 2-Fluoro-N-(2-(2-hydrazinyl-2-oxoethyl)-4-phenylpyrimidin-5-yl)-5-(1-methyl-1H-pyrazol-3-yl)-4-(trifluoromethyl)benzamide To a suspension of methyl 2-(5-(2-fluoro-5-(1-methyl-1H-pyrazol-3-yl)-4-(trifluoromethyl)benzamido)-4-phenylpyrimidin-2-yl)acetate (800 mg, 1.56 mmol) in MeOH (6 mL) was added hydrazine monohydrate (0.38 mL, 7.8 mmol), and the resulting mixture was heated to 60° C. After 5 h, the mixture was cooled and concentrated. The residue was purified by silica gel chromatography (RediSep-Rf-40 g, 100% EtOH) to give the title compound. $^1$H NMR (500 MHz, CDCl$_3$): δ 9.82 (s, 1H), 8.66 (d, J=14.2 Hz, 1H), 8.47 (d, J=7.8 Hz, 1H), 8.40 (s, 1H), 7.67-7.65 (m, 2H), 7.59-7.58 (m, 3H), 7.50 (s, 1H), 7.48 (s, 1H), 7.41 (d, J=2.3 Hz, 1H), 6.46 (s, 1H), 4.04 (s, 2H), 3.97-3.96 (m, 4H).

Step B: (E)-N-(2,4-Dimethoxybenzyl)-N,N-dimethylformimidamide (2,4-Dimethoxyphenyl)methanamine (1.00 mL, 6.66 mmol) and DMF-DMA (2.67 mL, 20.0 mmol) were combined in MeOH (20 mL), and the resulting mixture was heated to reflux. After 3 h, the mixture was cooled and concentrated to give the title compound. $^1$H NMR (500 MHz, CDCl$_3$): δ 7.36 (s, 1H), 7.21 (d, J=8.1 Hz, 1H), 6.46-6.43 (m, 2H), 4.38 (s, 2H), 3.80 (s, 3H), 3.79 (s, 3H), 2.87 (s, 6H).

Step C: N-(2-((4-(2,4-Dimethoxybenzyl)-4H-1,2,4-triazol-3-yl)methyl)-4-phenylpyrimidin-5-yl)-2-fluoro-5-(1-methyl-1H-pyrazol-3-yl)-4-(trifluoromethyl)benzamide To a solution of (E)-N-(2,4-dimethoxybenzyl)-N,N-dimethylformimidamide (162 mg, 0.730 mmol) in CH$_3$CN (5 mL) was added AcOH (0.100 mL, 1.75 mmol) followed by 2-fluoro-N-(2-(2-hydrazinyl-2-oxoethyl)-4-phenylpyrimidin-5-yl)-5-(1-methyl-1H-pyrazol-3-yl)-4-(trifluoromethyl) benzamide (300 mg, 0.584 mmol). The resulting mixture was stirred for 30 minutes at 23° C. then heated to 80° C. After 8 h the mixture was cooled, then was diluted with saturated aqueous NH$_4$Cl solution and extracted with EtOAc (3×). The combined organic layers were dried (MgSO$_4$), filtered, and concentrated. The residue was purified by silica gel chromatography (RediSep-Rf-24 g, 100% 3:1 EtOAc/EtOH) to give the title compound. $^1$H NMR (500 MHz, DMSO-d$_6$): δ 10.61 (s, 1H), 8.91 (s, 1H), 8.38 (s, 1H), 7.87-7.91 (m, 1H), 7.81 (s, 1H), 7.73 (s, 2H), 7.50 (s, 3H), 7.00 (d, J=8.3 Hz, 1H), 6.52 (d, J=2.4 Hz, 1H), 6.45 (s, 1H), 6.42 (d, J=8.4 Hz, 1H), 5.14 (s, 2H), 4.52 (s, 2H), 3.92 (s, 3H), 3.73 (s, 3H), 3.72 (s, 3H).

Step D: N-(2-((4H-1,2,4-Triazol-3-yl)methyl)-4-phenylpyrimidin-5-yl)-2-fluoro-5-(1-methyl-1H-pyrazol-3-yl)-4-(trifluoromethyl)benzamide N-(2-((4-(2,4-Dimethoxybenzyl)-4H-1,2,4-triazol-3-yl)methyl)-4-phenylpyrimidin-5-yl)-2-fluoro-5-(1-methyl-1H-pyrazol-3-yl)-4-(trifluoromethyl)benzamide (268 mg, 0.398 mmol) was dissolved in TFA (3 mL) and the mixture was heated to 60° C. After 1 h the mixture was cooled, diluted with MeOH, and concentrated. The residue was dissolved in DMSO (5 mL), filtered using a 0.45 μm PTFE syringe filter, then purified by preparative reversed-phase HPLC (21×100 mm Phenomenex AXIA-Gemini-NX (0.1% TFA), 10-50% CH$_3$CN/water over 18 min at 20 mL/min, 3 injections of ~1.7 mL each) to give the title compound. $^1$H NMR (500 MHz, CDCl$_3$): δ 9.90 (s, 1H), 8.73 (d, J=14.3 Hz, 1H), 8.45 (d, J=7.6 Hz, 1H), 8.20 (s, 1H), 7.67 (s, 3H), 7.62-7.61 (m, 3H), 7.50 (d, J=12.0 Hz, 1H), 7.42 (d, J=2.3 Hz, 1H), 6.46 (s, 1H), 4.79 (s, 2H), 3.99 (s, 3H). MS: m/z=523.3 (M+1).

EXAMPLE 130

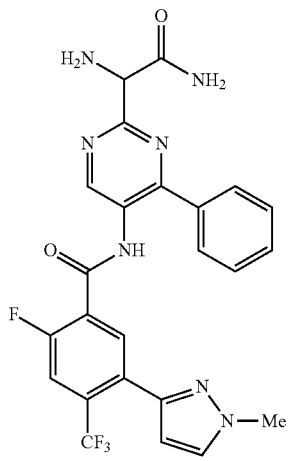 [SMILES: Cn1ccc(-c2cc(C(=O)Nc3cnc(C(N)C(N)=O)nc3-c3ccccc3)c(F)cc2C(F)(F)F)n1]

N-(2-(1,2-Diamino-2-oxoethyl)-4-phenylpyrimidin-5-yl)-2-fluoro-5-(1-methyl-1H-pyrazol-3-yl)-4-(trifluoromethyl)benzamide A solution of NaNO$_2$ (11 mg, 0.16 mmol) in H$_2$O (0.100 mL) was added to a mixture of N-(2-(2-amino-2-oxoethyl)-4-phenylpyrimidin-5-yl)-2-fluoro-5-(1-methyl-1H-pyrazol-3-yl)-4-(trifluoromethyl)benzamide (50 mg, 0.100 mmol) in AcOH (1 mL) at 23° C., and the resulting mixture was stirred for 20 h. Additional NaNO$_2$ (6 mg, 0.09 mmol) in H$_2$O (0.050 mL) was added and stirring was continued for 30 min. 10% Pd/C (11 mg, 0.010 mmol) was added, and the mixture was placed under an atmosphere of H$_2$ (balloon) and stirred rapidly at 23° C. for 3 h. The mixture was filtered directly using a 0.45 µm PTFE syringe filter, washing with AcOH, and the filtrate was concentrated. The residue was partitioned between saturated aqueous NaHCO$_3$ solution (20 mL) and DCM (3×30 mL). The combined organic layers were filtered through a pad of Celite®, washing with DCM, and concentrated. The residue was taken up in DMSO (0.5 mL), filtered using a 0.45 µm PTFE syringe filter, then purified by preparative reversed-phase HPLC (21×100 mm Phenomenex AXIA-Gemini-NX (0.1% TFA), 5-50% CH$_3$CN/water over 18 min at 20 mL/min) to give the title compound as a TFA salt. $^1$H NMR (500 MHz, DMSO-d$_6$): δ 10.79 (s, 1H), 9.14 (s, 1H), 8.78 (s, 3H), 8.09 (s, 1H), 7.87-7.95 (m, 6H), 7.82 (d, J=2.2 Hz, 1H), 7.56 (d, J=5.7 Hz, 3H), 6.45 (s, 1H), 5.21 (s, 1H), 3.92 (s, 3H). MS: m/z=514.3 (M+1).

EXAMPLE 131

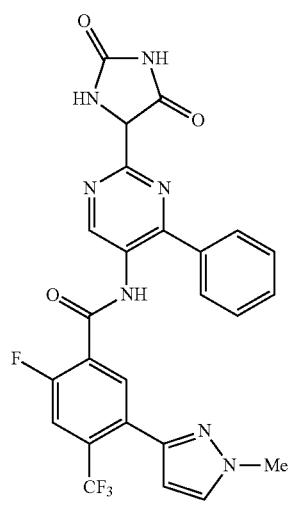 [SMILES: Cn1ccc(-c2cc(C(=O)Nc3cnc(C4NC(=O)NC4=O)nc3-c3ccccc3)c(F)cc2C(F)(F)F)n1]

N-(2-(2,5-Dioxoimidazolidin-4-yl)-4-phenylpyrimidin-5-yl)-2-fluoro-5-(1-methyl-1H-pyrazol-3-yl)-4-(trifluoromethyl)benzamide To a solution of N-(2-(1,2-diamino-2-oxoethyl)-4-phenylpyrimidin-5-yl)-2-fluoro-5-(1-methyl-1H-pyrazol-3-yl)-4-(trifluoromethyl)benzamide (50 mg, 0.097 mmol) in 2-MeTHF (0.5 ml) at 23° C. was added CDI (20 mg, 0.12 mmol). The resulting mixture was heated to 80° C. After 1 h the mixture was cooled and concentrated. The residue was taken up in DMSO (1.0 mL), filtered using a 0.45 µm PTFE syringe filter, then purified by preparative reversed-phase HPLC (21×100 mm Phenomenex AXIA-Gemini-NX (0.1% TFA), 20-65% CH$_3$CN/water over 18 min at 20 mL/min) to give the title compound. $^1$H NMR (500 MHz, DMSO-d$_6$): δ 11.86 (s, 1H), 10.30 (s, 1H), 8.52 (s, 1H), 7.88 (d, J=6.7 Hz, 1H), 7.79-7.84 (m, 5H), 7.52 (s, 1H), 7.47-7.51 (m, 3H), 6.43 (s, 1H), 3.92 (s, 3H). MS: m/z=540.2 (M+1).

EXAMPLE 132

N-(4-(3-(Acetamidomethyl)phenyl)-2-methylpyrimidin-5-yl)-2-fluoro-5-(1-methyl-1H-pyrazol-3-yl)-4-(trifluoromethyl)benzamide Step A: N-(4-(3-(Acetamidomethyl)phenyl)-6-chloro-2-methylpyrimidin-5-yl)-2-fluoro-5-(1-methyl-1H-pyrazol-3-yl)-4-(trifluoromethyl)benzamide A solution of N-(4,6-dichloro-2-methylpyrimidin-5-yl)-2-fluoro-5-(1-methyl-1H-pyrazol-3-yl)-4-(trifluoromethyl) benzamide (30 mg, 0.067 mmol), potassium phosphate tribasic (1M, 0.20 mL, 0.20 mmol) and dioxane (0.5 mL) was stirred at 23° C. for 10 min. The mixture was added to a microwave vial equipped with (3-(acetamidomethyl)phenyl)boronic acid (16 mg, 0.067 mmol), Pd(dppf)Cl$_2$—CH$_2$Cl$_2$ complex (10 mg, 0.012 mmol) and a stir bar. The vial was sealed and heated at 130° C. for 5 min in a microwave reactor. The reaction mixture was cooled, diluted with ethyl acetate and washed with saturated aqueous sodium bicarbonate solution. The organic layer was washed with brine, dried over sodium sulfate, filtered and concentrated to afford the title compound.

Step B: N-(4-(3-(Acetamidomethyl)phenyl)-2-methylpyrimidin-5-yl)-2-fluoro-5-(1-methyl-1H-pyrazol-3-yl)-4-(trifluoromethyl)benzamide To a microwave vial was added bis-pin (13 mg, 0.051 mmol), potassium acetate (5.0 mg, 0.051 mmol) and Pd(dppf)Cl$_2$—CH$_2$Cl$_2$ (20 mg, 0.024 mmol), and a solution of N-(4-(3-(acetamidomethyl)phenyl)-6-chloro-2-methylpyrimidin-5-yl)-2-fluoro-5-(1-methyl-1H-pyrazol-3-yl)-4-(trifluoromethyl)benzamide in 2-methyl-1-propanol (1 mL). The vial was sealed and heated at 130° C. for 5 min in a microwave reactor. The reaction mixture was cooled, diluted with ethyl acetate and washed with water. The organic layer was concentrated, and the residue was purified by reverse phase HPLC (CH$_3$CN/water with 0.1% TFA modifier) to give the title compound. MS: m/z=527.3 (M+1). $^1$H NMR (500 MHz, DMSO-d$_6$) δ 10.55 (s, 1H), 8.87 (s, 1H), 8.38 (s, 1H), 7.92-7.86 (m, 2H), 7.81 (d, J=2.3 Hz, 1H), 7.67 (d, J=9.9 Hz, 2H), 7.44 (t, J=7.6 Hz, 1H), 7.38 (d, J=7.7 Hz, 1H), 6.45 (s, 1H), 4.30 (d, J=5.9 Hz, 2H), 3.92 (s, 3H), 2.70 (s, 3H), 2.55 (s, 1H), 1.83 (s, 3H).

The following compounds were prepared in a similar fashion to the procedures described above. For the synthesis of compound 134, (2-(2-((tert-butoxycarbonyl)amino)ethyl) phenyl)boronic acid was utilized in the initial palladium-catalyzed cross-coupling reaction, and penultimate product was subsequently treated with TFA in dichloromethane to remove the Boc protecting group.

| Compound Number | Structure | Compound Name | LCMS (M + 1) |
|---|---|---|---|
| 133 | 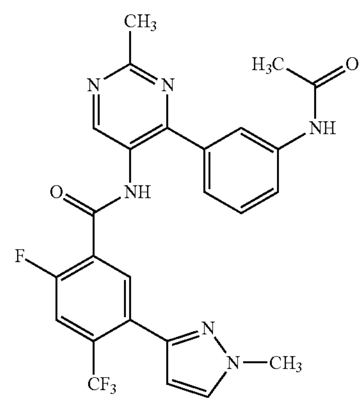 [SMILES: CC(=O)Nc1cccc(-c2nc(C)ncc2NC(=O)c2cc(-c3ccn(C)n3)c(C(F)(F)F)cc2F)c1] | N-(4-(3-acetamidophenyl)-2-methylpyrimidin-5-yl)-2-fluoro-5-(1-methyl-1H-pyrazol-3-yl)-4-(trifluoromethyl)benzamide | 513.3 |
| 134 | 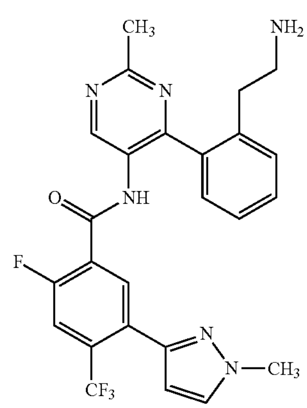 [SMILES: Cc1ncc(NC(=O)c2cc(-c3ccn(C)n3)c(C(F)(F)F)cc2F)c(-c2ccccc2CCN)n1] | N-(4-(2-(2-aminoethyl)phenyl)-2-methylpyrimidin-5-yl)-2-fluoro-5-(1-methyl-1H-pyrazol-3-yl)-4-(trifluoromethyl)benzamide | 498.9 |

EXAMPLE 135

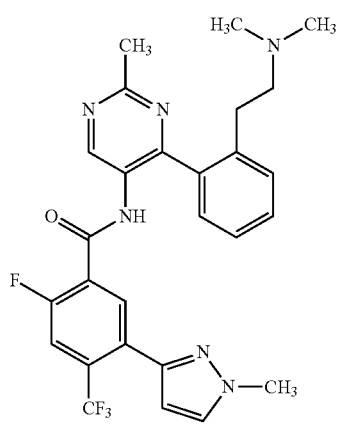 [SMILES: Cc1ncc(NC(=O)c2cc(-c3ccn(C)n3)c(C(F)(F)F)cc2F)c(-c2ccccc2CCN(C)C)n1]

N-(4-(2-(2-(Dimethylamino)ethyl)phenyl)-2-methyl-pyrimidin-5-yl)-2-fluoro-5-(1-methyl-1H-pyrazol-3-yl)-4-(trifluoromethyl)benzamide Formaldehyde (0.003 mL, 0.04 mmol) and sodium acetate (2.1 mg, 0.026 mmol) were added to a solution of N-(4-(2-(2-aminoethyl)phenyl)-2-methylpyrimidin-5-yl)-2-fluoro-5-(1-methyl-1H-pyrazol-3-yl)-4-(trifluoromethyl)benzamide (13 mg, 0.026 mmol) in MeOH (1 mL). The resulting mixture was stirred at 23° C. for 10 min. Sodium cyanoborohydride (1.6 mg, 0.026 mmol) was then added and after stirring for 1 h, the mixture was purified by reverse-phase HPLC (C-18), eluting with acetonitrile/water+0.1% TFA, to give the title compound. MS: m/z=527.0 (M+1). $^1$H NMR (400 MHz, CD$_3$OD) δ 9.00 (s, 1H), 7.80 (m, 1H), 7.65 (m, 2H), 7.50 (m, 2H), 7.40 (m, 2H), 6.40 (s, 1H), 4.00 (s, 3H), 3.22 (t, 2H), 3.10 (t, 2H), 2.82 (s, 6H), 2.80 (s, 3H).

REACTION SCHEME FOR EXAMPLE 136

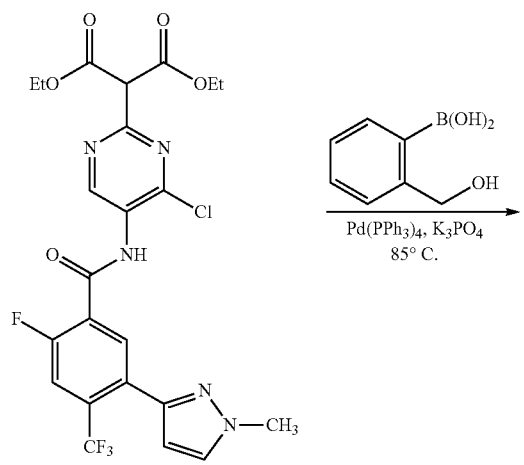

-continued

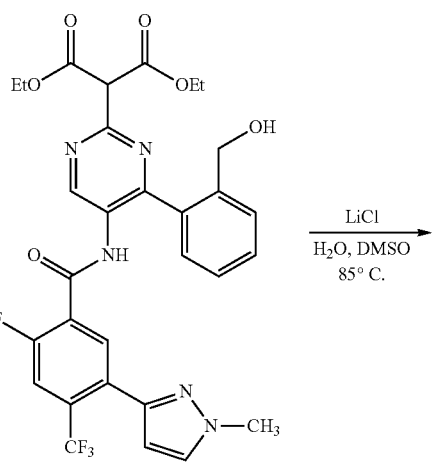

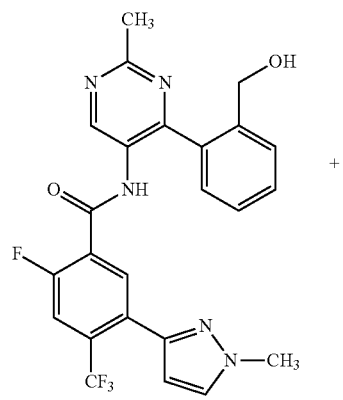

+

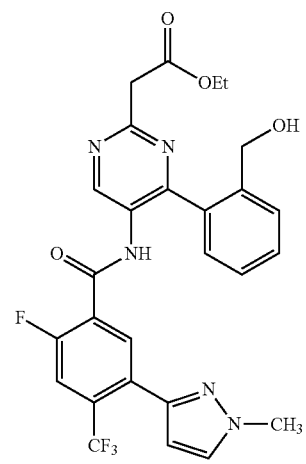

EXAMPLE 136

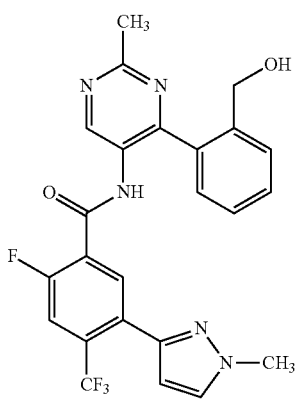 [SMILES: Cc1ncc(NC(=O)c2cc(-c3ccn(C)n3)c(C(F)(F)F)cc2F)c(-c2ccccc2CO)n1]

2-Fluoro-N-(4-(2-(hydroxymethyl)phenyl)-2-methyl-pyrimidin-5-yl)-5-(1-methyl-1H-pyrazol-3-yl)-4-(trifluoromethyl)benzamide Step A: Diethyl 2-(5-(2-fluoro-5-(1-methyl-1H-pyrazol-3-yl)-4-(trifluoromethyl)benzamido)-4-(2-(hydroxymethyl)phenyl)pyrimidin-2-yl)malonate A deoxygenated mixture of diethyl 2-(4-chloro-5-(2-fluoro-5-(1-methyl-1H-pyrazol-3-yl)-4-(trifluoromethyl)benzamido)pyrimidin-2-yl)malonate (0.38 g, 0.68 mmol), Pd(dppf)Cl$_2$—CH$_2$Cl$_2$ (0.028 g, 0.034 mmol), 2-(hydroxymethyl)phenyl boronic acid (0.16 g, 0.12 mmol), and aqueous potassium phosphate tribasic solution (1N, 2.04 mL, 2.04 mmol) in dioxane (5 mL) was heated at 85° C. for 1 h. The mixture was diluted with DCM, dried over Na$_2$SO$_4$ and concentrated. The residue was purified by column chromatography on silica gel, eluting with 10-90% EtOAc/hexanes, to give the title compound. MS: m/z=630.12 (M+1).

Step B: 2-Fluoro-N-(4-(2-(hydroxymethyl)phenyl)-2-methylpyrimidin-5-yl)-5-(1-methyl-1H-pyrazol-3-yl)-4-(trifluoromethyl)benzamide 2,2,2-trifluoroacetate To a solution of diethyl 2-(5-(2-fluoro-5-(1-methyl-1H-pyrazol-3-yl)-4-(trifluoromethyl)benzamido)-4-(2-(hydroxymethyl)phenyl)pyrimidin-2-yl)malonate (390 mg, 0.619 mmol) in DMSO (3.1 mL) was added H$_2$O (0.067 mL, 3.7 mmol) and lithium chloride (79 mg, 1.9 mmol). The resulting mixture was heated at 85° C. for 1 h then cooled and diluted with dichloromethane. The resulting mixture was washed with water, dried over Na$_2$SO$_4$ and concentrated. The residue was purified by reverse-phase HPLC (C-18), eluting with acetonitrile/water+0.1% TFA, to give separately ethyl 2-(5-(2-fluoro-5-(1-methyl-1H-pyrazol-3-yl)-4-(trifluoromethyl)benzamido)-4-(2-(hydroxymethyl)phenyl)pyrimidin-2-yl)acetate and the title compound. MS: m/z=486.0 (M+1). $^1$H NMR (400 MHz, CD$_3$OD) δ 9.20 (s, 1H), 7.90 (d, 1H), 7.65 (m, 3H), 7.52 (m, 1H), 7.40 (m, 1H), 7.38 (m, 1H), 6.40 (s, 1H), 4.55 (s, 2H), 3.98 (s, 3H), 2.75 (3H).

EXAMPLE 137

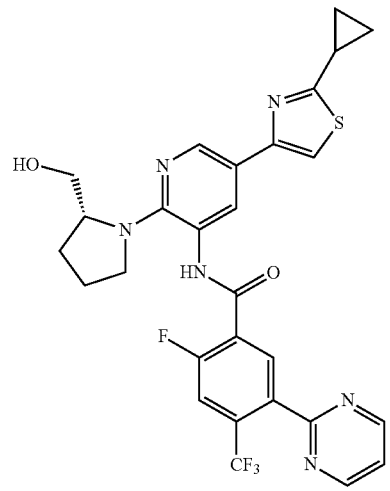 [SMILES: O=C(Nc1cc(-c2csc(C3CC3)n2)cnc1N1CCC[C@@H]1CO)c1cc(-c2ncccn2)c(C(F)(F)F)cc1F]

(R)—N-(5-(2-Cyclopropylthiazol-4-yl)-2-(2-(hydroxymethyl)pyrrolidin-1-yl)pyridin-3-yl)-2-fluoro-5-(pyrimidin-2-yl)-4-(trifluoromethyl)benzamide (R)—N-(5-bromo-2-(2-(hydroxymethyl)pyrolidin-1-yl)pyridin-3-yl)-2-fluoro-5-(pyrimidin-2-yl)-4-(trifluoromethyl)benzamide (30 mg, 0.056 mmol) and bis-pin (15 mg, 0.061 mmol) were added to a 1 dram vial. The vial was transferred to a glove box. In the glove box, KOAc (16 mg, 0.17 mmol), 2nd gen. XPHOS precatalyst (4 mg, 0.006 mmol) and anhydrous dioxane (0.3 mL) were added to the vial. The resulting mixture was heated at 100° C. for 2 h. In the glove box, 4-bromo-2-cyclopropyl-thiazole (14 mg, 0.067 mmol), potassium phosphate tribasic (2M, 0.083 mL, 0.17 mmol) and PdCl$_2$(dtbpf) (5 mg, 0.008 mmol) were added to the reaction vial. The resulting mixture was heated at 40° C. for 2 hours. The mixture was diluted with ethyl acetate and washed with water. The organic layer was washed with brine, dried over sodium sulfate, filtered and concentrated. The residue was purified by reverse-phase HPLC (CH$_3$CN/water with 0.1% TFA modifier) to give the title compound. MS: m/z=585 (M+1). $^1$H NMR (500 MHz, CD$_3$OD) δ 8.94 (dd, J=5.0, 2.7 Hz, 2H), 8.50 (s, 2H), 8.29 (d, J=6.8 Hz, 1H), 7.88 (d, J=10.7 Hz, 1H), 7.65 (d, J=2.6 Hz, 1H), 7.57-7.55 (m, 1H), 4.60 (s, 1H), 3.76 (t, J=10.0 Hz, 2H), 3.71-3.63 (m, 2H), 2.42-2.39 (m, 1H), 2.17-2.09 (m, 3H), 2.00-1.97 (m, 2H), 1.21-1.18 (m, 2H), 1.10-1.08 (m, 2H).

The following compound was prepared in a similar fashion to the procedures described above.

| Compound Number | Structure | Compound Name | LCMS (M + 1) |
|---|---|---|---|
| 138 | 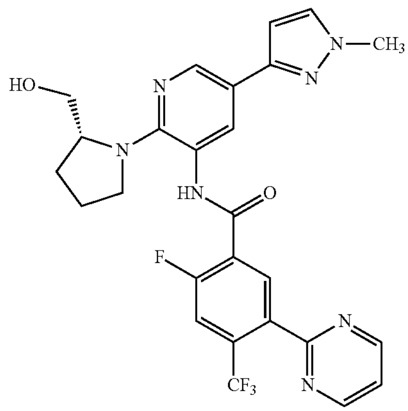 [SMILES: Cn1ccc(-c2cnc(N3CCC[C@@H]3CO)c(NC(=O)c3cc(-c4ncccn4)c(C(F)(F)F)cc3F)c2)n1] | (R)-2-fluoro-N-(2-(2-(hydroxymethyl)pyrrolidin-1-yl)-5-(1-methyl-1H-pyrazol-3-yl)pyridin-3-yl)-5-(pyrimidin-2-yl)-4-(trifluoromethyl)benzamide | 542 |

EXAMPLE 139

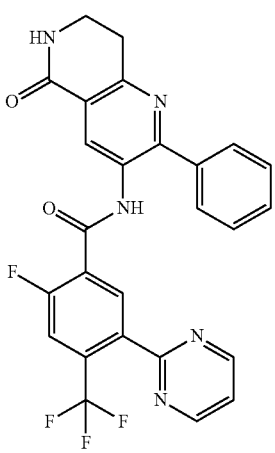 [SMILES: O=C(Nc1cc2c(nc1-c1ccccc1)CCNC2=O)c1cc(-c2ncccn2)c(C(F)(F)F)cc1F]

2-Fluoro-N-(5-oxo-2-phenyl-5,6,7,8-tetrahydro-1,6-naphthyridin-3-yl)-5-(pyrimidin-2-yl)-4-(trifluoromethyl)benzamide Step A: tert-Butyl 3-(2-fluoro-5-(pyrimidin-2-yl)-4-(trifluoromethyl)benzamido)-2-phenyl-7,8-dihydro-1,6-naphthyridine-6(5H)-carboxylate To a solution of tert-butyl 3-amino-2-phenyl-7,8-dihydro-1,6-naphthyridine-6(5H)-carboxylate (400 mg, 1.23 mmol) and 2-fluoro-5-(pyrimidin-2-yl)-4-(trifluoromethyl)benzoic acid (352 mg, 1.23 mmol) in pyridine (5 mL) at 19° C. was added phosphorus oxychloride (0.229 mL, 2.46 mmol). The resulting mixture was stirred for 5 min then diluted with water (20 mL) and extracted with ethyl acetate (20 mL×3). The combined organic layers were dried over $Na_2SO_4$ and concentrated, and the residue was purified by preparative TLC (PE/EtOAc=1/1) to give the title compound. MS: m/z=594.3 (M+1).

Step B: 2-Fluoro-N-(2-phenyl-5,6,7,8-tetrahydro-1,6-naphthyridin-3-yl)-5-(pyrimidin-2-yl)-4-(trifluoromethyl)benzamide To a solution of tert-butyl 3-(2-fluoro-5-(pyrimidin-2-yl)-4-(trifluoromethyl)benzamido)-2-phenyl-7,8-dihydro-1,6-naphthyridine-6(5H)-carboxylate (300 mg, 0.505 mmol) in ethyl acetate (5 mL) at 18° C. was added a 4 M solution of HCl in EtOAc (3 mL). The resulting mixture was stirred for 1 h then concentrated. The residue was purified by reverse-phase HPLC under basic conditions ($H_2O/CH_3CN$ gradient with 0.05% $NH_4OH$ present) to give the title compound. MS: m/z=494.1 (M+1). $^1$H NMR (400 MHz, DMSO) δ 10.49 (s, 1H), 9.05 (s, 2H), 8.96 (d, J=4.7 Hz, 2H), 7.95 (m, 3H), 7.59 (m, 2H), 7.40 (d, J=7.0 Hz, 2H), 4.38 (s, 2H), 3.53 (s, 2H), 3.11 (s, 2H).

Step C: 2-Fluoro-N-(5-oxo-2-phenyl-5,6,7,8-tetrahydro-1,6-naphthyridin-3-yl)-5-(pyrimidin-2-yl)-4-(trifluoromethyl)benzamide To a solution of tert-butyl 3-(2-fluoro-5-(pyrimidin-2-yl)-4-(trifluoromethyl)benzamido)-2-phenyl-7,8-dihydro-1,6-naphthyridine-6(5H)-carboxylate (200 mg, 0.337 mmol) in acetonitrile (3 mL) and water (3 mL) at 20° C. was added sodium periodate (216 mg, 1.011 mmol) and ruthenium (IV) oxide hydrate (10 mg, 0.067 mmol). The resulting mixture was stirred for 48 h then filtered and concentrated. The residue was purified by reverse-phase HPLC under acidic conditions ($H_2O/CH_3CN$ gradient with 0.1% TFA present) to give the title compound. MS: m/z=508.1 (M+1). $^1$H NMR (400 MHz, $CDCl_3$) δ 9.34 (s, 1H), 8.87 (d, J=5.1 Hz, 2H), 8.64 (d, J=13.7 Hz, 1H), 8.57 (d, J=7.4 Hz, 1H), 7.63-7.59 (m, 2H), 7.57-7.49 (m, 4H), 7.35 (t, J=4.7 Hz, 1H), 6.02 (s, 1H), 3.69 (s, 2H), 3.24 (t, J=6.5 Hz, 2H).

EXAMPLE 140

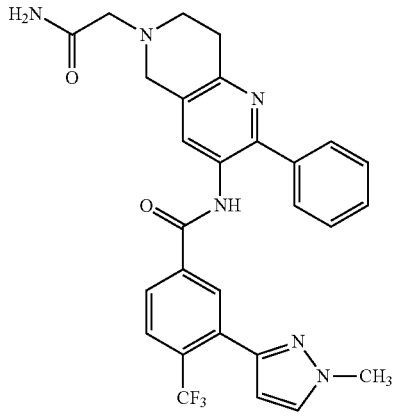 [SMILES: Cn1ccc(-c2cc(C(=O)Nc3cc4c(nc3-c3ccccc3)CCN(CC(N)=O)C4)ccc2C(F)(F)F)n1]

N-(6-(2-Amino-2-oxoethyl)-2-phenyl-5,6,7,8-tetrahydro-1,6-naphthyridin-3-yl)-3-(1-methyl-1H-pyrazol-3-yl)-4-(trifluoromethyl)benzamide Step A: Ethyl 2-(3-(3-(1-methyl-1H-pyrazol-3-yl)-4-(trifluoromethyl)benzamido)-2-phenyl-7,8-dihydro-1,6-naphthyridin-6(5H)-yl)acetate To a solution of 3-(1-methyl-1H-pyrazol-3-yl)-4-(trifluoromethyl) benzoic acid (850 mg, 3.15 mmol) in pyridine (5 mL) at 20° C. was added ethyl 2-(3-amino-2-phenyl-7,8-dihydro-1,6-naphthyridin-6(5H)-yl) acetate (980 mg, 3.15 mmol) and POCl$_3$ (0.440 mL, 4.72 mmol). The resulting mixture was stirred for 0.5 h then diluted with water (5 mL) and extracted with EtOAc (10 mL×3). The combined organic layers were dried over Na$_2$SO$_4$ and concentrated to give the title compound. MS: m/z=564.3 (M+1).

Step B: 2-(3-(3-(1-Methyl-1H-pyrazol-3-yl)-4-(trifluoromethyl)benzamido)-2-phenyl-7,8-dihydro-1,6-naphthyridin-6(5H)-yl)acetic acid To a solution of ethyl 2-(3-(3-(1-methyl-1H-pyrazol-3-yl)-4-(trifluoromethyl) benzamido)-2-phenyl-7,8-dihydro-1,6-naphthyridin-6(5H)-yl)acetate (200 mg, 0.355 mmol) in THF (2 mL) and water (2 mL) was added LiOH (17 mg, 0.70 mmol). The resulting mixture was stirred at 20° C. for 30 min then diluted water (5 mL), acidified to pH 6 by the addition of aqueous 6N HCl solution, and extracted with EtOAc (5 mL×4). The combined organic layers were dried over Na$_2$SO$_4$ and concentrated to give crude title compound. MS: m/z=536.2 (M+1).

Step C: N-(6-(2-Amino-2-oxoethyl)-2-phenyl-5,6,7,8-tetrahydro-1,6-naphthyridin-3-yl)-3-(1-methyl-1H-pyrazol-3-yl)-4-(trifluoromethyl)benzamide A solution of 2-(3-(3-(1-methyl-1H-pyrazol-3-yl)-4-(trifluoromethyl)benzamido)-2-phenyl-7,8-dihydro-1,6-naphthyridin-6(5H)-yl)acetic acid (174 mg, 0.325 mmol) in DCM (2 mL) at 20° C. was basified to pH 8 with DIEA. HATU (148 mg, 0.384 mmol) and NH$_4$Cl (85 mg, 1.6 mmol) were added and the resulting mixture was stirred for 1 h. The product mixture was partitioned between water (2 mL) and EtOAc (5 mL×3). The combined organic layers were dried over Na$_2$SO$_4$ and concentrated. The residue was purified by reverse-phase HPLC under basic conditions (H$_2$O/CH$_3$CN gradient with 0.05% NH$_4$OH present) to give the title compound. MS: m/z=535.2 (M+1). $^1$H NMR (400 MHz, CD$_3$OD) δ 7.99 (s, 1H), 7.93-7.85 (m, 2H), 7.80 (s, 1H), 7.67 (d, J=2.0 Hz, 1H), 7.59 (d, J=7.0 Hz, 2H), 7.48-7.39 (m, 3H), 6.45 (s, 1H), 3.97 (s, 3H), 3.87 (s, 2H), 3.35 (s, 2H), 3.16-3.08 (m, 2H), 3.04-2.97 (m, 2H).

EXAMPLE 141

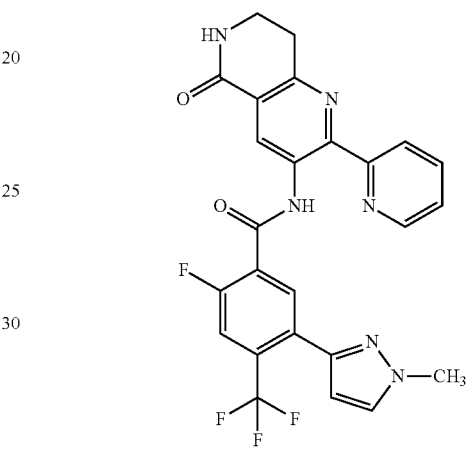

2-Fluoro-5-(1-methyl-1H-pyrazol-3-yl)-N-(5-oxo-2-(pyridin-2-yl)-5,6,7,8-tetrahydro-1,6-naphthyridin-3-yl)-4-(trifluoromethyl)benzamide Step A: 2-Fluoro-5-(1-methyl-1H-pyrazol-3-yl)-N-(5-oxo-2-(pyridin-2-yl)-5,6,7,8-tetrahydro-1,6-naphthyridin-3-yl)-4-(trifluoromethyl)benzamide To a solution of 3-amino-2-(pyridin-2-yl)-7,8-dihydro-1,6-naphthyridin-5(6H)-one (30 mg, 0.13 mmol) and 2-fluoro-5-(1-methyl-1H-pyrazol-3-yl)-4-(trifluoromethyl)benzoic acid (36.0 mg, 0.13 mmol) in pyridine (2 mL) at 25° C. was added phosphorus oxychloride (0.023 mL, 0.25 mmol). The resulting mixture was stirred for 10 min, diluted with ice water (20 mL), and extracted with ethyl acetate (10 mL×3). The combined organic layers were dried over Na$_2$SO$_4$ and concentrated. The residue was purified by reverse-phase HPLC under basic conditions (H$_2$O/CH$_3$CN gradient with 0.05% NH$_4$OH present) to give the title compound. MS: m/z=511.1 (M+1). $^1$H NMR (400 MHz, CDCl$_3$) δ 9.77 (s, 1H), 8.77-8.71 (m, 2H), 8.47 (d, J=7.5 Hz, 1H), 7.99 (t, J=8.5 Hz, 1H), 7.67 (d, J=11.0 Hz, 1H), 7.48-7.43 (m, 2H), 6.54 (s, 1H), 6.06 (s, 1H), 4.04 (s, 3H), 3.79-3.72 (m, 2H), 3.30 (t, J=6.8 Hz, 2H).

EXAMPLE 142

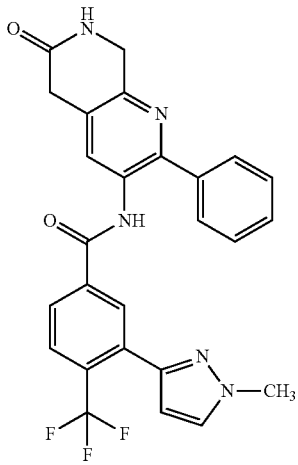 [SMILES: Cn1ccc(-c2cc(C(=O)Nc3cc4c(nc3-c3ccccc3)CNC(=O)C4)ccc2C(F)(F)F)n1]

3-(1-Methyl-1H-pyrazol-3-yl)-N-(6-oxo-2-phenyl-5, 6,7,8-tetrahydro-1,7-naphthyridin-3-yl)-4-(trifluoromethyl)benzamide Step A: Methyl 2-(2-cyano-5-(3-(1-methyl-1H-pyrazol-3-yl)-4-(trifluoromethyl)benzamido)-6-phenylpyridin-3-yl)acetate To a stirred solution of ethyl 2-(5-amino-2-cyano-6-phenylpyridin-3-yl)acetate (83 mg, 0.29 mmol) and 3-(1-methyl-1H-pyrazol-3-yl)-4-(trifluoromethyl)benzoic acid (80 mg, 0.28 mmol) in pyridine (3 mL) at 25° C. was added dropwise $POCl_3$ (0.040 mL, 0.43 mmol). The resulting mixture was stirred at 25° C. for 15 min, then carefully diluted with saturated aqueous $NaHCO_3$ solution (20 mL) and extracted with EtOAc (30 mL×3). The combined organic layers was dried over $Na_2SO_4$ and concentrated, and the residue was purified by preparative TLC (PE/EtOAc=1/1) to give the title compound. MS: m/z=534.2 (M+1).

Step B: 3-(1-Methyl-1H-pyrazol-3-yl)-N-(6-oxo-2-phenyl-5,6,7,8-tetrahydro-1,7-naphthyridin-3-yl)-4-(trifluoromethyl)benzamide A solution of ethyl 2-(2-cyano-5-(3-(1-methyl-1H-pyrazol-3-yl)-4-(trifluoromethyl)benzamido)-6-phenylpyridin-3-yl)acetate (80 mg, 0.15 mmol) and Raney-Ni (17.6 mg, 0.03 mmol) in MeOH (10 mL) was stirred under $H_2$ (50 psi) at 25° C. for 5 h. The mixture was filtered and the filtrate was concentrated. The residue was purified by reverse-phase HPLC under basic conditions ($H_2O/CH_3CN$ gradient with 0.05% $NH_4OH$ present) to give the title compound. MS: m/z=492.2 (M+H). $^1H$ NMR (400 MHz, $CD_3OD$) δ 8.03 (s, 1H), 7.97 (s, 1H), 7.94-7.86 (m, 2H), 7.68 (d, J=2.5 Hz, 1H), 7.64 (d, J=6.5 Hz, 2H), 7.49-7.41 (m, 3H), 6.47 (s, 1H), 4.64 (s, 2H), 3.98 (s, 3H), 3.76 (s, 2H).

EXAMPLE 143

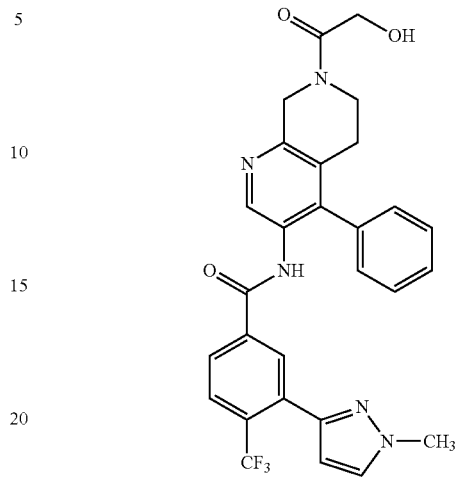

N-(7-(2-Hydroxyacetyl)-4-phenyl-5,6,7,8-tetrahydro-1,7-naphthyridin-3-yl)-3-(1-methyl-1H-pyrazol-3-yl)-4-(trifluoromethyl)benzamide Step A: tert-Butyl 3-(3-(1-methyl-1H-pyrazol-3-yl)-4-(trifluoromethyl)benzamido)-4-phenyl-5,6-dihydro-1,7-naphthyridine-7(8H)-carboxylate To a solution of tert-butyl 3-amino-4-phenyl-5,6-dihydro-1,7-naphthyridine-7(8H)-carboxylate (500 mg, 1.54 mmol) and 3-(1-methyl-1H-pyrazol-3-yl)-4-(trifluoromethyl)benzoic acid (415 mg, 1.54 mmol) in pyridine (5 mL) at 20° C. was added phosphoryl trichloride (236 mg, 1.54 mmol). The resulting mixture was stirred for 10 min then partitioned between water (20 mL) and ethyl acetate (20 mL×3). The combined organic layers were dried over $Na_2SO_4$ and concentrated. The residue was purified by reverse-phase HPLC under basic conditions ($H_2O/CH_3CN$ gradient with 0.05% $NH_4OH$ present) to give the title compound. MS: m/z=578.3 (M+1). $^1H$ NMR (400 MHz, $CD_3OD$) δ 8.59 (s, 1H), 7.84-7.77 (m, 2H), 7.73 (d, J=7.8 Hz, 1H), 7.64 (d, J=2.0 Hz, 1H), 7.48-7.41 (m, 2H), 7.38 (d, J=7.0 Hz, 1H), 7.26 (d, J=7.0 Hz, 2H), 6.40 (s, 1H), 4.71 (s, 2H), 3.94 (s, 3H), 3.59 (s, 2H), 2.59 (t, J=5.3 Hz, 2H), 1.48 (s, 9H).

Step B: 3-(1-Methyl-1H-pyrazol-3-yl)-N-(4-phenyl-5,6,7,8-tetrahydro-1,7-naphthyridin-3-yl)-4-(trifluoromethyl)benzamide To a solution of tert-butyl 3-(3-(1-methyl-1H-pyrazol-3-yl)-4-(trifluoromethyl)benzamido)-4-phenyl-5,6-dihydro-1,7-naphthyridine-7(8H)-carboxylate (200 mg, 0.346 mmol) in dioxane (20 mL) at 20° C. was added a 4M solution of HCl in dioxane (20 mL). The resulting mixture was stirred for 10 min then concentrated. The residue was purified by reverse-phase HPLC under basic conditions ($H_2O/CH_3CN$ gradient with 0.05% $NH_4OH$ present) to give the title compound. MS: m/z=478.2 (M+1). $^1H$ NMR (400 MHz, CD₃OD) δ 8.54 (s, 1H), 7.82-7.76 (m, 2H), 7.71 (d, J=8.2 Hz, 1H), 7.63 (d, J=2.0 Hz, 1H), 7.47-7.40 (m, 2H), 7.39-7.32 (m, 1H), 7.24 (d, J=7.0 Hz, 2H), 6.39 (s, 1H), 4.08 (s, 2H), 3.94 (s, 3H), 3.01 (t, J=5.7 Hz, 2H), 2.56 (t, J=5.5 Hz, 2H).

Step C: N-(7-(2-Hydroxyacetyl)-4-phenyl-5,6,7,8-tetrahydro-1,7-naphthyridin-3-yl)-3-(1-methyl-1H-pyrazol-3-yl)-4-(trifluoromethyl)benzamide A mixture of 2-hydroxyacetic acid (29 mg, 0.38 mmol), HATU (143 mg, 0.38 mmol) and triethylamine (0.053 mL, 0.38 mmol) in DMF (5 mL) was stirred at 20° C. for 10 min before 3-(1-methyl-1H-pyrazol-3-yl)-N-(4-phenyl-5,6,7,8-tetrahydro-1,7-naphthyridin-3-yl)-4-(trifluoromethyl)benzamide (90 mg, 0.19 mmol) was added. The resulting mixture was stirred for 2 h then filtered and purified by reverse-phase HPLC under basic conditions (H₂O/CH₃CN gradient with 0.05% NH₄OH present) to give the title compound. MS: m/z=536.2 (M+1). ¹H NMR (400 MHz, DMSO) δ 10.08 (s, 1H), 8.46 (d, J=6.3 Hz, 1H), 7.85 (d, J=11.0 Hz, 2H), 7.80-7.69 (m, 2H), 7.43-7.28 (m, 3H), 7.23 (d, J=7.0 Hz, 2H), 6.38 (s, 1H), 4.69 (d, J=16.8 Hz, 3H), 4.20 (d, J=5.1 Hz, 2H), 3.88 (s, 3H), 3.64-3.51 (m, 2H), 2.56 (s, 2H).

EXAMPLE 144

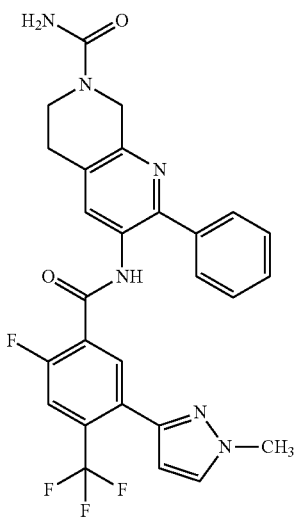 [SMILES: Cn1ccc(-c2cc(C(=O)Nc3cc4c(nc3-c3ccccc3)CN(C(N)=O)CC4)c(F)cc2C(F)(F)F)n1]

3-(2-Fluoro-5-(1-methyl-1H-pyrazol-3-yl)-4-(trifluoromethyl)benzamido)-2-phenyl-5,6-dihydro-1,7-naphthyridine-7(8H)-carboxamide Step A: tert-Butyl 3-(2-fluoro-5-(1-methyl-1H-pyrazol-3-yl)-4-(trifluoromethyl)benzamido)-2-phenyl-5,6-dihydro-1,7-naphthyridine-7(8H)-carboxylate To a stirred solution of tert-butyl 3-amino-2-phenyl-5,6-dihydro-1,7-naphthyridine-7(8H)-carboxylate (30 mg, 0.092 mmol) and 2-fluoro-5-(pyrimidin-2-yl)-4-(trifluoromethyl)benzoic acid (26 mg, 0.090 mmol) in pyridine (2 mL) at 25° C. was added dropwise POCl₃ (0.010 mL, 0.11 mmol). The resulting mixture was stirred for 15 min then carefully diluted with saturated aqueous NaHCO₃ solution (10 mL) and extracted with EtOAc (10 mL×3). The combined organic layers were dried over Na₂SO₄ and concentrated to give the title compound. MS: m/z=594.2 (M+1).

Step B: 2-Fluoro-5-(1-methyl-1H-pyrazol-3-yl)-N-(2-phenyl-5,6,7,8-tetrahydro-1,7-naphthyridin-3-yl)-4-(trifluoromethyl)benzamide A solution of tert-butyl 3-(2-fluoro-5-(pyrimidin-2-yl)-4-(trifluoromethyl)benzamido)-2-phenyl-5,6-dihydro-1,7-naphthyridine-7(8H)-carboxylate (70 mg, 0.12 mmol) in a 4M solution of HCl in dioxane (2 mL) was stirred at 26° C. for 2 h. The product mixture was concentrated and the residue was basified with saturated aqueous K₂CO₃ solution (2 mL). The aqueous mixture was extracted with DCM (4 mL×3), and the combined organic layers were dried over Na₂SO₄ and concentrated. The residue was purified by reverse-phase HPLC under acidic conditions (H₂O/CH₃CN gradient with 0.1% TFA present) to give the title compound. MS: m/z=496.2 (M+1). ¹H NMR (400 MHz, CD₃OD) δ 8.24 (s, 1H), 7.92 (d, J=7.0 Hz, 1H), 7.68-7.62 (m, 4H), 7.46-7.51 (m, 3H), 6.44 (s, 1H), 4.44 (s, 2H), 3.97 (s, 3H), 3.61 (t, J=6.3 Hz, 2H), 3.24 (t, J=6.1 Hz, 2H).

Step C: 3-(2-Fluoro-5-(1-methyl-1H-pyrazol-3-yl)-4-(trifluoromethyl)benzamido)-2-phenyl-5,6-dihydro-1,7-naphthyridine-7(8H)-carboxamide To a solution of 2-fluoro-5-(1-methyl-1H-pyrazol-3-yl)-N-(2-phenyl-5,6,7,8-tetrahydro-1,7-naphthyridin-3-yl)-4-(trifluoromethyl)benzamide (20 mg, 0.040 mmol) in DCM (0.5 mL) at 28° C. was added isocyanatotrimethylsilane (9 mg, 0.08 mmol). The resulting mixture was stirred for 1 h then partitioned between water (1 mL) and DCM (2 mL×3). The combined organic layers were combined dried over Na₂SO₄ and concentrated. The residue was purified by reverse-phase HPLC under basic conditions (H₂O/CH₃CN gradient with 0.05% NH₄OH present) to give the title compound. MS: m/z=539.1 (M+1). ¹H NMR (400 MHz, CD₃OD) δ 8.09 (s, 1H), 7.89 (d, J=7.0 Hz, 1H), 7.67-7.60 (m, 4H), 7.50-7.43 (m, 3H), 6.43 (s, 1H), 4.67 (s, 2H), 3.96 (s, 3H), 3.75 (t, J=5.7 Hz, 2H), 2.98 (t, J=5.5 Hz, 2H).

The following examples were prepared in similar fashion to the procedures described above.

| Compound Number | Structure | Compound Name | LCMS (M + 1) |
|---|---|---|---|
| 145 | 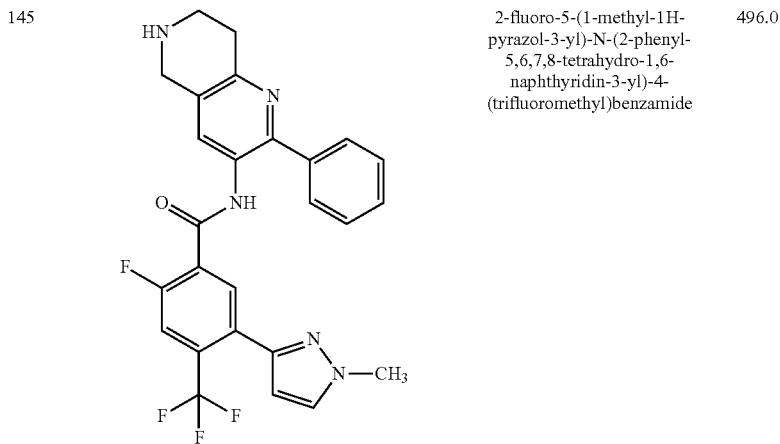 | 2-fluoro-5-(1-methyl-1H-pyrazol-3-yl)-N-(2-phenyl-5,6,7,8-tetrahydro-1,6-naphthyridin-3-yl)-4-(trifluoromethyl)benzamide | 496.0 |
| 146 | 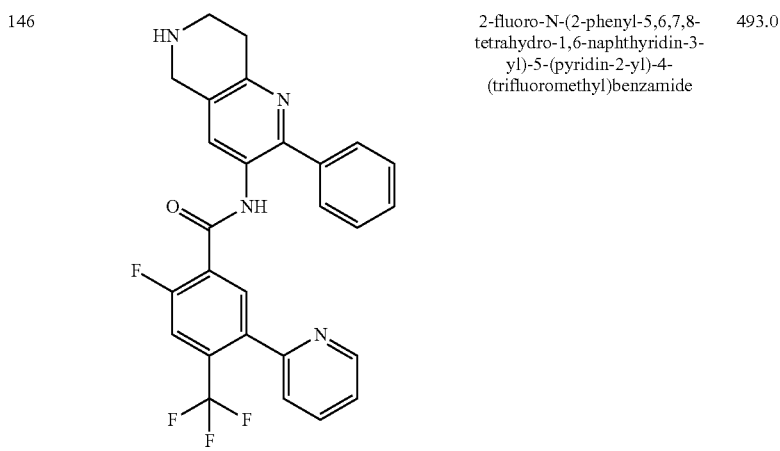 | 2-fluoro-N-(2-phenyl-5,6,7,8-tetrahydro-1,6-naphthyridin-3-yl)-5-(pyridin-2-yl)-4-(trifluoromethyl)benzamide | 493.0 |
| 147 | 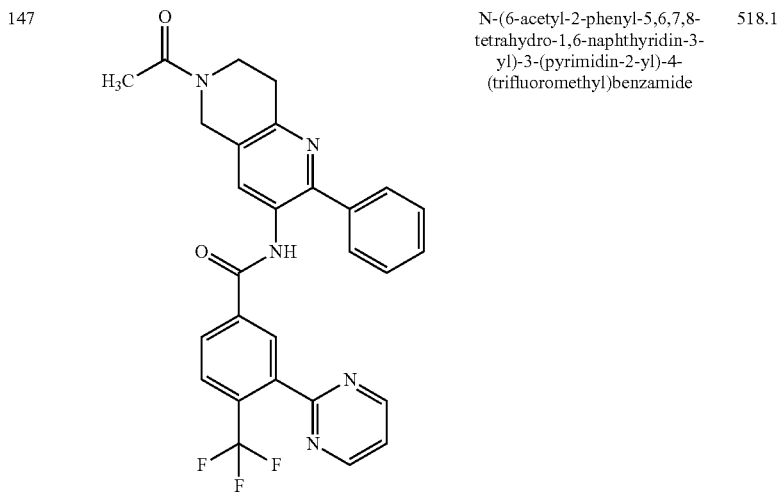 | N-(6-acetyl-2-phenyl-5,6,7,8-tetrahydro-1,6-naphthyridin-3-yl)-3-(pyrimidin-2-yl)-4-(trifluoromethyl)benzamide | 518.1 |

-continued

| Compound Number | Structure | Compound Name | LCMS (M + 1) |
|---|---|---|---|
| 148 | 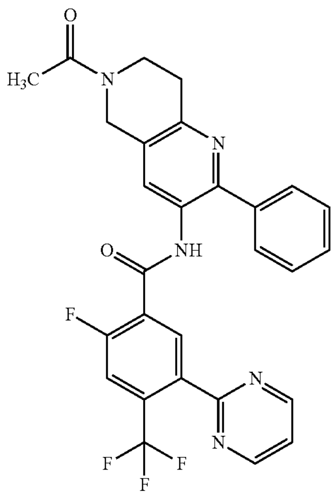 [SMILES: CC(=O)N1CCc2nc(-c3ccccc3)c(NC(=O)c3cc(-c4ncccn4)c(C(F)(F)F)cc3F)cc2C1] | N-(6-acetyl-2-phenyl-5,6,7,8-tetrahydro-1,6-naphthyridin-3-yl)-2-fluoro-5-(pyrimidin-2-yl)-4-(trifluoromethyl)benzamide | 536.1 |
| 149 | 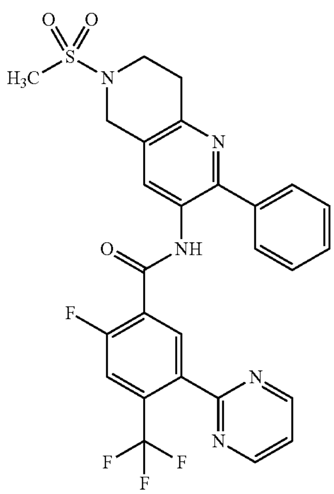 [SMILES: CS(=O)(=O)N1CCc2nc(-c3ccccc3)c(NC(=O)c3cc(-c4ncccn4)c(C(F)(F)F)cc3F)cc2C1] | 2-fluoro-N-(6-(methylsulfonyl)-2-phenyl-5,6,7,8-tetrahydro-1,6-naphthyridin-3-yl)-5-(pyrimidin-2-yl)-4-(trifluoromethyl)benzamide | 572.3 |
| 150 | 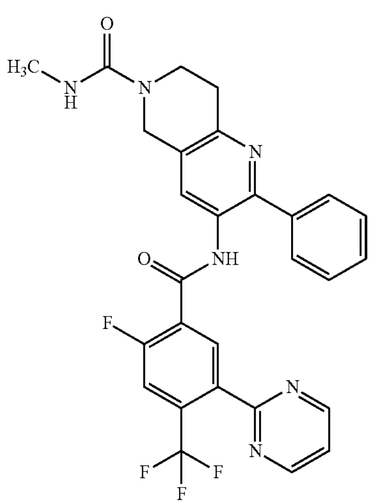 [SMILES: CNC(=O)N1CCc2nc(-c3ccccc3)c(NC(=O)c3cc(-c4ncccn4)c(C(F)(F)F)cc3F)cc2C1] | 3-(2-fluoro-5-(pyrimidin-2-yl)-4-(trifluoromethyl)benzamido)-N-methyl-2-phenyl-7,8-dihydro-1,6-naphthyridine-6(5H)-carboxamide | 551.2 |

| Compound Number | Structure | Compound Name | LCMS (M + 1) |
|---|---|---|---|
| 151 | 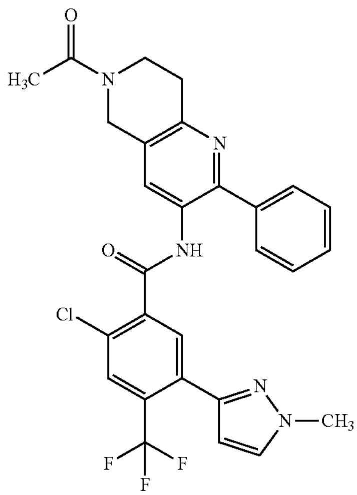 [SMILES: CC(=O)N1CCc2nc(-c3ccccc3)c(NC(=O)c3cc(-c4ccn(C)n4)c(C(F)(F)F)cc3Cl)cc2C1] | N-(6-acetyl-2-phenyl-5,6,7,8-tetrahydro-1,6-naphthyridin-3-yl)-2-chloro-5-(1-methyl-1H-pyrazol-3-yl)-4-(trifluoromethyl)benzamide | 554.1 |
| 152 | 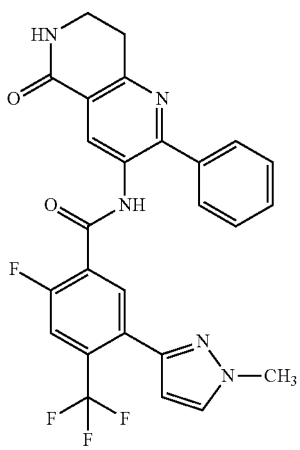 [SMILES: Cn1ccc(-c2cc(C(=O)Nc3cc4c(nc3-c3ccccc3)CCNC4=O)c(F)cc2C(F)(F)F)n1] | 2-fluoro-5-(1-methyl-1H-pyrazol-3-yl)-N-(5-oxo-2-phenyl-5,6,7,8-tetrahydro-1,6-naphthyridin-3-yl)-4-(trifluoromethyl)benzamide | 510.1 |
| 153 | 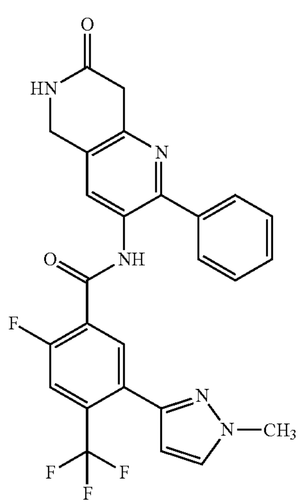 [SMILES: Cn1ccc(-c2cc(C(=O)Nc3cc4c(nc3-c3ccccc3)CC(=O)NC4)c(F)cc2C(F)(F)F)n1] | 2-fluoro-5-(1-methyl-1H-pyrazol-3-yl)-N-(7-oxo-2-phenyl-5,6,7,8-tetrahydro-1,6-naphthyridin-3-yl)-4-(trifluoromethyl)benzamide | 510.1 |

-continued

| Compound Number | Structure | Compound Name | LCMS (M + 1) |
|---|---|---|---|
| 154 | 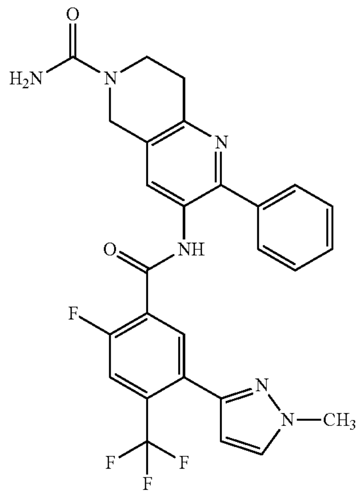 | 3-(2-fluoro-5-(1-methyl-1H-pyrazol-3-yl)-4-(trifluoromethyl)benzamido)-2-phenyl-7,8-dihydro-1,6-naphthyridine-6(5H)-carboxamide | 539.1 |
| 155 | 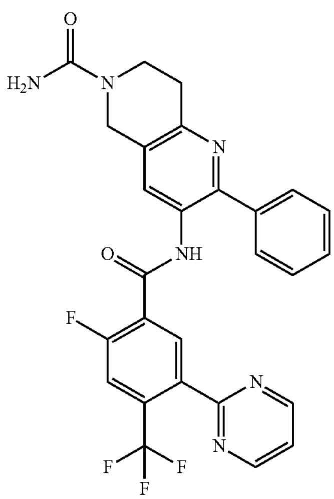 [SMILES: NC(=O)N1CCc2nc(-c3ccccc3)c(NC(=O)c3cc(-c4ncccn4)c(C(F)(F)F)cc3F)cc2C1] | 3-(2-fluoro-5-(pyrimidin-2-yl)-4-(trifluoromethyl)benzamido)-2-phenyl-7,8-dihydro-1,6-naphthyridine-6(5H)-carboxamide | 537.1 |
| 156 | 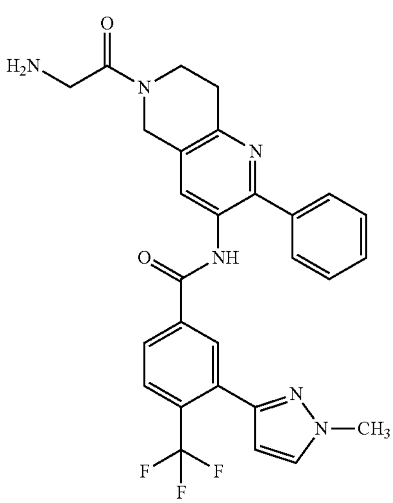 [SMILES: Cn1ccc(-c2cc(C(=O)Nc3cc4c(nc3-c3ccccc3)CCN(C(=O)CN)C4)ccc2C(F)(F)F)n1] | N-(6-glycyl-2-phenyl-5,6,7,8-tetrahydro-1,6-naphthyridin-3-yl)-3-(1-methyl-1H-pyrazol-3-yl)-4-(trifluoromethyl)benzamide | 535.1 |

-continued

| Compound Number | Structure | Compound Name | LCMS (M + 1) |
|---|---|---|---|
| 157 | 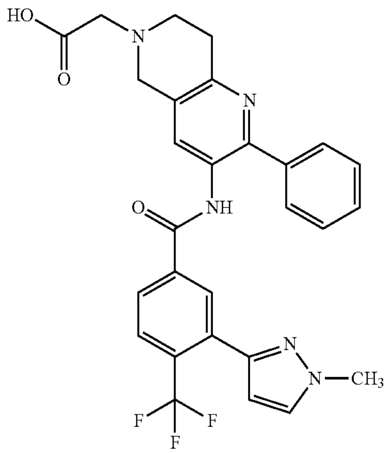 [SMILES: Cn1ccc(-c2cc(C(=O)Nc3cc4c(nc3-c3ccccc3)CCN(CC(=O)O)C4)ccc2C(F)(F)F)n1] | 2-(3-(3-(1-methyl-1H-pyrazol-3-yl)-4-(trifluoromethyl)benzamido)-2-phenyl-7,8-dihydro-1,6-naphthyridin-6(5H)-yl)acetic acid | 536.2 |
| 158 | 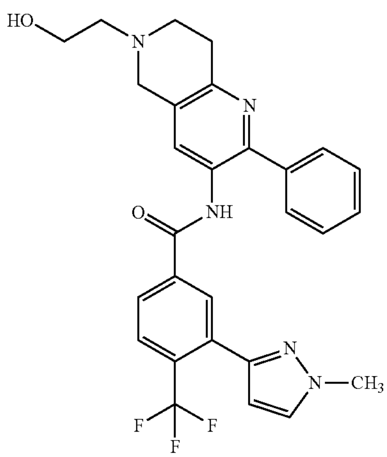 [SMILES: Cn1ccc(-c2cc(C(=O)Nc3cc4c(nc3-c3ccccc3)CCN(CCO)C4)ccc2C(F)(F)F)n1] | N-(6-(2-hydroxyethyl)-2-phenyl-5,6,7,8-tetrahydro-1,6-naphthyridin-3-yl)-3-(1-methyl-1H-pyrazol-3-yl)-4-(trifluoromethyl)benzamide | 522.2 |
| 159 | 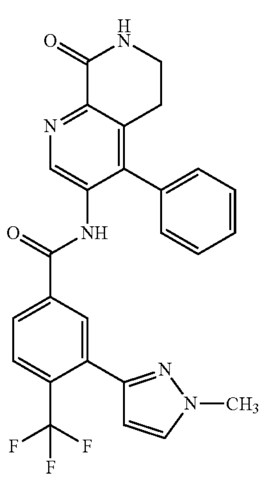 [SMILES: Cn1ccc(-c2cc(C(=O)Nc3cnc4c(c3-c3ccccc3)CCNC4=O)ccc2C(F)(F)F)n1] | 3-(1-methyl-1H-pyrazol-3-yl)-N-(8-oxo-4-phenyl-5,6,7,8-tetrahydro-1,7-naphthyridin-3-yl)-4-(trifluoromethyl)benzamide | 492.1 |

| Compound Number | Structure | Compound Name | LCMS (M + 1) |
|---|---|---|---|
| 160 | 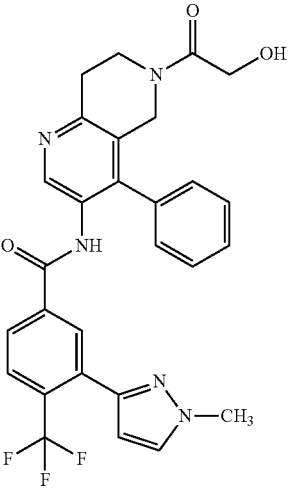 [SMILES: Cn1ccc(-c2cc(C(=O)Nc3cnc4c(c3-c3ccccc3)CN(C(=O)CO)CC4)ccc2C(F)(F)F)n1] | N-(6-(2-hydroxyacetyl)-4-phenyl-5,6,7,8-tetrahydro-1,6-naphthyridin-3-yl)-3-(1-methyl-1H-pyrazol-3-yl)-4-(trifluoromethyl)benzamide | 536.1 |
| 161 | 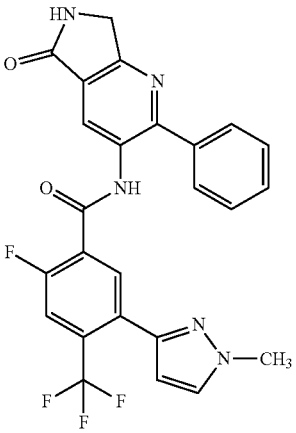 [SMILES: Cn1ccc(-c2cc(C(=O)Nc3cc4c(nc3-c3ccccc3)CNC4=O)c(F)cc2C(F)(F)F)n1] | 2-fluoro-5-(1-methyl-1H-pyrazol-3-yl)-N-(5-oxo-2-phenyl-6,7-dihydro-5H-pyrrolo[3,4-b]pyridin-3-yl)-4-(trifluoromethyl)benzamide | 496.1 |

-continued
| Compound Number | Structure | Compound Name | LCMS (M + 1) |
|---|---|---|---|
| 162 | 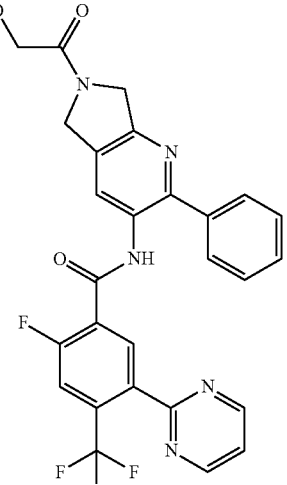 | 2-fluoro-N-(6-(2-hydroxyacetyl)-2-phenyl-6,7-dihydro-5H-pyrrolo[3,4-b]pyridin-3-yl)-5-(pyrimidin-2-yl)-4-(trifluoromethyl)benzamide | 538.1 |
| 163 | 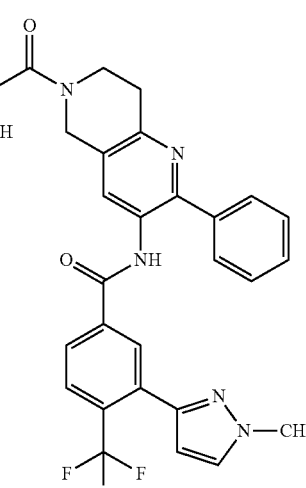 | (R)-N-(6-(2-hydroxypropanoyl)-2-phenyl-5,6,7,8-tetrahydro-1,6-naphthyridin-3-yl)-3-(1-methyl-1H-pyrazol-3-yl)-4-(trifluoromethyl)benzamide | 550.2 |

EXAMPLE 164

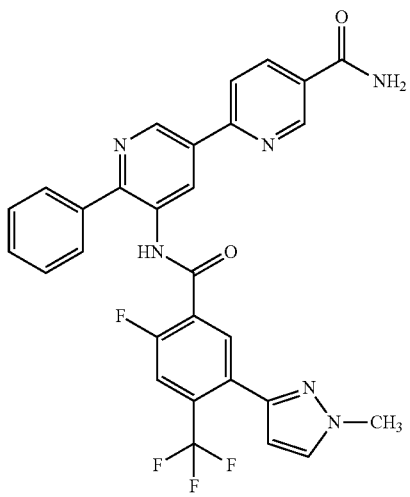 [SMILES: Cn1ccc(-c2cc(C(=O)Nc3cc(-c4ccc(C(N)=O)cn4)cnc3-c3ccccc3)c(F)cc2C(F)(F)F)n1]

5'-(2-Fluoro-5-(1-methyl-1H-pyrazol-3-yl)-4-(trifluoromethyl)benzamido)-6'-phenyl-[2,3'-bipyridine]-5-carboxamide Step A: N-(5-Cyano-6'-phenyl-[2,3'-bipyridin]-5'-yl)-2-fluoro-5-(1-methyl-1H-pyrazol-3-yl)-4-(trifluoromethyl)benzamide To a solution of 2-fluoro-5-(1-methyl-1H-pyrazol-3-yl)-4-(trifluoromethyl)benzoic acid (100 mg, 0.347 mmol) in pyridine (2 mL) at 15° C. was added 5'-amino-6'-phenyl-[2,3'-bipyridine]-5-carbonitrile (94 mg, 0.35 mmol) followed by $POCl_3$ (53 mg, 0.35 mmol). The resulting mixture was stirred for 1 h, then diluted with water (10 mL) and extracted with EtOAc (10 mL×3). The combined organic layers were dried with $Na_2SO_4$ and concentrated, and the residue was purified by preparative TLC (PE/EtOAc=1/1) to give the title compound. MS: m/z=543.2 (M+1).

Step B: 5'-(2-Fluoro-5-(1-methyl-1H-pyrazol-3-yl)-4-(trifluoromethyl)benzamido)-6'-phenyl-[2,3'-bipyridine]-5-carboxamide To a solution of N-(5-cyano-6'-phenyl-[2,3'-bipyridin]-5'-yl)-2-fluoro-5-(1-methyl-1H-pyrazol-3-yl)-4-(trifluoromethyl)benzamide (50 mg, 0.092 mmol) in DMSO (2 mL) at 15° C. was added LiOH (11 mg, 0.46 mmol) followed by aqueous $H_2O_2$ solution (37%, 0.008 mL, 0.09 mmol). The resulting mixture was stirred for 30 min then filtered and concentrated. The residue was purified by reverse-phase HPLC under acidic conditions ($H_2O/CH_3CN$ gradient with 0.1% TFA present) to give the title compound. MS: m/z=561.2 (M+1). $^1$H NMR (400 MHz, DMSO) δ 10.55 (br, 1H), 9.32 (br, 1H), 9.14 (br, 1H), 8.76 (br, 1H), 8.35 (d, J=8.2 Hz, 1H), 8.25 (d, J=7.4 Hz, 2H), 7.92-7.82 (m, 2H), 7.79 (d, J=1.6 Hz, 1H), 7.74 (d, J=6.7 Hz, 2H), 7.67 (br, 1H), 7.51-7.37 (m, 3H), 6.42 (br, 1H), 3.90 (s, 3H).

The following examples were prepared in similar fashion to the procedures described above.

| Compound Number | Structure | Compound Name | LCMS (M + 1) |
|---|---|---|---|
| 165 | 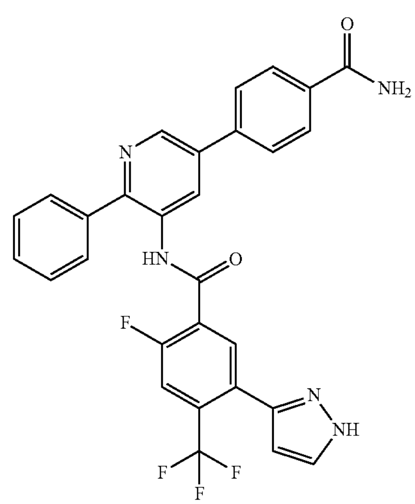 [SMILES: NC(=O)c1ccc(-c2cnc(-c3ccccc3)c(NC(=O)c3cc(-c4cc[nH]n4)c(C(F)(F)F)cc3F)c2)cc1] | N-(5-(4-carbamoylphenyl)-2-phenylpyridin-3-yl)-2-fluoro-5-(1H-pyrazol-3-yl)-4-(trifluoromethyl)benzamide | 546.2 |

-continued

| Compound Number | Structure | Compound Name | LCMS (M + 1) |
|---|---|---|---|
| 166 | 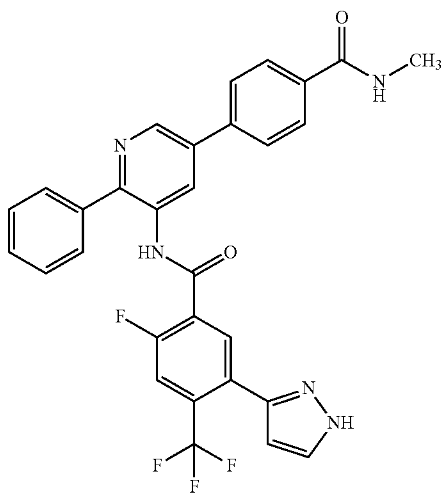 [SMILES: CNC(=O)c1ccc(-c2cnc(-c3ccccc3)c(NC(=O)c3cc(-c4cc[nH]n4)c(C(F)(F)F)cc3F)c2)cc1] | 2-fluoro-N-(5-(4-(methylcarbamoyl)phenyl)-2-phenylpyridin-3-yl)-5-(1H-pyrazol-3-yl)-4-(trifluoromethyl)benzamide | 560.2 |
| 167 | 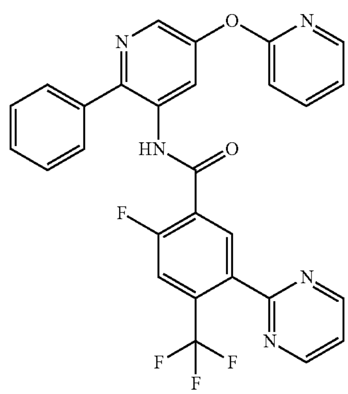 [SMILES: O=C(Nc1cc(Oc2ccccn2)cnc1-c1ccccc1)c1cc(-c2ncccn2)c(C(F)(F)F)cc1F] | 2-fluoro-N-(2-phenyl-5-(pyridin-2-yloxy)pyridin-3-yl)-5-(pyrimidin-2-yl)-4-(trifluoromethyl)benzamide | 532.1 |
| 168 | 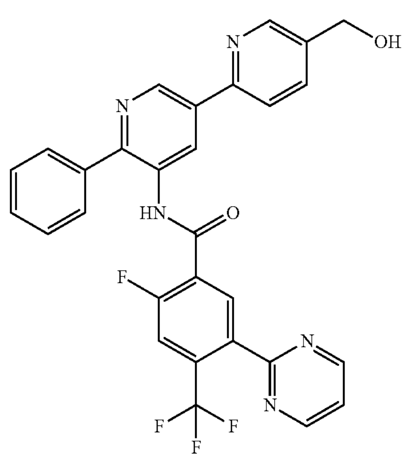 [SMILES: O=C(Nc1cc(-c2ccc(CO)cn2)cnc1-c1ccccc1)c1cc(-c2ncccn2)c(C(F)(F)F)cc1F] | 2-fluoro-N-(5-(hydroxymethyl)-6'-phenyl-[2,3'-bipyridin]-5'-yl)-5-(pyrimidin-2-yl)-4-(trifluoromethyl)benzamide | 546.1 |

-continued

| Compound Number | Structure | Compound Name | LCMS (M + 1) |
|---|---|---|---|
| 169 | 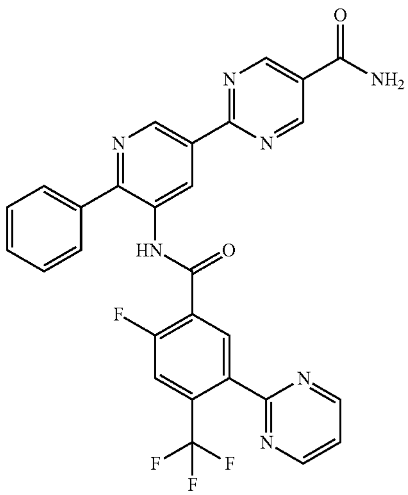 [SMILES: NC(=O)c1cnc(-c2cnc(-c3ccccc3)c(NC(=O)c3cc(-c4ncccn4)c(C(F)(F)F)cc3F)c2)nc1] | 2-(5-(2-fluoro-5-(pyrimidin-2-yl)-4-(trifluoromethyl)benzamido)-6-phenylpyridin-3-yl)pyrimidine-5-carboxamide | 560.1 |
| 170 | 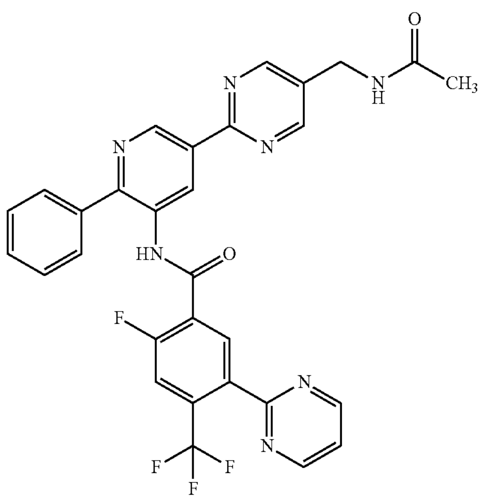 [SMILES: CC(=O)NCc1cnc(-c2cnc(-c3ccccc3)c(NC(=O)c3cc(-c4ncccn4)c(C(F)(F)F)cc3F)c2)nc1] | N-(5-(5-(acetamidomethyl)pyrimidin-2-yl)-2-phenylpyridin-3-yl)-2-fluoro-5-(pyrimidin-2-yl)-4-(trifluoromethyl)benzamide | 588.1 |
| 171 | 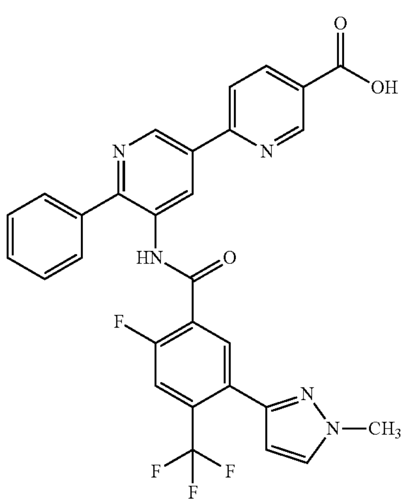 [SMILES: Cn1ccc(-c2cc(C(=O)Nc3cc(-c4ccc(C(=O)O)cn4)cnc3-c3ccccc3)c(F)cc2C(F)(F)F)n1] | 5'-(2-fluoro-5-(1-methyl-1H-pyrazol-3-yl)-4-(trifluoromethyl)benzamido)-6'-phenyl-[2,3'-bipyridine]-5-carboxylic acid | 562.1 |

-continued

| Compound Number | Structure | Compound Name | LCMS (M + 1) |
|---|---|---|---|
| 172 | 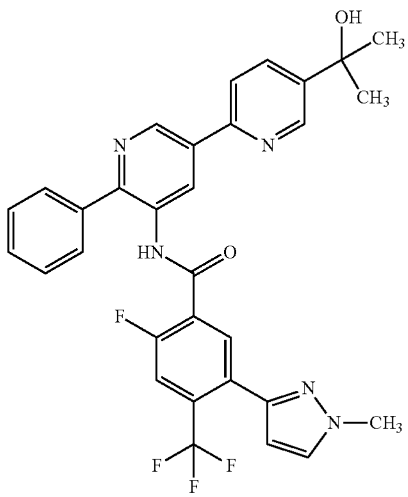 [SMILES: Cn1ccc(-c2cc(C(=O)Nc3cc(-c4ccc(C(C)(C)O)cn4)cnc3-c3ccccc3)c(F)cc2C(F)(F)F)n1] | 2-fluoro-N-(5-(2-hydroxypropan-2-yl)-6'-phenyl-[2,3'-bipyridin]-5'-yl)-5-(1-methyl-1H-pyrazol-3-yl)-4-(trifluoromethyl)benzamide | 576.1 |
| 173 | 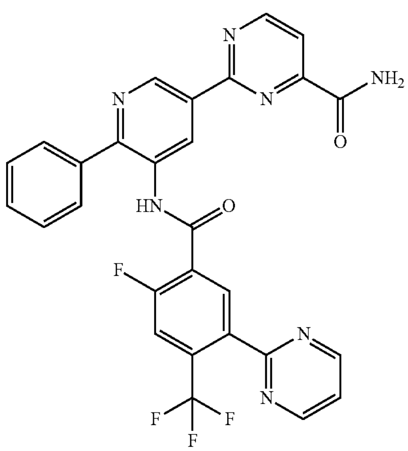 [SMILES: NC(=O)c1ccnc(-c2cnc(-c3ccccc3)c(NC(=O)c3cc(-c4ncccn4)c(C(F)(F)F)cc3F)c2)n1] | 2-(5-(2-fluoro-5-(pyrimidin-2-yl)-4-(trifluoromethyl)benzamido)-6-phenylpyridin-3-yl)pyrimidine-4-carboxamide | 560.1 |
| 174 | 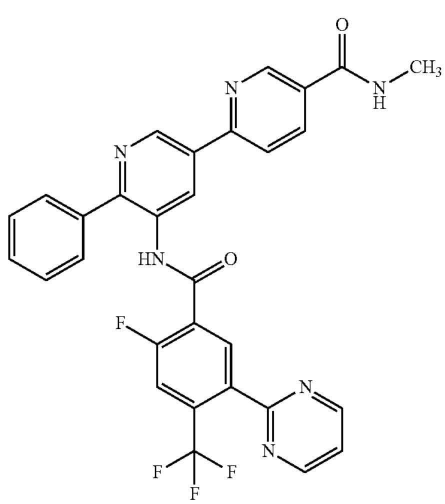 [SMILES: CNC(=O)c1ccc(-c2cnc(-c3ccccc3)c(NC(=O)c3cc(-c4ncccn4)c(C(F)(F)F)cc3F)c2)nc1] | 5'-(2-fluoro-5-(pyrimidin-2-yl)-4-(trifluoromethyl)benzamido)-N-methyl-6'-phenyl-[2,3'-bipyridine]-5-carboxamide | 573.1 |

-continued
| Compound Number | Structure | Compound Name | LCMS (M + 1) |
|---|---|---|---|
| 175 | 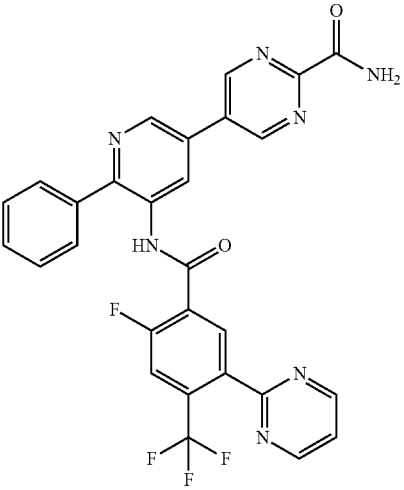 [SMILES: NC(=O)c1ncc(-c2cnc(-c3ccccc3)c(NC(=O)c3cc(-c4ncccn4)c(C(F)(F)F)cc3F)c2)cn1] | 5-(5-(2-fluoro-5-(pyrimidin-2-yl)-4-(trifluoromethyl)benzamido)-6-phenylpyridin-3-yl)pyrimidine-2-carboxamide | 560.1 |
| 176 | 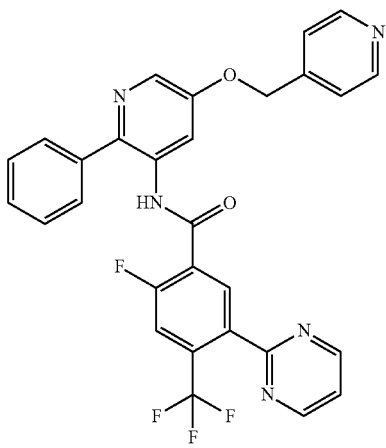 [SMILES: O=C(Nc1cc(OCc2ccncc2)cnc1-c1ccccc1)c1cc(-c2ncccn2)c(C(F)(F)F)cc1F] | 2-fluoro-N-(2-phenyl-5-(pyridin-4-ylmethoxy)pyridin-3-yl)-5-(pyrimidin-2-yl)-4-(trifluoromethyl)benzamide | 546.1 |

-continued
| Compound Number | Structure | Compound Name | LCMS (M + 1) |
|---|---|---|---|
| 177 | 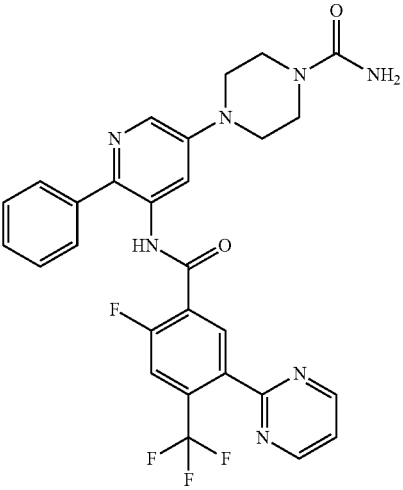 [SMILES: NC(=O)N1CCN(c2cnc(-c3ccccc3)c(NC(=O)c3cc(-c4ncccn4)c(C(F)(F)F)cc3F)c2)CC1] | 4-(5-(2-fluoro-5-(pyrimidin-2-yl)-4-(trifluoromethyl)benzamido)-6-phenylpyridin-3-yl)piperazine-1-carboxamide | 566.2 |
| 178 | 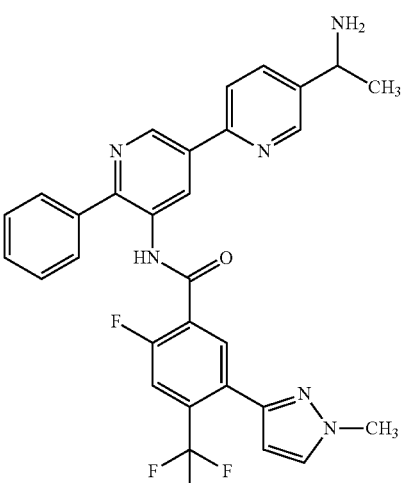 | N-(5-(1-aminoethyl)-6'-phenyl-[2,3'-bipyridin]-5'-yl)-2-fluoro-5-(1-methyl-1H-pyrazol-3-yl)-4-(trifluoromethyl)benzamide | 561.2 |

Example 179

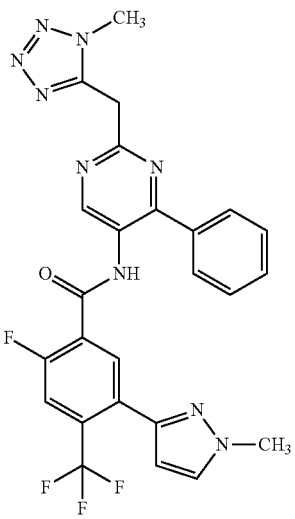 [SMILES: Cn1ccc(-c2cc(C(=O)Nc3cnc(Cc4nnnn4C)nc3-c3ccccc3)c(F)cc2C(F)(F)F)n1]

2-Fluoro-5-(1-methyl-1H-pyrazol-3-yl)-N-(2-((1-methyl-1H-tetrazol-5-yl)methyl)-4-phenylpyrimidin-5-yl)-4-(trifluoromethyl)benzamide To a solution of 2-((1-methyl-1H-tetrazol-5-yl)methyl)-4-phenylpyrimidin-5-amine (30 mg, 0.11 mmol) and 2-fluoro-5-(1-methyl-1H-pyrazol-3-yl)-4-(trifluoromethyl) benzoic acid (32 mg, 0.11 mmol) in pyridine (2 mL) at 19° C. was added $POCl_3$ (0.021 mL, 0.22 mmol). The resulting mixture was stirred for 5 min then diluted with water (5 mL) and extracted with ethyl acetate (5 mL×3). The combined organic layers were dried over anhydrous $Na_2SO_4$ and concentrated. The residue was purified by reverse-phase HPLC under basic conditions ($H_2O$/$CH_3CN$ gradient with 0.05% $NH_4OH$ present) to give the title compound. MS: m/z=538.2 (M+1). $^1$H NMR (400 MHz, DMSO-$d_6$) δ 10.65 (s, 1H), 8.93 (s, 1H), 7.86 (m, 2 H), 7.78 (d, J=1.6 Hz, 1H), 7.72 (m, 2H), 7.47 (d, J=3.5 Hz, 3H), 6.41 (s, 1H), 4.77 (s, 2H), 4.06 (s, 3H), 3.88 (s, 3H).

The following example was prepared in similar fashion to the procedures described above.

Example 181

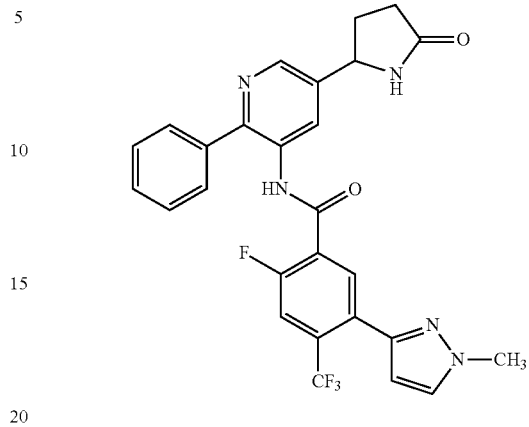

(R or S)-2-Fluoro-5-(1-methyl-1H-pyrazol-3-yl)-N-(5-(5-oxopyrrolidin-2-yl)-2-phenylpyridin-3-yl)-4-(trifluoromethyl)benzamide To a stirred solution of 5-(5-amino-6-phenylpyridin-3-yl) pyrrolidin-2-one (50 mg, 0.20 mmol) and 2-fluoro-5-(1-methyl-1H-pyrazol-3-yl)-4-(trifluoromethyl)benzoic acid (57 mg, 0.20 mmol) in pyridine (3 mL) at 20° C. was added dropwise $POCl_3$ (0.028 mL, 0.30 mmol). The resulting mixture was stirred for 10 min then diluted with water (15 mL) and extracted with EtOAc (15 mL×3). The combined organic layers were dried over $Na_2SO_4$ and concentrated, and the residue was purified by preparative TLC (EtOAc/MeOH=20/1), followed by SFC (250 mm×30 mm, Sum, OD column) eluting with 55% EtOH (0.1% $NH_3.H_2O$), at 80 mL/min to give the title compound (the second eluted isomer by SFC). MS: m/z=524.1 (M+1). $^1$H NMR (400 MHz, $CD_3OD$) δ 8.48 (d, J=1.6 Hz, 1H), 8.31 (s, 1H), 7.91 (d, J=6.7 Hz, 1H), 7.66-7.60 (m, 4H), 7.50-7.44 (m, 3H), 6.42 (bs, 1H), 4.99-4.96 (m, 1H), 3.95 (s, 3H), 2.70 (d, J=7.8 Hz, 1H), 2.52-2.48 (m, 2H), 2.05 (d, J=7.4 Hz, 1H).

| Compound Number | Structure | Compound Name | LCMS (M + 1) |
|---|---|---|---|
| 180 | 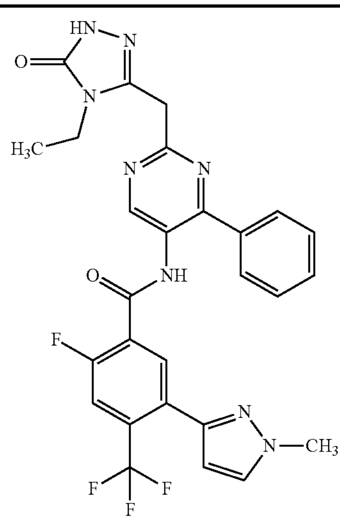 | N-(2-((4-ethyl-5-oxo-4,5-dihydro-1H-1,2,4-triazol-3-yl)methyl)-4-phenylpyrimidin-5-yl)-2-fluoro-5-(1-methyl-1H-pyrazol-3-yl)-4-(trifluoromethyl)benzamide | 567.2 |

Example 182

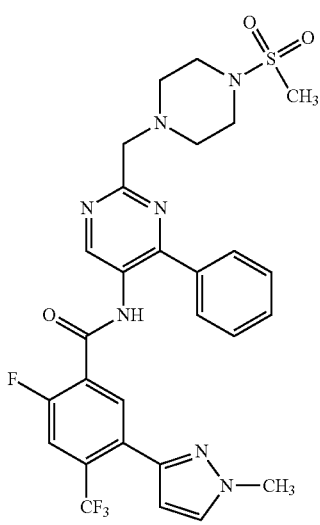 [SMILES: Cn1ccc(-c2cc(C(=O)Nc3cnc(CN4CCN(S(C)(=O)=O)CC4)nc3-c3ccccc3)c(F)cc2C(F)(F)F)n1]

2-Fluoro-5-(1-methyl-1H-pyrazol-3-yl)-N-(2-((4-(methylsulfonyl)piperazin-1-yl)methyl)-4-phenylpyrimidin-5-yl)-4-(trifluoromethyl)benzamide To a mixture of 2-fluoro-5-(1-methyl-1H-pyrazol-3-yl)-4-(trifluoromethyl)benzoic acid (46 mg, 0.16 mmol) in pyridine (5 mL) at 25° C. was added 2-((4-(methylsulfonyl)piperazin-1-yl)methyl)-4-phenylpyrimidin-5-amine (50 mg, 0.14 mmol) followed by $POCl_3$ (0.016 mL, 0.17 mmol). The resulting mixture was stirred for 15 min then diluted with water (5 mL) and extracted with DCM (10 mL×2). The combined organic layers were dried over $Na_2SO_4$ and concentrated, and the residue was purified by reverse-phase HPLC under basic conditions ($H_2O/CH_3CN$ gradient with 0.05% $NH_4OH$ present) to give the title compound. MS: m/z=618.2 (M+1). $^1$H NMR (400 MHz, $CD_3OD$) δ 9.13 (s, 1H), 7.95 (d, J=6.7 Hz, 1H), 7.79 (d, J=3.5 Hz, 2H), 7.71-7.64 (m, 2H), 7.54-7.48 (m, 3H), 6.43 (s, 1H), 3.98-3.90 (m, 5H), 3.26 (s, 4H), 2.83 (s, 3H), 2.76 (d, J=4.3 Hz, 3H).

The following examples were prepared in similar fashion to the procedures described above.

| Compound Number | Structure | Compound Name | LCMS (M + 1) |
|---|---|---|---|
| 183 | 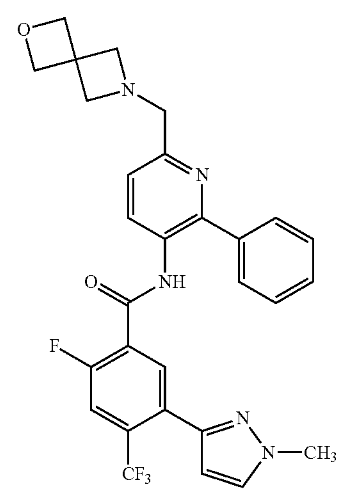 [SMILES: Cn1ccc(-c2cc(C(=O)Nc3ccc(CN4CC5(COC5)C4)nc3-c3ccccc3)c(F)cc2C(F)(F)F)n1] | N-(6-((2-oxa-6-azaspiro[3.3]heptan-6-yl)methyl)-2-phenylpyridin-3-yl)-2-fluoro-5-(1-methyl-1H-pyrazol-3-yl)-4-(trifluoromethyl)benzamide | 552.2 |
| 184 | 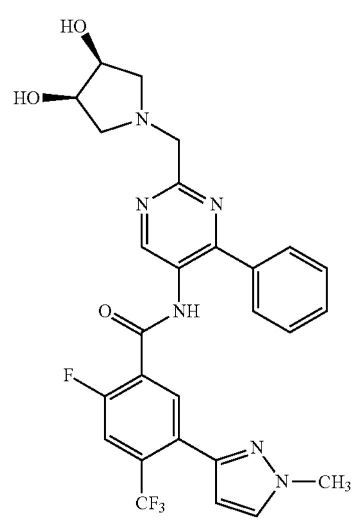 [SMILES: Cn1ccc(-c2cc(C(=O)Nc3cnc(CN4C[C@@H](O)[C@@H](O)C4)nc3-c3ccccc3)c(F)cc2C(F)(F)F)n1] | N-(2-(((3S,4R)-3,4-dihydroxypyrrolidin-1-yl)methyl)-4-phenylpyrimidin-5-yl)-2-fluoro-5-(1-methyl-1H-pyrazol-3-yl)-4-(trifluoromethyl)benzamide | 557.1 |

Example 185

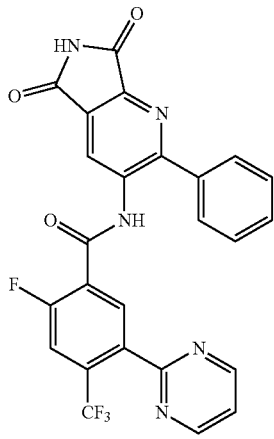 [SMILES: O=C(Nc1cc2c(nc1-c1ccccc1)C(=O)NC2=O)c1cc(-c2ncccn2)c(C(F)(F)F)cc1F]

N-(5,7-Dioxo-2-phenyl-6,7-dihydro-5H-pyrrolo[3,4-b]pyridin-3-yl)-2-fluoro-5-(pyrimidin-2-yl)-4-(trifluoromethyl)benzamide

Step A: Methyl 2-cyano-5-(2-fluoro-5-(pyrimidin-2-yl)-4-(trifluoromethyl)benzamido)-6-henylnicotinate To a solution of 2-fluoro-5-(pyrimidin-2-yl)-4-(trifluoromethyl)benzoic acid (113 mg, 0.40 mmol) in pyridine (3 mL) at 22° C. was added POCl$_3$ (0.18 mL, 2.0 mmol) followed by methyl 5-amino-2-cyano-6-phenylnicotinate (100 mg, 0.40 mmol). The resulting mixture was stirred for 10 min then diluted with water (10 mL) and extracted with EtOAc (10 mL×3). The combined organic layers were dried with Na$_2$SO$_4$ and concentrated to give the title compound. MS: m/z=522.2 (M+1).

Step B: N-(5,7-Dioxo-2-phenyl-6,7-dihydro-5H-pyrrolo[3,4-b]pyridin-3-yl)-2-fluoro-5-(pyrimidin-2-yl)-4-(trifluoromethyl)benzamide To a mixture of methyl 2-cyano-5-(2-fluoro-5-(pyrimidin-2-yl)-4-(trifluoromethyl) benzamido)-6-phenylnicotinate (60 mg, 0.12 mmol) in toluene (3 mL) was added acetaldehyde oxime (7 mg, 0.1 mmol) and indium (III) chloride tetrahydrate (34 mg, 0.12 mmol). The resulting mixture was heated at 120° C. for 24 h, then partitioned between water (10 mL) and EtOAc (10 mL×3). The combined organic layers were dried over Na$_2$SO$_4$ and concentrated. The residue was purified by reverse-phase HPLC under acidic conditions (H$_2$O/CH$_3$CN gradient with 0.1% TFA present) to give the title compound. MS: m/z=508.0 (M+1). $^1$H NMR (400 MHz, DMSO-d$_6$) δ 11.68 (s, 1H), 10.73 (s, 1H), 8.96 (d, J=4.7 Hz, 2H), 8.59 (br, 1H), 8.07 (d, J=5.9 Hz, 1H), 7.97 (d, J=10.2 Hz, 1H), 7.70 (br, 2H), 7.58 (t, J=4.9 Hz, 1H), 7.47 (br, 3H).

Example 186

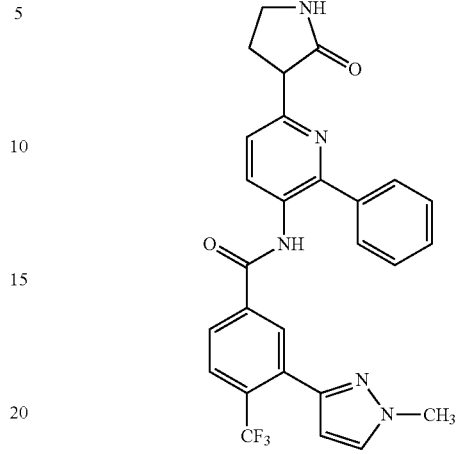

(R or S)-3-(1-Methyl-1H-pyrazol-3-yl)-N-(6-(2-oxopyrrolidin-3-yl)-2-phenylpyridin-3-yl)-4-(trifluoromethyl)benzamide

Step A: Ethyl 3-cyano-2-(5-(3-(1-methyl-1H-pyrazol-3-yl)-4-(trifluoromethyl)benzamido)-6-phenylpyridin-2-yl)propanoate To a solution of 3-(1-methyl-1H-pyrazol-3-yl)-4-(trifluoromethyl)benzoic acid (201 mg, 0.698 mmol) in pyridine (8 mL) at 25° C. was added phosphorus oxychloride (0.10 mL, 1.1 mmol) and ethyl 2-(5-amino-6-phenylpyridin-2-yl)-3-cyanopropanoate (220 mg, 0.75 mmol). The resulting mixture was stirred for 10 min then diluted with water (10 mL) and extracted with ethyl acetate (20 mL×3). The combined organic layers were dried over Na$_2$SO$_4$ and concentrated, and the residue was purified by preparative TLC (PE/EtOAc=5/1) to afford the title compound. $^1$H NMR (400 MHz, CD$_3$OD) δ 8.07 (d, J=8.2 Hz, 1H), 8.03 (br, 1H), 7.93 (d, J=7.8 Hz, 1H), 7.90-7.83 (m, 1H), 7.72-7.60 (m, 3H), 7.50 (d, J=8.2 Hz, 1H), 7.45-7.35 (m, 3H), 6.44 (s, 1H), 4.26-4.13 (m, 2H), 3.93 (s, 3H), 3.47 (s, 1H), 3.26-3.11 (m, 2H), 1.23-1.12 (m, 3H).

Step B: (R or S)-3-(1-Methyl-1H-pyrazol-3-yl)-N-(6-(2-oxopyrrolidin-3-yl)-2-phenylpyridin-3-yl)-4-(trifluoromethyl)benzamide A mixture of ethyl 3-cyano-2-(5-(3-(1-methyl-1H-pyrazol-3-yl)-4-(trifluoromethyl)benzamido)-6-phenylpyridin-2-yl)propanoate (160 mg, 0.28 mmol), triethylamine (0.080 mL, 0.57 mmol) and Raney-Ni (13 mg, 0.15 mmol) in methanol (30 mL) was stirred under hydrogen (50 psi) at 20° C. for 3 h. The mixture was filtered and filtrate concentrated. The residue was purified by preparative TLC (PE/EtOAc=1/1), followed by SFC (Column/AD(250 mm*30 mm, 5um); Mobile phase/A: Supercritical CO$_2$, B: EtOH(base), A:B=55/45 at 45 mL/min; Wavelength/220 nm) to give the title compound (the first eluted isomer by SFC). MS: m/z=506.1 (M+1). $^1$H NMR (400 MHz, CD$_3$OD) δ 8.10-8.00 (m, 2H), 7.93 (d, J=9.3 Hz, 2H), 7.68 (br, 3H), 7.44 (d, J=11.0 Hz, 4H), 6.48 (br, 1H), 4.06-3.89 (m, 4H), 3.60 (d, J=3.8 Hz, 1H), 3.49 (br, 1H), 2.62 (br, 2H).

Example 187

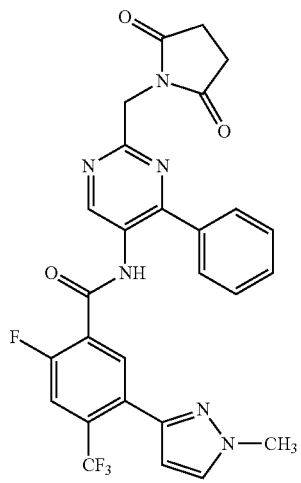 [SMILES: Cn1ccc(-c2cc(C(=O)Nc3cnc(CN4C(=O)CCC4=O)nc3-c3ccccc3)c(F)cc2C(F)(F)F)n1]

N-(2-((2,5-dioxopyrrolidin-1-yl)methyl)-4-phenylpyrimidin-5-yl)-2-fluoro-5-(1-methyl-1H-pyrazol-3-yl)-4-(trifluoromethyl)benzamide To a solution of 2-fluoro-5-(1-methyl-1H-pyrazol-3-yl)-4-(trifluoromethyl) benzoic acid (100 mg, 0.34 mmol) in pyridine (5 mL) at 26° C. was added POCl₃ (0.040 mL, 0.52 mmol) and 1-(5-amino-4-phenylpyrimidin-2-yl)methyl)pyrrolidine-2,5-dione (98 mg, 0.34 mmol). The resulting mixture was stirred for 0.5 h then diluted with water (5 mL) and extracted with EtOAc (10 mL×3). The combined organic layers were concentrated, and the residue was purified by reverse-phase HPLC under basic conditions (H₂O/CH₃CN gradient with 0.05% NH₄OH present) to give the title compound. MS: m/z=553.2 (M+1). ¹H NMR (400 MHz, CD₃OD) δ 9.06 (s, 1H), 7.96 (d, J=7.0 Hz, 1H), 7.77 (d, J=3.5 Hz, 2H), 7.71-7.65 (m, 2H), 7.51 (br, 3H), 6.44 (s, 1H), 4.96 (s, 2H), 3.96 (s, 3H), 2.83 (s, 4H).

Example 188

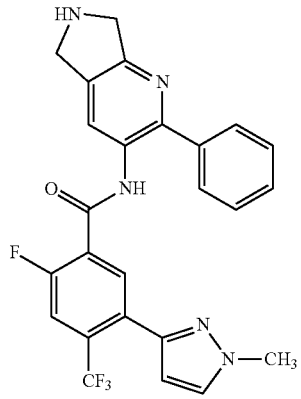 [SMILES: Cn1ccc(-c2cc(C(=O)Nc3cc4c(nc3-c3ccccc3)CNC4)c(F)cc2C(F)(F)F)n1]

2-Fluoro-5-(1-methyl-1H-pyrazol-3-yl)-N-(2-phenyl-6,7-dihydro-5H-pyrrolo[3,4-b]pyridin-3-yl)-4-(trifluoromethyl)benzamide Step A: tert-Butyl 3-(2-fluoro-5-(1-methyl-1H-pyrazol-3-yl)-4-(trifluoromethyl)benzamido)-2-phenyl-5H-pyrrolo[3,4-b]pyridine-6(7H)-carboxylate To a solution of 2-fluoro-5-(1-methyl-1H-pyrazol-3-yl)-4-(trifluoromethyl)benzoic acid (42 mg, 0.14 mmol) in pyridine (2 mL) at 25° C. was added POCl₃ (22 mg, 0.14 mmol) and tert-butyl 3-amino-2-phenyl-5H-pyrrolo[3,4-b]pyridine-6(7H)-carboxylate (45 mg, 0.14 mmol). The resulting mixture was stirred for 10 min then carefully diluted with saturated aqueous NaHCO₃ solution (2 mL) and extracted with EtOAc (2 mL×3). The combined organic layers were dried with Na₂SO₄ and concentrated to give the title compound. MS: m/z=528.2 (M+1).

Step B: 2-Fluoro-5-(1-methyl-1H-pyrazol-3-yl)-N-(2-phenyl-6,7-dihydro-5H-pyrrolo[3,4-b]pyridin-3-yl)-4-(trifluoromethyl)benzamide A solution of tert-butyl 3-(2-fluoro-5-(1-methyl-1H-pyrazol-3-yl)-4-(trifluoromethyl)benzamido)-2-phenyl-5H-pyrrolo[3,4-b]pyridine-6(7H)-carboxylate (50 mg, 0.086 mmol) in a 4 M solution of HCl in dioxane (10 mL, 40 mmol) was stirred at 26° C. for 30 min. The product mixture was concentrated, and the residue was purified by reverse-phase HPLC under basic conditions (H₂O/CH₃CN gradient with 0.05% NH₄OH present) to give the title compound. MS: m/z=482.1 (M+1). ¹H NMR (400 MHz, CD₃OD) δ 8.18-8.12 (m, 1H), 7.87 (d, J=6.7 Hz, 1H), 7.68-7.57 (m, 4H), 7.50-7.43 (m, 3H), 6.43 (br, 1H), 4.33 (s, 2H), 4.21 (s, 2H), 3.96 (s, 3H).

Example 189

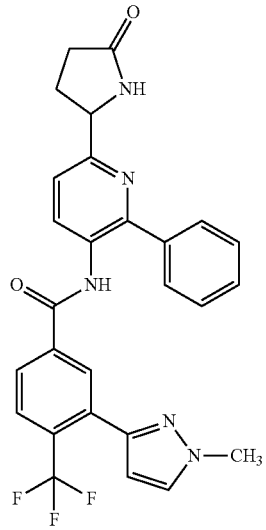 [SMILES: Cn1ccc(-c2cc(C(=O)Nc3ccc(C4CCC(=O)N4)nc3-c3ccccc3)ccc2C(F)(F)F)n1]

(R or S)-3-(1-Methyl-1H-pyrazol-3-yl)-N-(6-(5-oxopyrrolidin-2-yl)-2-phenylpyridin-3-yl)-4-(trifluoromethyl)benzamide To a solution of 3-(1-methyl-1H-pyrazol-3-yl)-4-(trifluoromethyl)benzoic acid (25 mg, 0.093 mmol) in pyridine (1 mL) at 30° C. was added POCl₃ (0.030 mL, 0.28 mmol). The resulting mixture was stirred for 15 min before a solution of 5-(5-amino-6-phenylpyridin-2-yl)pyrrolidin-2-one (35 mg, 0.14 mmol) in pyridine (2 mL) was added dropwise. The resulting mixture was stirred for 30 min then diluted with water (5 mL) and extracted with EtOAc (5 mL×3). The combined organic layers were dried over Na₂SO₄ and concentrated. The residue was dissolved in a mixture of THF (2 mL) and saturated aqueous K₂CO₃ solution (2 mL), and the resulting mixture was stirred at 30° C. for 1 h. The product mixture was extracted with EtOAc (5 mL×3) and the combined organic layers were dried over Na₂SO₄ and concentrated. The residue was purified by preparative TLC (100% EtOAc), followed by SFC ((250 mm×30 mm, Sum AD column) eluting with 40% MeOH (0.1% NH$_4$OH), 60% CO$_2$ at 50 mL/min)), then reverse-phase HPLC under basic conditions (H$_2$O/CH$_3$CN gradient with 0.05% NH$_4$OH present) to give the title compound (the second eluted isomer by SFC). MS: m/z=506.1 (M+1). $^1$H NMR (400 MHz, CD$_3$OD) δ 8.07 (d, J=8.0 Hz, 1H), 8.02 (s, 1H), 7.91-7.89 (m, 2H), 7.66-7.65 (m, 3H), 7.48-7.42 (m, 4H), 6.45 (s, 1H), 4.95-4.92 (m, 1H), 3.96 (s, 3H), 2.67-2.50 (m, 1H), 2.49-2.42 (m, 2H), 2.19-2.17 (m, 1H).

Example 190

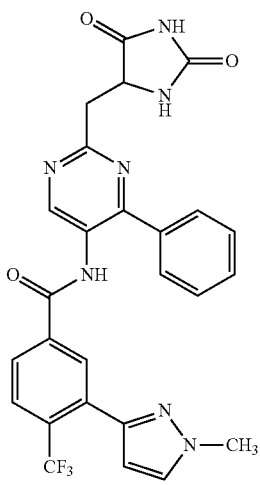 [SMILES: Cn1ccc(-c2cc(C(=O)Nc3cnc(CC4NC(=O)NC4=O)nc3-c3ccccc3)ccc2C(F)(F)F)n1]

(R or S)—N-(2-(2,5-Dioxoimidazolidin-4-yl)methyl)-4-phenylpyrimidin-5-yl)-3-(1-methyl-1H-pyrazol-3-yl)-4-(trifluoromethyl)benzamide To a solution of 3-(1-methyl-1H-pyrazol-3-yl)-4-(trifluoromethyl)benzoic acid (57 mg, 0.21 mmol) in pyridine (3 mL) at 26° C. was added POCl$_3$ (39 mg, 0.25 mmol). The resulting mixture was stirred for 10 min before 5-((5-amino-4-phenylpyrimidin-2-yl)methyl)imidazolidine-2,4-dione (60 mg, 0.21 mmol) was added. After stirring for 20 min, the product mixture was diluted with water (5 mL) and extracted with ethyl acetate (3×5 mL). The combined organic layers were dried over sodium sulfate and concentrated, and the residue was purified by reverse-phase HPLC under basic conditions (H$_2$O/CH$_3$CN gradient with 0.05% NH$_4$OH present), followed by SFC ((2.5 cm×3 cm, 10 um AD column) eluting with 50% EtOH (0.1% NH$_3$.H$_2$O), 50% CO$_2$ at 80 mL/min) to give the title compound (the second eluted isomer in SFC). MS: m/z=536.1 (M+1). $^1$H NMR (400 MHz, CD$_3$OD) δ 8.90 (s, 1H), 8.08 (s, 1H), 8.01-7.95 (m, 1H), 7.92-7.87 (m, 1H), 7.77 (d, J=3.9 Hz, 2H), 7.65 (d, J=1.6 Hz, 1H), 7.46 (d, J=3.1 Hz, 3H), 6.46 (s, 1H), 4.76-4.66 (m, 1H), 3.95 (s, 3H), 3.60-3.52 (m, 1H), 3.46-3.36 (m, 1H).

Example 191

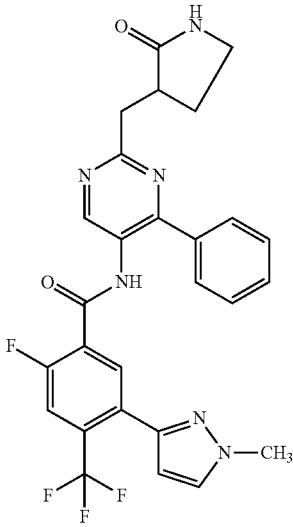 [SMILES: Cn1ccc(-c2cc(C(=O)Nc3cnc(CC4CCNC4=O)nc3-c3ccccc3)c(F)cc2C(F)(F)F)n1]

(R or S)-2-Fluoro-5-(1-methyl-1H-pyrazol-3-yl)-N-(2-(2-oxopyrrolidin-3-yl)methyl)-4-phenylpyrimidin-5-yl)-4-(trifluoromethyl)benzamide To a solution of 2-fluoro-5-(1-methyl-1H-pyrazol-3-yl)-4-(trifluoromethyl)benzoic acid (25 mg, 0.087 mmol) in pyridine (2 mL) at 26° C. was added POCl$_3$ (20 mg, 0.13 mmol) and 3-((5-amino-4-phenylpyrimidin-2-yl)methyl)pyrrolidin-2-one (23 mg, 0.086 mmol). The resulting mixture was stirred 0.5 h then diluted with water (3 mL) and extracted with CH$_2$Cl$_2$ (5 mL×3). The combined organic layers were concentrated, and the residue was purified by reverse-phase HPLC under acidic conditions (H$_2$O/CH$_3$CN gradient with 0.1% TFA present), followed by SFC ((250×30 mm OJ column) eluting with 35% MeOH (0.1% NH$_3$H$_2$O), 65% CO$_2$ at 60 mL/min) to give the title compound (the first eluted isomer by SFC). MS: m/z=539.1 (M+1). $^1$H NMR (400 MHz, CD$_3$OD) δ 8.97 (s, 1H), 7.90 (d, J=7.0 Hz, 1H), 7.80-7.73 (m, 2H), 7.67-7.59 (m, 2H), 7.45 (d, J=3.1 Hz, 3H), 6.39 (s, 1H), 3.90 (s, 3H), 3.44 (dd, J$_1$=14.5 Hz, J$_2$=3.5 Hz, 1H), 3.29 (dd, J$_1$=8.2 Hz, J$_2$=5.5 Hz, 2H), 3.12-2.96 (m, 2H), 2.34-2.24 (m, 1H), 1.97-1.88 (m, 1H).

Example 192

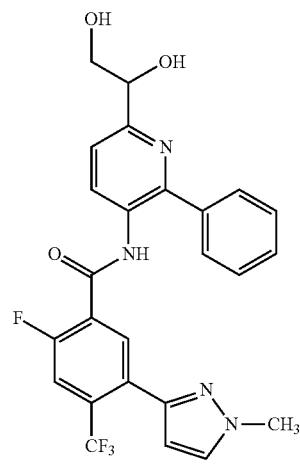 [SMILES: Cn1ccc(-c2cc(C(=O)Nc3ccc(C(O)CO)nc3-c3ccccc3)c(F)cc2C(F)(F)F)n1]

(R or S)—N-(6-(1,2-Dihydroxyethyl)-2-phenylpyridin-3-yl)-2-fluoro-5-(1-methyl-1H-pyrazol-3-yl)-4-(trifluoromethyl)benzamide Step A: N-(6-Chloro-2-phenylpyridin-3-yl)-2-fluoro-5-(1-methyl-1H-pyrazol-3-yl)-4-(trifluoromethyl)benzamide To a solution of 6-chloro-2-phenylpyridin-3-amine (197 mg, 0.96 mmol) and 2-fluoro-5-(1-methyl-1H-pyrazol-3-yl)-4-(trifluoromethyl)benzoic acid (277 mg, 0.96 mmol) in pyridine (5 mL) at 25° C. was added $POCl_3$ (211 mg, 1.44 mmol). The resulting mixture was stirred for 2 h then carefully diluted with saturated aqueous $NaHCO_3$ solution (20 mL) and extracted with EtOAc (20 mL). The organic layer was dried over $Na_2SO_4$ and concentrated. The residue was purified by silica gel column chromatography (PE/EtOAc=3/1) to give the title compound. MS: m/z=475.2 (M+1).

Step B: 2-Fluoro-5-(1-methyl-1H-pyrazol-3-yl)-N-(2-phenyl-6-vinylpyridin-3-yl)-4-(trifluoromethyl)benzamide To a deoxygenated mixture of N-(6-chloro-2-phenylpyridin-3-yl)-2-fluoro-5-(1-methyl-1H-pyrazol-3-yl)-4-(trifluoromethyl)benzamide (70 mg, 0.15 mmol), $K_2CO_3$ (41 mg, 0.30 mmol) and potassium trifluoro(vinyl)borate (40 mg, 0.30 mmol) in DME (7 mL) was added $Pd(dppf)_2Cl_2$ (30 mg). The resulting mixture was heated at 100° C. for 2 h then cooled and concentrated. The residue was purified by preparative TLC (PE/EtOAc=4/1) to give the title compound. MS: m/z=467.2 (M+1). $^1H$ NMR (400 MHz, DMSO) δ 8.19-8.09 (m, 1H), 8.05-7.87 (m, 3H), 7.84-7.75 (m, 1H), 7.69 (d, J=7.5 Hz, 1H), 7.59 (d, J=8.5 Hz, 1H), 7.47-7.32 (m, 3H), 6.89 (dd, J=10.8, 17.3 Hz, 1H), 6.46 (s, 1H), 6.27 (d, J=17.6 Hz, 1H), 5.52 (d, J=11.5 Hz, 1H), 3.92 (s, 3H).

Step C: (R or S)—N-(6-(1,2-Dihydroxyethyl)-2-phenylpyridin-3-yl)-2-fluoro-5-(1-methyl-1H-pyrazol-3-yl)-4-(trifluoromethyl)benzamide To a solution of 2-fluoro-5-(1-methyl-1H-pyrazol-3-yl)-N-(2-phenyl-6-vinylpyridin-3-yl)-4-(trifluoromethyl)benzamide (47 mg, 0.10 mmol) and NMO (117 mg, 1.00 mmol) in a mixture of THF (5 mL) and $H_2O$ (1 mL) at 25° C. was added $OsO_4$ (100 mg, 0.39 mmol). The resulting mixture was stirred for 2 h then partitioned between saturated aqueous $Na_2SO_3$ solution (20 mL) and EtOAc (20 mL). The organic layer was concentrated and the residue was purified by preparative TLC (PE/EtOAc=1/4), followed by SFC ((250×30 mm IC column) eluting with 35% EtOH (0.05% DEA), 65% $CO_2$ at 70 mL/min) to give the title compound (the first eluted isomer by SFC). MS: m/z=501.2 (M+1). $^1H$ NMR (400 MHz, $CD_3OD$) δ 8.14 (d, J=8.6 Hz, 1H), 7.80 (d, J=7.0 Hz, 1H), 7.71-7.56 (m, 5H), 7.44-7.29 (m, 3H), 6.34 (s, 1H), 4.74-4.71 (m, 1H), 3.87 (s, 3H), 3.81 (dd, $J_1$=11.2 Hz, $J_2$=4.1 Hz, 1H), 3.66 (dd, $J_1$=11.3 Hz, $J_2$=6.7 Hz, 1H).

Example 193

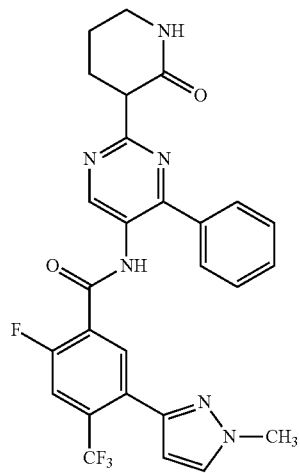 [SMILES: Cn1ccc(-c2cc(C(=O)Nc3cnc(C4CCCNC4=O)nc3-c3ccccc3)c(F)cc2C(F)(F)F)n1]

2-Fluoro-5-(1-methyl-1H-pyrazol-3-yl)-N-(2-(2-oxopiperidin-3-yl)-4-phenylpyrimidin-5-yl)-4-(trifluoromethyl)benzamide To a solution of 2-fluoro-5-(1-methyl-1H-pyrazol-3-yl)-4-(trifluoromethyl)benzoic acid (65 mg, 0.22 mmol) and 3-(5-amino-4-phenylpyrimidin-2-yl)piperidin-2-one (60 mg, 0.22 mmol) in pyridine (2 mL) at 25° C. was added $POCl_3$ (0.031 mL, 0.34 mmol). The resulting mixture was stirred for 0.5 h then carefully diluted with saturated aqueous $NaHCO_3$ solution (10 mL) and EtOAc (10 mL×3). The combined organic layers were dried over sodium sulfate and concentrated. The residue was dissolved in a mixture of THF (5 mL) and water (5 mL) and lithium hydroxide monohydrate (28 mg, 0.67 mmol) was added. The resulting mixture was stirred at 25° C. for 10 min then extracted with EtOAc (10 mL×3). The combined organic layers were dried over sodium sulfate and concentrated, and the residue was purified by reverse-phase HPLC under basic conditions ($H_2O$/$CH_3CN$ gradient with 0.05% $NH_4OH$ present) to give the title compound. MS: m/z=539.1 (M+1). $^1HNMR$ (400 MHz, $CD_3OD$) δ 9.00 (s, 1H), 7.88 (d, J=6.7 Hz, 1H), 7.72 (d, J=3.5 Hz, 2H), 7.64-7.55 (m, 2H), 7.43 (d, J=3.1 Hz, 3H), 6.36 (s, 1H), 3.94 (t, J=7.8 Hz, 1H), 3.88 (s, 3H), 3.43-3.28 (m, 2H), 2.28-2.08 (m, 2H), 1.94 (d, J=4.7 Hz, 1H), 1.79 (td, J=4.6, 9.1 Hz, 1H).

Example 194

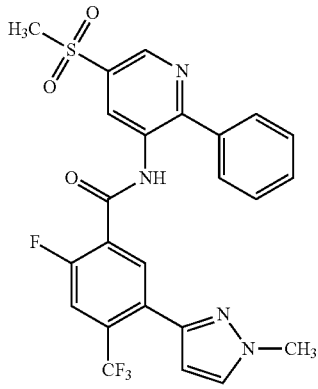 [SMILES: Cn1ccc(-c2cc(C(=O)Nc3cc(S(C)(=O)=O)cnc3-c3ccccc3)c(F)cc2C(F)(F)F)n1]

2-Fluoro-5-(1-methyl-1H-pyrazol-3-yl)-N-(5-(methylsulfonyl)-2-phenylpyridin-3-yl)-4-(trifluoromethyl)benzamide To a solution of 2-fluoro-5-(1-methyl-1H-pyrazol-3-yl)-4-(trifluoromethyl)benzoic acid (58 mg, 0.20 mmol) and 5-(methylsulfonyl)-2-phenylpyridin-3-amine (50 mg, 0.20 mmol) in pyridine (3 mL) at 23° C. was added phosphorus oxychloride (0.038 mL, 0.40 mmol). The resulting mixture was stirred for 10 min then diluted with water (10 mL) and extracted with ethyl acetate (10 mL×3). The combined organic layers were dried over anhydrous sodium sulfate and concentrated. The residue was purified by reverse-phase HPLC under basic conditions (H$_2$O/CH$_3$CN gradient with 0.05% NH$_4$OH present) to give the title compound. MS: m/z=519.2 (M+1). $^1$H NMR (400 MHz, CDCl$_3$) δ 9.51 (d, J=1.8 Hz, 1H), 9.03 (d, J=2.0 Hz, 1H), 8.91 (d, J=14.6 Hz, 1H), 8.48 (d, J=7.8 Hz, 1H), 7.68-7.59 (m, 5H), 7.50 (d, J=12.0 Hz, 1H), 7.44 (d, J=2.3 Hz, 1H), 6.48 (s, 1H), 4.00 (s, 3H), 3.24 (s, 3H).

The following example was prepared in similar fashion to the procedures described above.

(R or S)-2-Fluoro-5-(1-methyl-1H-pyrazol-3-yl)-N-(6-(2-oxooxazolidin-4-yl)-2-phenylpyridin-3-yl)-4-(trifluoromethyl)benzamide To a stirred solution of 2-fluoro-5-(1-methyl-1H-pyrazol-3-yl)-4-(trifluoromethyl)benzoic acid (43 mg, 0.15 mmol) and 4-(5-amino-6-phenylpyridin-2-yl)oxazolidin-2-one (38 mg, 0.15 mmol) in pyridine (2 mL) at 25° C. was added dropwise POCl$_3$ (0.021 mL, 0.22 mmol). The resulting mixture was stirred for 15 min then diluted with aqueous 2M LiOH solution (10 mL) and extracted with EtOAc (10 mL×3). The combined organic layers were dried over Na$_2$SO$_4$ and concentrated, and the residue was purified by preparative TLC (PE/EtOAc=2/1), followed by SFC ((250× 30 mm AS column) eluting with 35% MeOH (0.05% DEA), 65% CO$_2$ at 80 mL/min to 100% MeOH) to give the title compound (the first eluted isomer by SFC). MS: m/z=526.1 (M+1). $^1$H NMR (400 MHz, CD$_3$OD) δ 8.22 (d, J=8.2 Hz, 1H), 7.82 (d, J=6.7 Hz, 1H), 7.60-7.55 (m, 4H), 7.44 (d, J=8.2 Hz, 1H), 7.41-7.34 (m, 3H), 6.34 (s, 1H), 5.03 (dd, J$_1$=9.0 Hz, J$_2$=5.5 Hz, 1H), 4.73-4.71 (m, 1H), 4.38 (dd, J$_1$=8.4 Hz, J$_2$=5.7 Hz, 1H), 3.87 (s, 3H).

| Compound Number | Structure | Compound Name | LCMS (M + 1) |
|---|---|---|---|
| 195 | 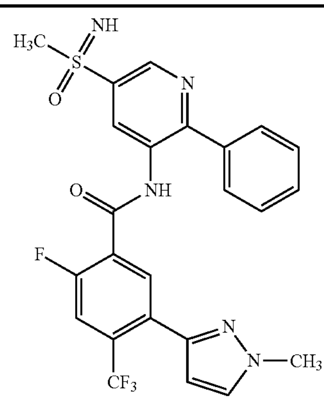 | 2-fluoro-5-(1-methyl-1H-pyrazol-3-yl)-N-(5-(S-methylsulfonimidoyl)-2-phenylpyridin-3-yl)-4-(trifluoromethyl)benzamide | 518.1 |

Example 196

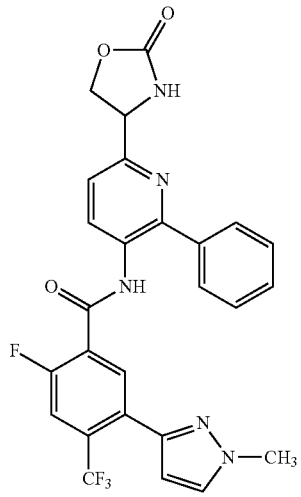 [SMILES: Cn1ccc(-c2cc(C(=O)Nc3ccc(C4COC(=O)N4)nc3-c3ccccc3)c(F)cc2C(F)(F)F)n1]

Example 197

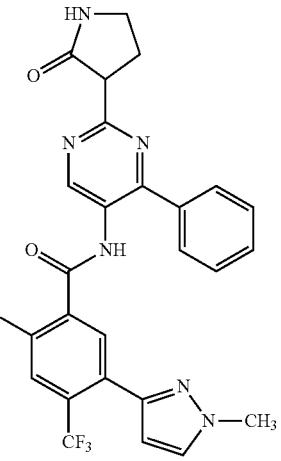

(R or S)-2-Fluoro-5-(1-methyl-1H-pyrazol-3-yl)-N-
(2-(2-oxopyrrolidin-3-yl)-4-phenylpyrimidin-5-yl)-
4-(trifluoromethyl)benzamide Step A: Methyl 3-cyano-2-(5-(2-fluoro-5-(1-methyl-
1H-pyrazol-3-yl)-4-(trifluoromethyl) benzamido)-4-
phenylpyrimidin-2-yl)propanoate To a solution of 2-fluoro-5-(1-methyl-1H-pyrazol-3-yl)-4-(trifluoromethyl)benzoic acid (67 mg, 0.23 mmol) and methyl 2-(5-amino-4-phenylpyrimidin-2-yl)-3-cyanopropanoate (70 mg, 0.23 mmol) in pyridine (3 mL) at 25° C. was added POCl$_3$ (0.043 mL, 0.47 mmol). The resulting mixture was stirred for 10 min then diluted with water (20 mL) and extracted with EtOAc (10 mL×3). The combined organic layers were dried over Na$_2$SO$_4$ and concentrated. The residue was purified by preparative TLC (PE/EtOAc=1/1) to give the title compound. MS: m/z=574.9 (M+1). $^1$H NMR (400 MHz, CDCl$_3$) δ 9.86 (s, 1H), 8.71 (d, J=14.1 Hz, 1H), 8.46 (d, J=7.4 Hz, 1H), 7.68 (d, J=3.5 Hz, 2H), 7.58 (d, J=3.5 Hz, 3H), 7.48 (d, J=12.1 Hz, 1H), 7.39 (d, J=2.0 Hz, 1H), 6.44 (s, 1H), 4.42 (t, J=7.4 Hz, 1H), 3.96 (s, 3H), 3.77 (s, 3H), 3.29-3.14 (m, 2H).

Step B: Methyl 4-amino-2-(5-(2-fluoro-5-(1-methyl-
1H-pyrazol-3-yl)-4-(trifluoromethyl) benzamido)-4-
phenylpyrimidin-2-yl)butanoate To a deoxygenated solution of methyl 3-cyano-2-(5-(2-fluoro-5-(1-methyl-1H-pyrazol-3-yl)-4-(trifluoromethyl)benzamido)-4-phenylpyrimidin-2-yl)propanoate (67 mg, 0.10 mmol) in EtOAc (2 mL) at 25° C. was added Et$_3$N (0.044 mL, 0.31 mmol) and Raney-Ni (6 mg, 0.1 mmol). The resulting mixture was stirred under H$_2$ (50 psi) at 25° C. for 2 h, then filtered and concentrated to give the title compound. MS: m/z=557.2 (M+1).

Step C: (R or S)-2-Fluoro-5-(1-methyl-1H-pyrazol-
3-yl)-N-(2-(2-oxopyrrolidin-3-yl)-4-phenyl pyrimi-
din-5-yl)-4-(trifluoromethyl)benzamide To a solution of methyl 4-amino-2-(5-(2-fluoro-5-(1-methyl-1H-pyrazol-3-yl)-4-(trifluoromethyl)benzamido)-4-phenylpyrimidin-2-yl)butanoate (53 mg, 0.095 mmol) in CH$_3$CN (2 mL) at 28° C. was added K$_2$CO$_3$ (40 mg, 0.29 mmol). The resulting mixture was heated at 80° C. for 18 h then cooled, filtered and purified by reverse-phase HPLC under basic conditions (H$_2$O/CH$_3$CN gradient with 0.05% NH$_4$OH present) followed by SFC ((250×30 mm AS column) eluting with 35% MeOH (0.05% DEA), 65% CO$_2$ at 80 mL/min to 100% MeOH) to give the title compound (the second eluted isomer by SFC). MS: m/z=525.1 (M+1). $^1$HNMR (400 MHz, CDCl$_3$) δ 9.81 (s, 1H), 8.63 (d, J=13.7 Hz, 1H), 8.46 (d, J=4.3 Hz, 1H), 7.68 (d, J=3.5 Hz, 2H), 7.56 (s, 3H), 7.48 (d, J=11.7 Hz, 1H), 7.40 (s, 1H), 6.45 (s, 1H), 5.79 (s, 1H), 4.15-4.05 (m, 1H), 3.97 (s, 3H), 3.64 (s, 1H), 3.50 (d, J=0.8 Hz, 1H), 2.79-2.60 (m, 2H).

Example 198

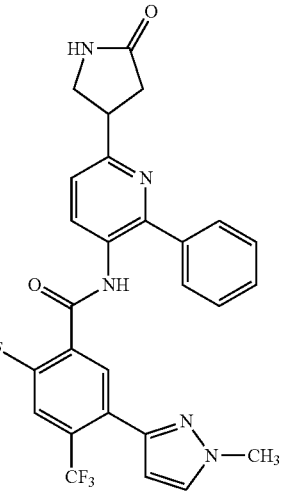

(R or S)-2-Fluoro-5-(1-methyl-1H-pyrazol-3-yl)-N-
(6-(5-oxopyrrolidin-3-yl)-2-phenylpyridin-3-yl)-4-
(trifluoromethyl)benzamide Step A: Ethyl 3-cyano-3-(5-(2-fluoro-5-(1-methyl-
1H-pyrazol-3-yl)-4-(trifluoromethyl)benzamido)-6-
phenylpyridin-2-yl)propanoate To a solution of 2-fluoro-5-(1-methyl-1H-pyrazol-3-yl)-4-(trifluoromethyl)benzoic acid (110 mg, 0.381 mmol) in pyridine (5 mL) at 22° C. was added POCl$_3$ (0.10 mL, 1.1 mmol). After stirring for 5 min, ethyl 3-(5-amino-6-phenylpyridin-2-yl)-3-cyanopropanoate (125 mg, 0.381 mmol) was added. The resulting mixture was stirred for 20 min then diluted with water (10 mL) and extracted with ethyl acetate (10 mL×3). The combined organic layers were dried over sodium sulfate and concentrated, and the residue was purified by preparative TLC (PE/EtOAc=1/1) to give the title compound. MS: m/z=566.2 (M+1).

Step B: Ethyl 4-amino-3-(5-(2-fluoro-5-(1-methyl-
1H-pyrazol-3-yl)-4-(trifluoromethyl)benzamido)-6-
phenylpyridin-2-yl)butanoate A mixture of ethyl 3-cyano-3-(5-(2-fluoro-5-(1-methyl-1H-pyrazol-3-yl)-4-(trifluoromethyl)benzamido)-6-phenylpyridin-2-yl)propanoate (30 mg, 0.048 mmol) and Raney-Ni (0.4 mg, 0.005 mmol) in EtOH (10 mL) was stirred under hydrogen (50 psi) at 26° for 2 h. The mixture was filtered and the filtrate was concentrated to give the title compound. MS: m/z=570.3 (M+1).

Step C: (R or S)-2-Fluoro-5-(1-methyl-1H-pyrazol-
3-yl)-N-(6-(5-oxopyrrolidin-3-yl)-2-phenylpyridin-
3-yl)-4-(trifluoromethyl)benzamide To a solution of ethyl 4-amino-3-(5-(2-fluoro-5-(1-methyl-1H-pyrazol-3-yl)-4-(trifluoromethyl)benzamido)-6-phenylpyridin-2-yl)butanoate (10 mg, 0.012 mmol) in EtOH (1 mL) at 22° C. was added potassium carbonate (5 mg, 0.04 mmol). The resulting mixture was stirred for 12 h then partitioned between water (5 mL) and ethyl acetate (5 mL×3). The combined organic layers were dried over sodium sulfate and concentrated. The residue was purified by preparative TLC (CH$_2$Cl$_2$/MeOH=10/1), followed by SFC ((2.5 cm×3 cm, 5 um AD column) eluting with 50% EtOH (0.1% NH$_4$OH), 50% CO$_2$ at 50 mL/min) to give the title compound (the first eluted isomer by SFC). MS: m/z=524.2 (M+1). $^1$H NMR (400 MHz, CD$_3$OD) δ 8.09 (d, J=8.2 Hz, 1H), 7.81 (d, J=6.7 Hz, 1H), 7.58 (d, J=6.3 Hz, 4H), 7.43-7.28 (m, 4H), 6.34 (s, 1H), 3.93-3.82 (m, 4H), 3.73 (t, J=9.0 Hz, 1H), 3.53 (dd, J=7.0, 9.8 Hz, 1H), 2.75-2.60 (m, 2H).

Example 199

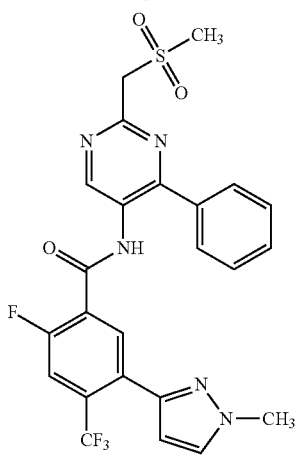 [SMILES: Cn1ccc(-c2cc(C(=O)Nc3cnc(CS(C)(=O)=O)nc3-c3ccccc3)c(F)cc2C(F)(F)F)n1]

2-Fluoro-5-(1-methyl-1H-pyrazol-3-yl)-N-(2-((methylsulfonyl)methyl)-4-phenylpyrimidin-5-yl)-4-(trifluoromethyl)benzamide To a mixture of 2-fluoro-5-(1-methyl-1H-pyrazol-3-yl)-4-(trifluoromethyl)benzoic acid (80 mg, 0.278 mmol) in pyridine (3 mL) at 25° C. was added $POCl_3$ (0.039 mL, 0.41 mmol) followed by 2-((methylsulfonyl)methyl)-4-phenylpyrimidin-5-amine (88 mg, 0.33 mmol). The resulting mixture was stirred for 50 min then diluted with water (5 mL) and extracted with DCM (5 mL×2). The combined organic layers were dried over $Na_2SO_4$ and concentrated, and the residue was purified by reverse-phase HPLC under basic conditions ($H_2O/CH_3CN$ gradient with 0.05% $NH_4OH$ present) to give the title compound. MS: m/z=534.1 (M+1). $^1H$ NMR (400 MHz, $CD_3OD$) δ 9.23 (s, 1H), 7.99 (d, J=7.0 Hz, 1H), 7.81 (d, J=3.5 Hz, 2H), 7.68-7.64 (m, 2H), 7.51 (d, J=3.1 Hz, 3H), 6.44 (s, 1H), 4.82-4.72 (m, 2H), 3.94 (s, 3H), 3.20 (s, 3H).

The following example was prepared in similar fashion to the procedures described above.

Example 201

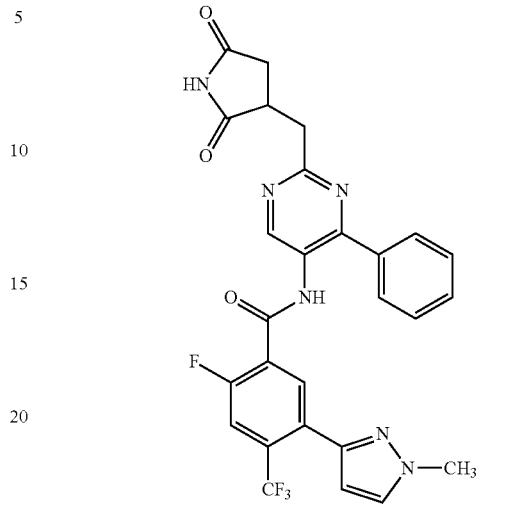

N-(2-((2,5-Dioxopyrrolidin-3-yl)methyl)-4-phenylpyrimidin-5-yl)-2-fluoro-5-(1-methyl-1H-pyrazol-3-yl)-4-(trifluoromethyl)benzamide To a solution of 2-fluoro-5-(1-methyl-1H-pyrazol-3-yl)-4-(trifluoromethyl)benzoic acid (10 mg, 0.035 mmol) in pyridine (0.2 mL) at 18° C. was added phosphoryl trichloride (8 mg, 0.05 mmol). After stirring for 5 min, 3-((5-amino-4-phenylpyrimidin-2-yl)methyl)pyrrolidine-2,5-dione (10 mg, 0.035 mmol) was added. The resulting mixture was stirred for 20 min then concentrated. The residue was purified by reverse-phase HPLC ($H_2O/CH_3CN$ gradient with 0.1% TFA present) to give the title compound. MS: m/z=553.2 (M+1). $^1H$ NMR (400 MHz, $CD_3OD$) δ 9.01 (s, 1H), 7.95-7.93 (m, 1H), 7.80-7.65 (m, 4H), 7.58-7.45 (m, 3H), 6.43 (s, 1H), 3.94 (s, 3H), 3.48 (s, 3H), 2.93-2.89 (m, 1H), 2.69-2.49 (m, 1H).

| Compound Number | Structure | Compound Name | LCMS (M + 1) |
|---|---|---|---|
| 200 | 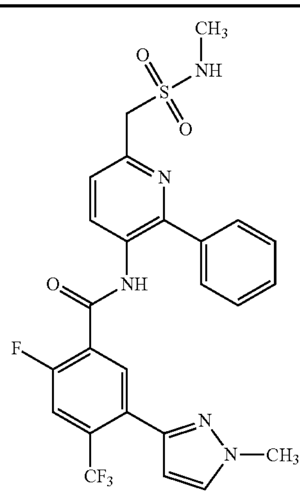 | 2-fluoro-5-(1-methyl-1H-pyrazol-3-yl)-N-(6-((N-methylsulfamoyl)methyl)-2-phenylpyridin-3-yl)-4-(trifluoromethyl)benzamide | 548.1 |

Example 202

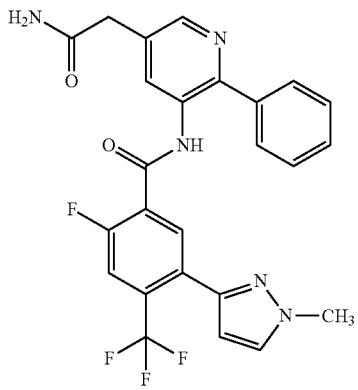 [SMILES: Cn1ccc(-c2cc(C(=O)Nc3cc(CC(N)=O)cnc3-c3ccccc3)c(F)cc2C(F)(F)F)n1]

N-(5-(2-Amino-2-oxoethyl)-2-phenylpyridin-3-yl)-2-fluoro-5-(1-methyl-1H-pyrazol-3-yl)-4-(trifluoromethyl)benzamide Step A: Ethyl 2-(5-(2-fluoro-5-(1-methyl-1H-pyrazol-3-yl)-4-(trifluoromethyl)benzamido)-6-phenylpyridin-3-yl)acetate To a solution of ethyl 2-(5-amino-6-phenylpyridin-3-yl)acetate (103 mg, 0.321 mmol) (80%) and 2-fluoro-5-(1-methyl-1H-pyrazol-3-yl)-4-(trifluoromethyl)benzoic acid (93 mg, 0.32 mmol) in pyridine (3 mL) at 25° C. was added phosphorus oxychloride (0.060 mL, 0.64 mmol). The resulting mixture was stirred for 10 min then partitioned between water (20 mL) and ethyl acetate (10 mL×3). The combined organic layers were dried over sodium sulfate and concentrated. The residue was purified by preparative TLC (PE/EtOAc=1/2) to give the title compound. MS: m/z=527.1 (M+1). $^1$H NMR (400 MHz, CDCl$_3$) δ 8.87 (s, 1H), 8.65 (d, J=13.7 Hz, 1H), 8.40 (s, 2H), 7.61-7.36 (m, 7H), 6.43 (s, 1H), 4.20 (q, J=7.0 Hz, 2H), 3.95 (s, 3H), 3.72 (s, 2H), 1.29 (t, J=7.0 Hz, 3H).

Step B: 2-(5-(2-Fluoro-5-(1-methyl-1H-pyrazol-3-yl)-4-(trifluoromethyl)benzamido)-6-phenyl pyridin-3-yl)acetic acid To a solution of ethyl 2-(5-(2-fluoro-5-(1-methyl-1H-pyrazol-3-yl)-4-(trifluoromethyl) benzamido)-6-phenylpyrid in-3-yl)acetate (60 mg, 0.11 mmol) in ethanol (3 mL) and water (1 mL) at 25° C. was added lithium hydroxide (8 mg, 0.3 mmol). The resulting mixture was stirred for 50 min then partitioned between water (20 mL) and ethyl acetate (10 mL×3). The combined organic layers were dried over sodium sulfate, filtered and concentrated to give the title compound. MS: m/z=499.1 (M+1).

Step C: N-(5-(2-Amino-2-oxoethyl)-2-phenylpyridin-3-yl)-2-fluoro-5-(1-methyl-1H-pyrazol-3-yl)-4-(trifluoromethyl)benzamide To a solution of 2-(5-(2-fluoro-5-(1-methyl-1H-pyrazol-3-yl)-4-(trifluoromethyl) benzamido)-6-phenylpyridin-3-yl)acetic acid (10 mg, 0.020 mmol) in DMF (3 mL) at 25° C. was added triethylamine (8 µL, 0.06 mmol), and HATU (11 mg, 0.030 mmol). The mixture was stirred at 10 min before ammonium chloride (2 mg, 0.04 mmol) was added. The resulting mixture was stirred for 1 h then filtered and purified by reverse-phase HPLC under basic conditions (H$_2$O/CH$_3$CN gradient with 0.05% NH$_4$OH present) to give the title compound. MS: m/z=498.1 (M+1). $^1$H NMR (400 MHz, CDCl$_3$) δ 8.86 (s, 1H), 8.46-8.36 (m, 2H), 7.60-7.49 (m, 5H), 7.44 (d, J=11.9 Hz, 1H), 7.39 (s, 1H), 6.43 (s, 1H), 3.95 (s, 3H), 3.68 (s, 2H).

The following examples were prepared in similar fashion to the procedures described above.

| Compound Number | Structure | Compound Name | LCMS (M + 1) |
|---|---|---|---|
| 203 | 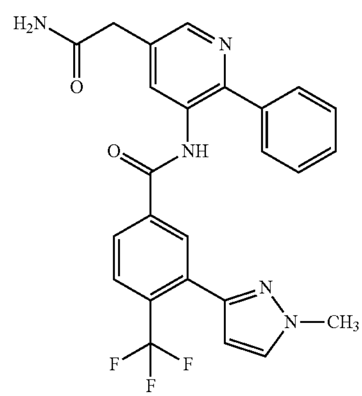 [SMILES: Cn1ccc(-c2cc(C(=O)Nc3cc(CC(N)=O)cnc3-c3ccccc3)ccc2C(F)(F)F)n1] | N-(5-(2-amino-2-oxoethyl)-2-phenylpyridin-3-yl)-3-(1-methyl-1H-pyrazol-3-yl)-4-(trifluoromethyl)benzamide | 480.1 |

| Compound Number | Structure | Compound Name | LCMS (M + 1) |
|---|---|---|---|
| 204 | 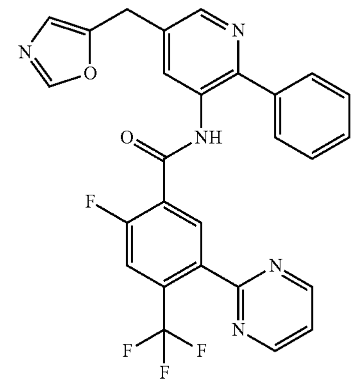 [SMILES: O=C(Nc1cc(Cc2cnco2)cnc1-c1ccccc1)c1cc(-c2ncccn2)c(C(F)(F)F)cc1F] | 2-fluoro-N-(5-(oxazol-5-ylmethyl)-2-phenylpyridin-3-yl)-5-(pyrimidin-2-yl)-4-(trifluoromethyl)benzamide | 520.0 |

Example 205

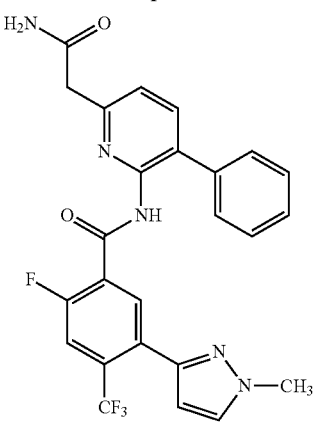

N-(6-(2-Amino-2-oxoethyl)-3-phenylpyridin-2-yl)-2-fluoro-5-(1-methyl-1H-pyrazol-3-yl)-4-(trifluoromethyl)benzamide Step A: Ethyl 2-(6-(2-fluoro-5-(1-methyl-1H-pyrazol-3-yl)-4-(trifluoromethyl)benzamido)-5-phenylpyridin-2-yl)acetate To a solution of ethyl 2-(6-amino-5-phenylpyridin-2-yl)acetate (400 mg, 1.56 mmol) and 2-fluoro-5-(1-methyl-1H-pyrazol-3-yl)-4-(trifluoromethyl)benzoic acid (495 mg, 1.72 mmol) in pyridine (5 mL) at 20° C. was added POCl₃ (0.15 mL, 1.6 mmol). The resulting mixture was stirred for 30 min then carefully diluted with saturated aqueous NaHCO₃ solution (30 mL) and extracted with ethyl acetate (20 mL×3). The combined organic layers were washed with saturated aqueous NaHCO₃ solution and brine, dried over Na₂SO₄ and concentrated. The residue was purified by flash silica gel chromatography (ISCO; 12 g SepaFlash® Silica Flash Column, EtOAc in petroleum ether: 0-50%, 30 mL/min, dry loaded) to give the title compound. MS: m/z=527.2 (M+1). ¹H NMR (400 MHz, CDCl₃) δ 8.42 (br., 1H), 8.16 (br., 1H), 7.75 (d, J=6.0 Hz, 1H), 7.69 (d, J=7.0 Hz, 1H), 7.52-7.42 (m, 4H), 7.41-7.36 (m, 2H), 6.43 (d, J=18.6 Hz, 2H), 3.98-3.91 (m, 4H), 1.25 (q, J=7.0 Hz, 3H).

Step B: N-(6-(2-Amino-2-oxoethyl)-3-phenylpyridin-2-yl)-2-fluoro-5-(1-methyl-1H-pyrazol-3-yl)-4-(trifluoromethyl)benzamide To a solution of ethyl 2-(6-(2-fluoro-5-(1-methyl-1H-pyrazol-3-yl)-4-(trifluoromethyl)benzamido)-5-phenylpyridin-2-yl)acetate (200 mg, 0.380 mmol) in MeOH (2 mL) at 20° C. was added aqueous ammonium hydroxide solution (35%, 1 mL, 7 mmol). The resulting mixture was stirred for 16 h then partitioned between saturated aqueous NaHCO₃ solution (30 mL) and ethyl acetate (20 mL×3). The combined organic layers were washed with brine, dried over Na₂SO₄ and concentrated. The residue was purified by reverse-phase HPLC under basic conditions (H₂O/CH₃CN gradient with 0.05% NH₄OH present) to give the title compound. MS: m/z=498.1 (M+1). ¹H NMR (400 MHz, CD₃OD) δ 7.84 (d, J=8.0 Hz, 1H), 7.79 (d, J=7.0 Hz, 1H), 7.67-7.61 (m, 2H), 7.52-7.47 (m, 2H), 7.46-7.40 (m, 3H), 7.38-7.33 (m, 1H), 6.42 (s, 1H), 3.96 (s, 3H), 3.78 (s, 2H).

Example 206

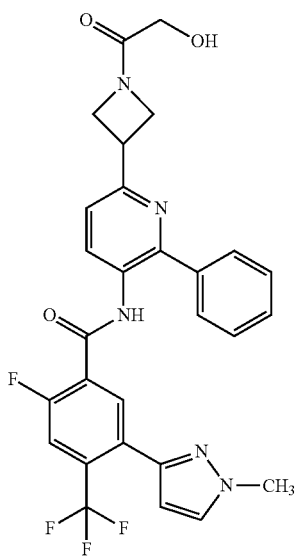

2-Fluoro-N-(6-(1-(2-hydroxyacetyl)azetidin-3-yl)-2-phenylpyridin-3-yl)-5-(1-methyl-1H-pyrazol-3-yl)-4-(trifluoromethyl)benzamide

Step A: tert-Butyl 3-(5-(2-fluoro-5-(1-methyl-1H-pyrazol-3-yl)-4-(trifluoromethyl)benzamido)-6-phenylpyridin-2-yl)azetidine-1-carboxylate To a solution of tert-butyl 3-(5-amino-6-phenylpyridin-2-yl)azetidine-1-carboxylate (40 mg, 0.12 mmol) and 2-fluoro-5-(1-methyl-1H-pyrazol-3-yl)-4-(trifluoromethyl)benzoic acid (39 mg, 0.14 mmol) in pyridine (2 mL) at 26° C. was added phosphoryl trichloride (19 mg, 0.12 mmol). The resulting mixture was stirred for 30 min then carefully diluted with saturated aqueous NaHCO$_3$ solution (30 mL) and ethyl acetate (20 mL×3). The combined organic layers were washed with brine, dried over Na$_2$SO$_4$ and concentrated. The residue was purified by preparative TLC (PE/EtOAc=3/1) to give the title compound. $^1$H NMR (400 MHz, CDCl$_3$) δ 8.70 (d, J=5.1 Hz, 1H), 8.36 (d, J=7.8 Hz, 1H), 8.03 (d, J=12.9 Hz, 1H), 7.57-7.47 (m, 4H), 7.42 (d, J=2.3 Hz, 4H), 6.47 (br., 1H), 4.32 (t, J=8.2 Hz, 2H), 4.07-3.93 (m, 6H), 1.46 (s, 9H).

Step B: N-(6-(Azetidin-3-yl)-2-phenylpyridin-3-yl)-2-fluoro-5-(1-methyl-1H-pyrazol-3-yl)-4-(trifluoromethyl)benzamide To a solution of tert-butyl 3-(5-(2-fluoro-5-(1-methyl-1H-pyrazol-3-yl)-4-(trifluoromethyl)benzamido)-6-phenylpyridin-2-yl)azetidine-1-carboxylate (22 mg, 0.035 mmol) in DCM (2 mL) at 26° C. was added TFA (0.027 mL, 0.35 mmol), and the resulting mixture was stirred for 1 h. The product mixture was partitioned between saturated aqueous NaHCO$_3$ solution (30 mL) and DCM (20 mL×3). The combined organic layers were washed with brine, dried over Na$_2$SO$_4$ and concentrated. The residue was purified by reverse-phase HPLC under acidic conditions (H$_2$O/CH$_3$CN gradient with 0.1% TFA present) to give the title compound. MS: m/z=496.2 (M+1). $^1$H NMR (400 MHz, CDCl$_3$) δ 8.89 (d, J=7.8 Hz, 1H), 8.74 (d, J=14.1 Hz, 1H), 8.42 (d, J=7.4 Hz, 1H), 7.66-7.55 (m, 5H), 7.48 (d, J=11.7 Hz, 1H), 7.42 (s, 1H), 6.46 (s, 1H), 4.47 (br., 4H), 4.29 (br., 1H), 3.98 (s, 3H).

Step C: 2-Fluoro-N-(6-(1-(2-hydroxyacetyl)azetidin-3-yl)-2-phenylpyridin-3-yl)-5-(1-methyl-1H-pyrazol-3-yl)-4-(trifluoromethyl)benzamide To a solution of 2-hydroxyacetic acid (21 mg, 0.28 mmol) in CH$_2$Cl$_2$ (4 mL) at 15° C. was added HOBt (54 mg, 0.35 mmol), DIEA (0.062 mL, 0.35 mmol), EDC (60 mg, 0.31 mmol), and N-(6-(azetidin-3-yl)-2-phenylpyridin-3-yl)-2-fluoro-5-(1-methyl-1H-pyrazol-3-yl)-4-(trifluoromethyl)benzamide (70 mg, 0.14 mmol). The resulting mixture was stirred for 16 h then partitioned between water (10 mL) and DCM (10 mL×4). The combined organic layers were dried over sodium sulfate and concentrated. The residue was purified by reverse-phase HPLC under acidic conditions (H$_2$O/CH$_3$CN gradient with 0.1% TFA present) to give the title compound. MS: m/z=554.2 (M+1). $^1$H NMR (400 MHz, CDCl$_3$) δ 8.97 (d, J=8.0 Hz, 1H), 8.72 (d, J=13.6 Hz, 1H), 8.39 (d, J=8.0 Hz, 1H), 7.66-7.53 (m, 5H), 7.47 (d, J=12.0 Hz, 1H), 7.43 (d, J=2.0 Hz, 1H), 7.38 (d, J=8.5 Hz, 1H), 6.46 (s, 1H), 4.58-4.34 (m, 4H), 4.20 (d, J=6.5 Hz, 1H), 4.08 (br s, 2H), 4.00 (s, 3H).

The following examples were prepared in similar fashion to the procedures described above.

| Compound Number | Structure | Compound Name | LCMS (M + 1) |
|---|---|---|---|
| 207 | 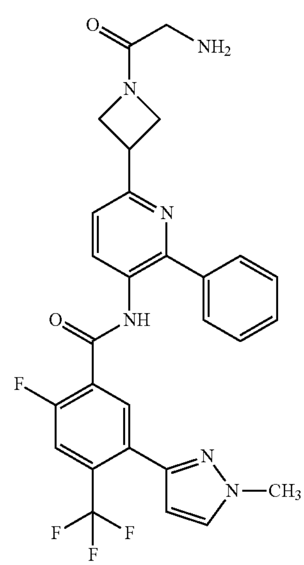 [SMILES: Cn1ccc(-c2cc(C(=O)Nc3ccc(C4CN(C(=O)CN)C4)nc3-c3ccccc3)c(F)cc2C(F)(F)F)n1] | 2-fluoro-N-(6-(1-glycylazetidin-3-yl)-2-phenylpyridin-3-yl)-5-(1-methyl-1H-pyrazol-3-yl)-4-(trifluoromethyl)benzamide | 553.2 |

| Compound Number | Structure | Compound Name | LCMS (M + 1) |
|---|---|---|---|
| 208 | 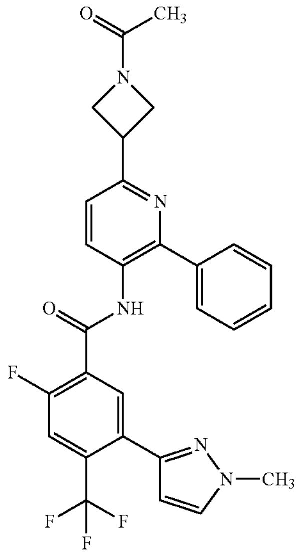 [SMILES: CC(=O)N1CC(c2ccc(NC(=O)c3cc(-c4ccn(C)n4)c(C(F)(F)F)cc3F)c(-c3ccccc3)n2)C1] | N-(6-(1-acetylazetidin-3-yl)-2-phenylpyridin-3-yl)-2-fluoro-5-(1-methyl-1H-pyrazol-3-yl)-4-(trifluoromethyl)benzamide | 538.2 |

Example 209

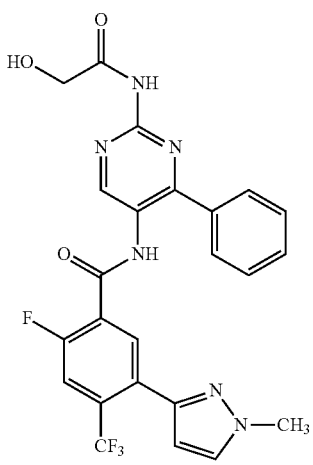 [SMILES: Cn1ccc(-c2cc(C(=O)Nc3cnc(NC(=O)CO)nc3-c3ccccc3)c(F)cc2C(F)(F)F)n1]

2-Fluoro-N-(2-(2-hydroxyacetamido)-4-phenylpyrimidin-5-yl)-5-(1-methyl-1H-pyrazol-3-yl)-4-(trifluoromethyl)benzamide

Step A: N-(2-Chloro-4-phenylpyrimidin-5-yl)-2-fluoro-5-(1-methyl-1H-pyrazol-3-yl)-4-(trifluoromethyl)benzamide To a stirred solution of 2-chloro-4-phenylpyrimidin-5-amine (206 mg, 1.00 mmol) and 2-fluoro-5-(1-methyl-1H-pyrazol-3-yl)-4-(trifluoromethyl)benzoic acid (289 mg, 1.00 mmol) in pyridine (4 mL) at 20° C. was added phosphoryl trichloride (184 mg, 1.20 mmol). The resulting mixture was stirred for 5 min then carefully diluted with saturated sodium bicarbonate solution (5 mL) and extracted with ethyl acetate (5 mL×3). The combined organic layers were dried over sodium sulfate and concentrated. The residue was purified by column chromatography on silica gel (PE/EtOAc=1/1) to afford the title compound. MS: m/z=476.2 (M+1).

Step B: 2-Fluoro-N-(2-(2-hydroxyacetamido)-4-phenylpyrimidin-5-yl)-5-(1-methyl-1H-pyrazol-3-yl)-4-(trifluoromethyl)benzamide To a deoxygenated mixture of N-(2-chloro-4-phenylpyrimidin-5-yl)-2-fluoro-5-(1-methyl-1H-pyrazol-3-yl)-4-(trifluoromethyl)benzamide (110 mg, 0.231 mmol), 2-hydroxyacetamide (52 mg, 0.69 mmol) and potassium phosphate dibasic (121 mg, 0.694 mmol) in dioxane (2 mL) was added Xantphos (13 mg, 0.023 mmol) and $Pd_2(dba)_3$ (21 mg, 0.023 mmol). The resulting mixture was heated at 100° C. for 15 min in microwave reactor then cooled and partitioned between water (5 mL) and ethyl acetate (5 mL×3). The combined organic layers were dried over sodium sulfate and concentrated. The residue was purified by preparative TLC (ethyl acetate) followed by reverse-phase HPLC under basic conditions ($H_2O/CH_3CN$ gradient with 0.05% $NH_4OH$ present) to afford the title compound. MS: m/z=515.1 (M+1). $^1H$ NMR (400 MHz, $CD_3OD$) δ 8.79 (s, 1H), 7.92 (d, J=6.8 Hz, 1H), 7.81 (d, J=3.5 Hz, 2H), 7.69 (d, J=10.6 Hz, 1H), 7.64 (d, J=2.0 Hz, 1H), 7.49 (d, J=2.3 Hz, 3H), 6.43 (s, 1H), 4.92 (s, 2H), 3.95 (s, 3H).

The following examples were prepared in similar fashion to the procedures described above.

| Compound Number | Structure | Compound Name | LCMS (M + 1) |
|---|---|---|---|
| 210 | 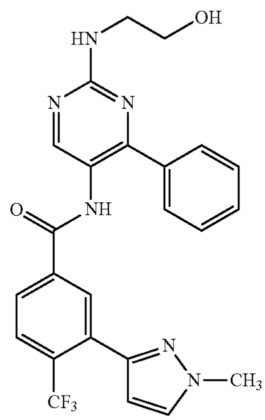 [SMILES: Cn1ccc(-c2cc(C(=O)Nc3cnc(NCCO)nc3-c3ccccc3)ccc2C(F)(F)F)n1] | N-(2-((2-hydroxyethyl)amino)-4-phenylpyrimidin-5-yl)-3-(1-methyl-1H-pyrazol-3-yl)-4-(trifluoromethyl)benzamide | 483.2 |
| 211 | 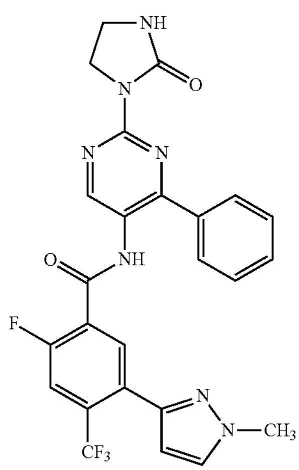 [SMILES: Cn1ccc(-c2cc(C(=O)Nc3cnc(N4CCNC4=O)nc3-c3ccccc3)c(F)cc2C(F)(F)F)n1] | 2-fluoro-5-(1-methyl-1H-pyrazol-3-yl)-N-(2-(2-oxoimidazolidin-1-yl)-4-phenylpyrimidin-5-yl)-4-(trifluoromethyl)benzamide | 526.1 |
| 212 | 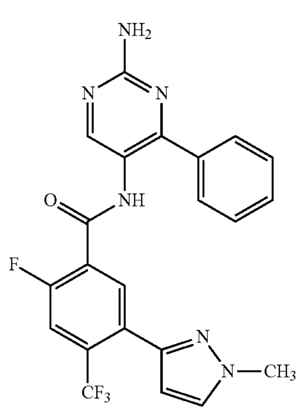 [SMILES: Cn1ccc(-c2cc(C(=O)Nc3cnc(N)nc3-c3ccccc3)c(F)cc2C(F)(F)F)n1] | N-(2-amino-4-phenylpyrimidin-5-yl)-2-fluoro-5-(1-methyl-1H-pyrazol-3-yl)-4-(trifluoromethyl)benzamide | 457.1 |

-continued

| Compound Number | Structure | Compound Name | LCMS (M + 1) |
|---|---|---|---|
| 213 | 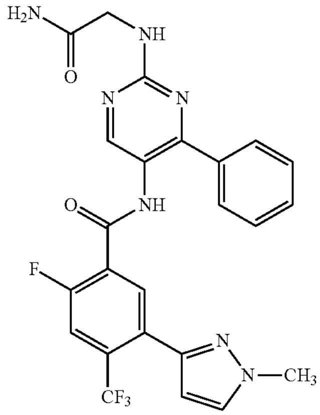 [SMILES: Cn1ccc(-c2cc(C(=O)Nc3cnc(NCC(N)=O)nc3-c3ccccc3)c(F)cc2C(F)(F)F)n1] | N-(2-((2-amino-2-oxoethyl)amino)-4-phenylpyrimidin-5-yl)-2-fluoro-5-(1-methyl-1H-pyrazol-3-yl)-4-(trifluoromethyl)benzamide | 514.2 |

Example 214

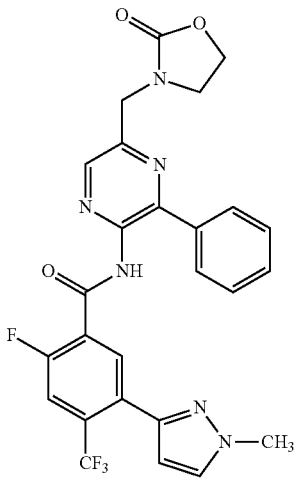 [SMILES: Cn1ccc(-c2cc(C(=O)Nc3ncc(CN4CCOC4=O)nc3-c3ccccc3)c(F)cc2C(F)(F)F)n1]

2-Fluoro-5-(1-methyl-1H-pyrazol-3-yl)-N-(5-((2-oxooxazolidin-3-yl)methyl)-3-phenylpyrazin-2-yl)-4-(trifluoromethyl)benzamide Step A: tert-Butyl ((5-(2-fluoro-5-(1-methyl-1H-pyrazol-3-yl)-4-(trifluoromethyl)benzamido)-6-phenylpyrazin-2-yl)methyl)carbamate To a solution of 2-fluoro-5-(1-methyl-1H-pyrazol-3-yl)-4-(trifluoromethyl)benzoic acid (202 mg, 0.700 mmol) in pyridine (6 mL) at 20° C. was added phosphoryl trichloride (129 mg, 0.840 mmol) followed by tert-butyl ((5-amino-6-phenylpyrazin-2-yl)methyl)carbamate (290 mg, 0.966 mmol). The resulting mixture was stirred for 30 min then diluted with water (3 mL) and extracted with EtOAc (5 mL×3). The combined organic layers were dried over sodium sulfate and concentrated, and the residue was purified by silica gel column chromatography (PE/EtOAc=5/1, 2/1, 1/1) to give the title compound. MS: m/z=571.3 (M+1).

Step B: N-(5-(Aminomethyl)-3-phenylpyrazin-2-yl)-2-fluoro-5-(1-methyl-1H-pyrazol-3-yl)-4-(trifluoromethyl)benzamide A mixture of tert-butyl ((5-(2-fluoro-5-(1-methyl-1H-pyrazol-3-yl)-4-(trifluoromethyl)benzamido)-6-phenylpyrazin-2-yl)methyl)carbamate (220 mg, 0.355 mmol) in a 4M solution of HCl in dioxane (5 mL, 20 mmol) was heated at 50° C. for 30 min. The product mixture was concentrated. The residue was dissolved in water (5 mL) and this mixture was basified to pH 7 with the addition of saturated aqueous $K_2CO_3$ solution and extracted with EtOAc (4 mL×3). The combined organic layers were dried over sodium sulfate and concentrated to give the title compound. MS: m/z=471.2 (M+1).

Step C: 2-Chloroethyl ((5-(2-fluoro-5-(1-methyl-1H-pyrazol-3-yl)-4-(trifluoromethyl)benzamido)-6-phenylpyrazin-2-yl)methyl)carbamate To a solution of N-(5-(aminomethyl)-3-phenylpyrazin-2-yl)-2-fluoro-5-(1-methyl-1H-pyrazol-3-yl)-4-(trifluoromethyl)benzamide (20 mg, 0.043 mmol) in THF (1 mL) at 0° C. was added triethylamine (0.018 mL, 0.13 mmol) and 2-chloroethyl carbonochloridate (12 mg, 0.085 mmol). The resulting mixture was stirred for 30 min then partitioned between water (2 mL) and EtOAc (3 mL×3). The combined organic layers were dried over sodium sulfate and concentrated to give the title compound. MS: m/z/577.2 (M+1).

Step D: 2-Fluoro-5-(1-methyl-1H-pyrazol-3-yl)-N-(5-(2-oxooxazolidin-3-yl)methyl)-3-phenylpyrazin-2-yl)-4-(trifluoromethyl)benzamide To a solution of 2-chloroethyl ((5-(2-fluoro-5-(1-methyl-1H-pyrazol-3-yl)-4-(trifluoromethyl)benzamido)-6-phenylpyrazin-2-yl)methyl)carbamate (45 mg, 0.058 mmol) in THF (1 mL) at 0° C. was added sodium hydride (7 mg, 0.2 mmol). The resulting mixture was stirred for 2 h then diluted with water (1 mL) and extracted with EtOAc (2 mL×3). The combined organic layers were dried over sodium sulfate and concentrated, and the residue was purified by reverse-phase HPLC under basic conditions ($H_2O/CH_3CN$ gradient with 0.05% $NH_4OH$ present) to give the title compound. MS: m/z=541.1 (M+1). $^1$H NMR (400 MHz, $CD_3OD$) δ 8.40 (s, 1H), 7.72 (d, J=7.2 Hz, 3H), 7.61-7.55 (m, 2H), 7.39-7.32 (m, 3H), 6.34 (s, 1H), 4.60 (s, 2H), 4.32 (t, J=8.0 Hz, 2H), 3.86 (s, 3H), 3.67 (t, J=8.1 Hz, 2H).

Example 215

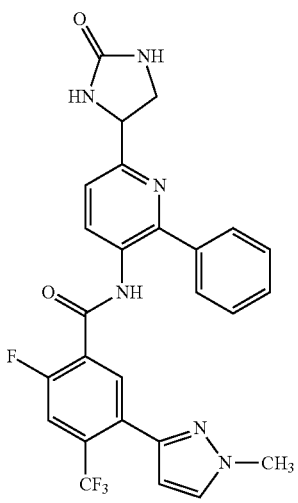 [SMILES: Cn1ccc(-c2cc(C(=O)Nc3ccc(C4CNC(=O)N4)nc3-c3ccccc3)c(F)cc2C(F)(F)F)n1]

2-Fluoro-5-(1-methyl-1H-pyrazol-3-yl)-N-(6-(2-oxoimidazolidin-4-yl)-2-phenylpyridin-3-yl)-4-(trifluoromethyl)benzamide Step A: Di-tert-butyl (1-(5-(2-fluoro-5-(1-methyl-1H-pyrazol-3-yl)-4-(trifluoromethyl)benzamido)-6-phenylpyridin-2-yl)ethane-1,2-diyl)dicarbamate To a stirred solution of 2-fluoro-5-(1-methyl-1H-pyrazol-3-yl)-4-(trifluoromethyl)benzoic acid (200 mg, 0.693 mmol) and di-tert-butyl (1-(5-amino-6-phenylpyridin-2-yl)ethane-1,2-diyl)dicarbamate (270 mg, 0.630 mmol) in pyridine (3 mL) at 15° C. was added dropwise $POCl_3$ (0.088 mL, 0.95 mmol). The resulting mixture was stirred for 15 min then partitioned between saturated aqueous LiOH (10 mL) solution and EtOAc (10 mL×3). The combined organic layers were dried over sodium sulfate and concentrated, and the residue was purified by preparative TLC (PE/EtOAc=1/1) to give the title compound. MS: m/z=699.2 (M+1). $^1$H NMR (400 MHz, $CDCl_3$) δ 8.77 (d, J=8.0 Hz, 1H), 8.57 (d, J=13.3 Hz, 1H), 8.35 (d, J=7.4 Hz, 1H), 7.57-7.43 (m, 5H), 7.38 (d, J=11.7 Hz, 1H), 7.34-7.25 (m, 4H), 6.37 (s, 1H), 3.48 (d, J=5.3 Hz, 3H), 1.38 (s, 18H).

Step B: N-(6-(1,2-Diaminoethyl)-2-phenylpyridin-3-yl)-2-fluoro-5-(1-methyl-1H-pyrazol-3-yl)-4-(trifluoromethyl)benzamide A stirred solution of di-tert-butyl (1-(5-(2-fluoro-5-(1-methyl-1H-pyrazol-3-yl)-4-(trifluoromethyl)benzamido)-6-phenylpyridin-2-yl)ethane-1,2-diyl)dicarbamate (280 mg, 0.401 mmol) in a 4M solution of HCl in EtOAc (10 mL) was stirred at 15° C. for 30 min. The mixture was concentrated to give the title compound as an HCl salt. MS: m/z=499.2 (M+1).

Step C: 2-Fluoro-5-(1-methyl-1H-pyrazol-3-yl)-N-(6-(2-oxoimidazolidin-4-yl)-2-phenylpyridin-3-yl)-4-(trifluoromethyl)benzamide To a stirred solution of N-(6-(1,2-diaminoethyl)-2-phenylpyridin-3-yl)-2-fluoro-5-(1-methyl-1H-pyrazol-3-yl)-4-(trifluoromethyl)benzamide hydrochloride (70 mg, 0.12 mmol) in THF (5 mL) at 15° C. was added CDI (39.7 mg, 0.245 mmol). The mixture was stirred for 15 min before $K_2CO_3$ (51 mg, 0.37 mmol) was added. The resulting mixture was heated at 60° C. for 2 h then cooled and partitioned between water (30 mL) and EtOAc (30 mL×3). The combined organic layers were dried over $Na_2SO_4$ and concentrated, and the residue was purified by reverse-phase HPLC under basic conditions ($H_2O/CH_3CN$ gradient with 0.05% $NH_4OH$ present) to give the title compound. MS: m/z=525.1 (M+1). $^1$H NMR (400 MHz, $CD_3OD$) δ 8.30 (d, J=8.4 Hz, 1H), 7.91 (d, J=7.1 Hz, 1H), 7.69-7.64 (m, 4H), 7.59 (d, J=8.4 Hz, 1H), 7.51-7.43 (m, 3H), 6.43 (s, 1H), 5.01 (dd, $J_1$=9.4 Hz, $J_2$=6.3 Hz, 1H), 4.00-3.97 (m, 1H), 3.97 (s, 3H), 3.50 (dd, $J_1$=9.2 Hz, $J_2$=6.3 Hz, 1H).

Example 216

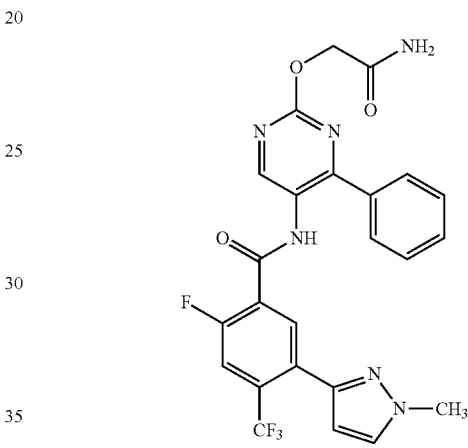

N-(2-(2-Amino-2-oxoethoxy)-4-phenylpyrimidin-5-yl)-2-fluoro-5-(1-methyl-1H-pyrazol-3-yl)-4-(trifluoromethyl)benzamide Step A: Methyl 2-((5-(2-fluoro-5-(1-methyl-1H-pyrazol-3-yl)-4-(trifluoromethyl)benzamido)-4-phenylpyrimidin-2-yl)oxy)acetate To a stirred solution of methyl 2-((5-amino-4-phenylpyrimidin-2-yl)oxy)acetate hydrochloride (42 mg, 0.14 mmol) and 2-fluoro-5-(1-methyl-1H-pyrazol-3-yl)-4-(trifluoromethyl)benzoic acid (41 mg, 0.14 mmol) in pyridine (2 mL) at 15° C. was added phosphoryl trichloride (26 mg, 0.17 mmol). The resulting mixture was stirred for 15 min then carefully diluted with saturated aqueous sodium bicarbonate solution (5 mL) and extracted with ethyl acetate (5 mL×3). The combined organic layers were dried over sodium sulfate and concentrated, and the residue was purified by preparative TLC (PE/EtOAc=2/3) to afford the title compound. MS: m/z=530.2 (M+1).

Step B: N-(2-(2-Amino-2-oxo ethoxy)-4-phenylpyrimidin-5-yl)-2-fluoro-5-(1-methyl-1H-pyrazol-3-yl)-4-(trifluoromethyl)benzamide A solution of methyl 2-((5-(2-fluoro-5-(1-methyl-1H-pyrazol-3-yl)-4-(trifluoromethyl)benzamido)-4-phenylpyrimidin-2-yl)oxy)acetate (53 mg, 0.10 mmol) in a 2M solution of $NH_3$ in $CH_3OH$ (10 mL, 20 mmol) was stirred at 15°

C. for 10 h. The product mixture was concentrated, and the residue was purified by reverse-phase HPLC under basic conditions (H₂O/CH₃CN gradient with 0.05% NH₄OH present) to give the title compound. MS: m/z=514.1 (M+1). ¹H NMR (400 MHz, CD₃OD) δ 8.81 (s, 1H), 7.93 (d, J=6.8 Hz, 1H), 7.86-7.79 (m, 2H), 7.71 (d, J=10.6 Hz, 1H), 7.66 (d, J=2.0 Hz, 1H), 7.53-7.47 (m, 3H), 6.45 (s, 1H), 4.94 (s, 2H), 3.96 (s, 3H).

Example 217

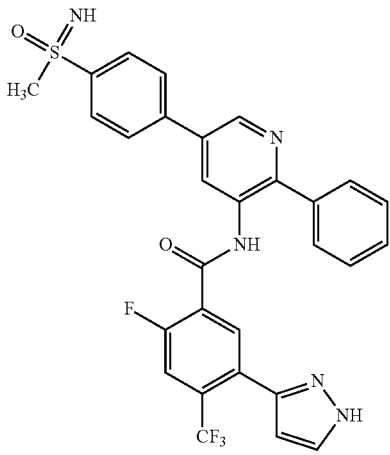 [SMILES: CS(=N)(=O)c1ccc(-c2cnc(-c3ccccc3)c(NC(=O)c3cc(-c4cc[nH]n4)c(C(F)(F)F)cc3F)c2)cc1]

(R or S)-2-Fluoro-N-(5-(4-(S-methylsulfonimidoyl) phenyl)-2-phenylpyridin-3-yl)-5-(1H-pyrazol-3-yl)-4-(trifluoromethyl)benzamide Step A: N-(5-bromo-2-phenylpyridin-3-yl)-2-fluoro-5-(1H-pyrazol-3-yl)-4-(trifluoromethyl)benzamide To a solution of 5-bromo-2-phenylpyridin-3-amine (1.5 g, 6.0 mmol) and 2-fluoro-5-(1H-pyrazol-3-yl)-4-(trifluoromethyl)benzoic acid (2.0 g, 6.0 mmol) in pyridine (20 mL) at 25° C. was added POCl₃ (915 mg, 6.0 mmol). The resulting mixture was stirred 2 h then concentrated. The residue was purified by column chromatography on silica gel (PE/EtOAc=3/1) to afford the title compound.

Step B: (R or S)-2-Fluoro-N-(5-(4-(S-methylsulfonimidoyl)phenyl)-2-phenylpyridin-3-yl)-5-(1H-pyrazol-3-yl)-4-(trifluoromethyl)benzamide To a deoxygenated solution of N-(5-bromo-2-phenylpyridin-3-yl)-2-fluoro-5-(1H-pyrazol-3-yl)-4-(trifluoromethyl)benzamide (150 mg, 0.30 mmol) in dioxane (2 mL) was added enantiomerically pure 4,4,5,5-tetramethyl-2-(4-(S-methylsulfonimidoyl)phenyl)-1,3,2-dioxaborolane (S or R, the second peak in SFC) (100 mg, 0.36 mmol), K₂CO₃ (102 mg, 0.75 mmol) and Pd(dppf)Cl₂ (22 mg, 0.03 mmol). The resulting mixture was heated at 80° C. for 16 h then cooled and partitioned between water (10 mL) and EtOAc (20 mL×3). The combined organic layers were dried over Na₂SO₄ and concentrated. The residue was purified by reverse-phase HPLC under acid conditions (H₂O/CH₃CN gradient with 0.1% TFA present) to give the title compound. MS: m/z=580.0 (M+1). ¹H NMR (400 MHz, CD₃OD) δ 8.90 (s, 1H), 8.78 (s, 1H), 8.28 (d, J=8.6 Hz, 2H), 8.18 (d, J=8.6 Hz, 2H), 7.96 (d, J=7.1 Hz, 1H), 7.79-7.66 (m, 4H), 7.57-7.43 (m, 3H), 6.50 (s, 1H), 3.73 (s, 3H).

Example 218

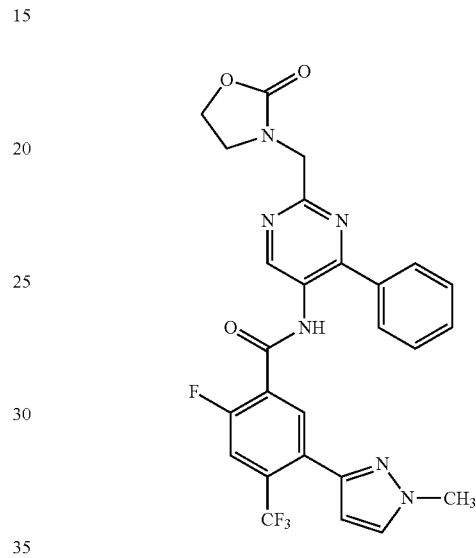

(R or S)-2-Fluoro-N-(5-(4-(S-methylsulfonimidoyl) phenyl)-2-phenylpyridin-3-yl)-5-(1H-pyrazol-3-yl)-4-(trifluoromethyl)benzamide A mixture of 3-((5-amino-4-phenylpyrimidin-2-yl) methyl)oxazolidin-2-one (35 mg, 0.13 mmol), 2-fluoro-5-(1-methyl-1H-pyrazol-3-yl)-4-(trifluoromethyl)benzoic acid (41 mg, 0.14 mmol), HATU (54 mg, 0.14 mmol) and 2,6-lutidine (0.022 mL, 0.19 mmol) in DMF (2 mL) was stirred at 23° C. for 3 d. The product mixture was purified by preparative HPLC (Separation COE, reverse-phase, Sun-Fire C-18) eluting with acetonitrile/water w/0.05% TFA (15% to 65% organic in 15 min, 50 mL/min) to give the title compound as a TFA salt. MS: m/z=541.0 (M+1). ¹H NMR (500 MHz, DMSO-d₆): δ 10.66 (s, 1H), 8.98 (s, 1H), 7.92-7.87 (m, 2H), 7.82-7.80 (m, 3H), 7.51-7.50 (m, 3H), 6.44 (s, 1H), 4.66 (s, 2H), 4.36 (t, J=8.0 Hz, 2H), 3.91 (s, 3H), 3.75 (t, J=8.0 Hz, 2H).

The following examples were prepared in similar fashion to the procedures described above.

| Compound Number | Structure | Compound Name | LCMS (M + 1) |
|---|---|---|---|
| 219 | 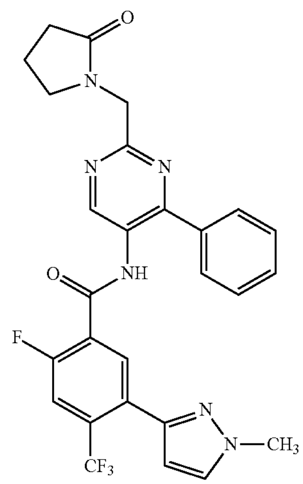 [SMILES: Cn1ccc(-c2cc(C(=O)Nc3cnc(CN4CCCC4=O)nc3-c3ccccc3)c(F)cc2C(F)(F)F)n1] | 2-fluoro-5-(1-methyl-1H-pyrazol-3-yl)-N-(2-((2-oxopyrrolidin-1-yl)methyl)-4-phenylpyrimidin-5-yl)-4-(trifluoromethyl)benzamide | 539.2 |
| 220 | 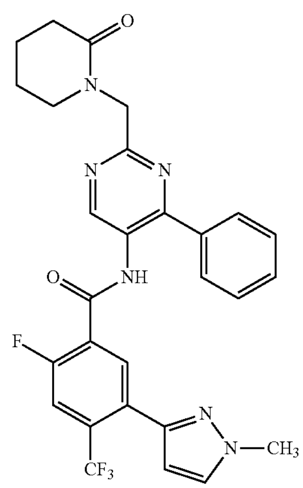 [SMILES: Cn1ccc(-c2cc(C(=O)Nc3cnc(CN4CCCCC4=O)nc3-c3ccccc3)c(F)cc2C(F)(F)F)n1] | 2-fluoro-5-(1-methyl-1H-pyrazol-3-yl)-N-(2-((2-oxopiperidin-1-yl)methyl)-4-phenylpyrimidin-5-yl)-4-(trifluoromethyl)benzamide | 553.2 |
| 221 | 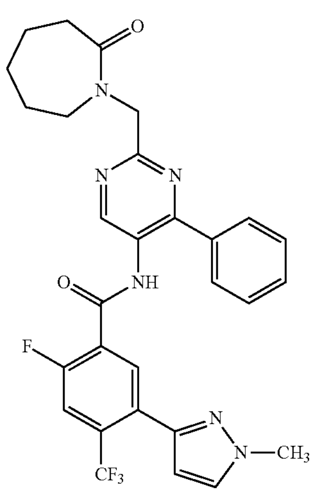 [SMILES: Cn1ccc(-c2cc(C(=O)Nc3cnc(CN4CCCCCC4=O)nc3-c3ccccc3)c(F)cc2C(F)(F)F)n1] | 2-fluoro-5-(1-methyl-1H-pyrazol-3-yl)-N-(2-((2-oxoazepan-1-yl)methyl)-4-phenylpyrimidin-5-yl)-4-(trifluoromethyl)benzamide | 567.1 |

| Compound Number | Structure | Compound Name | LCMS (M + 1) |
|---|---|---|---|
| 222 | 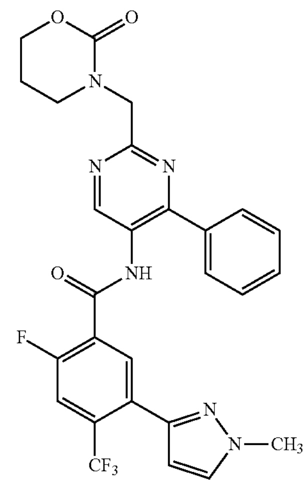 [SMILES: Cn1ccc(-c2cc(C(=O)Nc3cnc(CN4CCCOC4=O)nc3-c3ccccc3)c(F)cc2C(F)(F)F)n1] | 2-fluoro-5-(1-methyl-1H-pyrazol-3-yl)-N-(2-((2-oxo-1,3-oxazinan-3-yl)methyl)-4-phenylpyrimidin-5-yl)-4-(trifluoromethyl)benzamide | 555.1 |
| 223 | 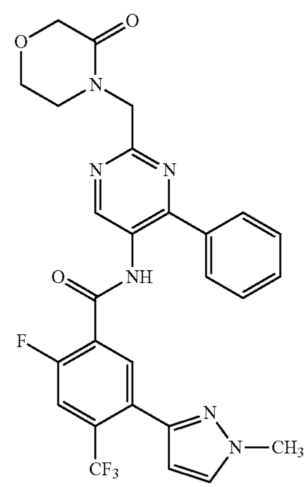 [SMILES: Cn1ccc(-c2cc(C(=O)Nc3cnc(CN4CCOCC4=O)nc3-c3ccccc3)c(F)cc2C(F)(F)F)n1] | 2-fluoro-5-(1-methyl-1H-pyrazol-3-yl)-N-(2-((3-oxomorpholino)methyl)-4-phenylpyrimidin-5-yl)-4-(trifluoromethyl)benzamide | 555.0 |
| 224 | 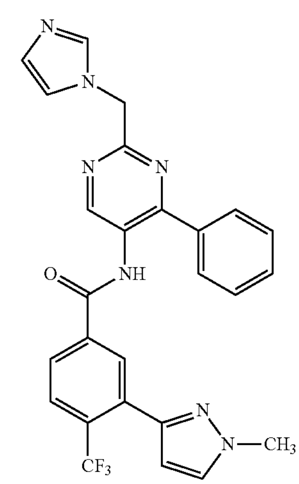 [SMILES: Cn1ccc(-c2cc(C(=O)Nc3cnc(Cn4ccnc4)nc3-c3ccccc3)ccc2C(F)(F)F)n1] | N-(2-((1H-imidazol-1-yl)methyl)-4-phenylpyrimidin-5-yl)-3-(1-methyl-1H-pyrazol-3-yl)-4-(trifluoromethyl)benzamide | 504.2 |

-continued

| Compound Number | Structure | Compound Name | LCMS (M + 1) |
|---|---|---|---|
| 225 | 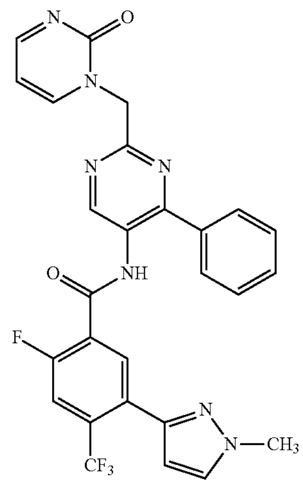 [SMILES: Cn1ccc(-c2cc(C(=O)Nc3cnc(Cn4cccnc4=O)nc3-c3ccccc3)c(F)cc2C(F)(F)F)n1] | 2-fluoro-5-(1-methyl-1H-pyrazol-3-yl)-N-(2-((2-oxopyrimidin-1(2H)-yl)methyl)-4-phenylpyrimidin-5-yl)-4-(trifluoromethyl)benzamide | 550.2 |
| 226 | 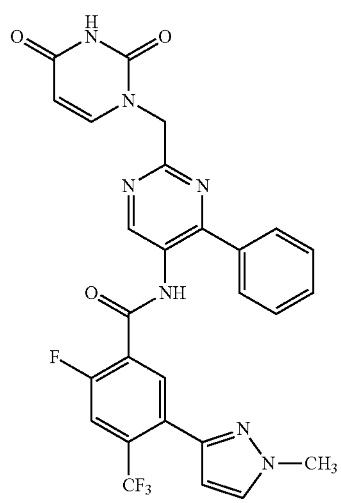 [SMILES: Cn1ccc(-c2cc(C(=O)Nc3cnc(Cn4ccc(=O)[nH]c4=O)nc3-c3ccccc3)c(F)cc2C(F)(F)F)n1] | N-(2-((2,4-dioxo-3,4-dihydropyrimidin-1(2H)-yl)methyl)-4-phenylpyrimidin-5-yl)-2-fluoro-5-(1-methyl-1H-pyrazol-3-yl)-4-(trifluoromethyl)benzamide | 566.1 |
| 227 | 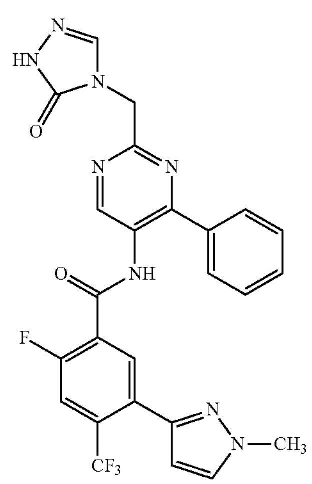 [SMILES: Cn1ccc(-c2cc(C(=O)Nc3cnc(Cn4cn[nH]c4=O)nc3-c3ccccc3)c(F)cc2C(F)(F)F)n1] | 2-fluoro-5-(1-methyl-1H-pyrazol-3-yl)-N-(2-((5-oxo-1,5-dihydro-4H-1,2,4-triazol-4-yl)methyl)-4-phenylpyrimidin-5-yl)-4-(trifluoromethyl)benzamide | 539.1 |

-continued

| Compound Number | Structure | Compound Name | LCMS (M + 1) |
|---|---|---|---|
| 228 | 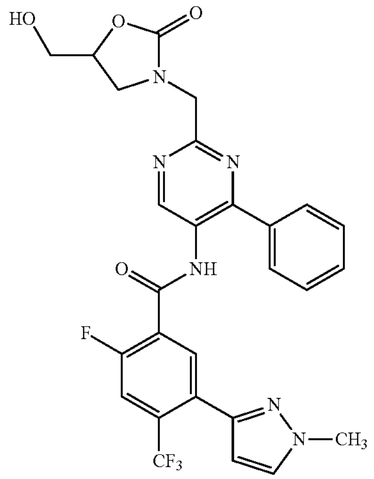 [SMILES: Cn1ccc(-c2cc(C(=O)Nc3cnc(CN4CC(CO)OC4=O)nc3-c3ccccc3)c(F)cc2C(F)(F)F)n1] | (R or S)-2-fluoro-N-(2-((5-(hydroxymethyl)-2-oxooxazolidin-3-yl)methyl)-4-phenylpyrimidin-5-yl)-5-(1-methyl-1H-pyrazol-3-yl)-4-(trifluoromethyl)benzamide | 571.3 |

Biological Utility

TrkA functional activity was measured using a DiscoverX PathHunter assay. In this assay, U2OS cells express the human TrkA receptor as a fusion with the weakly complementing fragment of B-galactosidase, which DiscoverX calls "Prolink (PK)"; additionally, Shc1 is fused with a larger fragment, which is called "Enzyme Acceptor (EA)". Activation of the TrkA receptor, upon NGF addition, results in the kinase domain being phosphorylated, resulting in subsequent recruitment of Shc1-EA protein. That recruitment results in an active B-galactosidase enzyme that is detected by addition of a chemiluminescent substrate. The human $p75^{NTR}$ protein was also expressed as a co-receptor for NGF.

All reagents were purchased from DiscoverX, except for the receptor agonists (NGF, BDNF, NT3) which were purchased from Peprotech. Cells were expanded and frozen into cryovials, and stored in the vapor phase of liquid nitrogen, and thawed immediately before use. Thawed cells were added to a 384-well plate at 7500 cells/well, and allowed to incubate overnight. Compound at various concentrations was added the following morning and allowed to incubate on cells for 1 h. Then, NGF was added at a concentration sufficient to elicit ~80% of a maximal response and allowed to incubate for 3 h at ambient temperature. DiscoverX PathHunter detection reagent was then added and the plate was further incubated for 1 h in the dark. The plate was then read via luminescence on the Perkin Elmer Envision.

The percent inhibition was calculated for each compound concentration, and the $IC_{50}$ was determined using Equation 1 below.

$$\% \text{ Inhibition} = \left( \text{Max} + \frac{(\text{Max} - \text{Min})}{1 + \left(\frac{Conc}{IC_{50}}\right)^{Hill}} \right) \quad \text{Equation 1}$$

$IC_{50}$ values from the aforementioned assay for the compounds of this invention range between 0.05 nM to 10000 nM. $IC_{50}$ values for particular compounds of this invention are provided below in Table 2 below.

TABLE 2

| Compound Number | TrkA $IC_{50}$ (nM) |
|---|---|
| 1 | 480 |
| 2 | 100 |
| 3 | 54 |
| 4 | 160 |
| 5 | 14 |
| 6 | 4900 |
| 7 | 4000 |
| 8 | 4300 |
| 9 | 140 |
| 10 | 1600 |
| 11 | 7500 |
| 12 | 36 |
| 13 | 910 |
| 14 | 590 |
| 15 | 3.0 |
| 16 | 66 |
| 17 | 15 |
| 18 | 330 |
| 19 | 25 |
| 20 | 15 |
| 21 | 35 |
| 22 | 64 |
| 23 | 1.1 |
| 24 | 2.2 |
| 25 | 83 |
| 26 | 210 |
| 27 | 1.0 |
| 28 | 9.6 |
| 29 | 4.0 |
| 30 | 130 |
| 31 | 5.5 |
| 32 | 8.3 |
| 33 | 56 |
| 34 | 0.69 |
| 35 | 7.3 |
| 36 | 24 |
| 37 | 4.0 |
| 38 | 25 |
| 39 | 70 |
| 40 | 12 |
| 41 | 5.0 |
| 42 | 21 |
| 43 | 55 |
| 44 | 20 |
| 45 | 16 |
| 46 | 24 |
| 47 | 1.3 |

TABLE 2-continued

| Compound Number | TrkA IC$_{50}$ (nM) |
|---|---|
| 48 | 1.1 |
| 49 | 3.6 |
| 50 | 3.6 |
| 51 | 4.9 |
| 52 | 1.6 |
| 53 | 5.7 |
| 54 | 9.3 |
| 55 | 14 |
| 56 | 0.45 |
| 57 | 1.1 |
| 58 | 0.19 |
| 59 | 0.23 |
| 60 | 1.1 |
| 61 | 0.64 |
| 62 | 0.79 |
| 63 | 1.8 |
| 64 | 0.44 |
| 65 | 3.3 |
| 66 | 1.2 |
| 67 | 1.6 |
| 68 | 0.40 |
| 69 | 18 |
| 70 | 0.53 |
| 71 | 3.6 |
| 72 | 0.57 |
| 73 | 1.0 |
| 74 | 2.0 |
| 75 | 12 |
| 76 | 0.84 |
| 77 | 1.0 |
| 78 | 1.1 |
| 79 | 1.1 |
| 80 | 0.49 |
| 81 | 14 |
| 82 | 11 |
| 83 | 1.1 |
| 84 | 1.2 |
| 85 | 0.58 |
| 86 | 19 |
| 87 | 8.5 |
| 88 | 1200 |
| 89 | 1.5 |
| 90 | 80 |
| 91 | 11 |
| 92 | 2.2 |
| 93 | 5.7 |
| 94 | 9.3 |
| 95 | 0.11 |
| 96 | 0.083 |
| 97 | 0.25 |
| 98 | 0.22 |
| 99 | 0.59 |
| 100 | 1.2 |
| 101 | 1.1 |
| 102 | 0.79 |
| 103 | 4.1 |
| 104 | 0.76 |
| 105 | 0.53 |
| 106 | 2.0 |
| 107 | 1.2 |
| 108 | 1.5 |
| 109 | 2.6 |
| 110 | 1.2 |
| 111 | 9.1 |
| 112 | 6.5 |
| 113 | 1.3 |
| 114 | 3.0 |
| 115 | 2.6 |
| 116 | 9.8 |
| 117 | 4.9 |
| 118 | 3.8 |
| 119 | 7.9 |
| 120 | 8.7 |
| 121 | 8.0 |
| 122 | 18 |
| 123 | 8.4 |
| 124 | 8.8 |
| 125 | 14 |
| 126 | 17 |
| 127 | 6.0 |
| 128 | 0.54 |
| 129 | 0.25 |
| 130 | 4.6 |
| 131 | 4.4 |
| 132 | 16 |
| 133 | 4.6 |
| 134 | 7.0 |
| 135 | 0.57 |
| 136 | 4.4 |
| 137 | 2.9 |
| 138 | 27 |
| 139 | 1.4 |
| 140 | 1.8 |
| 141 | 14 |
| 142 | 4.7 |
| 143 | 19 |
| 144 | 0.26 |
| 145 | 2.9 |
| 146 | 13 |
| 147 | 14 |
| 148 | 3.3 |
| 149 | 11 |
| 150 | 14 |
| 151 | 0.54 |
| 152 | 0.069 |
| 153 | 6.8 |
| 154 | 0.76 |
| 155 | 2.3 |
| 156 | 1.0 |
| 157 | 23 |
| 158 | 7.5 |
| 159 | 260 |
| 160 | 4.7 |
| 161 | 0.38 |
| 162 | 180 |
| 163 | 1.3 |
| 164 | 0.51 |
| 165 | 2.3 |
| 166 | 12 |
| 167 | 24 |
| 168 | 0.68 |
| 169 | 0.59 |
| 170 | 16 |
| 171 | 10 |
| 172 | 0.26 |
| 173 | 4.9 |
| 174 | 4.8 |
| 175 | 12.4 |
| 176 | 6.3 |
| 177 | 18 |
| 178 | 0.29 |
| 179 | 1.0 |
| 180 | 3.2 |
| 181 | 3.5 |
| 182 | 5.1 |
| 183 | 7.0 |
| 184 | 4.1 |
| 185 | 18 |
| 186 | 5.0 |
| 187 | 0.68 |
| 188 | 2.9 |
| 189 | 0.51 |
| 190 | 1.8 |
| 191 | 4.5 |
| 192 | 2.3 |
| 193 | 3.9 |
| 194 | 2.6 |
| 195 | 2.8 |
| 196 | 0.19 |
| 197 | 3.7 |
| 198 | 0.57 |
| 199 | 4.0 |
| 200 | 4.4 |
| 201 | 2.8 |
| 202 | 3.7 |
| 203 | 6.0 |

TABLE 2-continued

| Compound Number | TrkA IC$_{50}$ (nM) |
|---|---|
| 204 | 8.3 |
| 205 | 8.4 |
| 206 | 1.3 |
| 207 | 1.1 |
| 208 | 3.0 |
| 209 | 2.0 |
| 210 | 2.5 |
| 211 | 2.6 |
| 212 | 2.8 |
| 213 | 1.4 |
| 214 | 4.6 |
| 215 | 0.36 |
| 216 | 1.8 |
| 217 | 11 |
| 218 | 0.14 |
| 219 | 0.32 |
| 220 | 1.0 |
| 221 | 1.9 |
| 222 | 0.22 |
| 223 | 1.6 |
| 224 | 1.6 |
| 225 | 1.2 |
| 226 | 0.35 |
| 227 | 0.24 |
| 228 | 0.66 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula I:

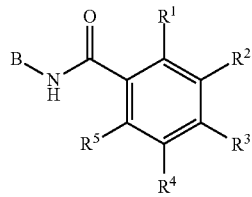

I or pharmaceutically acceptable salts thereof, wherein:
B represents a six membered heteroaryl having at least one heteroatom that is nitrogen, said heteroaryl optionally substituted with 1 to 3 groups of $R^a$;
R represents hydrogen, OH, or —$C_{1-6}$alkyl, said alkyl optionally substituted with 1 to 3 groups of $R^f$;
$R^1$ is selected from the group consisting of hydrogen, CN, OH, —$C_{1-6}$alkyl and halogen;
$R^2$ is hydrogen or (CHR)$_n$$C_{5-10}$ heterocycle, said heterocycle optionally substituted with 1 to 3 groups of $R^a$, wherein when $R^2$ is hydrogen then $R^4$ is (CHR)$_n$$C_{5-10}$ heterocycle;
$R^4$ is selected from the group consisting of hydrogen, halogen, $C_{1-6}$ alkyl, (CHR)$_n$$C_{6-10}$ aryl and (CHR)$_n$$C_{5-10}$ heterocycle, said alkyl, aryl, and heterocycle optionally substituted with 1 to 3 groups of $R^a$,
$R^3$ represents $C_{1-4}$ haloalkyl,
$R^5$ is hydrogen or halogen;

$R^a$ is selected from the group consisting of hydrogen, —CN, NO$_2$, —(CH$_2$)$_n$C(O)OR$^f$, —C$_{1-4}$haloalkyl, —OC$_{1-4}$haloalkyl, —C$_{1-6}$alkyl, —C$_{1-6}$alkenyl, —C$_{1-6}$alkynyl, —(CH$_2$)$_n$C$_{3-6}$cycloalkyl, —(CHR)$_n$C$_{6-10}$ aryl, —(CHR)$_n$C$_{4-10}$ heterocycle, —(CH$_2$)$_n$C(O)(CHR)$_n$C$_{4-10}$ heterocycle, —O—(CH$_2$)$_n$C$_{6-10}$ aryl, —O—(CH$_2$)$_n$C$_{4-10}$ heterocycle, —O—, —(CH$_2$)$_n$N(R$^d$)$_2$, —(CH$_2$)$_n$C(O)NH(CH$_2$)$_n$C$_{4-10}$heterocycle, SO$_2$R$^d$, (CH$_2$)$_n$NHSO$_2$R$^d$, —(CH$_2$)$_n$SO$_2$N(R$^d$)$_2$, S(O)(NH)R$^g$, —C(O)CF$_3$, COR, —(CH$_2$)$_n$halo, —(CH$_2$)$_n$NHC(O)R$^d$, —(CH$_2$)$_n$NRC(O)NHR$^d$, —(CH$_2$)$_n$NHC(O)OR$^d$, CHR)$_n$C(O)N(R$^d$)$_2$ —OC$_{1-6}$alkyl, —O—, and —OH, said alkyl, cycloalkyl, aryl and heterocycle optionally substituted with 1 to 3 groups of R$^b$, wherein when two R$^d$ groups are attached to a nitrogen atom they may combine with that nitrogen to from a 4-8 membered heterocyle that is optionally substituted with 1 to 3 groups of R$^f$;

$R^b$ is selected from the group consisting of halogen, —C$_{1-6}$alkyl, —C$_{1-6}$alkylOR, —C$_{1-4}$haloalkyl, —(CH$_2$)$_n$N(R$^d$)$_2$, —OR$^c$, —O—, —CN, S(O)(NH)R$^g$, —SO$_2$R, —SO$_2$N(R$^d$)$_2$, —(CH$_2$)$_n$C(O)N(R$^d$)$_2$, —(CH$_2$)$_n$NHC(O)R$^d$, COR, C(O)OR, C$_{3-6}$cycloalkyl, —O—(CH$_2$)$_n$C$_{4-10}$ heterocycle, and —C$_{1-6}$alkyl N(R$^d$)$_2$, said alkyl and heterocycle optionally substituted with 1 to 3 groups of R$^f$;

$R^c$ is selected from the group consisting of hydrogen, —C$_{1-6}$alkylORg, —C$_{1-4}$haloalkyl and —C$_{1-6}$alkyl;

$R^d$ is independently selected from the group consisting of hydrogen, halogen, —C$_{1-4}$haloalkyl —C$_{1-6}$alkyl, COR, —(CH$_2$)$_n$SO$_2$R, —(CH$_2$)$_n$NR$^f$C$_{4-10}$ heterocycle, —(CH$_2$)$_n$C$_{3-6}$cycloalkyl, —(CH$_2$)$_n$C$_{4-10}$heterocycle said alkyl, cycloalkyl and heterocycle optionally substituted with 1 to 3 groups of R$^f$; wherein when two R$^d$ groups are attached to a nitrogen atom they may combine with that nitrogen to from a 4-8 membered heterocyle that is optionally substituted with 1 to 3 groups of R$^f$;

$R^f$ is selected from the group consisting of hydrogen, C$_{1-6}$alkyl, OR$^c$, CN, —N(R$^c$)$_2$, C(O)N(R$^g$)$_2$, C(O)C$_{1-6}$alkyl, —SO$_2$R$^g$, —O—, —C$_{1-6}$alkylSO$_2$R$^g$, —C$_{1-6}$alkylOR$^g$, —C$_{1-6}$alkylN(R$^g$)$_2$, $R^g$ is selected from the group consisting of hydrogen, —C$_{1-6}$alkyl; and n represents 0-6.

2. The compound according to claim 1 wherein B is an unsubstituted or substituted six membered heterocycle selected from the group consisting of pyridyl, pyrimidinyl, pyradizinyl, and pyrazinyl.

3. The compound according to claim 2 wherein B is unsubstituted or substituted pyridyl.

4. The compound according to claim 2 wherein B is unsubstituted or substituted pyrimidinyl.

5. The compound according to claim 1 wherein one of $R^2$ and $R^4$ is hydrogen and the other is optionally substituted (CHR)$_n$C$_{5-10}$ heterocycle and $R^1$ and $R^5$ are independently selected from hydrogen and halogen.

6. The compound according to claim 5 wherein the heterocycle of $R^2$ and $R^4$ is selected from the group consisting of optionally substituted pyrazolyl, pyridyl, thiazolyl, triazolyl, oxazolyl, oxadiazolyl, and pyrimidinyl.

7. The compound according to claim 1 wherein $R^3$ is CF$_3$.

8. The compound according to claim 1 wherein B is a pyrimidinyl substituted with 1 to 3 groups of $R^a$ selected from the group consisting of —C$_{1-4}$haloalkyl, —OC$_{1-4}$haloalkyl, —C$_{1-6}$alkyl, —(CHR)$_n$C$_{6-10}$ aryl, —(CHR)$_n$C$_{4-10}$ heterocycle, —C(O)(CHR)$_n$C$_{4-10}$ heterocycle, —O—

$(CH_2)_nC_{6-10}$ aryl, $—O—(CH_2)_nC_{4-10}$ heterocycle, —O—, $—(CH_2)_nN(R^d)_2$, $—(CH_2)_nC(O)NH(CH_2)_nC_{4-10}$ heterocycle, COR, $—(CH_2)_n$halo, $—(CH_2)_nNHC(O)R^d$, $—(CH_2)_nNHC(O)NHR^d$, $—(CH_2)_nNHC(O)OR^d$, $—(CHR)_nC(O)N(R^d)_2$ $—(CH_2)_nNHSO_2R^d$, and —OR, said alkyl, aryl and heterocycle optionally substituted with 1 to 3 groups of $R^b$, wherein n=0-2.

9. The compound according to claim 1 wherein B is a pyridyl substituted with 1 to 3 groups of $R^a$ selected from the group consisting of $—C_{1-4}$haloalkyl, $—OC_{1-4}$haloalkyl, $—C_{1-6}$alkyl, $—(CHR)_nC_{6-10}$ aryl, $—(CHR)_nC_{4-10}$ heterocycle, $—C(O)(CHR)_nC_{4-10}$ heterocycle, $—O—(CH_2)_nC_{6-10}$ aryl, $—O—(CH_2)_nC_{4-10}$ heterocycle, —O—, $—(CH_2)_nN(R^d)_2$, $—(CH_2)_nC(O)NH(CH_2)_nC_{4-10}$ heterocycle, COR, $—(CH_2)_n$halo, $—(CH_2)_nNHC(O)R^d$, $—(CH_2)_nNHC(O)NHR^d$, $—(CH_2)_nNHC(O)OR^d$, $—(CHR)_nC(O)N(R^d)_2$ $—(CH_2)_nNHSO_2R^d$, and —OR, said alkyl, aryl and heterocycle optionally substituted with 1 to 3 groups of $R^b$, wherein n=0-2.

10. The compound according to claim 1 represented by structural formula Ia:

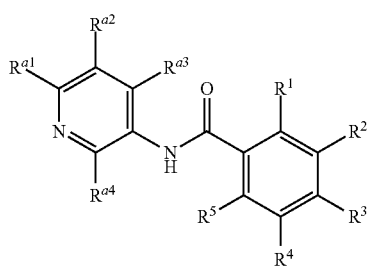

or a pharmaceutically acceptable salt thereof, wherein $R^1$, $R^2$, $R^3$, $R^4$, and $R^5$ are as originally described and $R^{a1}$, $R^{a2}$, $R^{a3}$, and $R^{a4}$ all equal $R^a$ and $R^a$ is as originally described.

11. The compound according to claim 10 wherein $R^{a1}$, $R^{a2}$, $R^{a3}$, and $R^{a4}$ are independently selected from hydrogen, $C_{1-4}$haloalkyl, $—OC_{1-4}$haloalkyl, $—C_{1-6}$alkyl, $—(CHR)_nC_{6-10}$ aryl, $—(CHR)_nC_{4-10}$ heterocycle, $—C(O)(CHR)_nC_{4-10}$ heterocycle, $—O—(CH_2)_nC_{6-10}$ aryl, $—O—(CH_2)_nC_{4-10}$ heterocycle, —O—, $—(CH_2)_nN(R^d)_2$, $—(CH_2)_nC(O)NH(CH_2)_nC_{4-10}$ heterocycle, COR, $—(CH_2)_n$halo, $—(CH_2)_nNHC(O)R^d$, $—(CH_2)_nNHC(O)NHR^d$, $—(CH_2)_nNHC(O)OR^d$, $—(CHR)_nC(O)N(R^d)_2$— $(CH_2)_nNHSO_2R^d$, and —OR, said alkyl, aryl and heterocycle optionally substituted with 1 to 3 groups of $R^b$, wherein at least two of $R^{a1}$, $R^{a2}$, $R^{a3}$, and $R^{a4}$ on the pryidyl are hydrogen, and one of $R^{a1}$, $R^{a2}$, $R^{a3}$, and $R^{a4}$ is phenyl, $R^1$ and $R^5$ are independently selected from hydrogen and halogen, $R^3$ is $CF_3$, or halogen, and one of $R^2$ and $R^4$ is hydrogen and the other is $(CHR)_nC_{5-10}$ heterocycle.

12. The compound according to claim 10 wherein $R^{a4}$ is phenyl, $R^1$ is hydrogen, $R^3$ is $CF_3$, $R^5$ is fluorine, $R^2$ is optionally substituted pyrazolyl, and $R^4$ is hydrogen.

13. The compound according to claim 1 represented by structural formula II:

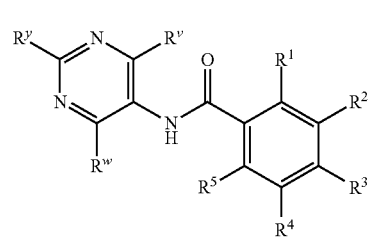

and pharmaceutically acceptable salts thereof, wherein $R^1$, $R^2$, $R^3$, $R^4$, and $R^5$ are as originally described, and $R^w$, $R^v$ and $R^y=R^a$.

14. The compound according to claim 13 wherein $R^w$, $R^v$, and $R^y$ are independently selected from hydrogen, $C_{1-4}$haloalkyl, $—OC_{1-4}$haloalkyl, $—C_{1-6}$alkyl, $—(CHR)_nC_{6-10}$ aryl, $—(CHR)_nC_{4-10}$ heterocycle, $—C(O)(CHR)_nC_{4-10}$ heterocycle, $—O—(CH_2)_nC_{6-10}$ aryl, $—O—(CH_2)_nC_{4-10}$ heterocycle, —O—, $—(CH_2)_nN(R^d)_2$, $—(CH_2)_nC(O)NH(CH_2)_nC_{4-10}$ heterocycle, COR, $—(CH_2)_n$halo, $—(CH_2)_nNHC(O)R^d$, $—(CH_2)_nNHC(O)NHR^d$, $—(CH_2)_nNHC(O)OR^d$, $—(CHR)_nC(O)N(R^d)_2$— $(CH_2)_nNHSO_2R^d$, and —OR, said alkyl, aryl and heterocycle optionally substituted with 1 to 3 groups of $R^b$, wherein at least two of $R^w$, $R^v$, and $R^y$ on the pryimidinyl are hydrogen, and one of $R^w$, $R^v$, and $R^y$ is phenyl, $R^1$ and $R^5$ are independently selected from hydrogen and halogen, $R^3$ is $CF_3$, or halogen, and one of $R^2$ and $R^4$ is hydrogen and the other is $(CHR)_nC_{5-10}$ heterocycle.

15. The compound according to claim 13 wherein $R^w$ is phenyl, $R^1$ is hydrogen, $R^3$ is $CF_3$, $R^5$ is fluorine, $R^2$ is optionally substituted pyrazolyl, and $R^4$ is hydrogen.

16. A pharmaceutical composition comprising a therapeutically effective amount of a compound of claim 1 or a pharmaceutically acceptable salt thereof, and a pharmaceutically acceptable carrier.

* * * * *